United States Patent
Joung et al.

(10) Patent No.: US 10,415,059 B2
(45) Date of Patent: *Sep. 17, 2019

(54) USING TRUNCATED GUIDE RNAS (TRU-GRNAS) TO INCREASE SPECIFICITY FOR RNA-GUIDED GENOME EDITING

(71) Applicant: The General Hospital Corporation, Boston, MA (US)

(72) Inventors: J. Keith Joung, Winchester, MA (US); Jeffry D. Sander, Ankeny, IA (US); Morgan Maeder, Brookline, MA (US); Yanfang Fu, Malden, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/430,218

(22) Filed: Feb. 10, 2017

(65) Prior Publication Data

US 2017/0152508 A1 Jun. 1, 2017

Related U.S. Application Data

(63) Continuation of application No. 14/213,723, filed on Mar. 14, 2014, now Pat. No. 9,567,604.

(60) Provisional application No. 61/799,647, filed on Mar. 15, 2013, provisional application No. 61/838,178, filed on Jun. 21, 2013, provisional application No. 61/838,148, filed on Jun. 21, 2013, provisional application No. 61/921,007, filed on Dec. 26, 2013.

(51) Int. Cl.
| | | |
|---|---|---|
| C12N 9/02 | (2006.01) | |
| C12N 9/10 | (2006.01) | |
| C12N 9/16 | (2006.01) | |
| C12N 9/22 | (2006.01) | |
| C12N 9/96 | (2006.01) | |
| C12N 15/01 | (2006.01) | |
| C12N 15/10 | (2006.01) | |
| C12N 15/11 | (2006.01) | |
| C12N 15/63 | (2006.01) | |
| C12N 15/85 | (2006.01) | |
| C12N 15/90 | (2006.01) | |
| C07K 14/005 | (2006.01) | |
| C07K 14/195 | (2006.01) | |

(52) U.S. Cl.
CPC .......... *C12N 15/907* (2013.01); *C07K 14/005* (2013.01); *C07K 14/195* (2013.01); *C12N 9/0071* (2013.01); *C12N 9/1007* (2013.01); *C12N 9/16* (2013.01); *C12N 9/22* (2013.01); *C12N 9/96* (2013.01); *C12N 15/01* (2013.01); *C12N 15/102* (2013.01); *C12N 15/1031* (2013.01); *C12N 15/11* (2013.01); *C12N 15/63* (2013.01); *C12N 15/85* (2013.01); *C12Y 301/21004* (2013.01); *C07K 2319/00* (2013.01); *C07K 2319/01* (2013.01); *C07K 2319/80* (2013.01); *C12N 2310/20* (2017.05); *C12N 2710/00033* (2013.01); *C12N 2770/00033* (2013.01); *C12N 2800/80* (2013.01); *C12Y 114/11* (2013.01); *C12Y 201/01* (2013.01); *C12Y 301/00* (2013.01)

(58) Field of Classification Search
None
See application file for complete search history.

(56) References Cited

U.S. PATENT DOCUMENTS

| | | | |
|---|---|---|---|
| 4,603,044 | A | 7/1986 | Geho et al. |
| 4,957,773 | A | 9/1990 | Spencer et al. |
| 5,436,150 | A | 7/1995 | Srinivasan |
| 6,007,988 | A | 12/1999 | Choo et al. |
| 6,013,453 | A | 1/2000 | Choo et al. |
| 6,503,717 | B2 | 1/2003 | Case et al. |
| 6,511,808 | B2 | 1/2003 | Wolffe et al. |
| 7,021,555 | B2 | 4/2006 | Bagnall |
| 7,220,719 | B2 | 5/2007 | Case |
| 7,914,796 | B2 | 3/2011 | Miller |
| 7,919,277 | B2 | 4/2011 | Russell et al. |
| 8,034,598 | B2 | 10/2011 | Miller |
| 8,071,370 | B2 | 12/2011 | Wolffe |
| 8,252,535 | B2 | 8/2012 | Biekle et al. |
| 8,282,920 | B2 | 10/2012 | Heo et al. |
| 8,361,725 | B2 | 1/2013 | Russell et al. |
| 8,697,359 | B1 | 4/2014 | Zhang |
| 8,771,986 | B2 | 7/2014 | Miller |
| 8,865,406 | B2 | 10/2014 | Zhang et al. |
| 8,962,281 | B2 | 2/2015 | Doyon |
| 8,993,233 | B2 | 3/2015 | Zhang et al. |
| 9,023,649 | B2 | 5/2015 | Mali et al. |

(Continued)

FOREIGN PATENT DOCUMENTS

| | | |
|---|---|---|
| CN | 103224947 | 7/2013 |
| CN | 103233028 | 8/2013 |

(Continued)

OTHER PUBLICATIONS

Ma et al. A Guide RNA Sequence Design Platform for the CRISPR/Cas9 System for Model Organism Genomes. BioMed Research International, 2013. Article ID 270805, 4 pages.*
Farboud and Meyer. Dramatic Enhancement of Genome Editing by CRISPR/Cas9 Through Improved Guide RNA Design. Genetics, 2015. 199:959-971.*
U.S. Appl. No. 61/799,647, Joung et al., filed Mar. 15, 2013.
U.S. Appl. No. 61/838,148, Joung et al., filed Jun. 21, 2013.
Addgene.org [Online]. CRISPR/Cas9 Guide on the web, Jan. 2016, [retrieved on Sep. 13, 2016]. Retrieved from the internet: URL<http://www.addgene.org/CRISPR/guide>/. 146 pages.

(Continued)

*Primary Examiner* — Christopher M Babic
*Assistant Examiner* — Kimberly A. Aron
(74) *Attorney, Agent, or Firm* — Fish & Richardson P.C.

(57) ABSTRACT

Methods for increasing specificity of RNA-guided genome editing, e.g., editing using CRISPR/Cas9 systems, using truncated guide RNAs (tru-gRNAs).

31 Claims, 28 Drawing Sheets

Specification includes a Sequence Listing.

(56) References Cited

U.S. PATENT DOCUMENTS

| | | |
|---|---|---|
| 9,074,199 B1 | 7/2015 | Chavez et al. |
| 9,322,037 B2 | 4/2016 | Liu et al. |
| 9,885,033 B2 | 2/2018 | Joung |
| 2002/0160940 A1 | 10/2002 | Case et al. |
| 2002/0164575 A1 | 11/2002 | Case et al. |
| 2006/0199190 A1 | 9/2006 | Russell et al. |
| 2007/0020627 A1 | 1/2007 | Barbas, III |
| 2008/0124725 A1 | 5/2008 | Barrangou et al. |
| 2008/0193470 A1 | 8/2008 | Masignani et al. |
| 2010/0034924 A1 | 2/2010 | Fremaux et al. |
| 2010/0055793 A1 | 3/2010 | Chandrasegaran |
| 2010/0076057 A1 | 3/2010 | Sontheimer et al. |
| 2010/0093617 A1 | 4/2010 | Barrangou et al. |
| 2010/0104690 A1 | 4/2010 | Barrangou et al. |
| 2010/0120043 A1 | 5/2010 | Sood et al. |
| 2010/0183559 A1 | 7/2010 | Van Sinderen et al. |
| 2010/0184624 A1 | 7/2010 | Samuel et al. |
| 2010/0209998 A1 | 8/2010 | Attwood et al. |
| 2010/0209999 A1 | 8/2010 | Altermann et al. |
| 2010/0221185 A1 | 9/2010 | Alterman et al. |
| 2010/0311061 A1 | 12/2010 | Korlach et al. |
| 2010/0317116 A1 | 12/2010 | Flusberg et al. |
| 2011/0002889 A1 | 1/2011 | Barrangou et al. |
| 2011/0092381 A1 | 4/2011 | Sood et al. |
| 2011/0143348 A1 | 6/2011 | Tomigahara et al. |
| 2011/0150852 A1 | 6/2011 | Chambaud et al. |
| 2011/0171647 A1 | 7/2011 | Tomigahara et al. |
| 2011/0189674 A1 | 8/2011 | Tomigahara et al. |
| 2011/0189776 A1 | 8/2011 | Terns et al. |
| 2011/0201007 A1 | 8/2011 | Waller et al. |
| 2011/0201118 A1 | 8/2011 | Yang et al. |
| 2011/0217739 A1 | 9/2011 | Terns et al. |
| 2011/0217791 A1 | 9/2011 | Tomigahara et al. |
| 2011/0223638 A1 | 9/2011 | Wiedenheft et al. |
| 2011/0236530 A1 | 9/2011 | Manoury et al. |
| 2011/0236894 A1 | 9/2011 | Rao et al. |
| 2011/0269119 A1 | 11/2011 | Hutchison et al. |
| 2011/0300528 A1 | 12/2011 | Jassim et al. |
| 2011/0300538 A1 | 12/2011 | Barrangou et al. |
| 2012/0027786 A1 | 2/2012 | Gupta et al. |
| 2012/0088676 A1 | 4/2012 | Weill et al. |
| 2012/0151635 A1 | 6/2012 | Coruzzi et al. |
| 2012/0214160 A1 | 8/2012 | Deng et al. |
| 2013/0011516 A1 | 1/2013 | Griffin et al. |
| 2013/0011828 A1 | 1/2013 | Barrangou et al. |
| 2013/0130248 A1 | 5/2013 | Haurwitz et al. |
| 2013/0145497 A1 | 6/2013 | Choi et al. |
| 2013/0150240 A1 | 6/2013 | Newman et al. |
| 2013/0158245 A1 | 6/2013 | Russell et al. |
| 2013/0253040 A1 | 9/2013 | Miller et al. |
| 2013/0288251 A1 | 10/2013 | Horvath et al. |
| 2013/0326645 A1 | 12/2013 | Cost et al. |
| 2013/0326725 A1 | 12/2013 | Shukla et al. |
| 2013/0330778 A1 | 12/2013 | Zeiner et al. |
| 2013/0337454 A1 | 12/2013 | Duchateau |
| 2014/0068797 A1 | 3/2014 | Doudna et al. |
| 2014/0093941 A1 | 4/2014 | Terns et al. |
| 2014/0113376 A1 | 4/2014 | Sorek et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0199767 A1 | 7/2014 | Barrangou et al. |
| 2014/0201857 A1 | 7/2014 | Fahrenkrug et al. |
| 2014/0212869 A1 | 7/2014 | Sampas et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0242702 A1 | 8/2014 | Chen et al. |
| 2014/0248702 A1 | 9/2014 | Zhang et al. |
| 2014/0256046 A1 | 9/2014 | Zhang et al. |
| 2014/0271987 A1 | 9/2014 | Manoury et al. |
| 2014/0273037 A1 | 9/2014 | Wu |
| 2014/0273226 A1 | 9/2014 | Wu |
| 2014/0273230 A1 | 9/2014 | Chen et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0273235 A1 | 9/2014 | Voytas et al. |
| 2014/0287938 A1 | 9/2014 | Zhang et al. |
| 2014/0294773 A1 | 10/2014 | Brouns et al. |
| 2014/0295556 A1 | 10/2014 | Joung et al. |
| 2014/0295557 A1 | 10/2014 | Joung et al. |
| 2014/0298547 A1 | 10/2014 | Sastry-Dent et al. |
| 2014/0304853 A1 | 10/2014 | Ainley et al. |
| 2014/0309487 A1 | 10/2014 | Lee et al. |
| 2014/0310828 A1 | 10/2014 | Lee et al. |
| 2014/0310830 A1 | 10/2014 | Zhang et al. |
| 2014/0315985 A1 | 10/2014 | May et al. |
| 2014/0335063 A1 | 11/2014 | Cannon et al. |
| 2014/0335620 A1 | 11/2014 | Zhang et al. |
| 2014/0349400 A1 | 11/2014 | Jakimo et al. |
| 2014/0356867 A1 | 12/2014 | Peter et al. |
| 2014/0356958 A1 | 12/2014 | Mali et al. |
| 2014/0357530 A1 | 12/2014 | Zhang et al. |
| 2014/0377868 A1 | 12/2014 | Joung et al. |
| 2015/0020223 A1 | 1/2015 | Zhang et al. |
| 2015/0024499 A1 | 1/2015 | Brouns et al. |
| 2015/0024500 A1 | 1/2015 | Yu et al. |
| 2015/0031134 A1 | 1/2015 | Zhang et al. |
| 2015/0044772 A1 | 2/2015 | Zhao |
| 2015/0045546 A1 | 2/2015 | Siksnys et al. |
| 2015/0050699 A1 | 2/2015 | Siksnys et al. |
| 2015/0056629 A1 | 2/2015 | Guthrie-Honea |
| 2015/0067922 A1 | 3/2015 | Yang et al. |
| 2015/0071899 A1 | 3/2015 | Liu et al. |
| 2015/0079681 A1 | 3/2015 | Zhang |
| 2015/0093473 A1 | 4/2015 | Barrangou et al. |
| 2015/0159174 A1 | 6/2015 | Frendeway et al. |
| 2015/0159175 A1 | 6/2015 | Frendeway et al. |
| 2015/0166969 A1 | 6/2015 | Takeuchi et al. |
| 2015/0167000 A1 | 6/2015 | Voytas et al. |
| 2015/0176064 A1 | 6/2015 | Fach et al. |
| 2015/0184139 A1 | 7/2015 | Zhang et al. |
| 2015/0191744 A1 | 7/2015 | Wolfe et al. |
| 2015/0203872 A1 | 7/2015 | Zhang |
| 2015/0232882 A1 | 8/2015 | Zhang et al. |
| 2015/0232883 A1 | 8/2015 | Dahlman et al. |
| 2015/0247150 A1 | 9/2015 | Zhang et al. |
| 2015/0252358 A1 | 9/2015 | Maeder et al. |
| 2015/0291965 A1 | 10/2015 | Zhang et al. |
| 2015/0315576 A1 | 11/2015 | Caliando et al. |
| 2015/0356239 A1 | 12/2015 | Zhang et al. |
| 2015/0376652 A1 | 12/2015 | Kuhn et al. |
| 2016/0010076 A1 | 1/2016 | Joung et al. |
| 2016/0010147 A1 | 1/2016 | Heron |
| 2016/0017301 A1 | 1/2016 | Khalili et al. |
| 2016/0017366 A1 | 1/2016 | Chen et al. |
| 2016/0024510 A1 | 1/2016 | Bikard et al. |
| 2016/0024523 A1 | 1/2016 | Joung et al. |
| 2016/0024524 A1 | 1/2016 | Joung et al. |
| 2016/0024529 A1 | 1/2016 | Carstens et al. |
| 2016/0312198 A1 | 10/2016 | Joung et al. |
| 2016/0362688 A1 | 12/2016 | May et al. |

FOREIGN PATENT DOCUMENTS

| | | |
|---|---|---|
| CN | 103343120 | 10/2013 |
| EP | 2325332 | 5/2011 |
| WO | WO 2003/072788 | 9/2003 |
| WO | WO 2004/099366 | 11/2004 |
| WO | WO 2007/014275 | 2/2007 |
| WO | WO 2007/025097 | 3/2007 |
| WO | WO 2008/108989 | 9/2008 |
| WO | WO 2010/054108 | 5/2010 |
| WO | WO 2011/017293 | 2/2011 |
| WO | WO 2011/143124 | 11/2011 |
| WO | WO 2012/093833 | 7/2012 |
| WO | WO 2012/164565 | 12/2012 |

(56) References Cited

FOREIGN PATENT DOCUMENTS

| | | |
|---|---|---|
| WO | WO 2013/012674 | 1/2013 |
| WO | WO 2013/098244 | 7/2013 |
| WO | WO 2013/141680 | 9/2013 |
| WO | WO 2013/142578 | 9/2013 |
| WO | WO 2013/169398 | 11/2013 |
| WO | WO 2013/176772 | 11/2013 |
| WO | WO 2014/0590255 | 4/2014 |
| WO | WO 2014/089290 | 6/2014 |
| WO | WO 2014/093655 | 6/2014 |
| WO | WO 2014/099744 | 6/2014 |
| WO | WO 2014/124284 | 8/2014 |
| WO | WO 2014/127287 | 8/2014 |
| WO | WO 2014/144288 | 9/2014 |
| WO | WO 2014/144592 | 9/2014 |
| WO | WO 2014/144761 | 9/2014 |
| WO | WO 2014/152432 | 9/2014 |
| WO | WO 2014/204578 | 12/2014 |
| WO | WO 2014/204724 | 12/2014 |
| WO | WO 2015/035162 | 3/2015 |
| WO | WO 2015/089364 | 6/2015 |
| WO | WO 2015/099850 | 7/2015 |
| WO | WO 2015/153940 | 10/2015 |
| WO | WO 2016/115355 | 6/2016 |

OTHER PUBLICATIONS

Al-Attar et al., "Clustered regularly interspaced short palindromic repeats (CRISPRs): the hallmark of an ingenious antiviral defense mechanism in prokaryotes," Biol Chem., Apr. 2011, 392:277-289.
Alexopoulou et al., "The CMV early enhancer/chicken β actin (CAG) promoter can be used to drive transgene expression during the differentiation of murine embryonic stem cells into vascular progenitors," BMC Cell Biology, Jan. 2008, 9:2.
Anders et al., "Structural basis of PAM-dependent target DNA recognition by the Cas9 endonuclease," Nature, Jul. 2014, 513:569-573.
Anonymous, "2013 Runners-Up. Genetic microsurgery for the masses," Science. Dec. 20, 2013;342(6165):1434-5.
Appela., "Non-natural nucleic acids for synthetic biology", Current Opinion in Chemical Biology, Dec. 2009,13(5-6): 687-696.
Arimondo et al., "Exploring the Cellular Activity of Camptothecin—Triple—Helix-Forming Oligonucleotide Conjugates," Mol. Cell. Biol. Jan. 2006, 26(1):324-33.
Arnould et al., "Engineering of large numbers of highly specific homing endonucleases that induce recombination on novel DNA targets," J Mol Biol., 355(3):443-458, Epub Nov. 15, 2005.
Arnould et al., "The I-CreI meganuclease and its engineered derivatives: applications from cell modification to gene therapy," Protein Eng Des Sel., 24(1-2):27-31, Epub Nov. 3, 2010.
Arora et al., "Residues 1-254 of anthrax toxin lethal factor are sufficient to cause cellular uptake of fused polypeptides," J. Biol. Chem., Feb. 1993, 268:3334-41.
Auer et al., "Highly efficient CRISPR/Case9-mediated known-in in zebrafish by homology-independent DNA repair," Genome Res., 2014, 24:142-153.
Bae et al., "Cas-OFFinder: a fast and versatile algorithm that searches for potential off-target sites of Cas9 RNA-guided endonucleases," Bioinformatics, Jan. 2014, 30:1473-1475.
Bae et al., "Human zinc fingers as building blocks in the construction of artificial transcription factors," Nat Biotechnol., 21(3):275-280, Epub Feb. 18, 2003.
Barker et al., "Increased DNA microarray hybridization specificity using sscDNA targets," BMC Genomics, Apr. 22, 2005, 2005, 6:57, 8 pages.
Baron-Benhamou et al., "Using the λN Peptide to Tether Proteins to RNAs," Methods Mole Biol., Jan. 2004, 257:135-153.
Barrangou & May, "Unraveling the potential of CRISPR-Cas9 for gene therapy," Expert Opin. Biol. Ther., Mar. 2015, 15:311-314.
Barrangou et al., "CRISPR Provides Acquired Resistance Against Viruses in Prokaryotes," Sci., 2007, 315:1709-1712.
Barrangou, "RNA-mediated programmable DNA cleavage," Nature Biotechnol., 2012, 30(9):836-838.
Bassett et al., "Highly efficient targeted mutagenesis of Drosophila with the CRISPR/Cas9 system," Cell Reports, 2013, 4:220-228.
Beerli and Barbas, "Engineering polydactyl zinc-finger transcription factors," Nat Biotechnol., 20(2):135-141, Feb. 2002.
Beerli et al., "Toward controlling gene expression at will: specific regulation of the erbB-2/HER-2 promoter by using polydactyl zinc finger proteins constructed from modular building blocks," PNAS USA, 1998, 95:14628-14633.
Belhaj et al., "Plant genome editing made easy: targeted mutagenesis in model and crop plants using the CRISPR/Cas system," Plant Methods, 2013, 9:39, 10 pages.
Bello et al., "Hypermethylation of the DNA repair gene MGMT: association with TP53 G:C to A:T transitions in a series of 469 nervous system tumors," Mutat. Res., Oct. 2004, 554:23-32.
Berg, "Proposed structure for the zinc-binding domains from transcription factor IIIA and related proteins," Proc Natl Acad Sci U S A., 85(1):99-102, Jan. 1988.
Bikard et al., "Programmable repression and activation of bacterial gene expression using an engineered CRISPR-Cas system," Nucleic Acid Res., Jun. 2013 41(15):7429-7437.
Bitinaite et al., "FokI dimerization is required for DNA cleavage," Proc. Natl. Acad. Sci. USA, 1998, 95:10570-10575.
Blackburn et al., "The CRISPR System-Keeping Zebrafish Gene Targeting Fresh," Zebrafish, 2013, 10(1):116-118.
Blaese et al., "T lymphocyte-directed gene therapy for ADA-SCID: initial trial results after 4 years," Science, Oct. 1995, 270:475-480.
Boch et al., "Breaking the code of DNA binding specificity of TAL-type III effectors," Science, Dec. 11, 2009;326(5959):1509-12.
Bogdanove & Voytas, "TAL Effectors: Customizable Proteins for DNA Targeting," Science Sep. 2011, 333:1843-1846.
Bogdanove et al., "TAL effectors: finding plant genes for disease and defense," Curr. Opin. Plant Biol. Aug. 2010, 13:394-401.
Burgess, "A CRISPR genome-editing tool," Nature Reviews Genetics 14, 80-81 (Feb. 2013).
Burnett et al., "Conditional macrophage ablation in transgenic mice expressing a Fas-based suicide gene," J. Leukoc. Biol., Apr. 2004, 75(4):612-623.
Butler and Kadonaga, "The RNA polymerase II core promoter: a key component in the regulation of gene expression," Genes & Dev., Oct. 2002, 16:2583-2592.
Canadian Office Action in Canadian Application No. 2907198, dated Jul. 8, 2016, 4 pages.
Carbonetti et al., "Use of pertussis toxin vaccine molecule PT19K/129G to deliver peptide epitopes for stimulation of a cytotoxic T lymphocyte response," Abstr. Annu. Meet. Am. Soc. Microbiol., 1995, 95:295.
Carroll et al., "Design, construction and in vitro testing of zinc finger nucleases," Nat Protoc. Oct. 2006, 1(3):1329-1341.
Carroll, "A CRISPR Approach to Gene Targeting," Molecular Therapy, 2012, 20(9):1658-1660.
Carroll, "Progress and prospects: zinc-finger nucleases as gene therapy agents," Gene Ther., 15(22):1463-1468, Epub Sep. 11, 2008.
Carroll, "Staying on target with CRISPR-Case," Nat Biotechnol., 2013, 31(9):807-809.
Castellano et al., "Inducible recruitment of Cdc42 or WASP to a cell-surface receptor triggers actin polymerization and filopodium formation," Curr. Biol., Apr. 1999, 9(7): 351-360.
Cathomen and Joung, "Zinc-finger nucleases: the next generation emerges," Mol. Ther., 2008, 16:1200-1207.
Cermak et al., "Efficient design and assembly of custom TALEN and other TAL effector-based constructs for DNA targeting," Nucleic Acids Res. Jul. 2011, 39:e82, p. 1-11.
Chaikind et al., "Targeted DNA Methylation Using an Artificially Bisected M.HhaI Fused to Zinc Fingers," PLoS ONE Sep. 2012, 7(9):E44852 pp. 1-11.
Chang et al., "Genome editing with RNA-guided Cas9 nuclease in zebrafish embryos," Cell Res., 2013, 23:465-472.
Chen & Zhao, "A highly sensitive selection method for directed evolution of homing endonucleases," Nucleic Acids Res., Oct. 2005, 33(18):e154.

(56) References Cited

OTHER PUBLICATIONS

Chen et al., "Cut Site Selection by the Two Nuclease Domains of the Cas9 RNA-guided Endonuclease," J Biol Chem. May 9, 2014; 289(19):13284-94.

Chen et al., "Dynamic imaging of genomic loci in living human cells by an optimized CRISPR/Cas system," Cell, 2013, 155(7):1479-1491.

Chen et al., "Efficient genome editing in Caenorhabditis elegans by CRISPR-targeted homologous recombination," Nucleic Acids Res., 2013, 41(20):e193, 6 pages.

Chen et al., "Induced DNA demethylation by targeting Ten-Eleven Translocation 2 to the human ICAM-1 promoter," Nucleic Acids Res., 42(3):1563-1574, Epub Nov. 4, 2013.

Cheng et al., "Multiplexed activation of endogenous genes by CRISPR-on, an RNA-guided transcriptional activator system," Cell Res., Oct. 2013, 23(10):1163-71.

Chim et al., "Methylation profiling in multiple myeloma," Leuk. Res., Apr. 2004, 28:379-85.

Chiu et al., "Transgene-free genome editing in Caenorhabditis elegans using CRISPR-Cas," Genetics, Nov. 2013, 195(3):1167-71.

Cho et al., "Analysis of off-target effects of CRISPR/Case-derived RNA-guided endonucleases and nickases," Genome Res., 2014, 24:132-141.

Cho et al., "Targeted genome engineering in human cells with the Cas9 RNA-guided endonuclease," Nat Biotechnol., 2013, 31:230-232.

Choo and Klug, "Toward a code for the interactions of zinc fingers with DNA: selection of randomized fingers displayed on phage," Proc Natl Acad Sci U S A., 91(23):11163-11167, Nov. 8, 1994.

Christian et al., "Targeting DNA Double-Strand Breaks with TAL Effector Nucleases," Genetics, Oct. 2010, 186:757-761.

Chylinski et al., "Classification and evolution of type II CRISPR-Cas systems," Nucleic Acids Res. 2014;42(10):6091-105.

Chylinski et al., "The tracrRNA and Cas9 families of type II CRISPR-Cas immunity systems," RNA Biol., 2013, 10(5):726-737.

Clark-Curtiss and Curtiss, "Analysis of recombinant DNA using *Escherichia coli* minicells," Methods in Enzymology, 1983, 101:347-362.

Colley et al., "Conversion of a Golgi Apparatus Sialyltransferase to a Secretory Protein by Replacement of the NH2-terminall Signal Anchor with a Signal Peptide," J. Biol. Chem., 1989, 264:17619-22.

Cong et al., "Multiplex genome engineering using CRISPR/Cas systems," Science, 2013, 339:819-823 (Author Manuscript).

Conklin, "Sculpting genomes with a hammer and chisel," Nature Methods, 2013, 10(9):839-840.

Costa et al., "REELIN and schizophrenia: a disease at the interface of the genome and the epigenome," Mol. Interv., Feb. 2002, 2:47-57.

Crabtree and Schreiber, "Three-part inventions: intracellular signaling and induced proximity," Trends Biochem. Sci., Nov. 1996, 21(11):418-422.

Cradick et al., "CRISPR/Cas9 systems targeting beta-globin and CCR5 genes have substantial off-target activity," Nucleic Acids Res., 2013, 41(20):9584-92.

d'Avignon et al., "Site-specific experiments on folding/unfolding of Jun coiled coils: thermodynamic and kinetic parameters from spin inversion transfer nuclear magnetic resonance at leucine-18," Biopolymers, 83(3):255-267, Oct. 15, 2006.

de Souza, "RNA-guided gene editing," Nat Methods, Mar. 2013, 10(3):189.

De Zhu, "The altered DNA methylation pattern and its implications in liver cancer," Cell. Res., Apr. 2005, 15:272-80.

Deltcheva et al., "CRISPR RNA maturation by trans-encoded small RNA and host factor Rnase III," Nature, 2011, 471(7340):602-607 (Author Manuscript).

Deveau et al., "Phage response to CRISPR-encoded resistance in *Streptococcus thermophilus*," J Bacteriol., Feb. 2008, 190(4):1390-400.

Dicarlo et al., "Genome engineering in *Saccharomyces cerevisiae* using CRISPR-Cas systems," Nucleic Acids Res., 2013, 41(7):4336-43.

Dickinson et al., "Engineering the *Caenorhabditis elegans* genome using Cas9-triggered homologous recombination," Nat Methods., Oct. 2013, 10(10):1028-34.

Ding et al., "Enhanced efficiency of human pluripotent stem cell genome editing through replacing TALENs with CRISPRs," Cell Stem Cell., Apr. 4, 2013, 12(4):393-4 (Author Manuscript).

Donnelly et al., "Targeted delivery of peptide epitopes to class I major histocompatibility molecules by a modified Pseudomonas exotoxin," PNAS, Apr. 1993, 90:3530-34.

Doudna and Charpentier, "Genome editing. The new frontier of genome engineering with CRISPR-Cas9," Science, Nov. 2014, 346:1258096, 11 pages.

Doyon et al., "Directed Evolution and Substrate Specificity Profile of Homing Endonuclease I-Scel," J. Am. Chem. Soc., Feb. 2006, 128:2477-2484.

Doyon et al., "Heritable targeted gene disruption in zebrafish using designed zinc-finger nucleases," Nat Biotechnol., Jun. 2008, 26:702-708.

Dranoff et al., "A phase I study of vaccination with autologous, irradiated melanoma cells engineered to secrete human granulocyte-macrophage colony stimulating factor," Hum. Gene Ther., Jan. 1997, 8(1):111-23.

Dunbar et al., "Retrovirally Marked CD34-Enriched Peripheral Blood and Bone Marrow Cells Contribute to Long-Term Engraftment After Autologous Transplantation ," Blood, Jun. 1995, 85:3048-3057.

Eisenschmidt et al., "Developing a programmed restriction endonuclease for highly specific DNA cleavage," Nucleic Acids Res. Dec. 2005, 33(22):7039-47.

Ellem et al., "A case report: immune responses and clinical course of the first human use of granulocyte/macrophage-colony-stimulating—factor-transduced autologous melanoma cells for immunotherapy," Immunol Immunother., Mar. 1997, 44:10-20.

Elrod-Erickson et al., "High-resolution structures of variant Zif268-DNA complexes: implications for understanding zinc finger-DNA recognition," Structure, 6(4):451-464, Apr. 15, 1998.

Esteller et al., "A Gene Hypermethylation Profile of Human Cancer," Cancer Res., Apr. 2001, 61:3225-9.

Esteller et al., "Promoter Hypermethylation and BRCA1 Inactivation in Sporadic Breast and Ovarian Tumors," J. Natl. Cancer Inst., Apr. 2000, 92:564-9.

Esvelt et al., "Orthogonal Cas9 proteins for RNA-guided gene regulation and editing," Nat Methods, Nov. 2013, 10(11):1116-21.

European Partial Supplementary Search Report in European Application No. 14764117.9, dated Aug. 11, 2016, 7 pages.

European Search Report in European Application No. 14763916.5, dated Jul. 27, 2016, 10 pages.

Extended European Search Report in European Application No. 14764159.1, dated Aug. 10, 2016.

Extended European Search Report in European Application No. 14768877.4, dated Aug. 10, 2016.

Fisher et al., "A scalable, fully automated process for construction of sequence-ready human exome targeted capture libraries," Genome Biol., Jan. 2011, 12-R1.

Fonfara et al., "Phylogeny of Cas9 determines functional exchange-ability of dual-RNA and Cas9 among orthologous type II CRISPR-Cas systems." Nucleic Acids Res., Feb. 2014, 42(4):2577-90.

Freeman et al., "Inducible Prostate Intraepithelial Neoplasia with Reversible Hyperplasia in Conditional FGFR1-Expressing Mice," Cancer Res., Dec. 2003, 63(23):8256-8563.

Friedland et al., "Heritable genome editing in *C. elegans* via a CRISPR-Cas9 system," Nature Methods 10(8): 741-743, 2013 (Author Manuscript).

Fu et al, Targeted genome editing in human cells using CRISPR/Cas nucleases and truncated guide RNAs, Methods in Enzymology, Nov. 2014, 546: 21-45.

Fu et al., "High-frequency off-target mutagenesis induced by CRISPR-Cas nucleases in human cells," Nat Biotechnol., 2013, 31:822-826 (Author Manuscript).

(56) References Cited

OTHER PUBLICATIONS

Fu et al., "Improving CRISPR-Cas nuclease specificity using truncated guide RNAs," Nat. Biotechnol. Mar. 2014, 32:279-284.
Gabriel et al., "An unbiased genome-wide analysis of zinc-finger nuclease specificity," Nat Biotechnol., 2011, 29:816-823.
Gagnon et al., "Efficient mutagenesis by Cas9 protein-mediated oligonucleotide insertion and large-scale assessment of single-guide RNAs," PLoS One, May 2014, 9, e98186.
Gaj et al., ZFN, TALEN, and CRISPR/Cas-based methods for genome engineering, Trends in Biotechnology, Jul. 2013, 31(7): 397-405.
Gao et al., "Hypermethylation of the RASSF1A gene in gliomas," Clin. Chim. Acta., Nov. 2004, 349:173-9.
Garcia-Bustos et al., "Nuclear protein localization," Biochim. Biophys. Acta, Mar. 1991, 1071:83-101.
Garneau et al., "The CRISPR/Cas bacterial immune system cleaves bacteriophage and plasmid DNA," Nature, Nov. 4, 2010, 468(7320):67-71.
Gasiunas and Siksnys, "RNA-dependent DNA endonuclease Cas9 of the CRISPR system: Holy Grail of genome editing?" Trends Microbiol., 2013, 21(11):562-567.
Gasiunas,"Cas9-crRNA ribonucleoprotein complex mediates specific DNA cleavage for adaptive immunity in bacteria," Proc Natl Acad Sci U S A, Sep. 25, 2012, 109(39):E2579-86.
Geibler et al., "Transcriptional Activators of Human Genes with Programmable DNA-Specificity ," PLoS ONE May 2011, 6:e19509.
Gilbert et al., "CRISPR-mediated modular RNA-guided regulation of transcription in eukaryotes," Cell, 2013, 154(2):442-51.
Gossen and Bujard, "Tight control of gene expression in mammalian cells by tetracycline-responsive promoters," Proc. Natl. Acad. Sci., Jun. 1992, 89:5547-5551.
Graef et al., "Proximity and orientation underlie signaling by the non-receptor tyrosine kinase ZAP70," Embo. J., Sep. 1997, 16(18):5618-5628.
Gratz et al., "CRISPR/Cas9-mediated genome engineering and the promise of designer flies on demand," Fly (Austin), Oct.-Dec. 2013, 7(4):249-55.
Gratz et al., "Genome engineering of *Drosophila* with the CRISPR RNA-guided Cas9 nuclease," Genetics, 2013, 194(4):1029-35.
Grizot et al., "Generation of redesigned homing endonucleases comprising DNA-binding domains derived from two different scaffolds," Nucleic Acids Res., 38(6):2006-2018, Epub Dec. 21, 2009.
Gross and Garrard, "Nuclease Hypersensitive Sites in Chromatin," Annu. Rev. Biochem., Jul. 1988, 57:159-97.
Guilinger et al., "Broad specificity profiling of TALENs results in engineered nucleases with improved DNA-cleavage specificity," Nat. Methods, Apr. 2014, 11:429-435.
Guilinger et al., "Fusion of catalytically inactive Cas9 to FokI nuclease improves the specificity of genome modification," Nat Biotechnol., Apr. 2014, 32(6):577-583.
Guo et el., "Hydroxylation of 5-Methylcytosine by TET1 Promotes Active DNA Demethylation in the Adult Brain ," Cell Apr. 2011, 145:423-434.
Haft et al., "A Guild of 45 CRISPR-Associated (Cas) Protein Families and Multiple CRISPER/cas Subtypes Exist in Prokaryotic Genomes," PLOS, 1(6):0474-0483 (2005).
Hale et al., "Essential features and rational design of CRISPR RNAs that function with the Case RAMP modlule complex to cleave RNAs," Mol Cell., 2012, 45(3):292-302 (Author Manuscript).
Han et al., "CTCF Is the Master Organizer of Domain-Wide Allele-Specific Chromatin at the H19/Igf2 Imprinted Region," Mol Cell Biol., Feb. 2008, 28(3):1124-35.
Han et al., "Ligand-directed retroviml targeting of human breast cancer cells," PNAS, Oct. 1995, 92:9747-51.
Harikrishna et al., "Construction and function of fusion enzymes of the human cytochrome P450scc system," DNA Cell Biol., 12(5):371-379, Jun. 1993.
Harrison, "A structural taxonomy of DNA-binding domains," Nature, 353(6346): 715-719, Oct. 24, 1991.

Haurwitz et al., "Sequence- and Structure-Specific RNA Processing by a CRISPR Endonuclease," Science, Sep. 2010, 329(5997):1355-8.
Haurwitz, R. "The CRISPR endoribonuclease Csy4 utilizes unusual sequence and structures pecific mechanisms to recognize and process crRNAs," Thesis. May 8, 2012 (May 8, 2012), University of California, Berkeley, pp. 1-120. Retrieved from the lnternet:<http://escholarship.org/uc/item/0rh5940p> on Dec. 26, 2014 (Dec. 26, 2014). entire document.
He et al., "Tet-Mediated Formation of 5-Carboxylcytosine and Its Excision by TDG in Mammalian DNA," Science, Sep. 2011, 333:1303-1307.
Hockemeyer et al., "Genetic engineering of human ES and iPS cells using TALE nucleases," Nat Biotechnol., 2011, 29:731-734 (Author Manuscript).
Horii et al., "Generation of an ICF Syndrome Model by Efficient Genome Editing of Human Induced Pluripotent Stem Cells using the CRISPR System," Int J Mol Sci., 2013, 14:19774-19781.
Horvath and Barrangou, "CRISPR/Cas, the immune system of bacteria and archaea," Science, 2010, 327:167-170.
Horvath et al., "Diversity, activity, and evolution of CRISPR loci in *Streptococcus thermophilus*," J. Bacteriol., Feb. 2008, 190:1401-1412.
Hou et al., "Efficient genome engineering in human pluripotent stem cells using Cas9 from Neisseria meningitidis," Proc Natl Acad Sci U S A, Sep. 24, 2013, 110(39):15644-9.
Hsu et al., "Development and Applications of CRISPR-Cas9 for Genome Engineering," Cell, 2014, 157(6): 1262-1278.
Hsu et al., "DNA targeting specificity of RNA-guided Cas9 nucleases," Nat Biotechnol., 2013, 31:827-832.
Huang et al., "Heritable gene targeting in zebrafish using customized TALENs," Nat. Biotechnol. Aug. 2011, 29:699-700.
Hwang et al., "Efficient In Vivo Genome Editing Using RNA-Guided Nucleases," Nat Biotechnol., 2013, 31:227-229 (Author Manuscript).
Hwang et al., "Heritable and Precise Zebrafish Genome Editing Using a CRISPR-Cas System," PLoS One, 2013, 8(7):e68708, 9 pages.
International Preliminary Report on Patentability in International Application No. PCT/US2013/043075, dated Dec. 2, 2014, 7 pages.
International Preliminary Report on Patentability in International Application No. PCT/US2014/028630, dated Sep. 15, 2015, 8 pages.
International Preliminary Report on Patentability in International Application No. PCT/US2014/029304, dated Sep. 22, 2015, 12 pages.
International Preliminary Report on Patentability in International Application No. PCT/US2014/056416, dated Jun. 28, 2016, 7 pages.
International Search Report and Written Opinion in International Application No. PCT/US2014/027335, dated Jul. 16, 2014, 13 pages.
International Search Report and Written Opinion in International Application No. PCT/US2014/028630, dated Jul. 24, 2014, 9 pages.
International Search Report and Written Opinion in International Application No. PCT/US2014/035162, dated Oct. 14, 2014, 10 pages.
International Search Report and Written Opinion in International Application No. PCT/US2014/029068, dated Nov. 5, 2014, 15 pages.
International Search Report and Written Opinion in International Application No. PCT/US2013/043075, dated Sep. 26, 2013, 10 pages.
International Search Report and Written Opinion in International Application No. PCT/US2013/074736, dated Sep. 17, 2014.
International Search Report in International Application No. PCT/US2014/054291, dated Mar. 27, 2015.
Invitation to Pay Additional Fees and, Where Applicable, Protest Fee in International Application No. PCT/US2014/029068, mailed Aug. 20, 2014, 3 pages.
Invitation to Pay Additional Fees and, Where Applicable, Protest Fee in International Application No. PCT/US2014/029304, mailed Jul. 30, 2014, 3 pages.

(56) References Cited

OTHER PUBLICATIONS

Isalan et al., "A rapid, generally applicable method to engineer zinc fingers illustrated by targeting the HIV-1 promoter," Nat. Biotechnol., 19(7):656-660, Jul. 2001.

Ishino et al., "Nucleotide sequence of the iap gene, responsible for alkaline phosphatase isozyme conversion in Escherichia coli, and identification of the gene product," J Bacteriol., Dec. 1987, 169(12):5429-33.

Iyer et al., "Prediction of novel families of enzymes involved in oxidative and other complex modifications of bases in nucleic acids," Cell Cycle, Jun. 1, 2009, 8(11):1698-710.

Iyer et al., Supplementary Material for "Prediction of novel families of enzymes involved in oxidative and other complex modifications of bases in nucleic acids," Cell Cycle, Jun. 1, 2009, 8(11):1698-710, [retrieved on Dec. 22, 2015]. Retrieved from the Internet: URL <ftp://ftp.ncbi.nih.gov/pub/aravind/DONS/supplementaly_material_DONS.html>.

Jansen et al., "Identification of genes that are associated with DNA repeats in prokaryotes," Mol Microbiol., Mar. 2002, 43(6):1565-75.

Jiang et al., "CRISPR-assisted editing of bacterial genomes," Nat Biotechnol., 2013, 31:233-239 (Author Manuscript).

Jiang et al., "Structural Biology. A Cas9-guide RNA complex preorganized for target DNA recognition," Science, Jun. 2015, 348:1477-1481.

Jinek et al., "A programmable dual-RNA-guided DNA endonuclease in adaptive bacterial immunity," Science, 2012, 337:816-821.

Jinek et al., "RNA-programmed genome editing in human cells," Elife, 2013, 2:e00471, 9 pages.

Jinek et al., "Structures of Cas9 Endonucleases Reveal RNA-Mediated Conformational Activation," Science. Mar. 14, 2014; 343(6176):1247997.

Josephs et al., "Structure and specificity of the RNA-guided endonuclease Cas9 during DNA interrogation, target binding and cleavage," Nucleic Acids Res., Sep. 2015, 43:8924-8941.

Joung and Sander, "TALENs: a widely applicable technology for targeted genome editing," Nat Rev Mol Cell Biol., 14(1):49-55, Epub Nov. 21, 2012.

Joung et al., "Reply to "Successful genome editing with modularly assembled zinc finger nucleases"," Nat. Methods, Jan. 2010, 7:91-92.

Karkare and Bhatnagar, "Promising nucleic acid analogs and mimics. characteristic features and applications of PNA, LNA, and morpholino", Applied Microbiology and Biotechnology, May 2006, 71(5): 575-586.

Karvelis et al., "crRNA and tracrRNA guide Cas9-mediated DNA interference in Streptococcus thermophilus," RNA Biol., 2013, 10(5):841-851.

Katic and Graβhans, "Targeted heritable mutation and gene conversion by Cas9-CRISPR in Caenorhabditis elegans," Genetics, Nov. 2013, 195(3):1173-6.

Kearns et al., "Recombinant adeno-associated virus (AAV-CFTR) vectors do not integrate in a site-specific fashion in an immortalized epithelial cell line," Gene Ther., Sep. 1996, 9:748-55.

Keryer-Bibens et al., "Tethering of proteins to RNAs by bacteriophage proteins," Biol Cell, Feb. 2008, 100:125-138.

Kiani et al., "Cas9 gRNA engineering for genome editing, activation and repression," Nat. Methods, Nov. 2015, 12:1051-1054.

Kim and Kim, "A guide to genome engineering with progmmmable nucleases," Nature Rev Genetics 15, 321-334 (2014).

Kim et al., "Highly efficient RNA-guided genome editing in human cells via delivery of purified Cas9 ribonucleoproteins," Genome Res. Jun. 2014; 24(6):1012-9.

Kim et al., "Targeted genome editing in human cells with zinc finger nucleases constructed via modular assembly," Genome Res., 19(7):1279-1288, Epub May 21, 2009.

Kim et al., "Genome editing with modularly assembled zinc-finger nucleases," Nat. Methods, 7(2):91-92, Feb. 2010.

Kleinstiver et al., "Engineered CRISPR-Cas9 nucleases with altered PAM specificities," Nature, Jul. 2015, 523(7561):481-5.

Klimpel et al., "Anthrax toxin protective antigen is activated by a cell surface protease with the sequence specificity and catalytic properties of furin," PNAS, Nov. 1992, 89:10277-81.

Koike-Yusa et al., "Genome-wide recessive genetic screening in mammalian cells with a lentiviral CRISPR-guide RNA library," Nat Biotechnol., Mar. 2014, 32(3):267-73.

Kondo and Ueda, "Highly improved gene targeting by germline-specific Cas9 expression in Drosophila," Genetics, Nov. 2013, 195(3):715-21.

Konermann et al., "Optical control of mammalian endogenous transcription and epigenetic states," Nature. Aug. 22, 2013; 500(7463):472-6. (Author Manuscript).

Kumar et al., "DNA-Prot: identification of DNA binding proteins from protein sequence information using random forest," J Biomol Struct Dyn., 26(6):679-686, Jun. 2009.

Kumar et al., "Identification of DNA-binding proteins using support vector machines and evolutionary profiles," BMC Bioinformatics, 8:463, Nov. 27, 2007.

Kurmasheva et al., "Upstream CpG island methylation of the PAX3 gene in human rhabdomyosarcomas," Pediatr. Blood Cancer, Apr. 2005, 44:328-37.

Lea et al., "Aberrant p16 methylation is a biomarker for tobacco exposure in cervical squamous cell carcinogenesis," Am. J. Obstet. Gynecol., Mar. 2004, 190:674-9.

Li et al., "Heritable gene targeting in the mouse and rat using a CRISPR-Cas system," Nat Biotechnol, Aug. 2013, 31(8):681-3.

Li et al., "Modularly assembled designer TAL effector nucleases for targeted gene knockout and gene replacement in eukaryotes," Nucleic Acids Res., 39(14):6315-6325, Epub Mar. 31, 2011.

Li et al., "Protein trans-splicing as a means for viral vector-mediated in vivo gene therapy," Hum Gene Ther., 19(9):958-964, Sep. 2008.

Li et al., "Simultaneous generation and germline transmission of multiple gene mutations in rat using CRISPR-Cas systems," Nat Biotechnol., Aug. 2013, 31(8):684-6.

Li et al., "TAL nucleases (TALNs): hybrid proteins composed of TAL effectors and FokI DNA-cleavage domain," Nucleic Acids Res., 2011, 39(1): 359-372.

Liu et al., "Validated zinc finger protein designs for all 16 GNN DNA triplet targets," J. Biol. Chem., 277(6):3850-3856, Epub Nov. 28, 2001.

Lo et al., "Precise and Heritable Genome Editing in Evolutionarily Diverse Nematodes Using TALENs and CRISPR/Cas9 to Engineer Insertions and Delections," Genetics, 2013, 195:331-348.

Maeder et al., "CRISPR RNA-guided activation of endogenous human genes," Nat Methods, Oct. 2013, 10:977-979 (Author Manuscript).

Maeder et al., "Rapid 'open-source' engineering of customized zinc-finger nucleases for highly efficient gene modification," Mol Cell, Jul. 2008, 31(2):294-301.

Majumdar et al., "Targeted Gene Knock in and Sequence Modulation Mediated by a Psoralen-linked Triplex-forming Oligonucleotide," J Biol Chem., Apr. 2008, 283(17):11244-52.

Makarova et al., "A putative RNA-interference-based immune system in prokaryotes: computational analysis of the predicted enzymatic machinery, functional analogies with eukaryotic RNAi, and hypothetical mechanisms of action," Biol. Direct, Mar. 2006, 1:7, 26 pages.

Makarova et al., "Evolution and classification of the CRISPR-Cas systems," Nat. Rev. Microbiol., 2011, 9(6):467-77 (Author Manuscript).

Makarova et al., "Unification of Cas protein families and a simple scenario for the origin and evolution of CRISPR-Cas systems," Biol. Direct, Jul. 2011, 6:38, 27 pages.

Malech et al., "Prolonged production of NADPH oxidase-corrected granulocytes after gene therapy of chronic granulomatous disease," PNAS, Oct. 1997, 94:12133-38.

Mali et al., "Cas9 as a versatile tool for engineering biology," Nature Methods, 2013, 10(10):957-963.

Mali et al., "CAS9 transcriptional activators for target specificity screening and paired nickases for cooperative genome engineering," Nat Biotechnol, Aug. 2013, 31:833-838.

Mali et al., "RNA-guided human genome engineering via Cas9," Science, Feb. 2013, 339:823-826 (Author Manuscript).

(56) References Cited

OTHER PUBLICATIONS

Mancini et al. "CpG methylation within the 5' regulatory region of the BRCA1 gene is tumor specific and includes a putative CREB binding site," Oncogene, 1998, 16:1161-9.
Mandell and Barbas et al., "Zinc Finger Tools: custom DNA-binding domains for transcription factors and nucleases," Nucleic Acids Res., 34(Web Server issue):W516-W523, Jul. 1, 2006.
Marraffini and Sontheimer, "CRISPR Interference Limits Horizontal Gene Transfer in *Staphylococci* by Targeting DNA," Science, Dec. 2008, 322(5909):1843-1845.
Marraffini and Sontheimer, "Self vs. non-self discrimination during CRISPR RNA-directed immunity," Nature, Jan. 2010, 463(7280):568-571 (Author Manuscript).
Mashiko et al., "Generation of mutant mice by pronuclear injection of circular plasmid expressing Cas9 and single guided RNA," Sci Reports, 2013, 3(3355):1-6.
McGarty, "CRISPRs and Cancer," White Paper No. 111, Apr. 2014, 22 pages.
Mendenhall et al., "Locus-specific editing of histone modifications at endogenous enhancers," Nat Biotechnol., 31(12):1133-1136, Epub Sep. 8, 2013.
Miller et al., "A TALE nuclease architecture for efficient genome editing," Nature Biotechnology, Feb. 2011, 29:143-148.
Miller et al., "An improved zinc-finger nuclease architecture for highly specific genome editing," Nat Biotechnol., Jul. 2007, 25:778-785.
Miyazaki et al., "Expression vector system based on the chicken beta-actin promoter directs efficient production of interleukin-5," Gene, Jul. 1989, 79(2):269-77.
Mojica et al., "Biological significance of a family of regularly spaced repeats in the genomes of Archaea, Bacteria and mitochondria," Mol Microbiol., Apr. 2000, 36(1):244-6.
Mojica et al., "Short motif sequences determine the targets of the prokaryotic CRISPR defense system," Microbiology, Mar. 2009, 155:733-740.
Moore et al., "Design of polyzinc finger peptides with structured linkers," Proc Natl Acad Sci USA, Feb. 2001, 98:1432-1436.
Morbitzer et al., "Regulation of selected genome loci using de novo-engineered transcription activator-like effector (TALE)-type transcription factors," Proc Natl Acad Sci U S A., 107(50):21617-21622, Epub Nov. 24, 2010.
Morbitzer et al., "Assembly of custom TALE-type DNA binding domains by modular cloning," Nucl Acids Res. Jul. 2011, 39:5790-5799.
Mussolino and Cathomen, "RNA guides genome engineering," Nat Biotechnol., Mar. 2013, 31(3):208-209.
Mussolino et al., "A novel TALE nuclease scaffold enables high genome editing activity in combination with low toxicity," Nucleic Acids Res., Nov. 2011, 39:9283-93.
Neering et al., "Transduction of Primitive Human Hematopoietic Cells With Recombinant Adenovirus Vectors," Blood, Aug. 1996, 88:1147-55.
Nishimasu et al., "Crystal structure of Cas9 in complex with guide RNA and target DNA," Cell, 2014, 156:935-949.
Niu et al., "Generation of gene-modified cynomolgus monkey via Cas9/RNA-mediated gene targeting in one-cell embryos," Cell, 2014, 156:836-843.
Oligino et al., "Drug inducible transgene expression in brain using a herpes simplex virus vector," Gene Ther., 1998, 5:491-496.
Pattanayak et al., "High-throughput profiling of off-target DNA cleavage reveals RNA-programmed Cas9 nuclease specificity," Nat Biotechnol., 2013, 31:839-843 (Author Manuscript).
Pattanayak et al., "Revealing off-target cleavage specificities of zinc-finger nucleases by in vitro selection," Nat Methods, Aug. 2011, 8:765-770 (Author Manuscript).
Pavletich and Pabo, "Zinc finger-DNA recognition: crystal structure of a Zif268-DNA complex at 2.1 A," Science, 252(5007):809-817, May 10, 1991.
Perez et al., "Establishment of HIV-1 resistance in CD4+ T cells by genome editing using zinc-finger nucleases," Nat Biotechnol., Jul. 2008, 26:808-816 (Author Manuscript).
Perez-Pinera et al., "RNA-guided gene activation by CRISPR-Case9-based transcription factors," Nat Methods, 2013, 10(10):973-976 (Author Manuscript).
Pingoud and Silva, "Precision genome surgery," Nat Biotechnol., 25(7):743-744, Jul. 2007.
Puchta and Fauser et al., "Synthetic nucleases for genome engineering in plants: prospects for a bright future," Plant J. Jun. 2014; 78(5):727-41.
Qi et al., "Repurposing CRISPR as an RNA-Guided Platform for Sequence-Specific Control of Gene Expression," Cell, Feb. 2013, 152:1173-1183.
Ramakrishna et al., "Gene disruption by cell-penetrating peptide-mediated delivery of Cas9 protein and guide RNA," Genome Res. Jun. 2014; 24(6): 1020-1027.
Ramakrishna et al., "Surrogate reporter-based enrichment of cells containing RNA-guided Cas9 nuclease-induced mutations," Nat Commun. Feb. 26, 2014; 5:3378.
Ramalingam et al., "A CRISPR way to engineer the human genome," Genome Biol., 2013, 14:107, 4 pages.
Ramirez et al., "Unexpected failure rates for modular assembly of engineered zinc fingers," Nat Methods., 5(5):374-375, May 2008.
Ran et al., "Double nicking by RNA-guided CRISPR Cas9 for enhanced genome editing specificity," Cell, Sep. 2013, 154:1380-1389.
Ran et al., "Genome engineering using the CRISPR-Cas9 system," Nature Protocols, Nov. 2013, 8(11):2281-2308.
Ran et al., "In vivo genome editing using *Staphylococcus aureus* Cas9," Nature, Apr. 2015, 520:186-191.
Rebar and Pabo, "Zinc finger phage: affinity selection of fingers with new DNA-binding specificities," Science, 263(5147):671-673, Feb. 4, 1994.
Ren et al., "Optimized gene editing technology for *Drosophila melanogaster* using germ line-specific Cas9," Proc Natl Acad Sci U S A, Nov. 19, 2013, 110(47):19012-7.
Rendahl et al., "Regulation of gene expression in vivo following transduction by two separate rAAV vectors," Nat. Biotechnol., Aug. 1998, 16:757-761.
Reyon et al., "FLASH assembly of TALENs for high-throughput genome editing," Nat Biotech, May 2012, 30:460-465 (Author Manuscript).
Rodenhiser and Mann, "Epigenetics and human disease: translating basic biology into clinical applications," CMAJ, Jan. 2006, 174(3):341-348.
Rohde et al., "BISMA—Fast and accurate bisulfite sequencing data analysis of individual clones from unique and repetitive sequences," BMC Bioinformatics, May 2010, 11:230 12 pages.
Rothman, "Mechanisms of intracellular protein transport," Nature, 372(6501):55-63, Nov. 3, 1994.
Rusk, "CRISPRs and epigenome editing," Nature Methods, Jan. 2014, 11(1):28.
Sander and Joung et al., "CRISPR-Cas systems for editing, regulating and targeting genomes," Nat Biotechnol., Apr. 2014, 32(4):347-55.
Sander et al., "ZiFiT (Zinc Finger Targeter): an updated zinc finger engineering tool," Nucleic Acids Res., Jul. 2010, 38:W462-468.
Sander et al., "Zinc Finger Targeter (ZiFiT): an engineered zinc finger/target site design tool," Nucleic Acids Res., Jul. 2007, 35:W599-605.
Sander et al., "Targeted gene disruption in somatic zebrafish cells using engineered TALENs," Nat. Biotechnol. Aug. 2011, 29:697-698.
Sanjana et al., A transcription activator-like effector toolbox for genome engineering, Nature Protocols, Jan. 2012, 7:171-192.
Sapranauskas et al., "The *Streptococcus thermophilus* CRISPR/Cas system provides immunity in *Escherichia coli*," Nucleic Acids Res., Nov. 2011, 39(21):9275-9282.
Schleifman et al., "Triplex-mediated gene modification," Methods Mol. Biol. 2008, 435:175-190.
Scholze & Boch, "TAL effectors are remote controls for gene activation," J. Curr. Opin. Microbiol Feb. 2011, 14:47-53.

(56) References Cited

OTHER PUBLICATIONS

Schwank et al., "Functional repair of CFTR by CRISPR/Cas9 in intestinal stem cell organoids of cystic fibrosis patients," Cell Stem Cell, Dec. 5, 2013, 13(6):653-8.
Sebo et al., "Cell-invasive activity of epitope-tagged adenylate cyclase of Bordetella pertussis allows in vitro presentation of a foreign epitope to CD8+ cytotoxic T cells," Infect. Immun Oct. 1995, 63:3851-57.
Segal et al., "Evaluation of a modular strategy for the construction of novel polydactyl zinc finger DNA-binding proteins," Biochemistry, 42(7):2137-2148, Feb. 25, 2003.
Shen et al., "Efficient genome modification by CRISPR-Cas9 nickase with minimal off-target effects," Nat Methods, 2014, 11(4):399-402.
Shen et al., "Generation of gene-modified mice via Cas9/RNA-mediated gene targeting," Cell Res., 2013, 23(5):720-3.
Silva et al., "Meganucleases and other tools for targeted genome engineering: perspectives and challenges for gene therapy," Curr Gene Ther., 11(1):11-27, Feb. 2011.
Silver, "How Proteins Enter the Nucleus," Cell, 64(3):489-497, Feb. 8, 1991.
Slaymaker et al. Rationally engineered Cas9 nucleases with improved specificity. Science Jan. 2016, 351(6268): 84-88.
Stenmark et al., "Peptides fused to the amino-terminal end of diphtheria toxin are translocated to the cytosol," J. Cell Biol., Jun. 1991, 113:1025-32.
Sternberg et al., "Conformational control of DNA target cleavage by CRISPR-Cas9" Nature, Nov. 2015, 527:110-113.
Sternberg et al., "DNA interrogation by the CRISPR RNA-guided endonuclease Cas9," Nature, Mar. 2014, 507:62-67.
Stoddard, "Homing endonuclease structure and function," Q. Rev. Biophys., 38(1): 49-95, Epub Dec. 9, 2005.
Storrs, "A CRISPR Fore-Cas-t: A newcomer's guide to the hottest gene-editing tool on the block," Scientist Magazine, Mar. 2014, 4 pages.
Sugimoto et al., "Thermodynamic parameters to predict stability of RNA/DNA hybrid duplexes," Biochemistry, 1995, 34:11211-11216.
Sugimoto et al., "Thermodynamics-structure relationship of single mismatches in RNA/DNA duplexes," Biochemistry, Sep. 19, 2000, 39(37):11270-81.
Swarts el al., "CRISPR Interference Directed Strand Specific Spacer Acquisition," PLOS, Apr. 2012, 7(4):1-7.
Szczepek et al., "Structure-based redesign of the dimerization interface reduces the toxicity of zinc-finger nucleases," Nat Biotechnol., 2007, 25:786-793.
Szyf et al., "DNA methylation and breast cancer," Biochem. Pharmacol., Sep. 2004, 68:1187-97.
Tan et al., "Efficient nonmeiotic allele introgression in livestock using custom endonucleases," Proc Natl Acad Sci U S A, Oct. 8, 2013, 110(41):16526-31.
Terns and Terns, "CRISPR-based adaptive immune systems," Curr Opin Microbiol., Jun. 2011, 14:321-327.
Tesson et al., "Knockout rats generated by embryo microinjection of TALENs," Nat. Biotechnol. Aug. 2011, 29:695-696.
Tsai et al., "Dimeric CRISPR RNA-guided FokI nucleases for highly specific genome editing," Nat Biotechnol., Apr. 2014, 32(6):569-576.
Tsai et al., "GUIDE-Seq enables genome-wide profiling of off-target cleavage by CRISPR-Cas nucleases," Nat Biotechnol, Feb. 2015, 33:187-197.
Tzur et al., "Heritable Custom Genomic Modifications in Caenorhabditis elegans via a CRISPR-Cas9 System," Genetics, 2013, 195:1181-1185.
Tzur et al., "Heritable Custom Genomic Modifications in Caenorhabditis elegans via a CRISPR-Cas9 System," Genetics, Nov. 2013, 195:1181-1185.
Uhlmann et al., "Distinct methylation profiles of glioma subtypes," Int. J. Cancer, Aug. 2003, 106:52-9.
U.S. Final Office Action in U.S. Appl. No. 14/211,117, dated Jun. 30, 2016, 26 pages.
U.S. Non-Final Office Action in U.S. Appl. No. 14/211,117, dated Sep. 8, 2015, 20 pages.
U.S. Non-Final Office Action in U.S. Appl. No. 14/213,723, dated Mar. 2, 2016, 39 pages.
U.S. Non-Final Office Action in U.S. Appl. No. 13/838,520, dated Oct. 6, 2014, 38 pages.
Van der Oost et al., "Unraveling the Structural and Mechanistic Basis of CRISPR-Cas Systems," Nature Reviews Microbiology, 12:479-492 (2014).
Ventura et al., "Cre-lox-regulated conditional RNA interference from transgenes," PNAS, Jul. 2004, 101:10380-10385 Ventura et al., "Cre-lox-regulated conditional RNA interference from transgenes," PNAS, Jul. 2004, 101:10380-10385.
Wagers et al., "CRISPR/Cas9-Targeted Mutagenesis in Caenorhabditis elegans," Genetics, 2013, 195:1187-1191.
Wagner et al., "Efficient and persistent gene transfer of AAV-CFTR in maxillary sinus," Lancet, Jun. 1998, 351:1702-1703.
Wang et al., "One-Step Generation of Mice Carrying Mutations in Multiple Genes by CRISPR/Cas-Mediated Genome Engineering," Cell, May 2013, 153:910-918.
Wang et al., "Positive and negative regulation of gene expression in eukaryotic cells with an inducible transcriptional regulator," Gene Ther., May 1997, 4:432-441.
Wang et al., "The CRISPR/Cas system mediates efficient genome engineering in Bombyx mori," Cell Res., Dec. 2013, 23(12):1414-6.
Weber et al., "Assembly of Designer TAL Effectors by Golden Gate Cloning," PLoS ONE, May 2011, 6:e19722.
Widschwendter and Jones, "DNA methylation and breast carcinogenesis," Oncogene, Aug. 2002, 21:5462-82.
Wiedenheft, "RNA-guided genetic silencing systems in bacteria and archaea," Nature, Feb. 2012, 482:331-338.
Wolfe et al., "DNA recognition by Cys2His2 zinc finger proteins," Annu Rev Biophys Biomol Struct Jun. 2000, 29:183-212.
Wong et al., "Detection of aberrant p16 methylation in the plasma and serum of liver cancer patients," Cancer Res., 59(1):71-73 Jan. 1, 1999.
Wood et al., "Targeted Genome Editing Across Species Using ZFNs and TALENs," Science, Jul. 2011, 333:307.
Wright et al., "Standardized reagents and protocols for engineering zinc finger nucleases by modular assembly," Nat Protoc., 2006, 1(3):1637-1652.
Wu et al., "Building zinc fingers by selection: toward a therapeutic application," Proc Natl Acad Sci U S A., 92(2):344-348, Jan. 17, 1995.
Wu et al., "Correction of a genetic disease in mouse via use of CRISPR-Cas9," Cell Stem Cell., Dec. 5, 2013, 13(6):659-62.
Wu et al., "Genome-wide binding of the CRISPR endonuclease Cas9 in mammalian cells," Nat Biotechnol. Jul. 2014; 32(7):670-6.
Xu et al., "Genome-wide regulation of 5hmC, 5mC, and gene expression by Tet1 hydroxylase in mouse embryonic stem cells," Mol Cell., 42(4):451-464, Epub Apr. 21, 2011.
Yang et al., "One-step generation of mice carrying reporter and conditional alleles by CRISPR/Cas-mediated genome engineering," Cell, Sep. 12, 2013; 154(6):1370-9.
Yin et al., "Genome editing with Cas9 in adult mice corrects a disease mutation and phenotype," Nature Biotechnology 32, 551-553 (Jun. 2014).
Zetsche et al., "Cpf1 Is a Single RNA-Guided Endonuclease of a Class 2 CRISPR-Cas System," Cell, Oct. 2015, 163:759-771.
Zhang et al., "Efficient construction of sequence-specific TAL effectors for modulating mammalian transcription," Nat Biotechnol., 29(2):149-153, Epub Jan. 19, 2011.
Zhang et al., "TET1 is a DNA-binding protein that modulates DNA methylation and gene transcription via hydroxylation of 5-methylcytosine," Cell Res., 20(12):1390-1393, Epub Nov. 16, 2010.
Zhou et al., "High-throughput screening of a CRISPR/Cas9 library for functional genomics in human cells," Nature. May 22, 2014; 509(7501):487-91.
Office Action in European Application No. 14764159.1, dated Jun. 16, 2017, 4 pages.
Office Action in European Application No. 14764117.9, dated Jul. 6, 2017, 4 pages.

(56) References Cited

OTHER PUBLICATIONS

Office Action in European Application No. 14768877.4, dated Jul. 14, 2017, 4 pages.
Office Action in U.S. Appl. No. 14/775,930, dated Sep. 21, 2017, 23 pages.
Office Action in Canadian Application No. 2907198, dated Aug. 24, 2017, 10 pages.
Office Action in U.S. Appl. No. 14/776,620, dated Sep. 28, 2017, 8 pages.
Office Action in European Application No. 14763916.5, dated Oct. 26, 2017, 5 pages.
Ito et al., "Tet proteins can convert 5-methylcytosine to 5-formylcytosine and 5-carboxylcytosine," Science, 333(6047):1300-1303, Sep. 2, 2011.
Jamieson et al., "In vitro selection of zinc fingers with altered DNA-binding specificity," Biochemistry, 33(19):5689-5695, May 17, 1994.
Jinek et al., "Supplementary Materials for a Programmable Dual-RNA-Guided DNA Endonuclease in Adaptive Bacterial Immunity," Science Express, pp. 1-37, Jun. 28, 2012.
Karmirantzou and Harnodrakas, "A Web-based classification system of DNA-binding protein families," Protein Eng. 14(7):465-472, Jul. 2001.
Klug, "Co-chairman's remarks: protein designs for the specific recognition of DNA," Gene, 135(1-2):83-92, Dec. 15, 1993.
Kummerfeld and Teichmann, "DBD: a transcription factor prediction database," Nucleic Acids Res., 34 (Database issue): D74-D81, Jan. 1, 2006.
Lee et al., "Three-dimensional solution structure of a single zinc finger DNA-binding domain," Science., 245(4918):635-637, Aug. 11, 1989.
Li et al., "DNA methylation in prostate cancer," Biochim. Biophys. Acta., 1704:87-102, Sep. 2004.
Lin et al., "CRISPR/Cas9 systems have off-target activity with insertions or deletions between target DNA and guide RNA sequences," Nucleic Acids Res., 42:7473-7485, Jun. 2014.
Lin et al., "iDNA-Prot: identification of DNA binding proteins using random forest with grey model," PLoS One., 6(9):e24756, Epub Sep. 15, 2011.
Liu et al., "Regulation of an Endogenous Locus Using a Panel of Designed Zinc Finger Proteins Targeted to Accessible Chromatin Regions," J. Biol. Chem., 276(14):11323-34, Apr. 200.
Lund et al., "DNA Methylation Polymorphisms Precede Any Histological Sign of Atherosclerosis in Mice Lacking Apolipoprotein E," J. Biol. Chem., 279:29147-54, Jul. 2004.
Mabaera et al., "Developmental- and differentiation-specific patterns of human γ- and β-globin promoter DNA methylation," Blood, 110(4):1343-52, Aug. 2007.
Maeder et al., "Robust, synergistic regulation of human gene expression using TALE activators," Nat. Methods, 10:243-245, Mar. 2013.
Mahfouz et al., "De novo-engineered transcription activator-like effector (TALE) hybrid nuclease with novel DNA binding specificity creates double-strand breaks," Proc Natl Acad Sci U S A, 108:2623-2628, Feb. 2011.
Maiti and Drohat, "Thymine DNA glycosylase can rapidly excise 5-formylcytosine and 5-carboxylcytosine: potential implications for active demethylation of CpG sites," J Biol Chem., 286(41):35334-35338, Epub Aug. 23, 2011.
Majumdar et al., "Targeted Gene Knock in and Sequence Modulation Mediated by a Psoralen-linked Triplex-forming Oligonucleotide," J Biol Chem., 283(17):11244-52, Apr. 2008.
Miller et al., "Repetitive zinc-binding domains in the protein transcription factor IIIA from Xenopus oocytes," EMBO J., 4(6):1609-1614, Jun. 1985.
Morrison, "Transformation in *Escherichia coli*: Cryogenic Preservation of Competent Cells," J. Bacteriol., 132:349-351, Oct. 1977.
Moscou and Bogdanove, "A simple cipher governs DNA recognition by TAL effectors," Science, 326(5959):1501, Dec. 11, 2009.

Muthuswamy et al., "Controlled Dimerization of ErbB Receptors Provides Evidence for Differential Signaling by Homo- and Heterodimers," Mol. Cell. Biol., 19(10):6845-6857, Oct. 1999.
Needleman and Wunsch, "A General Method Applicable to the Search for Similarities in the Amino Acid Sequence of Two Proteins," J. Mol. Biol., 48:444-453, Mar. 1970.
Nissim et al., "Multiplexed and Programmable Regulation of Gene Networks with an Integrated RNA and CRISPR/Cas Toolkit in Human Cells," Molecular Cell, 54:698-710, May 2014.
Niwa et al., "Efficient selection for high-expression transfectants with a novel eukaryotic vector," Gene, 108(2):193-9, Dec. 1991.
Novak et al., "Functional Characterization of Protease-treated Bacillus anthracia Protective Antigen," J. Biol. Chem., 267:17186-93, Aug. 1992.
Palva et al., "Secretion of interferon by Bacillus subtilis," Gene, 22:229-235, May-Jun. 1983.
Perelle et al., "Characterization of Clostridium perfringens Iota-Toxin Genes and Expression in *Escherichia coli*," Infect. Immun., 61:5147-56, Dec. 1993.
Ro et al., "Adenovirus-based short hairpin RNA vectors containing an EGFP marker and mouse U6, human H1, or human U6 promoter," BioTechniques, 38(4):625-627, Apr. 2005.
Sander et al., "In silico abstraction of zinc finger nuclease cleavage profiles reveals an expanded landscape of off-target sites," Nucleic Acids Res., 41:e181, Oct. 2013.
Shah et al., "Protospacer recognition motifs," RNA Biol., 10:891-899, 2013.
Sharma, "Schizophrenia, epigenetics and ligand-activated nuclear receptors: a framework for chromatin therapeutics," Schizophr. Res., 72:79-90, Jan. 2005.
Shmakov et al., "Discovery and Functional Characterization of Diverse Class 2 CRISPR-Cas Systems," Molecular Cell, 60:385-397, Nov. 2015.
Simon et al., "Sequence-specific DNA cleavage mediated by bipyridine polyamide conjugates," Nucl. Acids Res., 36(11):3531-8, Jun. 2008.
Sterman et al., "Adenovirus-mediated herpes simplex virus thymidine kinase/ganciclovir gene therapy in patients with localized malignancy: results of a phase I clinical trial in malignant mesothelioma," Hum. Gene Ther., 7:1083-89, May 1998.
Sternberg et al., "Mechanism of substrate selection by a highly specific CRISPR endoribonuclease," RNA, 18:661-672, Apr. 2012.
Tahiliani et al., "Conversion of 5-Methylcytosine to 5-Hydroxymethylcytosine in Mammalian DNA by MLL Partner TET1," Science, 324:930-935, May 2009.
Tan et al., "Zinc-finger protein-targeted gene regulation: genomewide single-gene specificity," Proc Natl Acad Sci U S A., 100(21):11997-2002, Epub Sep. 26, 2003.
Tjong and Zhou, "DISPLAR: an accurate method for predicting Dna-binding sites on protein surfaces," Nucleic Acids Res., 35(5):1465-1477, Epub Feb. 6, 2007.
Tsai et al., "Dimeric CRISPR RNA-guided FokI nucleases for highly specific genome editing," Nat Biotechnol., 32(6):569-576, Apr. 2014.
Tsai et al., "GUIDE-Seq enables genome-wide profiling of off-target cleavage by CRISPR-Cas nucleases," Nat Biotechnol, 33:187-197, Feb. 2015.
U.S. Final Office Action in U.S. Appl. No. 13/838,520, dated Jul. 15, 2015, 35 pages.
U.S. Non-Final Office Action in U.S. Appl. No. 14/213,479, dated Dec. 9, 2015, 39 pages.
Wu et al., "Custom-designed zinc finger nucleases: what is next?," Cell Mol Life Sci., 64(22):2933-2944, Nov. 2007.
Xu et al., "Optimization of transcriptional regulatory elements for constructing plasmid vectors," Gene. 272(1-2):149-56, Jul. 2001.
Yang et al., "Optimization of scarless human stem cell genome editing," Nucleic Acids Res., 41:9049-9061, Oct. 2013.
Zitzewitz et al., "Probing the folding mechanism of a leucine zipper peptide by stopped-flA4:A48ism spectroscopy," Biochemistry, 34(39):12812-12819, Oct. 3, 1995.
Extended European Search Report in European Application No. 14764159.1, dated Aug. 10, 2016, 7 pages.

(56) References Cited

OTHER PUBLICATIONS

International Search Report and Written Opinion in International Application No. PCT/US2013/074736, dated Sep. 17, 2014, 4 pages.
Gaj et al., "ZFN, TALEN, and CRISPR/Cas-based methods for genome engineering," Trends in Biotechnology, 31(7): 397-405, Jul. 2013.
International Search Report in International Application No. PCT/US2014/054291, dated Mar. 27, 2015, 6 pages.
Slaymaker et al., "Rationally engineered Cas9 nucleases with improved specificity," Science 351(6268): 84-88, Jan. 2016.
Invitation to Pay Additional Fees and, Where Applicable, Protest Fee in International application No. PCT/US2016/49147, mailed on Oct. 31, 2016, 2 pages.
Office Action in Australian Application No. 2014227653, dated Nov. 18, 2016, 3 pages.
International Search Report and Written Opinion in International Application No. PCT/US16/49147, dated Dec. 23, 2016, 12 pages.
Kleinstiver et al., "High-fidelity CR1SPR-Cas9 nucleases with no detectable genome-wide off target effects," Nature, Jan. 2016, 529: 490-495.
Office Action in U.S. Appl. No. 14/775,930, dated Feb. 27, 2017, 55 pages.
Office Action in U.S. Appl. No. 14/776,620, dated Mar. 31, 2017.
Office Action in European Application No. 14763916.5, dated Mar. 27, 2017, 6 pages.
Chinese Office Action in Application No. 2014800261133.4, dated May 31, 2017, 21 pages (with English abstract).
Extended European Search Report in Application No. 14875819.6, dated Jun. 8, 2017, 11 pages.
Blast sequence alignment: Query = Applicants SEQ ID No. 26 and Subject = Jinek et al.'s SEQ ID No. 8 from WO2013176772 (Retrieved from the Internet <https://blast.nchi.nlm.nih.gov/Blast.cgi>, retrieved on Feb. 1, 2018, 3 pages.
International Preliminary Report on Patentability in International Application No. PCT/US2016/49147, dated Mar. 6, 2018, 8 pages.
Office Action in Chinese Application No. 201480026133.4, dated Feb. 12, 2018, 22 pages (with English translation).
Office Action in European Application No. 14764117.9, dated Jan. 4, 2018, 4 pages.
Office Action in European Application No. 14764159.1, dated Nov. 21, 2017, 3 pages.
Office Action in European Application No. 14768877.4, dated Jan. 8, 2018, 4 pages.
Office Action in U.S. Appl. No. 14/211,117, dated Jan. 9, 2017, 12 pages.
Office Action in U.S. Appl. No. 14/211,117, dated Nov. 3, 2017, 11 pages.
Office Action in U.S. Appl. No. 14/775,869, dated Sep. 11, 2017, 43 pages.
Office Action in U.S. Appl. No. 15/107,550, dated Mar. 9, 2018, 21 pages.
Sequence Alignment instant SEQ ID No. 1 with SEQ ID No. 103. Search conducted on Feb. 15, 2018, 1 page.
Jiang et al., "RNA-guided editing of bacterial genomes using CRISPR-Cas systems," Nature Biotechnology, Mar. 2013, 31: 233-239.
Kim et al., "Hybrid restriction enzymes: zinc finger fusions to Fok I cleavage domain," PNAS, Feb. 1996, 93: 1156-1160.
Melo et al., "eRNAs are required for p53-dependent enhancer activity and gene transcription," Mol Cell, Feb. 2013, 49: 524-535.
Mino et al., "Efficient double-strand DNA cleavage by artificial zinc-finger nucleases composed of one zinc-finger protein and a single-chain FokI dimer," Journal of biotechnology, Mar. 2009, 140: 156-161.
Nielsen et al., "Interaction with members of the heterochromatin protein 1 (HP1) family and histone deacetylation are differentially involved in transcriptional silencing by members of the TIF1 family," EMBO J., Nov. 1999, 18: 6385-6395.
Office Action in Canadian Application No. 2907198, dated May 14, 2018, 3 pages.
Office Action in Chinese Application No. 201480026276.5, dated Apr. 17, 2018, 12 pages (with English tmnslation).
Office Action in Chinese Application No. 201480027950.1, dated Mar. 23, 2018, 13 pages (with English tmnslation).
Office Action in Japanese Application No. 2016-502406, dated Jun. 12, 2018, 23 pages (with English tmnslation).
Office Action in Japanese Application No. 2016-502853, dated Jun. 12, 2018, 15 pages (with English tmnslation).
Office Action in Japanese Application No. 2016-502976, dated May 8, 2018, 16 pages (with English translation).
Qi et al., "Repurposing CRISPR as an RNA-Guided Platform for Sequence-Specific Control of Gene Expression," Supplemental Information, Cell, Feb. 2013, 152(5): 1173-1183.
Williams et al., "Tet1 and hydroxymethylcytosine in transcription and DNA methylation fidelity," Nature, May 2011, 473: 343-349.

* cited by examiner

EMX1 truncated gRNA

```
GAAGCTGGAGGAGGAAGGGCCTGAGTCCGAGCAGAAGAAGAAgGGCTCCCATCACATCAACCGGTGG   wild-type x24
GAAGCTGGAGGAGGA                                                       Δ365
                                                      TCAACCGGTGG     Δ181
GAAGCTGGAGGAGGAAGG                                                    Δ138
                                                                      Δ126
                                          GGGCTCCCATCACATCAACCGGTGG   Δ114
GAAGCTGGAGGAGGAAGGGCCTGA                                              Δ101
GAAGCTGGAGGA                                                   GG     Δ53
GAAGCTGGAGGAGGAAGGG                       CCCATCACATCAACCGGTGG        Δ28
GAAGCTGGAGGAGGAAGGGC                      TCGCACACATCAACCGGTGG        Δ27
GAAGCTGGAGGAGGAAGGGC                      CTTCCATCACATCAACCGGTGG      Δ25
GAAGCTGGAGGAGGAAGGGCCTGAG                 TCCCATCACATCAACCGGTGG       Δ21 x2
GAAGCTGGAGGAGGAAGGGCCTGAGTCCGAG           TCCCATCACATCAACCGGTGG       Δ15
GAAGCTGGAGGAGGAAGGGCCTGAGTCCGAGCAGAAG     TCCCATCACATCAACCGGTGG       Δ9
GAAGCTGGAGGAGGAAGGGCCTGAGTCCTGCCGTTTGTAG  CCATCACATCAACCGGTGG         Δ8
GAAGCTGGAGGAGGAAGGGCCTGAGTCCGAGCAGAAGA    GCTCCCATCACATCAACCGGTGG     Δ6
GAAGCTGGAGGAGGAAGGGCCTGAGTCCGAGCAGAAGAA   CTCCCATCACATCAACCGGTGG      Δ6
GAAGCTGGAGGAGGAAGGGCCTGAGTCCGAGC AGAAGAAGGGCTCCCATCACATCAACCGGTGG     Δ3 x3
GAAGCTGGAGGAGGAAGGGCCTGAGTCCGAGCAGAAGA AAGGGCTCCCATCACATCAACCGGTGG    Δ2
GAAGCTGGAGGAGGAAGGGCCTGAGTCCGAGCAGAAGAaGAAGGGCTCCCATCACATCAACCGGT     +2
```

EMX1 full-length gRNA

```
GAAGCTGGAGGAGGAAGGGCCTGAGTCCGAGCAGAAGAAGAAgGGCTCCCATCACATCAACCGGTGG   wild-type x35
GAAGCTGGAGGAGGAAGGGCCTGAGTCCGAG                                       Δ202
                                                                      Δ115
GAA                                                                   Δ94
                                                                      Δ78
GAAGCTGGAGG                                                           Δ72
GAAGCTGGA                                                  GG         Δ56
GAAGCTGGAGGAGGAAGGGCCTGA                                   GTGG       Δ39
GAAGCTGGAGGAG                      GAAGGGCTCCCATCACATCAACCGGTGG       Δ26 x2
GAAGCTGGAGGAGGAAGGGCCTGAGT         CCATCACATCAACCGGTGG                Δ22
GAAGCTGGAGGAGGAAGGGCCTGAG          TCCATCACATCAACCGGTGG               Δ21 x3
GAAGCTGGAGGAGGAAGGGCCTGAGTCCGA     CATCACATCAACCGGTGG                 Δ18
GAAGCTGGAGGAGGAAGGGCCTGAGTCCGA     GCTCCCATCACATCAACCGGTGG            Δ14
GAAGCTGGAGGAGGAAGGGCCTGAGTCCGAGC   AGAAGGGCTCCCATCACATCAACCGGTGG      Δ6 x3
GAAGCTGGAGGAGGAAGGGCCTGAGTCCGAGC AGAAGAAGGGCTCCCATCACATCAACCGGTGG     Δ3 x3
GAAGCTGGAGGAGGAAGGGCCTGAGTCCGAGCAGA AAGAAGGGCTCCCATCACATCAACCGGTGG    Δ2 x2
GAAGCTGGAGGAGGAAGGGCCTGAGTCCGAGCAGAAGAaGAAGGGCTCCCATCACATCAACCGGT     +3
```

FIG. 3C

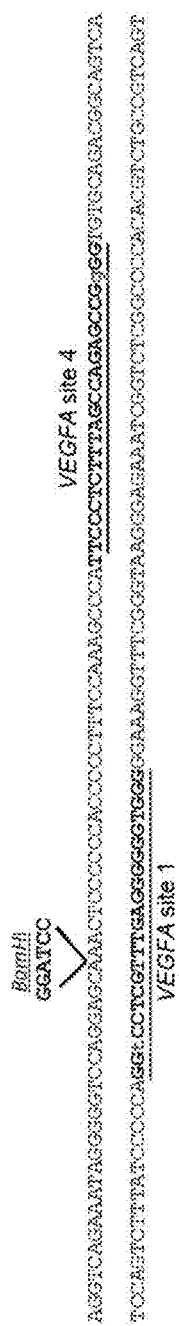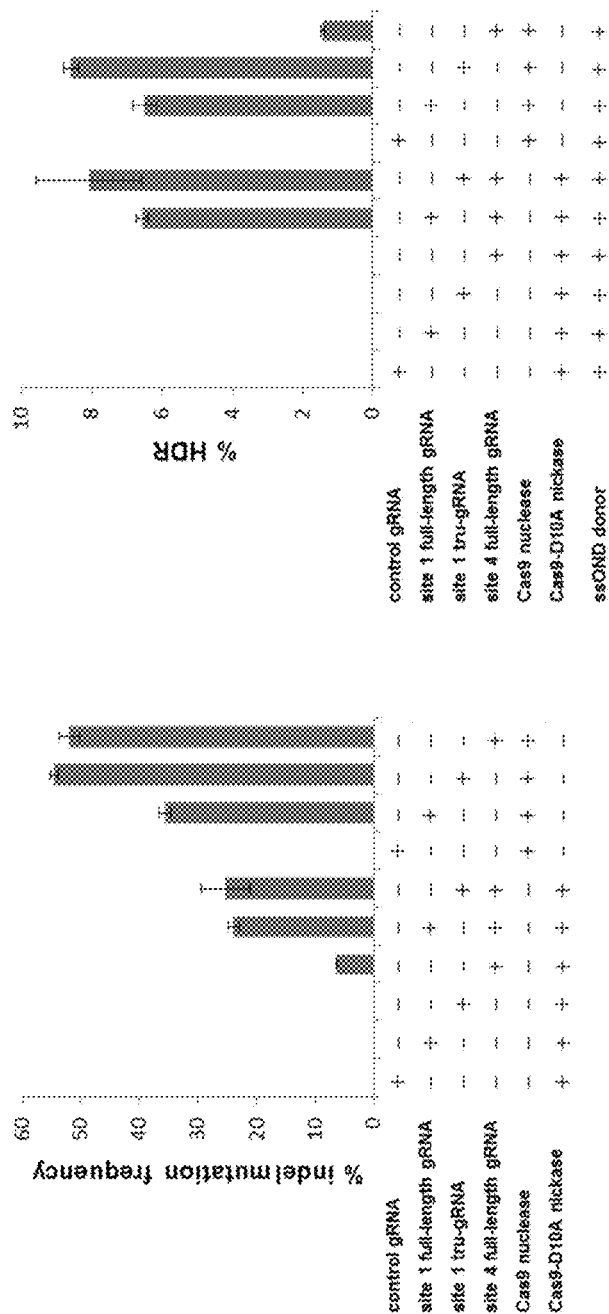
FIG. 4A
FIG. 4B
FIG. 4C

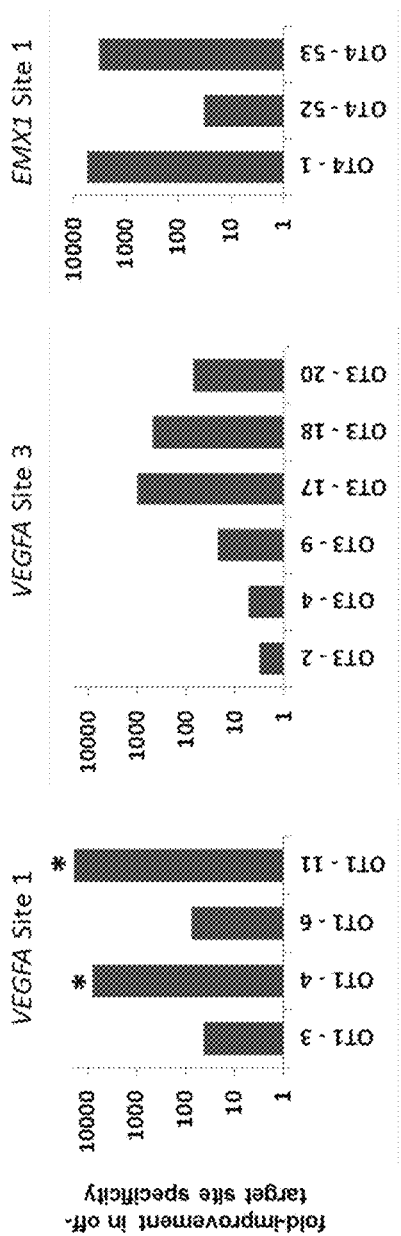

Figure 7A

```
VEGFA site1 full-length gRNA
TAGCTGTTTGGGAGGTCAGAAATAGGGGTCCaGGAGCAAACTCCCCCCACCCCCTTTCCAAAGCCC Wild-
Type x87
TAGCTGTT░░░░░░░░░░░░░░░░░░░░░░░░░░░░░░░░░░░░░░░░░░░░░░░░░░░░░░░░░ Δ205
░░░░░░░░░░░░░░░░░░░░░░░░░░░░░░░░░░░░░░░░░░░░░░░░░░░░CCTTTCCAAAGCCC Δ71
░░░░░░░░░░░░░░░░░░░░░░░░░░░░░░░░░░░░░░░░░░░░░░░░░░░░░░CCAAAGCCC Δ67
░░░░░░░░░░░░░░░░░░░░░░░░░░░░░░░░░░░░░░░░░░░░░░░░CCCCACCCCCTTTCCAAAGCCC Δ55
TAGCTG░░░░░░░░░░░░░░░░░░░░░░░░░░░░░░░░░░░░░░░░░░░TTTCCAAAGCCC Δ49
TAG░░░░░░░░░░░░░░░░░░░░░░░░░░░░░░░░░░░░░░░░░░░░░CCCTTTCCAAAGCCC Δ49
TAGCTGTTTGGGAGGTCAGA░░░░░░░░░░░░░░░░░░░░░░░░░░░░░░░░░░░░░░░░░░░░ Δ47
TAGCTGTT░░░░░░░░░░░░░░░░░░░░░░░░░░░░░░░░░░░░░░░CCCCTTTCCAAAGCCC Δ43
TAGCTGTTTGGGAGGTCAGAAAT░░░░░░░░░░░░░░░░░░░░░░░░░░░░░░░░░AGCCC Δ39
TAGCTGTTTGGGTGG░░░░░░░░░░░░░░░░░░░░░░░░░░░░░░░░░CCTTTCCAAAGCCC Δ38
TAGCTGTTTGGGAGGTCAGAAATAGG░░░░░░░░░░░░░░░░░░░░░░░░░░░CAAAGCCC Δ33
TAGCTGTTTGGGAGGT░░░░░░░░░░░░░░░░░░░░░░░░░░░CACCCCTTTCCAAAGCCC Δ32
TAGCTGTTTCTGA░░░░░░░░░░░░░░░░░░░░░░░CCTCCCACCCCTTTCCNAAGCCC Δ30
TAGCTGTTTGGGAGGTCAGAAATAGGGGTCCAG░░░░░░░░░░░░░░░░░░░░░░ANCCC Δ28
TAGCTGTTTGGGAGGTCAGAAAT░░░░░░░░░░░░░░░░░ACCCCCTTTCCAAAGCCC Δ26
TAGCTGTTTGGGAGGTCAGAAATAGGGGT░░░░░░░░░░░░░CCCTTTCCAAAGCCC Δ22
TAGCTGTTTGGGAGGTCAG░░░░░░░░░░AAACTCCCCCCACCCCCTTTCCAAAGCCC Δ19 x2
TAGCTGTTTGGGAGGTCAGAAATAGGGGT░░░░░░░░░░CCACCCCCTTTCCAAAGCCC Δ17
TAGCTGTTTGGGAGGTCAGAAATAGGGGT░░░░░░░░░CCCACCCCCTTTCCAAAGCCC Δ16
TAGCTGTTTGGGAGGTCAGAAATAGGG░░░░░░░░░TCCCCCCNCCCCCTTTCCNAANCCC Δ15
TAGCTGTTTGGGAGGTCAGA░░░░░░░░░░AGCAAACTCCCCCCACCCCCTTTCCAAAGCCC Δ15
TAGCTGTTTGGGAGGTCAGAAAT░░░░░░░░░AAACTCCCCCCACCCCCTTTCCAAAGCCC Δ15
NAGCTGNTTGGGAGGNCNNA░░░░░░░░░░NNGCAAACTCCCCCCACCCCCTTTCCAAANCCC Δ14
TAGCTGTTTGGGAGGTCAGAAATAGGGGT░░░░░░░░░CCCCACCCCCTTTCCAAAGCCC Δ14
TAGCTGTTTGGGAGGTCAGAAATAGGGGTCCA░░░░░░░░░CCCACCCCCTTTCCAAAGCCC Δ13
TAGCTGTTTGGGAGGTCAGAAAT░░░░░░░░░AGCAAACTCCCCCCACCCCCTTTCCAAAGCCC Δ12
TAGCTGTTTGGGAGGTCAGAAATAGGGGTCCAGGA░░░░░░░░CCCCACCCCCTTTCCAAAGCCC Δ9
TAGCTGTTTGGGAGGTCAGAAATAGGGGTCC░░░░░░AACTCCCCCACCCCCTTTCCAAAGCCC Δ7
TAGCTGTTTGGGAGGTCAGAAATAGGGGTC░░░░░░CACCCCTTTCCACCCCCTTTCCAAAGCCC Δ6
TAGCTGTTTGGGAGGTCAGAAATAGGGGTCCAGG░░░░░ACTCCCCCACCCCCTTTCCAAAGCCC Δ5 x2
TAGCTGTTTGGGAGGTCAGAAATAGGGGTCCAGG░░░░AACTCCCCCACCCCCTTTCCAAAGCCC Δ4 X2
TAGCTGTTTGGGAGGTCAGAAATAGGGGTCC░░░AGCAAACTCCCCCCACCCCCTTTCCAAAGCCC Δ3
TAGCTGTTTGGGAGGTCAGAAATAGGGGTCCAG░░GCAAACTCCCCCCACCCCCTTTCCAAAGCCC Δ2 X3

TAGCTGTTTGGGAGGTCAGAAATAGGGGTCCAGGAGTGCTAGATCTTCATCTAAAGACATTTCTGA +191
GAAAAATGTATCTGTTTTCTTTTCAGAAGAAATTTACACTTAATAGATATTATGGTAACTAAAGTAAG
GCAGATAATTTTGGCCATCAGCTTATATTGTGGGATAATCTCTTTTTGCTGACCTTGAAAAGNTGTG
GCATATTCACAACAAGTAGGAAAATTGCAAACTCCCCCACCCCCTTTCCAAAGCCC
```

Figure 7B

```
VEGFA site1 truncated gRNA
TGGGAGGTCAGAAATAGGGGGTCCaGGAGCAAACTCCCCCCACCCCCTTTCCAAAGCCCATTCCCTC  Wild-
Type x85
TGGGAGGTCAGAAATAGGGGGTCCAGGA--------------------------------------> Δ144
<------------------------------------CACCCTCTTTCCAAAGCCCATTCCCTC Δ112
<------------------------------CAAACTCCCCCCACCCCCTTTCCAAAGCCCATTCCCTC Δ111
<-----------------------------------------------AAGCCCATTCCCTC Δ80
<-------------------------------------------------------TCCCTC Δ80
<--------------------------------------------TTCCAAAGCCCATTCCCTC Δ61
TGGGAGGTC---------------------------------------------------------> Δ61
<-----------------------------CCCACCCCCTTTCCAAAGCCCATTCCCTC Δ56
<-----------------------------CCCACCCCCTTTCCAAAGCCCATTCCCTC Δ44
TGGG--------------------------------CCCCTTTCCAAAGCCCATTCCCTC Δ39
TGGGAG------------------------------CCCCCTTTCCAAAGCCCATTCCCTC Δ36
TGGGAGGTCAGAAA----------------------CACCCCCTTTCCAAAGCCCATTCCCTC Δ26
TGGGAGGTCAGAAATAGGGGT----------------CCCCTTTCCAAAGCCCATTCCCTC Δ20
TGGGAGGTCAGAA-------------AAACTCCCCCCACCCCCTTTCCNAAGCCCATTCCCTC Δ17
TGGGAGGTCAGAAATAGGGGT-----------CCACCCCCTTTCCAAAGCCCATTCCCTC Δ17
TGGGAGGTCAGAAATAGGGGT----------CCCACCCCCTTTCCAAAGCCCATTCCCTC Δ16
TGGGAGGTCAGAAATAGG-------------TCCCCCCACCCCCTTTCCAAAGCCCATTCCCTC Δ16
TGNGAGGTCAGA---------AGCAAACTCCCCCCACCCCCTTTCCAAAGCCCATTCCCTC Δ15
TGGGAGGTCAGAAATAGGGGT----------CCCCACCCCCTTTCCAAAGCCCATTCCCTC Δ15
TGGGAGGTCAGAAATAGGGGG---------TCCCCCCACCCCCTTTCCAAAGCCCATTCCCTC Δ13 x2
TGGGAGGTCAGAAATAGGGGGTCCAGGA----------CACCCCCTTTCCAAAGCCCATTCCCTC Δ12
TGGGAGGTCAGAAATAG--------GCAAACTCCCCCCACCCCCTTTCCAAAGCCCATTCCCTC Δ11 x2
TGGGAGGTCAGAAATAGGGGGTCCAGGA---------CCCCACCCCCTTTCCAAAGCCCATTCCCTC Δ9
TGGGAGGTCAGAAATAGGGGGTCCAGG-------NCCCCCACCCCCTTTCCAAAGCCCATTCCCTC Δ8
TGGGAGGTCAGAAATAGGGGGTCCAG------CTGGCCCCACCCCCTTTCCAAAGCCCATTCCCTC Δ7
TGGGAGGTCAGAAATAGGGGGTC------CAAACTCCCCCCACCCCCTTTCCAAAGCCCATTCCCTC Δ6 x5
TGGGAGGTCANAAATAGGGGGTCCAG------ACTCCCCCCACCCCCTTTCCAAAGCCCATTCCCTC Δ6
TGGGAGGTCAGAAATAGGGGGTCCAGG-----ACTCCCCCCACCCCCTTTCCAAAGCCCATTCCCTC Δ5
TGGGAGGTCAGAAATAGGGGGTCC------AGCAAACTCCCCCCACCCCCTTTNNNNNCCCATTNNNTC Δ3
TGNGAGGTCAGAAATAGGGGGTCCAGGA----AAACTCCCCCCACCCCCTTTCCAAAGCCCATTCCCTC Δ2

TGGGAGGTCA-----------------------CCCCTTTCCAAAGCCCACCCCCTTTCCAAAGCC Δ9 (+14
Δ23)
TGGGAGGTCAGAAATAGGGGGTCCAGGAAAGCAAACTCCCCCCACCCCCTTTCCAAAGCCCATTCCC +2
```

Figure 7C

```
VEGFA site3 full-length gRNA
GAGGACGTGTGTGTCTGTGTGGGGTGAGTGAGTGTGTGCGTGtGGGGTTGAGGGTGTTGGAGCGGGGA  Wild-
                                                                       type x35
GAGGACGTGTGTGTCTGTGTG░░░░░░░░░░░░░░░░░░░░░░░░░░░░░░░░░░░░░░░░░░░░░░  Δ117
GAGGACGTGTGTGTTGG░░░░░░░░░░░░░░░░░░░░░░░░░░░░░░░░░░░░░░░░░░░░░░░░░░  Δ84
GAGGACGTGTGTGTCTGTGTG░░░░░░░░░░░░░░░░░░░░░░░░░░░░░░░░░░░░░░░░░░░░░░  Δ75
GAGGACGTGTGTGTCTGTGTG░░░░░░░░░░░░░░░░░░░░░░░░░░░░░░░░░░░░░░░░░░░░░░  Δ49
GAGGACGTGTGTGTCTGTGTGGGTGAGTGAGTGTGTG░░░░░░░░░░░░░░░░░░░░░░░░░░░░░░  Δ43
GAGGACGTGTGTGTCTGTGTGGGTGAGTG░░░░░░░░░░░░░░░░░░░░░░░░░░░░░░░░░░░░░░  Δ40
GAGGACGTGTGTGTCTGTGTGAGT░░░░░░░░░░░░░░░░░░░░░░░░░░░░░░░░░░░░░░░GGGA  Δ39
GAGGACGTGTGTGTCTGTGTGGGTGAGTGAGTGTNNG░░░░░░░░░░░░░░░░░░░░░░░░░░░░░░  Δ37
GAGGACGTGTGTGTCTGTGTGGGTGAGT░░░░░░░░░░░░░░░░░░░░░░░░░░░░░GAGNGNGGN  Δ30 x2
GAGGACGTGTGTGTCTGTGTGGGTGAGTGAG░░░░░░░░░░░░░░░░░░░░░░░░TGGGGCGGGGA  Δ25
GAGGACGTGTGTGTCTGTGTGGGTGAGTGAGTG░░░░░░░░░░░░░░░░░░░░░░TGGAGCGGGGA  Δ23
GAGGACGTGTGTGTCTGTGTGGGTGAGTGAGT░░░░░░░░░░░░░░░░░░░░░GTTGGAGCGGGGA  Δ22
GAGGACGTGTGTGTCTGTGTGGGTGAGTGAGTGT░░░░░░░░░░░░░░░░░░░GTTGGAGCGGGGA  Δ20
GAGGACGTGTGTGTCTGTGTGGGTGAG░░░░░░░░░░░░░░░░░░░░░░░TGAGGGTGTTGGAGCGGGGA  Δ20 x2
GAGGACGTGTGTGTCTGTGTGGGTGAGTGAGT░░░░░░░░░░░░░░░░░░GGGCGTTGGAGCGGGGA  Δ18
GAGGACGTGTGTGTCTGTGTGGGTGA░░░░░░░░░░░░░NNGTGGGGTTGAGGGTGTTGGAGCGGGGA  Δ12
GAGGACGTGTGTGTCTGTGTGGGTGAGTGA░░░░░░░GTGTGGGGTTGAGGGCGTTGGAGCGGGGA  Δ8 x3
GAGGACGTGTGTGTCTGTGTGGGTGAGTGAGTGTGT░░░░░GGGTTGAGGGCGTTGGAGCGGGGA  Δ7
GAGGACGTGTGTGTCTGTGTGG-TGAGTGAGTGTGT░░░░░GGGGTTGAGGGTGTTGGAGCGGGGA  Δ6
GAGGACGTGTGTGTCTGTGTGGGTGAGTGAGT░░░░░░GNGTGGGGTTGAGGGTGTTGGAGCGGGGA  Δ6 x5
GAGGACGTGTGTGTCTGTGTGGGTGAGTGAGTGT░░░░GTGTGGGGTTGAGGGTGTTGGAGCGGGGA  Δ4
GAGGACGTGTGTGTCTGTGTGGGTGAGTGAGTGTGC░░TGGGGTTGAGGGTGTTGGAGCGGGGA  Δ3

GAGGANGNGTGTGTCTGTGTGGGTGAGTGAGTGTGTGTGGGTGAGTGAGTGTGTGTCTGTGGGGTTG  +20
GAGGACGTGTGTGTCTGTGTGGGTGAGTGAGTGTGTGCGTCGTGTGGGGTTGAGGGTGTTGGAGCGG  +3
GAGGACGTGTGTGTCTGTGTGGGTGAGTGAGTGTGTGCAAGTGTGGGGTTGAGGGTGTTGGAGCGG  +3
GAGGACGTGTGTGTCTGTGTGGGTGAGTGAGTGTGTGCGTGGGGGGTTGAGGGTGTTGGAGCGGG  +2
```

Figure 7D

VEGFA site3 truncated gRNA

```
TGAGGACGTGTGTGTCTGTGTGGGTGAGTGAGTGTGTGCCGTGtGGGGTTGAGGGTGTTGGAGCGGGG  Wild-
type x47
GGGAGGTCAGAAATAGGGGGT                                                  Δ324
                                                                       Δ201
TGAGGACGTGTGTGTCTGTGTGGGTGAGTGAGTGTGTG                                 Δ157
TGAGGACGTGTGTGT                                                        Δ153
TGAGGACGTGTGTGTCTGTGTGGGAGANNGANNGNGNG                                 Δ88
TGAGGACGTGTGTG                                                         Δ87
TGAGGACGTGTGTGTCTGTGTGG                                                Δ83
TGAGGACGTGTGTGT                                                    GG  Δ50
TGAGGACGTGTGTGTCTGTGTGGGTGAGTG                                         Δ40
TGAGGACGTGTGTGTCTGTGTGGGTGA                                        GG  Δ38
TGAGGACGTGTGTGTCTGTGTGGGTGAGT                                       G  Δ37
TGAGGACGTGTGTGTCTGTGTGGGTGAGTGA                              GGAGCGGGG Δ27
TGAGGACGTGTGTGTCTGTGTGGGTGAGTGA                              GTTGGAGCGGGG Δ24
TGAGGACGTGTGTGTCTGTGTGGGTGAGT                                GTGTTGGAGCGGGG Δ24
TGAGGACGTGTGTGTCT                        GTGTGGGGTTGAGGGCGTTGGAGCGGGG  Δ22
TGAGGACGTGTGTGTCTGTGTGGGTGAGTGAGT                            GTTGGAGCGGGG Δ22
TGAGGACGTGTGTGTCTGTGTGGGTGAGTGAGTGT                          GTTGGAGCGGGG Δ20 X2
TGAGGACGTGTGTGTCTGTGTGGGTGAG                         TGAGGGCGTTGGAGCGGGG Δ20 X2
TGAGGACGTGTGTGTCTGTGTGGGTGAGTGA                     GTTGAGGGTGTTGGAGCGGGG Δ15
TGAGGACGTGTGTGTCTGTGTGGGTGAGTGAGT                   GTTGAGGGCGTTGGAGCGGGG Δ13
TGAGGACGTGTGTGTCTGTGTGGGTGAGTGAGTGT                 GTTGAGGGCGTTGGAGCGGGG Δ11
TGAGGACGTGTGTGTCTGTGTGGGTGAGT              NNNGGGGGGNNGANGGNGTTGNNNNNGGG  Δ9
TGAGGACGTGTGTGTCTGTGTGGGTGAGTGA            NNNGGGGNTGAGGGTGTTGGAGCGGGG    Δ9
TGAGGACGTGTGTGTCTGTGTGGGTGAGTGA           GTGTGGGGTTGAGGGGGNTGNNNNNNGGG   Δ8 X3
TGAGGACGTGTGTGTCTGTGTGGGTGAGTGAGTGT       GGGTTGAGGGCGTTGGAGCGGGG         Δ7
TGAGGACGTGTGTGTCTGTGTGGGTGAGTGAGT         GTGTGGGGTTGAGGGTGTTGGAGCGGGG   Δ6 X5
TGAGGACGTGTGTGTCTGTGTGGGTGAGTGAGTGTGTGNGGNTGNGGTTGA        NGGAGNNGGA   Δ6
TGAGGACGTGTGTGTCTGTGTGGGTGAGTGAGTGT      GTGTGGGGTTGAGGGTGTTGGAGCGGGG   Δ4
TGAGGACGTGTGTGTCTGTGTGGGTGAGTGAGTG      CGTGTGGGGTTGAGGGTGTTGGAGCGGGG   Δ4
TGAGGACGTGTGTGTCTGTGTGGGTGAGTGAGTGAGT    GTGTGGGGTTGAGGGCGTTGGAGCGGGG   Δ2

TGAGGACGTGTGTGTCTGTGTGGGTGAGTGAGTGAGTGAGTGNGTGGGGTTGAGGGCGTTGGAGCGG    +2

TGAGGACGTGTGTGTCTGTGTGGGTGAGTGAGTGTGTGCTCGTGTGGGGTTGAGGGCGTTGGAGCGG    +2

GGGTGAATGGAGCGAGCAGCGTCTTCGNGNGNGAGGACGTGNNNGTCTGNGTGNGTNNGNGAGTGTG    +234 x2
TGCTAGGGTTAGGGTTAGGGTTAGGGTTAGGGTTAGGGTTAGGGTTAGGGTTAGGGTTAGGGTTAGG
GTTAGGGTTAGGGTTAGGGTTAGGGTTAGGGTTAGGGTTAGGGTTAGGGTTAGGGTTAGGGTNANNN
TTAGGGTTNNNNNNAGGNNNANNGTTANGGTTAGGGTTAGGGTTAGGGTTAGGGNTAGGGTTAGGGT
TAGGGTTAGGGTTAGGGTTAGGGTTAGGGTAGGGTGTGTGGGGTTGAGGGCGTTGGAGCGG
```

Fig. 8A

Target 1 (*VEGFA* Site 1):

OT1-3
AGACAGGACATTCTGACACCCCAGGAGCAAACTCCCTCCATCCCACAAATCCGTCCTTAGATGTGCA Wild-type x18
................................AACTCCCTCCATCCCACAAATCCGTCCTTAGATGTGCA Δ53
AGACAGGACATTCTGACACC........................CCATCCCACAAATCCGTCCTTAGATGTGCA Δ17
AGACAGGACATTCTGACACCCCAGGA....................CCCACAAATCCGTCCTTAGATGTGCA Δ15
AGACAGGACATTCTGACACCCCAG..GCAAACTCCCTCCATCCCACAAATCCGTCCTTAGATGTGCA Δ2

AGACAGGACATTCTGACACCCCAGGAGGGCAAACTCCCTCCATCCCACAAATCCGTCCTTAGATGTGCA +2

OT1-6
GAGAGAGGCTCCCATCACGGGGGAGGGAGTTTGCTCCTGGGGAACCTGTGATCCCCACAGGGAACA Wild-type x87
GAGAGAGGCTCCCATCACGGGGG...............................................AGGGAACA Δ35 x3
GAGAGAGGCTCCCATCACGGGGGA..........................GGGGAACCTGTGATCCCCACAGGGAACA Δ14 x1

OT1-11
TGGACTCTACCCACTGAATGCCAGGAGCAAACTTCCCCTCCCCGAGTTGTGACAGCAAAAATGTCTC Wild-type x27
TGGACTCTACCCACTG.....................................................AATGTCTC Δ43
TGGACTCTA..........................................CCCCTCCCCGAGTTGTGACAGCAAAAATGTCTC Δ25
TGGACTCTAC..........................................CCCCTCCCCGAGTTGTGACAGCAAAAATGTCTC Δ24
TGGACTCTACCCACTGAATG.........................CCCTCCCCGAGTTGTGACAGCAAAAATGTCTC Δ15
TGGACTCTACCCACTGAATG.........................CCCTCCCCGAGTTGTGACAGCAAAAATGTCTC Δ15
TGGACTCTACCCACTGAAT........GCAAACTTCCCCTCCCCGAGTTGTGACAGCAAAAATGTCTC Δ7
TGGACTCTACCCACTGAATGCCAGGA.........TTCCCCTCCCCGAGTTGTGACAGCAAAAATGTCTC Δ6
TGGACTCTACCCACTGAATGCCTGG..........CATCCCTCCCCGAGTTGTGACAGCAAAAATGTCTC Δ6
TGGACTCTACCCACTGAATGCCAGG......AAACTTCCCCTCCCCGAGTTGTGACAGCAAAAATGTCTC Δ3

TGGACTCTACCCACTGAATGCCAGGATGGAAGATAATTTTTTCCATAGACCAGGGTGGCGGAATGGTTTCGGGATGATTCAAGCACATCACATTTATTGTGCACTTTATTTCTATTACTATTATATTGTAATGTATACTAAAAATAATTAACAACTCACCATAAGTGTAGAACCAGTCGGAGCCGCAAACTTCCCCTCCCCGAGTTGTGACAGCAAAAATGTCTCA +158

TGGACTCTACCCACTGAATGCCAGGCAAACTTCCCCTCCCCGAGTTGTGACAGCAAAAATGTCTGGCCTAATGTCTGGCAAAAATGTCTCAAGACATTGCCAAATGTCCCCT +23 (Δ2 +25)

Fig. 8B
Target 2 (VEGFA Site 2):

OT2-2
ACCCACCTCCCTATCCTCAAAACTTGGCCAGAGCCGGGGTGGAGGGGCCCCTAGGAGCGCCTTGGTG Wild-type x30
ACCCAC━━━━━━━━━━━━━━━━━━━━━━━━━━━━━━━━━━━━━━━━━━━━━━━━━━CGCCTTGGTG Δ51
ACCCACCTCC━━━━━━━━━━━━━━━━━━━━━━━━━━━━━━━━━━━━━━━TATCCTAGGAGCGCCTTGGTG Δ36
ACCCACCTCCCTATCCTCAAAACTT━━━━━━━━━━━━━━━━━━━━━━━━━━━━━━━CCCTTGGTG Δ33
ACCCACCTCCCTATCCTCAAAACTTGGCCAGAG━━━━━━━━━━━━━━━━━━━TAGGAGCGCCTTGGTG Δ18
ACCCACCTCCCTATCCTCAAAACTT━━━━━━━━GGGGTGGAGGGGCCCCTAGGAGCGCCTTGGTG Δ10
ACCCACCTCCCTATCCTCAAAACTT━━━━━GGCGGGTTGGAGGGGCCCCTAGGAGCGCCTTGGTG Δ7
ACCCACCTCCCTATCCTCAAAACTTGGCCAGA━━━━━GTGGAGGGGCCCCTAGGAGCGCCTTGGTG Δ6
ACCCACCTCCCTATCCTCAAAACT━━━━━━━━━━━━━━━━━━━━━━━━━━━━━━━━━━━━━━━━━
CTGGCAGTCTGTCAGTGCGTTATCTTGTCACACTTCTACAAGGGGGCTCTCCCTGCATTCTGA +21 (Δ40, +61)
ACCCACCTCCCTATCCTCAAAACTTGGCCAGAGGGGCGCCTCGCCCAGGAAGTGCTCCGGCCAGCCCAGGGTAAACA
GGCTAGCCCTGCCCCTCTGGGACCATAGCCCGGGGACCCAGACTCTTGGCCACGCTCATTCCCACCGCGGGGTGG
AGGGGCCCCTAGGAGCGCCTTGGTG +108

OT2-15
TGACTGTCGGTGCCCCACATGTGGCAGATGCCCAGAGCCGGGGTGTGGGGGGTACTTTGTGGGCGTT Wild-type X71
TGACTGTC━━━━━━━━━━━━━━━━━━━━━━━━━━━━━━━━━━━━GGTGTGGGGGGTACTTTGTGGGCGTT Δ33
TGACTGTCGGTGCCCCACATGTGGCAGATGCCCAGAG━━━━━━━━━━━━━━━━━━━GGGCGTT Δ23
TGACTGTCGGTGCCCCACATGTGGCAGA━━━━━━━━━━━━━━TGTGGGGGGTACTTTGTGGGCGTT Δ15
TGACTGTCGGTGCCCCACATGT━━━━━━━━━━━━━GGCGGGGTGTGGGGGGTACTTTGTGGGCGTT Δ14
TGACTGTCGGTGCCCCACATGTGGCAGATG━━━━━GAGGCGGGTGTGGGGGGTACTTTGTGGGCGTT Δ4
TGACTGTCGGTGCCCCACATGTGGCAGATGCCCAGA━━━━GGGTGTGGGGGGTACTTTGTGGGCGTT Δ4
TGACTGTCGGTGCCCCACATGTGGCAGATGCCCAGAG━━GGGGTGTGGGGGGTACTTTGTGGGCGTT Δ2
TGACTGTCGGTGCCCCACATGTGGCAGATGCCCAGAGTTGCGGGGTGTGGGGGGTACTTTGTGGGCGTT +2
TGACTGTCGGTGCCCCACATGTGGCAGATGCCCAGAGCTGCGCGGGGTGTGGGGGGTACTTTGTGGGCGTT +2

OT2-24
ACAAGATGACTATGTCCCTCTGGGCCCCATCCTCCCCTCCCCACCCACCCCGCCTCAGGCTTGAAGA Wild-type x8
ACAAGA━━━━━━━━━━━━━━━━━━━━━━━━━━━━━━━━━━━━━━━━━━━━━━━━━━━━━━━━━ Δ121
━━━━━━━━━━━━━━━━━━━━━━━━━━━━━━━━━━━━━━━━━━━━━━━━━━CTCAGGCTTGAAGA Δ82
ACAAGATG━━━━━━━━━━━━━━━━━━━━━━━━━━━━━━━━━━━━━━━━━━━━━━━━━━━━━━━ Δ80
━━━━━━━━━━━━━━━━━━━━━━━━━━━━━━━━━━━━━━━━━━━━━━━━━━━━━━━━━━━━━━━ Δ79
ACAAGATGACTATGTCCCTCTGGGCCCCATCCTCC━━━━━━━━━━━━━━━━━━━━━━━━━━━━━ Δ42
ACAAGATGACTATGTCCCTCTGGGC━━━━━━━━━━━━━━━━━━━━━━━━━━━━━━━CTTGAAGA Δ34
ACAAGATGACTATGTCCCTCTGGGCCCCATCCTCCCCTCCC━━━━━━━━━━━━━CAGGCTTGAAGA Δ14
ACAAGATGACTATGTCCCTCTGGGCCCCATCCTCCCCTCC━━━━━━━━━━━CCTCAGGCTTGAAGA Δ12
ACAAGATGACTATGTCCCTCTGGGCCCCATCCTCCCCTCCCCA━━━━━━━━GCAGGCTTGAAGA Δ11
ACAAGATGACTATGTCCCTCTGGGCCCCATCCTCCCCTCCCCACCCAC━━━━━━━CTTGAAGA Δ11
ACAAGATGACTATGTCCCTCTGGGCCCCATCCTCCCCTCCC━━━━━━━━GCTCAGGCTTGAAGA Δ11

ACAAGATGACTATGTCCCTCTGGGCCCGCCTCAAGTGATCCAGCTGCCTTGCCCTCCAAAAGTGCTAGCAGTACA
GATGTGAGCCTCCATGCCCTGGCCTATTGCAACATCCCATCTCTGTGAAGCAGGCTTTTCTGCACTGACACCAAGA
AGAGCACAGGGCCAAAAAAACTTTGTCCTTTAGAAAGGATCTACCTTTTAGGCTGAGAATGGCA +76 (Δ43 +119)

Fig. 8C

Target 3 (*VEGFA* Site 3):

OT3-2
GAGTGAGAGAGCGAGTGAGTGAGTGAGTGAGTGTGTGTGTGGGGGGACTCGGCTTGTTGTTGTCGG Wild-type x14
GAGTGAGAGAGCGAGTGAGTGAGTGAGTGA████GTGTGTGGGGGGGACTCGGCTTGTTGTTGTCGG Δ4
GAGTGAGAGAGCGAGTGAGTGAGTGAGTGA████GTGTGGGGGGGACTCGGCTTGTTGTTGTCGG Δ6 x2

OT3-9
GTGTTGGGATGCGGGAGTGGGTGAGTGAGTGCGTGCGGGTGGCGATGCAAGCGTGTGCGAATGCGTG x173
GTGTTGGGATGCGGGA████████████████████████████████████████ Δ80
GTGTTGGGATGC████████████████████████████████████████GCGTG Δ50
GTGTTGGGATGCGGGAGTGGGTGAGTGA████████GTGGCGATGCAAGCGTGTGCGAATGCGTG Δ10

GTGTTGGGATGCGGGAGTGGGTGAGTGAGTGCAAGTGCGGGTGGCGATGCAAGCGTGTGCGAATGCGTG +2

OT3-18
TTTCAAAGACAGTAGATCTTAAATGTCCTCACCCACACACTCACCCACACATAAAAGGTGGTAACTG Wild-type x27
TTTCAAAGACAGTAGATCT████████████████████████████TAAAAGGTGGTAACTG Δ32
TTTCAAAGACAGTAGATCTTAAATGT████████████████████CATAAAAGGTGGTAACTG Δ23
TTTCAAAGACAGTAGATCTTAAATGTCCT████████████████CACATAAAAGGTGGTAACTG Δ18 x4
TTTCAAAGACAGTAGATCTTAAATGTCCT████████████████CCACACATAAAAGGTGGTAACTG Δ15
TTTCAAAGACAGTAGATCTTAAATGTC████████████████CTCACCCACACATAAAAGGTGGTAACTG Δ12
TTTCAAAGACAGTAGATCTTAAATGTCCTCA██CACACACTCACCCACACATAAAAGGTGGTAACTG Δ2

TTTCAAAGACAGTAGATCTTAAATGTCCTCACAGGCTGGAGTACAGTGGCATGATATCAGCTCACTGCAATCTCG
GGCTCCCGGGTTCAAGCCATGCACACACTCACCCACACATAAAAGGTGGTAAC +63

Target 4 (*EMX1*):

OT4-1
ACCTGTACATCTGCACAAGATTGCCTTTACTCCATGCCTTCTTCTTCTGCTCTAACTCTGACAATC Wild-type x20
████████████████████████████████████████████████████████████ATC Δ64
ACCTGTACATCTGCACAAGATTGCCTTTACTCC████████████████████████ACAATC Δ28
ACCTGTACATCTGCACAAGATTGCCTTTACTCCAT████████████████ACTCTGACAATC Δ20
ACCTGTACATCTGCACAAGATTGC████████████████CTTCTGCTCTAACTCTGACAATC Δ20
ACCTGTACATCTGCACAAGATTGCCTTTACTCCATGCCTTCT████████████████CAATC Δ19
ACCTGTACATCTGCACAAGATTGCCTTTACTCCA██████████TGCTCTAACTCTGACAATC Δ14
TCCTGTACATCTGCACAAGATTGCCTTTACTCC████████CTTCTTCTGCTCTAACTCTGACAATC Δ8

Fig. 9A

Target 1 (*VEGFA* Site 1):

```
OT1-3
TCAGACAGGACATTCTGACACCCCAGGAGCAAACTCCCTCCATCCCACAAATCCGTCCTTAGATGTG Wild-type x41
TCAGACAGGACATT                     CAAACTCCCTCCATCCCACAAATCCGTCCTTAGATGTG Δ15
TCAGACAGGACATTCT              GAGCAAACTCCCTCCATCCCACAAATCCGTCCTTAGATGTG Δ10
TCAGACAGGACATTCTGAC           GCAAACTCCCTCCATCCCACAAATCCGTCCTTAGATGTG Δ9
TCAGACAGGACATCCTGACAC         GCAAACTCCCTCCATCCCACAAATCCGTCCTTAGATGTG Δ7
TCAGACAGGACATTCTGACACCCCAG    GCAAACTCCCTCCATCCCACAAATCCGTCCTTAGATGTG Δ2 x6

TCAGACAGGACATTCTGACACCCCAGGAIGTCCTCCTCCCTCCATCCCACAAATCCGTCCTTAGATGTG +2

TCAGNCAGGACATTNNGNCACCCCAGGAAACNNGAGTTTCGNTNCNNNCANNGTCAGACCCAGNAGCAAACTCCCTCCATC
CCACAAATCCGTCCTTAGATGTG +38

TCAGACAGGACATTNTGACACCCCAGGAGTNTGCACNTCAGTTTTCTTANTATGTNCNNNNGGGGCANGNACAAANNCTTN
GCAAACTCCCTCCATCCCACAAATCCGTCCTTAGATGTG +54

TCAGACAGGACATTCTGACACCCCAGGAATGTTTGTTTGAGTCAGAGTCTCTCTTTTGTCACCCAGGCTGGAGTGCACTGGAA
NCTGTGCCTTTTGTATAATCCTCTTTGAAGGTTAAAGAGTCATLATGCATCANCNNCATAAAGCAAACTCCNTCCATCC
+116

TCAGACAGGACATTCTGACACCCCAGGATAAGCGGCAGGCGTCGGAACAGGAGAGCGCACCGAGGGAGCTTCCAGGGGGAAACC
CCTGGCTATCTTTATAGTCCTGTCCGGTTTCGCCACCTCTAGGGGAGTTCTGAGCTCGACCCCGGCCGTGTTAGGAGATAGC
AGGCCGTTAATGACCATCGCAGCCGAATTCCTCACTGTGCAGATGAGGAAGTGAGCTCAGGCAGGCTGAGTGTCCCAGGCCT
GTTGCCAGATGAGGCCACGCTGAGACTGTGCAAACTCCCTCCATCCCACAAATCCGTCCTTAGATGTG +247

OT1-6
TGGAGAGAGGCTCCCATCACGGGGGAGGGAGTTTGCTCCTGGGGAACCTGTGATCCCCACAGGGAAC Wild-type x88
TGGAGAGAGGCTCCCATCACGGGGGAGGGAGTTTC        CCTGTGATCCCCACAGGGAAC Δ11
TGGAGAGAGGCTCCCATCACGGGGGAGGGAGTTT        GGGAACCTGTGATCCCCACAGGGAAC Δ7

OT1-11
AGCATCGCTGGACTCTACCCACTGAATGCCAGGAGCAAACTTCCCCTCCCCGAGTTGTGACAGCAAA Wild-type x84
AGCATCGCTGGACTCTACCCACTGAATGCCAGGA        CCCGAGTTGTGACAGCAAA Δ14
AGCATCGCTGGACTCTACCCACTGA        GCAAACTTCCCCTCCCCGAGTTGTGACAGCAAA Δ9
AGCATCGCTGGACTCTACCCACTGAATGCCAG   GCAAACTTCCCCTCCCCGAGTTGTGACAGCAAA Δ2

AGCATCGCTGGACTCTACCCACTGAATGCCAGGAGTTCAGACGATTGAATGTATCAACTTGGCACATTGCCTATCAACTGGT
GAGTGCTCAAAAATATCCATTGCTGTGATCAGTAATGCCACAGGGTGACCATTTAAGGACAGAGTCCATGTTTTATCCATCC
TTAGCAAACTTCCCCTCCCCGAGTTGTGACAGCAAA +133

AGCATCGCTGGACTCTACCCACTGAATGCCAGAGCCCTTCCTTCTCCCTCTCTTCCTTCAGAGGTCCTGCCGAGATCAGGTT
GGAGGTCCTCTTTGTTCTTATGCCCATTCCTCCCCCAGGCACTTGGAGGAGGCCACTGTTTTTGAGTGTGCAAGTCTTTCT
TGTTACTGTTGGGCAAACTTCCCCTCCCCGAGTTGTGACAGCAAA +142

AGCATCGCTGGACTCTACCCACTGAATGCCAGGATGTTTCTTTGCGACGGANTCTCACTCTGTCGNCCGGGCTGGAGTGCA
NNGGCACANTTCCTCANCTGACTGCNATGCTGCCCTTCCCGGATTCAAGTGATTCTCCTGCCCCAGCCTCCCCAGTAGCTGGG
ATTATAGCTGCCTGCCACCATGCCTGGCTAATTTTTTTTTTTTTAAATGGAGTCTCACTCTGTGCCCCCGAGTTGTGA
CAGCAAA +186
```

Fig. 9B

**Target 2 (*VEGFA* Site 2):**

OT2-2
```
CACCTCCCTATCCTCAAAACTTGGCCAGAGGCGGGGTGGAGGGGCCCCTAGGAGCGCCTTGGTGGGA
CACCTCCCTATCCTCAAAACTTGGCCAGAGGCGGGGT--------GGAGCGCCTTGGTGGGA  Δ13
CACCTCCCTATCCTCAAAACTT--------GGCGGGGTGGAGGGGCCCCTAGGAGCGCCTTGGTGGGA  Δ7
CACCTCCCTATCCTCAAAACTTG--------GACGGGGTGGAGGGGCCCCTAGGAGCGCCTTGGTGGGA  Δ6
CACCTCCCTATCCTCAAAACTTGGCC--AGGCGGGGTGGAGGGGCCCCTAGGAGCGCCTTGGTGGGA  Δ2

CACCTCCCTATCCTCAAAACTTGGCCAGAGACTTANACCTAANACCTCAAACTATGAGACTGCTACNAGAGAACA
TCANAAAAACTTTCCAGGACATTCTTCTGGNGGGGTGGAGGGGCCCCTANGAGCGCCTTGNNGGGA  +74

CACCTCCCTATCCTCAAAACTTGGCCAGAGTCTACAGATTTATAAAATATTACCAGTTAATCATGACACATATTG
TTTATTTTCAAATATTTTTTCTAGTTAAACCCACCATTTATATAACCAATTATATTTGATATAATTTAAAATTTT
TGTATTAACACCCCACCAAATCATTTTACAGCGGGGTGGAGGGGCCCCTAGGAGCGCCTTGGTGGGA  +150
```

OT2-15
```
GTCGGTGCCCCACATGTGGCAGATGCCCAGAGCCGGGGTGTGGGGGGTACTTTGTGGGCGTTTTGGG  Wild-type x79
GTCGGTGCCCCAC--------------GCGGGGTGTGGGGGGTACTTTGTGGGCGTTTTGGG  Δ19
GTCGGTGCCCCACATGTGGC--------GCGGGGTGTGGGGGGTACTTTGTGGGCGTTTTGGG  Δ12
GTCGGTGCCCCACATGTGGCAGATGCCCAGA-----GGTGTGGGGGGTACTTTGTGGGCGTTTTGGG  Δ5
GTCGGTGCCCCACATGTGGCAGATGCCCA-----GGGGTGTGGGGGGTACTTTGTGGGCGTTTTGGG  Δ5
GTCGGTGCCCCACATGTGGCAGATGCCCAGA----GGGTGTGGGGGGTACTTTGTGGGCGTTTTGGG  Δ4
GTCGGTGCCCCACATGTGGCAGATGCCC----GCGGGGTGTGGGGGGTACTTTGTGGGCGTTTTGGG  Δ4
GTCGGTGCCCCACATGTGGCAGATGCCC--AGGCGGGGTGTGGGGGGTACTTTGTGGGCGTTTTGGG  Δ2 x2
```

OT2-24
```
GTCCCTCTGGGCCCCATCCTCCCCTCCCCACCCACCCCGGCCTCAGGCTTGAAGAGGAAAGAAGAGCA
GTCCCTCTGGGCCCC-------------------------ANAGNANNNANNANNN  Δ36
GTCCCTCTGGGCCCCATCCTCCCCTCCCC-------------TGAAGAGGAAAGAAGAGCG  Δ19
GTCCCTCTGGGCCCCATCCTCCCCTCCCC-----CCNCNCCTCAGGCTTGAAGAGGAAAGAAGAGCG  Δ17
GTCCCTCTGGGCCCCATCCTCCCCTC-----------CCTCAGGCTTGAAGAGGAAAGAAGAGCG  Δ13
GTCCCTCTGGGCCCCATCCTCCCCTCCCCA--------CTCAGGCTTGAAGAGGAAAGAAGAGCG  Δ10
GTCCCTCNNNNNNNCCTCCTCCCC--------NNCCCNCNCTCAGGCTTGAAGAGGAAAGAAGAGCG  Δ8
GTCCCTCTGGGCCCCATCCTCCCCTCCCCACCCA-----CTCAGGCTTGAAGAGGAAAGAAGAGCG  Δ6
GTCCCTCTGGGCCCCATCCTCCCCTCCCCACCCA-----CCTCAGGCTTGAAGAGGAAAGAAGAGCG  Δ5

GTCCCTCTGGGCCCCATCCTCCCCTCCCCACCCACCCCGCATCGTACGTGTCCTTATAAGCTGCAATTTGCCAT
CTTCAGCTAAGTCGAAGTTCGACCTCAGGCTTGAAGAGGAAAGAAGAGCG  +58
```

Fig. 9C

Target 3 (*VEGFA* Site 3):

OT3-2*
GAGAGCGAGTGAGTGAGTGAGTGAGTGTGTGTGTGGGGGGACTCGGCTTGTTGTTGTCGGTGACTT Wild-type x26
GAGAGCGAGTGAGTGAGTGAGTGAGTGAGTGTGNGTNTNNNNATTTCACAACATACGAGCCGGAAGCATAAAGTGTA
AAGCCTAGGGTGCCTAATGAGTGAGCTAACTCACATTAATTGCCTTGCGCTCACTGCCCGCTTTCCAGTCGGGAA
ACCTGTCGTGCCAGCTGCATTAATGAATCGGCCAANNNNNGNNNAGAGGCGGTTTGCGTATTGGGCGCTCTTCCG
CTTCCTCGCTCACTGACTCGCTGCGCTCGGTCGTTCGGCTGCGGCGAGCGGTATCAGCTCACTCAAAGGCGGTAA
TACGGTTATCCACANAANGGGACTCGGCTTGTTGTTGTCGGTGACTT +280

OT3-9
TGGAGGTGTTGGGATGCGGGAGTGGGTGAGTGAGTGCGTGCGGTCGCGATGCAAGCGTGTGCGAAT Wild-type x101
TGGAGGTGTTGGGATGCGGGAGTGG--------GTGCGTGCGGGTGGCGATGCAAGCGTGTGCGAAT Δ8
TGGAGGTGTTGGGATGCGGGAGTGGGTGA--------GTGCGGGTGGCGATGCAAGCGTGTGCGAAT Δ8

OT3-18
CAAAGACAGTAGATCTTAAATGTCCTCACGCACACACTCACCCACACATAAAAGGTGGTAACTGTGT Wild-type x64
CAAAGACAGTAGATCTTAA--------GCACACACTCACCCACACATAAAAGGTGGTAACTGTGT Δ10
CAAAGACAGTAGATCTTAAATGTCCTCACG--------TCACCCACACATAAAAGGTGGTAACTGTGT Δ7
CAAAGACAGTAGATCTTAAATGTC--------GCACACACTCACCCACACATAAAAGGTGGTAACTGTGT Δ5
CAAAGACAGTAGATCTTAAATGTCCTCACGCCGACNATTGCATGAAGAATCTGCTTAGGGTTAGGCGTTTTGCCG
TGCTTCGCGATGTACGGGCCAGATAGCACACACTCACCCACACATAAAAGGTGGTAACTGTGT +71

CAAAGACAGTAGATCTTAAATGTCCTCACGCAAATTTTATTTTGGTTCATGATATGGCTTGGCCGTGTATGCTTTT
CATTTCTAAAATTGCTGTTCTTTGACAATTTAACGTGACTGTTTCATTGACTACAAGTTTGAAAATAAAAATTAA
TTAAGAAAAAATTCCAATGACTGTGCTGTGGTTGGGCACACACTCACCCACACATAAAAGGTGGTAACTGTGT +157

CAAAGACAGTAGATCTTAAATGTCCTCACGTGGAAACATAGTACATGAGGTGGCATATCATGAAAGTACCCAAC
GATTTATCACCTCAAAAAAAGCTAGTTGACTCAACTGATAAAGCGGACCTGAGCTTAATCTACTTGGCTCTTGC
CCATATGATAAAGTTCCCTGGGCACTTTCTCATTGAGGCTGATCTAAATCCGGACAACTCGGATGTCGAGCACAC
ACTCACCCACACATAAAAGGTGGTAACTGTGT +190
CAAAGACAGTAGATCTTAAATGTCCTCACG--------
TTATTTAGAGACAGAGTCTCACTCTGTTGCCCAGGCTGGGGTGCAGTGGTACGAACTCGGCTCACTGCAACCTCC
GTCTCCTGGGCTCAAGTGATTATCCTGCCTCAGCCTCCCGAGTAGCTGGGATTACAGGTGCCCACCACCACACCC
GGCTAATTTTTGTATTTTCAGTAGAGCTGGGGTTTCACCATGTTGGCCAGCCTGTTCTCGGCACACACTCACCCA
CACATAAAAGGTGGTAACTGTGT +211 (Δ16 +227)

Target 4 (*EMX1*):

OT4-1
GATTGCCTTTACTCCATGCCTTCTTCTTGCTCTAACTCTGACAATCTGTCTTGCCATGCCATAA Wild-type x74
GATTGCCTTTACTC--------CTTCTTCTGCTCTAACTCTGACAATCTGTCTTGCCATGCCATAA Δ9
GATTGCCTTTACTCCATGCCT--------TTCTGCTCTAACTCTGACAATCTGTCTTGCCATGCCATAA Δ6 x2
GATTGCCTTTACTCCATGC--------TCTTCTGCTCTAACTCTGACAATCTGTCTTGCCATGCCATAA Δ6
GATTGCCTTTACTCCATGCCT--------TTCTTCTGCTCTAACTCTGACAATCTGTCTTGCCATGCCATAA Δ3 x3

USING TRUNCATED GUIDE RNAS (TRU-GRNAS) TO INCREASE SPECIFICITY FOR RNA-GUIDED GENOME EDITING

CLAIM OF PRIORITY

This application is a continuation of U.S. patent application Ser. No. 14/213,723, filed on Mar. 14, 2014, which claims the benefit of U.S. Patent Application Ser. No. 61/799,647, filed on Mar. 15, 2013; 61/838,178, filed on Jun. 21, 2013; 61/838,148, filed on Jun. 21, 2013, and 61/921,007, filed on Dec. 26, 2013. The entire contents of the foregoing are hereby incorporated by reference.

FEDERALLY SPONSORED RESEARCH OR DEVELOPMENT

This invention was made with Government support under Grant Nos. DPI GM105378 awarded by the National Institutes of Health. The Government has certain rights in the invention.

TECHNICAL FIELD

Methods for increasing specificity of RNA-guided genome editing, e.g., editing using CRISPR/Cas9 systems, using truncated guide RNAs (tru-gRNAs).

BACKGROUND

Recent work has demonstrated that clustered, regularly interspaced, short palindromic repeats (CRISPR)/CRISPR-associated (Cas) systems (Wiedenheft et al., Nature 482, 331-338 (2012); Horvath et al., Science 327, 167-170 (2010); Terns et al., Curr Opin Microbiol 14, 321-327 (2011)) can serve as the basis for performing genome editing in bacteria, yeast and human cells, as well as in vivo in whole organisms such as fruit flies, zebrafish and mice (Wang et al., Cell 153, 910-918 (2013); Shen et al., Cell Res (2013); Dicarlo et al., Nucleic Acids Res (2013); Jiang et al., Nat Biotechnol 31, 233-239 (2013); Jinek et al., Elife 2, e00471 (2013); Hwang et al., Nat Biotechnol 31, 227-229 (2013); Cong et al., Science 339, 819-823 (2013); Mali et al., Science 339, 823-826 (2013c); Cho et al., Nat Biotechnol 31, 230-232 (2013); Gratz et al., Genetics 194(4):1029-35 (2013)). The Cas9 nuclease from S. pyogenes (hereafter simply Cas9) can be guided via base pair complementarity between the first 20 nucleotides of an engineered guide RNA (gRNA) and the complementary strand of a target genomic DNA sequence of interest that lies next to a protospacer adjacent motif (PAM), e.g., a PAM matching the sequence NGG or NAG (Shen et al., Cell Res (2013); Dicarlo et al., Nucleic Acids Res (2013); Jiang et al., Nat Biotechnol 31, 233-239 (2013); Jinek et al., Elife 2, e00471 (2013); Hwang et al., Nat Biotechnol 31, 227-229 (2013); Cong et al., Science 339, 819-823 (2013); Mali et al., Science 339, 823-826 (2013c); Cho et al., Nat Biotechnol 31, 230-232 (2013); Jinek et al., Science 337, 816-821 (2012)). Previous studies performed in vitro (Jinek et al., Science 337, 816-821 (2012)), in bacteria (Jiang et al., Nat Biotechnol 31, 233-239 (2013)) and in human cells (Cong et al., Science 339, 819-823 (2013)) have shown that Cas9-mediated cleavage can, in some cases, be abolished by single mismatches at the gRNA/target site interface, particularly in the last 10-12 nucleotides (nts) located in the 3' end of the 20 nt gRNA complementarity region.

SUMMARY

CRISPR-Cas genome editing uses a guide RNA, which includes both a complementarity region (which binds the target DNA by base-pairing) and a Cas9-binding region, to direct a Cas9 nuclease to a target DNA (see FIG. 1). The nuclease can tolerate a number of mismatches (up to five, as shown herein) in the complementarity region and still cleave; it is hard to predict the effects of any given single or combination of mismatches on activity. Taken together, these nucleases can show significant off-target effects but it can be challenging to predict these sites. Described herein are methods for increasing the specificity of genome editing using the CRISPR/Cas system, e.g., using Cas9 or Cas9-based fusion proteins. In particular, provided are truncated guide RNAs (tru-gRNAs) that include a shortened target complementarity region (i.e., less than 20 nts, e.g., 17-19 or 17-18 nts of target complementarity, e.g., 17, 18 or 19 nts of target complementarity), and methods of using the same. As used herein, "17-18 or 17-19" includes 17, 18, or 19 nucleotides.

In one aspect, the invention provides a guide RNA molecule (e.g., a single guide RNA or a crRNA) having a target complementarity region of 17-18 or 17-19 nucleotides, e.g., the target complementarity region consists of 17-18 or 17-19 nucleotides of consecutive target complementarity. In some embodiments, the guide RNA includes a complementarity region consisting of 17-18 or 17-19 nucleotides that are complementary to 17-18 or 17-19 consecutive nucleotides of the complementary strand of a selected target genomic sequence. In some embodiments, the target complementarity region consists of 17-18 nucleotides (of target complementarity). In some embodiments, the complementarity region is complementary to 17 consecutive nucleotides of the complementary strand of a selected target sequence. In some embodiments, the complementarity region is complementary to 18 consecutive nucleotides of the complementary strand of a selected target sequence.

In another aspect, the invention provides a ribonucleic acid consisting of the sequence:

(SEQ ID NO: 2404)
$(X_{17-18}$ or $X_{17-19})$ GUUUUAGAGCUA;

(SEQ ID NO: 2407)
$(X_{17-18}$ or $X_{17-19})$ GUUUUAGAGCUAUGCUGUUUUG;
or (SEQ ID NO: 2408)
$(X_{17-18}$ or $X_{17-19})$ GUUUUAGAGCUAUGCU;

(SEQ ID NO: 1)
$(X_{17-18}$ or $X_{17-19})$ GUUUUAGAGCUAGAAAUAGCAAGUUAAAAUAA
GGCUAGUCCG $(X_N)$ ;

(SEQ ID NO: 2)
$(X_{17-18}$ or $X_{17-19})$ GUUUUAGAGCUAUGCUGAAAAGCAUAGCAAG
UUAAAAUAAGGCUAGUCCGUUAUC $(X_N)$ ;

(SEQ ID NO: 3)
$(X_{17-18}$ or $X_{17-19})$ GUUUUAGAGCUAUGCUGUUUUGGAAACAAAA
CAGCAUAGCAAGUUAAAAUAAGGCUAGUCCGUUAUC $(X_N)$ ;

(SEQ ID NO: 4)
$(X_{17-18})$ GUUUUAGAGCUAGAAAUAGCAAGUUAAAAUAAGGCUAGUCCG
UUAUCAACUUGAAAAAGUGGCACCGAGUCGGUGC $(X_N)$ ,

-continued (SEQ ID NO: 5)
($X_{17-18}$ or $X_{17-19}$) GUUUAAGAGCUAGAAAUAGCAAGUUUAAAUA

AGGCUAGUCCGUUAUCAACUUGAAAAAGUGGCACCGAGUCGGUGC;

(SEQ ID NO: 6)
($X_{17-18}$ or $X_{17-19}$) GUUUAGAGCUAUGCUGGAAACAGCAUAGCA

AGUUUAAAUAAGGCUAGUCCGUUAUCAACUUGAAAAAGUGGCACCGAGUC

GGUGC;

or (SEQ ID NO: 7)
($X_{17-18}$ or $X_{17-19}$) GUUUAAGAGCUAUGCUGGAAACAGCAUAGCA

AGUUUAAAUAAGGCUAGUCCGUUAUCAACUUGAAAAAGUGGCACCGAGU

CGGUGC;

wherein X17-18 or X17-19 is a sequence (of 17-18 or 17-19 nucleotides) complementary to the complementary strand of a selected target sequence, preferably a target sequence immediately 5' of a protospacer adjacent motif (PAM), e.g., NGG, NAG, or NNGG (see, for example, the configuration in FIG. 1), and $X_N$ is any sequence, wherein N (in the RNA) can be 0-200, e.g., 0-100, 0-50, or 0-20, that does not interfere with the binding of the ribonucleic acid to Cas9. In no case is the $X_{17-18}$ or $X_{17-19}$ identical to a sequence that naturally occurs adjacent to the rest of the RNA. In some embodiments the RNA includes one or more U, e.g., 1 to 8 or more Us (e.g., U, UU, UUU, UUUU, UUUUU, UUUUUU, UUUUUUU, UUUUUUUU) at the 3' end of the molecule, as a result of the optional presence of one or more Ts used as a termination signal to terminate RNA PolIII transcription. In some embodiments the RNA includes one or more, e.g., up to 3, e.g., one, two, or three, additional nucleotides at the 5' end of the RNA molecule that is not complementary to the target sequence. In some embodiments, the target complementarity region consists of 17-18 nucleotides (of target complementarity). In some embodiments, the complementarity region is complementary to 17 consecutive nucleotides of the complementary strand of a selected target sequence. In some embodiments, the complementarity region is complementary to 18 consecutive In another aspect, the invention provides DNA molecules encoding the ribonucleic acids described herein, and host cells harboring or expressing the ribonucleic acids or vectors.

In a further aspect, the invention provides methods for increasing specificity of RNA-guided genome editing in a cell, the method comprising contacting the cell with a guide RNA that includes a complementarity region consisting of 17-18 or 17-19 nucleotides that are complementary to 17-18 or 17-19 consecutive nucleotides of the complementary strand of a selected target genomic sequence, as described herein.

In yet another aspect, the invention provides methods for inducing a single or double-stranded break in a target region of a double-stranded DNA molecule, e.g., in a genomic sequence in a cell. The methods include expressing in or introducing into the cell: a Cas9 nuclease or nickase; and a guide RNA that includes a sequence consisting of 17 or 18 or 19 nucleotides that are complementary to the complementary strand of a selected target sequence, preferably a target sequence immediately 5' of a protospacer adjacent motif (PAM), e.g., NGG, NAG, or NNGG, e.g., a ribonucleic acid as described herein.

Also provided herein are methods for modifying a target region of a double-stranded DNA molecule in a cell. The methods include expressing in or introducing into the cell: a dCas9-heterologous functional domain fusion protein (dCas9-HFD); and a guide RNA that includes a complementarity region consisting of 17-18 or 17-19 nucleotides that are complementary to 17-18 or 17-19 consecutive nucleotides of the complementary strand of a selected target genomic sequence, as described herein.

In some embodiments, the guide RNA is (i) a single guide RNA that includes a complementarity region consisting of 17-18 or 17-19 nucleotides that are complementary to 17-18 or 17-19 consecutive nucleotides of the complementary strand of a selected target genomic sequence, or (ii) a crRNA that includes a complementarity region consisting of 17-18 or 17-19 nucleotides that are complementary to 17-18 or 17-19 consecutive nucleotides of the complementary strand of a selected target genomic sequence, and a tracrRNA.

In some embodiments, the target complementarity region consists of 17-18 nucleotides (of target complementarity). In some embodiments, the complementarity region is complementary to 17 consecutive nucleotides of the complementary strand of a selected target sequence. In some embodiments, the complementarity region is complementary to 18 consecutive In no case is the $X_{17-18}$ or $X_{17-19}$ of any of the molecules described herein identical to a sequence that naturally occurs adjacent to the rest of the RNA. In some embodiments the RNA includes one or more U, e.g., 1 to 8 or more Us (e.g., U, UU, UUU, UUUU, UUUUU, UUUUUU, UUUUUUU, UUUUUUUU) at the 3' end of the molecule, as a result of the optional presence of one or more Ts used as a termination signal to terminate RNA PolIII transcription. In some embodiments the RNA includes one or more, e.g., up to 3, e.g., one, two, or three, additional nucleotides at the 5' end of the RNA molecule that is not complementary to the target sequence.

In some embodiments, one or more of the nucleotides of the RNA is modified, e.g., locked (2'-O-4'-C methylene bridge), is 5'-methylcytidine, is 2'-O-methyl-pseudouridine, or in which the ribose phosphate backbone has been replaced by a polyamide chain, e.g., one or more of the nucleotides within or outside the target complementarity region $X_{17-18}$ or $X_{17-19}$. In some embodiments, some or all of the tracrRNA or crRNA, e.g., within or outside the $X_{17-18}$ or $X_{17-19}$ target complementarity region, comprises deoxyribonucleotides (e.g., is all or partially DNA, e.g. DNA/RNA hybrids).

In an additional aspect, the invention provides methods for modifying a target region of a double-stranded DNA molecule, e.g., in a genomic sequence in a cell. The methods include expressing in or introducing into the cell:
a dCas9-heterologous functional domain fusion protein (dCas9-HFD); and a guide RNA that includes a sequence consisting of 17-18 or 17-19 nucleotides that are complementary to the complementary strand of a selected target sequence, preferably a target sequence immediately 5' of a protospacer adjacent motif (PAM), e.g., NGG, NAG, or NNGG, e.g., a ribonucleic acid as described herein. In no case is the $X_{17-18}$ or $X_{17-19}$ identical to a sequence that naturally occurs adjacent to the rest of the RNA. In some embodiments the RNA includes one or more, e.g., up to 3, e.g., one, two, or three, additional nucleotides at the 5' end of the RNA molecule that is not complementary to the target sequence.

In another aspect, the invention provides methods for modifying, e.g., introducing a sequence specific break into, a target region of a double-stranded DNA molecule, e.g., in a genomic sequence in a cell. The methods include expressing in or introducing into the cell: a Cas9 nuclease or nickase, or a dCas9-heterologous functional domain fusion protein (dCas9-HFD);

a tracrRNA, e.g., comprising or consisting of the sequence GGAACCAUUCAAAACAGCAUAGCAAGUUAAAA U-AAGGCUAGUCCGUUA UCAACUUGAAAAAGUGGC-ACCGAGUCGGUGC (SEQ ID NO:8) or an active portion thereof;

UAGCAAGUUAAAAUAAGGCUAGUCCGUUAUCAA-CUUGAAAAAGUGGCA CCGAGUCGGUGC (SEQ ID NO:2405) or an active portion thereof;

AGCAUAGCAAGUUAAAAUAAGGCUAGUCCGU-UAUCAACUUGAAAAAGUGGCACCGAGUCGGUGC (SEQ ID NO:2407) or an active portion thereof;

CAAAACAGCAUAGCAAGUUAAAAUAAGGCUAGU-CCGUUAUCAACUUGA AAAAGUGGCACCGAGUCG-GUGC (SEQ ID NO:2409) or an active portion thereof;

UAGCAAGUUAAAAUAAGGCUAGUCCGUUAU-CAACUUGAAAAAGUG (SEQ ID NO:2410) or an active portion thereof;

UAGCAAGUUAAAAUAAGGCUAGUCCGUUAUCA (SEQ ID NO:2411) or an active portion thereof; or UAGCAAGUUAAAAUAAGGCUAGUCCG (SEQ ID NO:2412) or an active portion thereof; and a crRNA that includes a sequence consisting of 17-18 or 17-19 nucleotides that are complementary to the complementary strand of a selected target sequence, preferably a target sequence immediately 5' of a protospacer adjacent motif (PAM), e.g., NGG, NAG, or NNGG; in some embodiments the crRNA has the sequence:

($X_{17-18}$ or $X_{17-19}$)GUUUUAGAGCUA (SEQ ID NO:2404);

($X_{17-18}$ or $X_{17-19}$) GUUUUAGAGCUAUGCUGUUUUG (SEQ ID NO:2407); or ($X_{17-18}$ or $X_{17-19}$)GUUUUAGAGCUAUGCU (SEQ ID NO:2408).

In some embodiments the crRNA is ($X_{17-18}$ or $X_{17-19}$) GUUUUAGAGCUAUGCUGUUUUG (SEQ ID NO:2407) and the tracrRNA is GGAACCAUUCAAAACAGCAUAG-CAAGUUAAAAUAAGGCUAGUCCGUUA UCAACUU-GAAAAAGUGGCACCGAGUCGGUGC (SEQ ID NO:8); the cRNA is ($X_{17-18}$ or $X_{17-19}$)GUUUUAGAGCUA (SEQ ID NO:2404) and the tracrRNA is UAGCAAGUU-AAAAUAAGGCUAGUCCGUUAUCAACUUGAAAA-AGUGGCA CCGAGUCGGUGC (SEQ ID NO:2405); or the cRNA is ($X_{17-18}$ or $X_{17-19}$) GUUUUAGAGCUAUGCU (SEQ ID NO:2408) and the tracrRNA is AGCAUAG-CAAGUUAAAAUAAGGCUAGUCCGUUAUCAACU-UGAAAAAGU GGCACCGAGUCGGUGC (SEQ ID NO:2406).

In no case is the $X_{17-18}$ or $X_{17-19}$ identical to a sequence that naturally occurs adjacent to the rest of the RNA. In some embodiments the RNA (e.g., tracrRNA or crRNA) includes one or more U, e.g., 2 to 8 or more Us (e.g., U, UU, UUU, UUUU, UUUUU, UUUUUU, UUUUUUU, UUUUUUUU) at the 3' end of the molecule, as a result of the optional presence of one or more Ts used as a termination signal to terminate RNA PolIII transcription. In some embodiments the RNA (e.g., tracrRNA or crRNA) includes one or more, e.g., up to 3, e.g., one, two, or three, additional nucleotides at the 5' end of the RNA molecule that is not complementary to the target sequence. In some embodiments, one or more of the nucleotides of the crRNA or tracrRNA is modified, e.g., locked (2'-O-4'-C methylene bridge), is 5'-methylcytidine, is 2'-O-methyl-pseudouridine, or in which the ribose phosphate backbone has been replaced by a polyamide chain, e.g., one or more of the nucleotides within or outside the sequence $X_{17-18}$ or $X_{17-19}$. In some embodiments, some or all of the tracrRNA or crRNA, e.g., within or outside the $X_{17-18}$ or $X_{17-19}$ target complementarity region, comprises deoxyribonucleotides (e.g., is all or partially DNA, e.g. DNA/RNA hybrids).

In some embodiments, the dCas9-heterologous functional domain fusion protein (dCas9-HFD) comprises a HFD that modifies gene expression, histones, or DNA, e.g., transcriptional activation domain, transcriptional repressors (e.g., silencers such as Heterochromatin Protein 1 (HP1), e.g., HP1α or HP1β), enzymes that modify the methylation state of DNA (e.g., DNA methyltransferase (DNMT) or TET proteins, e.g., TET1), or enzymes that modify histone subunit (e.g., histone acetyltransferases (HAT), histone deacetylases (HDAC), or histone demethylases). In preferred embodiments, the heterologous functional domain is a transcriptional activation domain, e.g., a VP64 or NF-κB p65 transcriptional activation domain; an enzyme that catalyzes DNA demethylation, e.g., a TET protein family member or the catalytic domain from one of these family members; or histone modification (e.g., LSD1, histone methyltransferase, HDACs, or HATs) or a transcription silencing domain, e.g., from Heterochromatin Protein 1 (HP1), e.g., HP1α or HP1 (3; or a biological tether, e.g., MS2, CRISPR/Cas Subtype Ypest protein 4 (Csy4) or lambda N protein. dCas9-HFD are described in a U.S. Provisional Patent Application Ser. No. 61/799,647, Filed on Mar. 15, 2013, U.S. Ser. No. 61/838, 148, filed on Jun. 21, 2013, and PCT International Application No. PCT/US14/27335, all of which are incorporated herein by reference in its entirety.

In some embodiments, the methods described herein result in an indel mutation or sequence alteration in the selected target genomic sequence.

In some embodiments, the cell is a eukaryotic cell, e.g., a mammalian cell, e.g., a human cell.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

```
EGFP Site 1
                                (SEQ ID NO: 9)
GGGCACGGGCAGCTTGCCGGTGG EGFP Site 2
                                (SEQ ID NO: 10)
GATGCCGTTCTTCTGCTTGTCGG EGFP Site 3
                                (SEQ ID NO: 11)
GGTGGTGCAGATGAACTTCAGGG
```

Figure 2A:
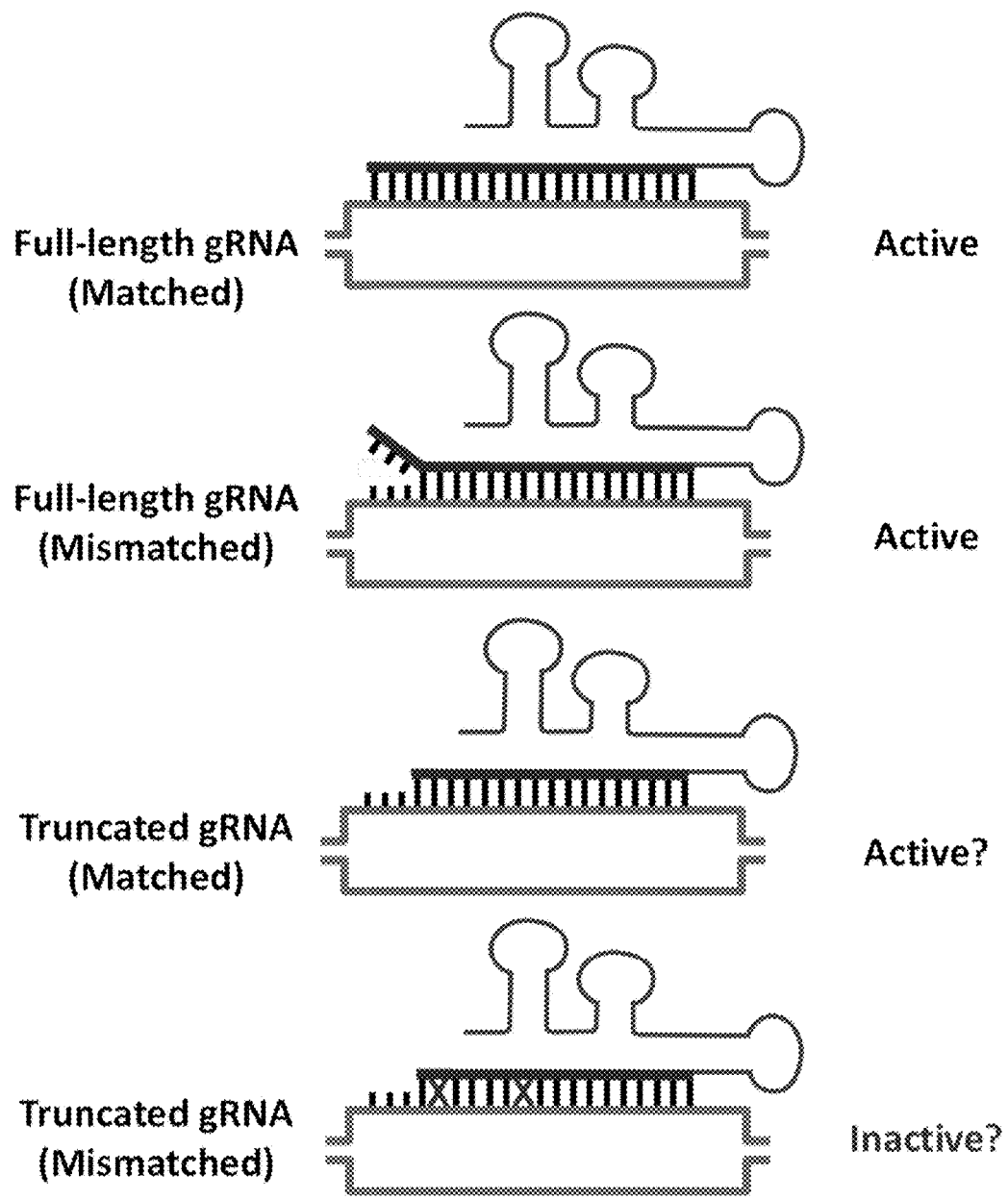
FIG. 2A: Schematic illustrating a rationale for truncating the 5' complementarity region of a gRNA. Thick grey lines=target DNA site, thin dark grey line structure=gRNA, black lines show base pairing (or lack thereof) between gRNA and target DNA site.
Figure 2B:
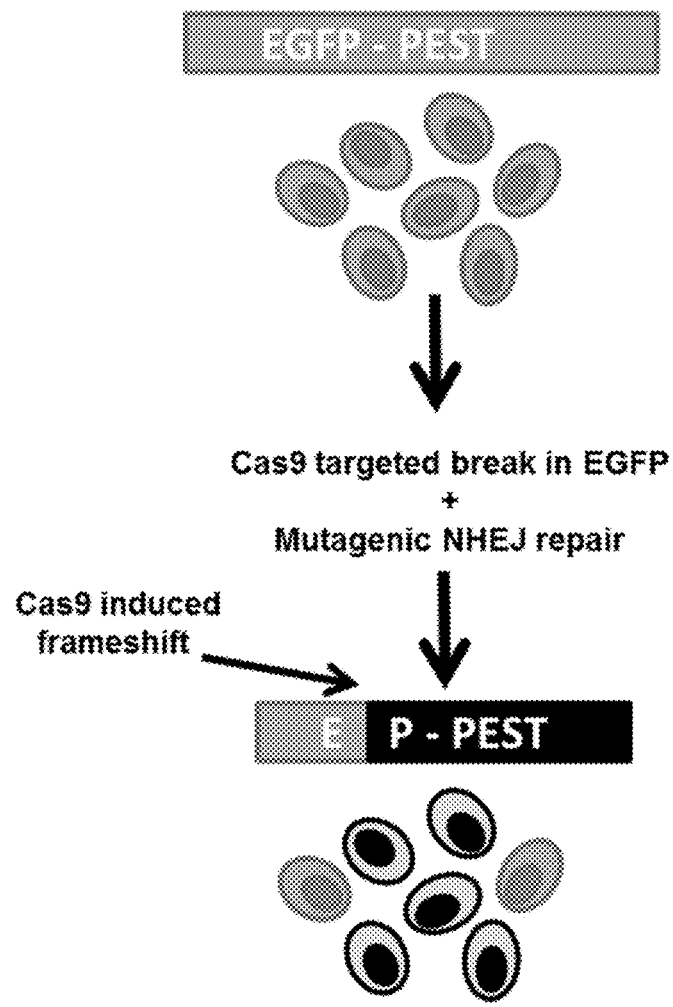
FIG. 2B: Schematic overview of the EGFP disruption assay. Repair of targeted Cas9-mediated double-stranded breaks in a single integrated EGFP-PEST reporter gene by error-prone NHEJ-mediated repair leads to frame-shift mutations that disrupt the coding sequence and associated loss of fluorescence in cells.
Figures 2C, 2D:
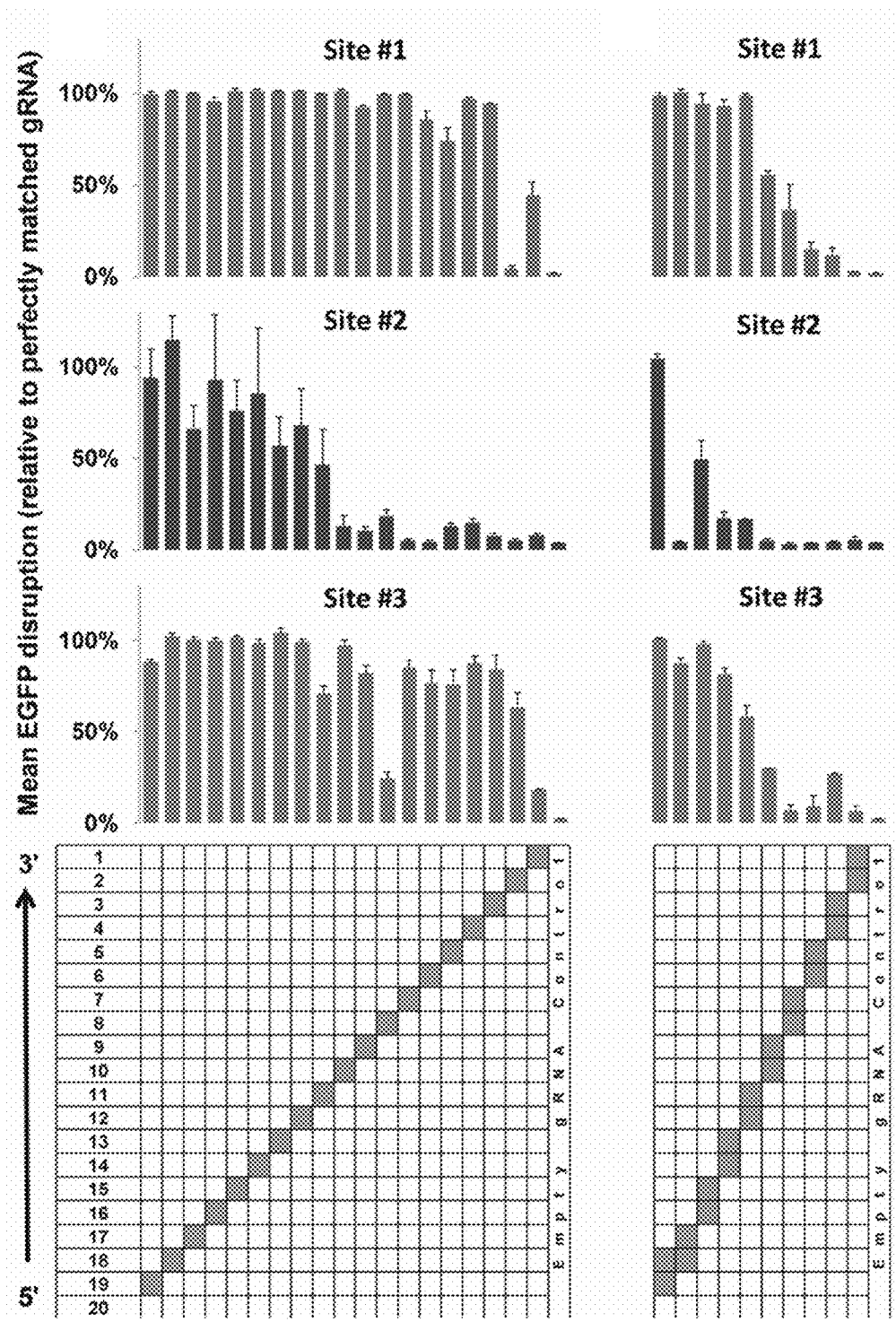
FIGS. 2C-F: Activities of RNA-guided nucleases (RGNs) harboring single guide RNAs (gRNAs) bearing (C) single mismatches, (D) adjacent double mismatches, (E) variably spaced double mismatches, and (F) increasing numbers of adjacent mismatches assayed on three different target sites in the EGFP reporter gene sequence. Mean activities of replicates are shown, normalized to the activity of a perfectly matched single gRNA. Error bars indicate standard errors of the mean. Positions mismatched in each single gRNA are highlighted in grey in the grid below. Sequences of the three EGFP target sites were as follows.
Figure 2E:
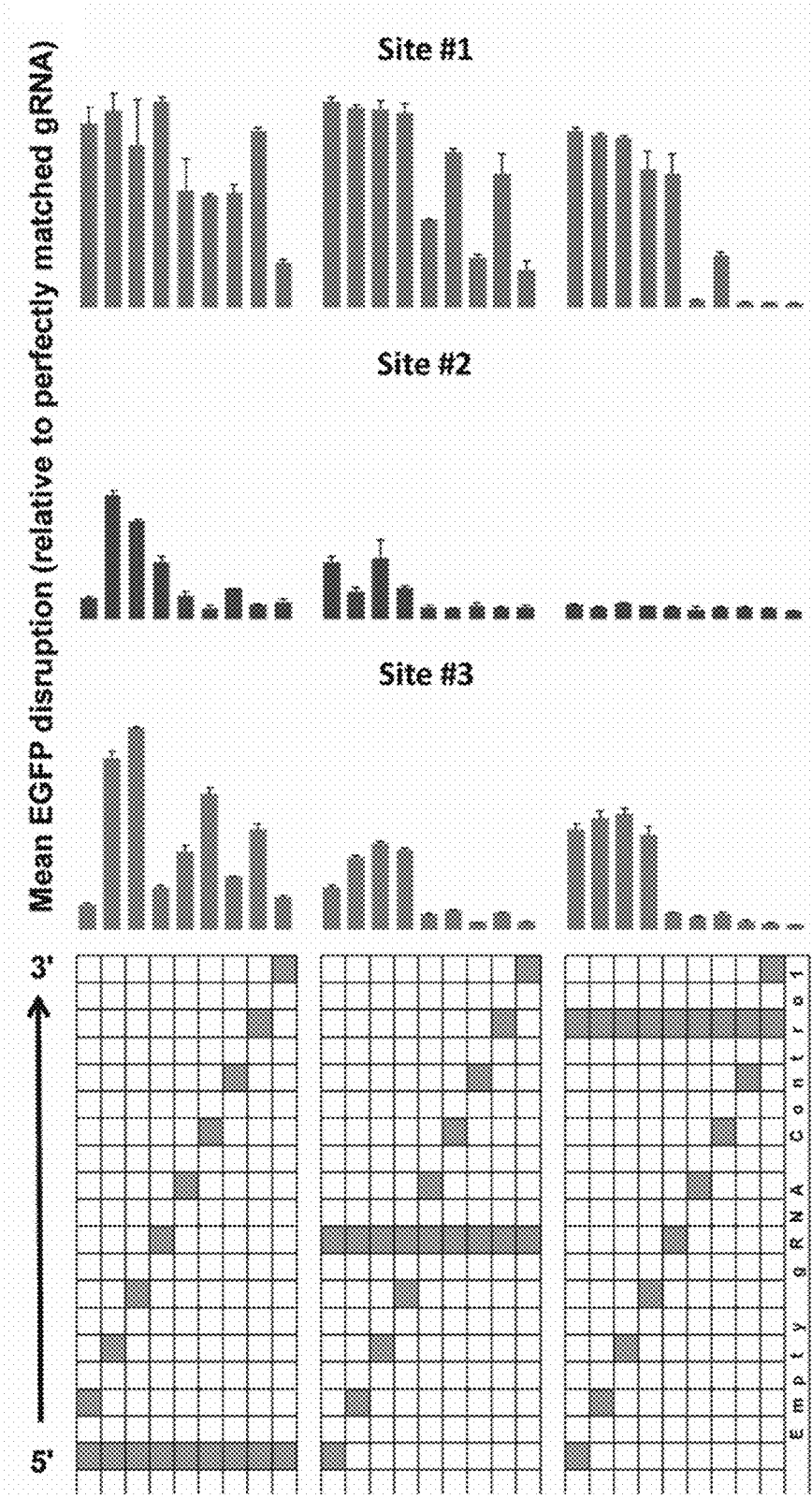
Figure 2F:
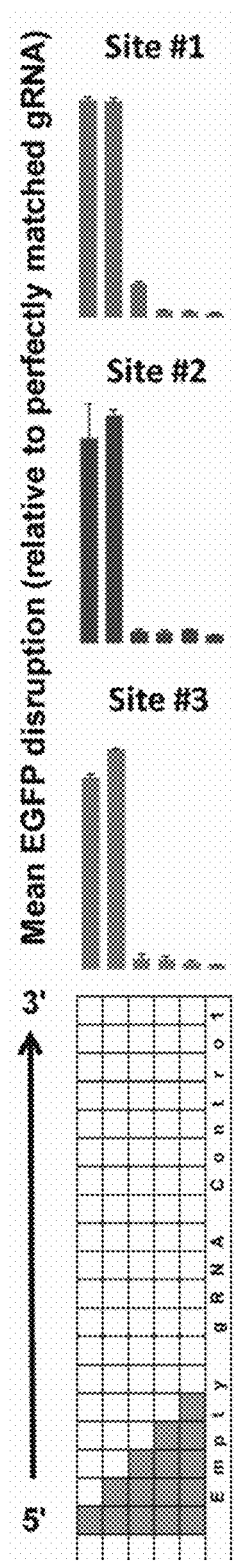
Figure 2G:
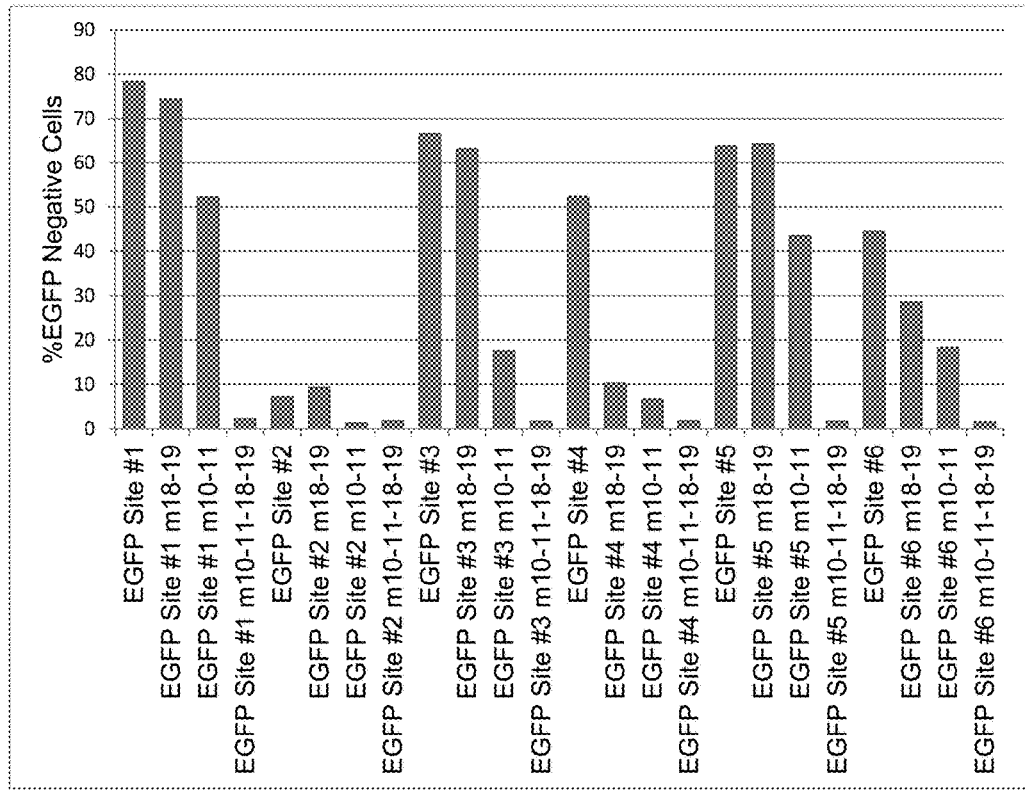

FIG. 2G: Mismatches at the 5' end of the gRNA make CRISPR/Cas more sensitive more 3' mismatches. The gRNAs Watson-Crick base pair between the RNA&DNA with the exception of positions indicated with an "m" which are mismatched using the Watson-Crick transversion (i.e., EGFP Site#2 M18-19 is mismatched by changing the gRNA to its Watson-Crick partner at positions 18 & 19. Although positions near the 5' of the gRNA are generally very well tolerated, matches in these positions are important for nuclease activity when other residues are mismatched. When all four positions are mismatched, nuclease activity is no longer detectable. This further demonstrates that matches at these 5' position can help compensate for mismatches at other more 3' positions. Note these experiments were performed with a non-codon optimized version of Cas9 which can show lower absolute levels of nuclease activity as compared to the codon optimized version.

Figure 2H:
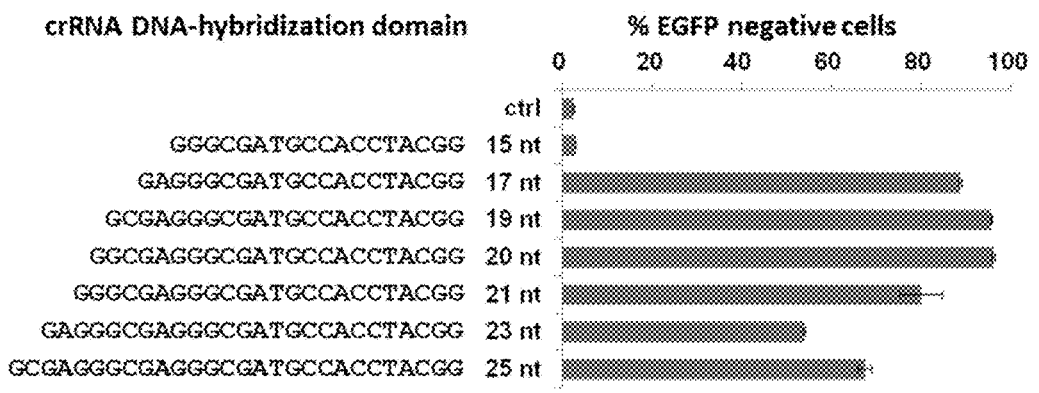

FIG. 2H: Efficiency of Cas9 nuclease activities directed by gRNAs bearing variable length complementarity regions ranging from 15 to 25 nts in a human cell-based U2OS EGFP disruption assay. Expression of a gRNA from the U6 promoter requires the presence of a 5' G and therefore it was only possible to evaluate gRNAs harboring certain lengths of complementarity to the target DNA site (15, 17, 19, 20, 21, 23, and 25 nts).

Figure 3A:
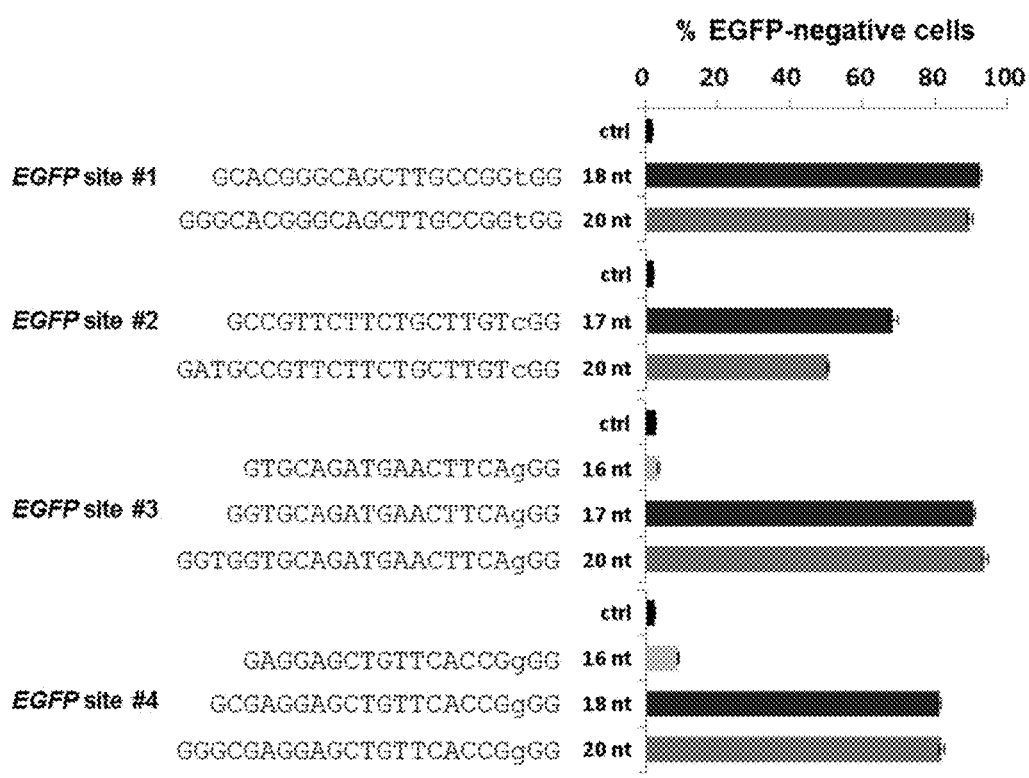

FIG. 3A: Efficiencies of EGFP disruption in human cells mediated by Cas9 and full-length or shortened gRNAs for four target sites in the EGFP reporter gene. Lengths of complementarity regions and corresponding target DNA sites are shown. Ctrl=control gRNA lacking a complementarity region.

Figure 3B:
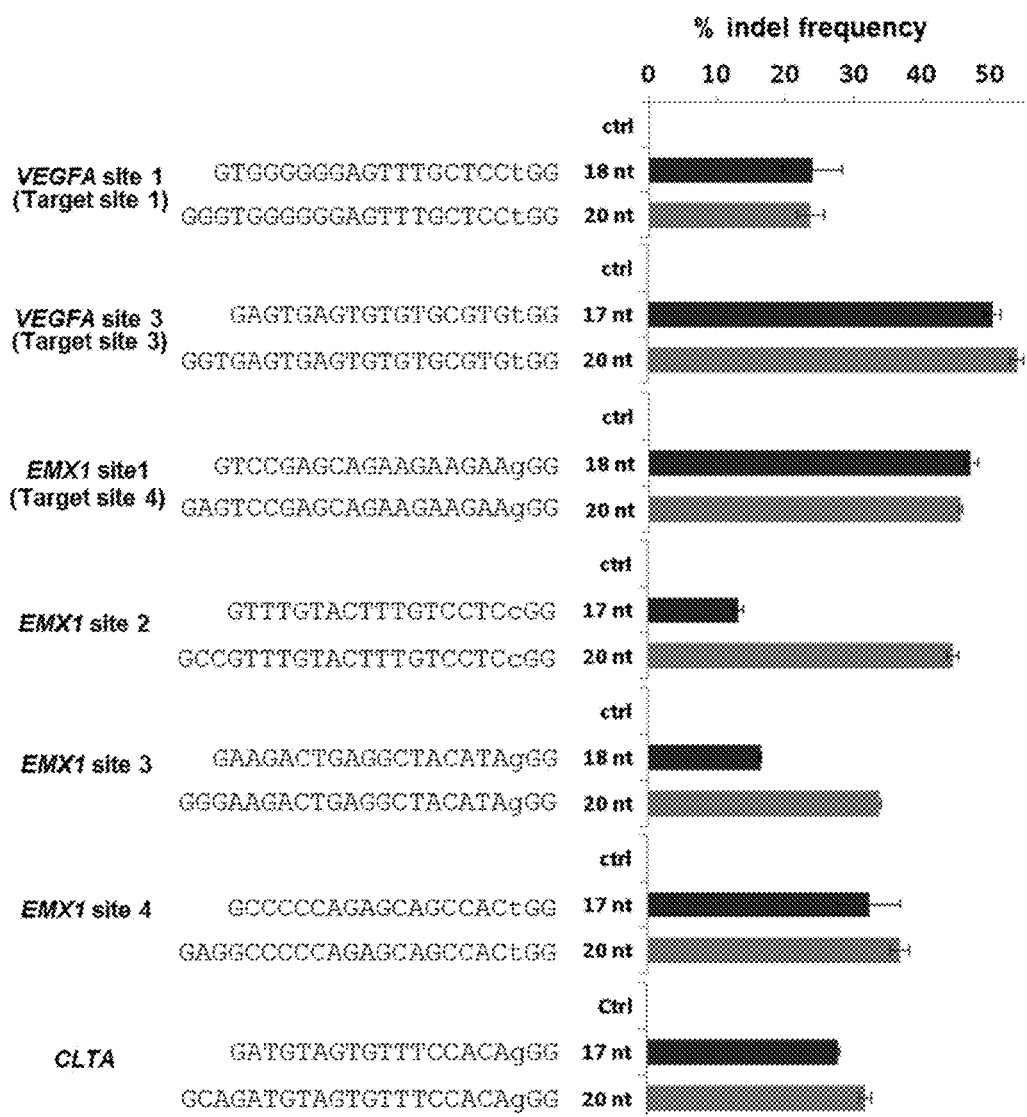

FIG. 3B: Efficiencies of targeted indel mutations introduced at seven different human endogenous gene targets by matched standard RGNs (Cas9 and standard full-length gRNAs) and tru-RGNs (Cas9 and gRNAs bearing truncations in their 5' complementarity regions). Lengths of gRNA complementarity regions and corresponding target DNA sites are shown. Indel frequencies were measured by T7EI assay. Ctrl=control gRNA lacking a complementarity region.

FIG. 3C: DNA sequences of indel mutations induced by RGNs using a tru-gRNA or a matched full-length gRNA targeted to the EMX1 site. The portion of the target DNA site that interacts with the gRNA complementarity region is highlighted in grey with the first base of the PAM sequence shown in lowercase. Deletions are indicated by dashes highlighted in grey and insertions by italicized letters highlighted in grey. The net number of bases deleted or inserted and the number of times each sequence was isolated are shown to the right.

Figure 3D:
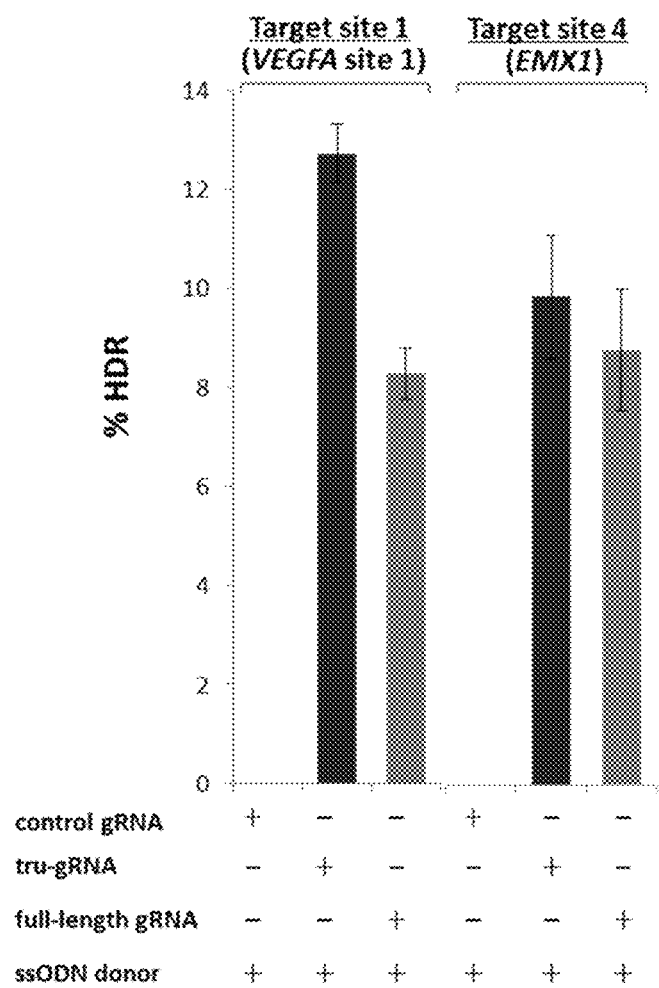

FIG. 3D: Efficiencies of precise HDR/ssODN-mediated alterations introduced at two endogenous human genes by matched standard and tru-RGNs. % HDR was measured using a BamHI restriction digest assay (see the Experimental Procedures for Example 2). Control gRNA=empty U6 promoter vector.

Figures 3E, 3F:
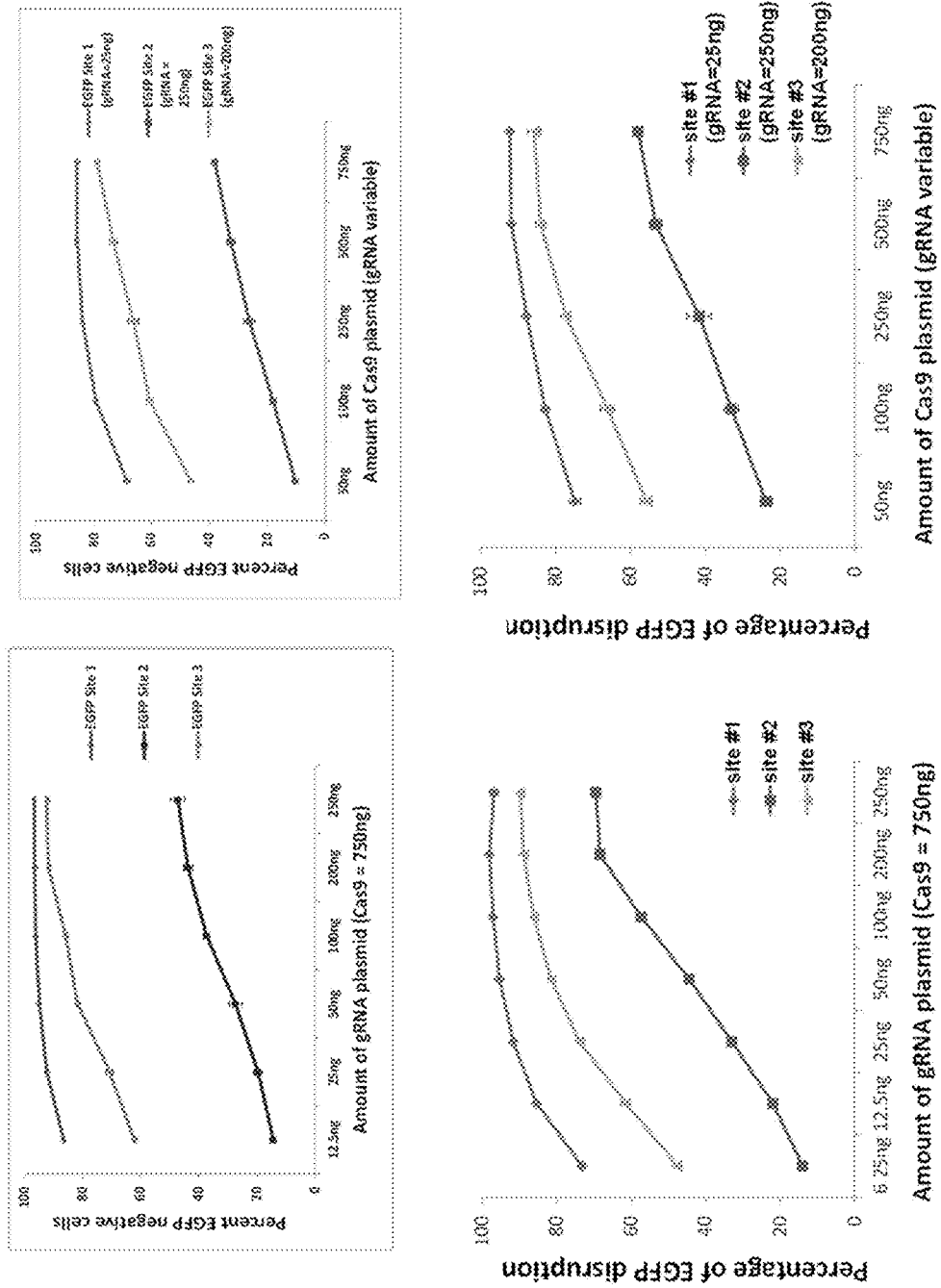

FIG. 3E: U2OS.EGFP cells were transfected with variable amounts of full-length gRNA expression plasmids (top) or tru-gRNA expression plasmids (bottom) together with a fixed amount of Cas9 expression plasmid and then assayed for percentage of cells with decreased EGFP expression. Mean values from duplicate experiments are shown with standard errors of the mean. Note that the data obtained with tru-gRNA matches closely with data from experiments performed with full-length gRNA expression plasmids instead of tru-gRNA plasmids for these three EGFP target sites.

FIG. 3F: U2OS.EGFP cells were transfected with variable amount of Cas9 expression plasmid together with fixed amounts of full-length gRNA expression plasmids (top) or tru-gRNA expression plasmids (bottom) for each target (amounts determined for each tru-gRNA from the experiments of FIG. 3E). Mean values from duplicate experiments are shown with standard errors of the mean. Note that the data obtained with tru-gRNA matches closely with data from experiments performed with full-length gRNA expression plasmids instead of tru-gRNA plasmids for these three EGFP target sites. The results of these titrations determined the concentrations of plasmids used in the EGFP disruption assays performed in Examples 1 and 2.

FIG. 4A: Schematic illustrating locations of VEGFA sites 1 and 4 targeted by gRNAs for paired double nicks. Target sites for the full-length gRNAs are underlined with the first base in the PAM sequence shown in lowercase. Location of the BamHI restriction site inserted by HDR with a ssODN donor is shown.

FIG. 4B: A tru-gRNA can be used with a paired nickase strategy to efficiently induce indel mutations. Substitution of a full-length gRNA for VEGFA site 1 with a tru-gRNA does not reduce the efficiency of indel mutations observed with a paired full-length gRNA for VEGFA site 4 and Cas9-D10A nickases. Control gRNA used is one lacking a complementarity region.

FIG. 4C: A tru-gRNA can be used with a paired nickase strategy to efficiently induce precise HDR/ssODN-mediated sequence alterations. Substitution of a full-length gRNA for VEGFA site 1 with a tru-gRNA does not reduce the efficiency of indel mutations observed with a paired full-length gRNA for VEGFA site 4 and Cas9-D10A nickases with an ssODN donor template. Control gRNA used is one lacking a complementarity region.

Figure 5A:
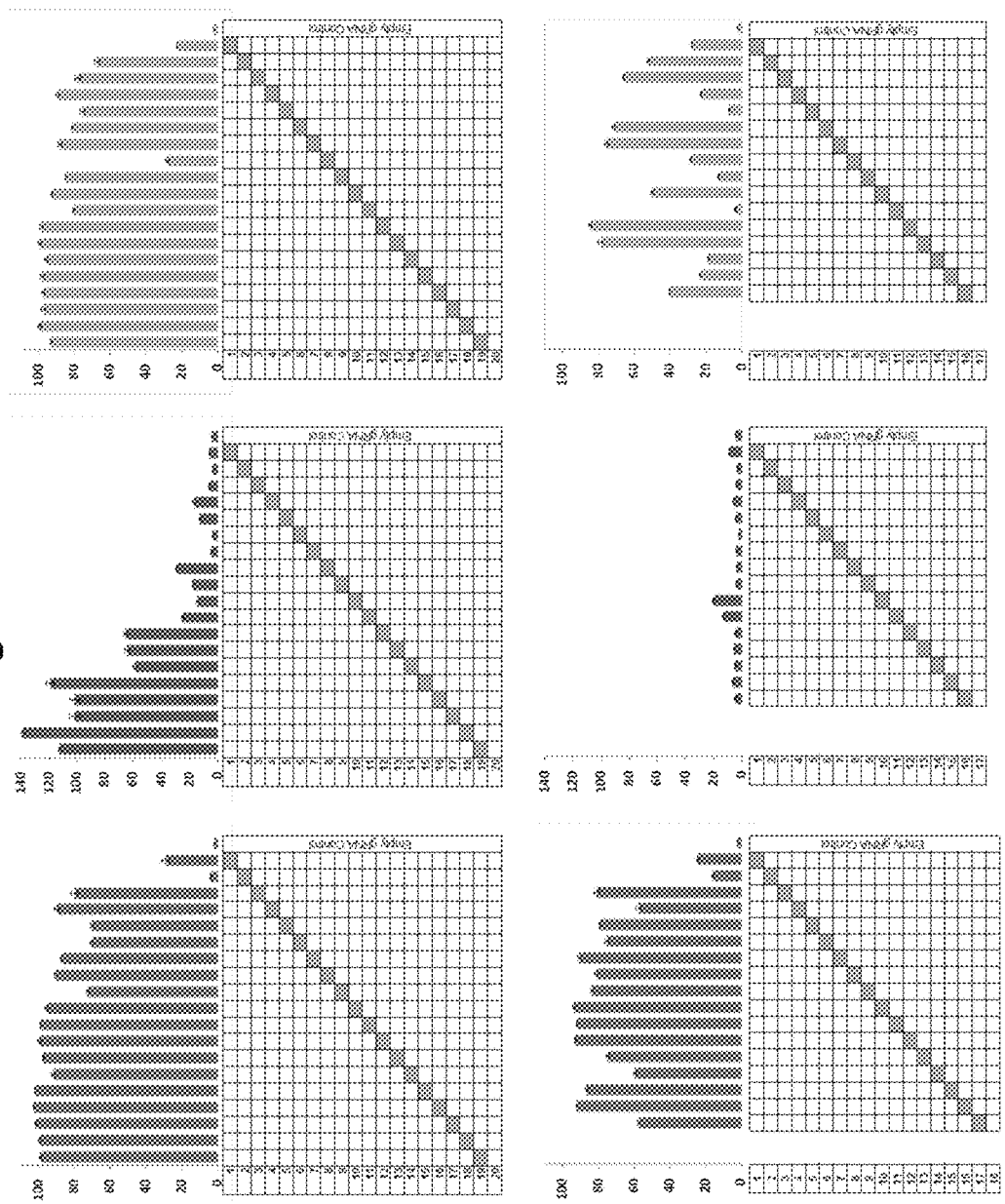

FIG. 5A: Activities of RGNs targeted to three sites in EGFP using full-length (top) or tru-gRNAs (bottom) with single mismatches at each position (except at the 5'-most base which must remain a G for efficient expression from the U6 promoter). Grey boxes in the grid below represent positions of the Watson-Crick transversion mismatches. Empty gRNA control used is a gRNA lacking a complementarity region. RGN activities were measured using the EGFP disruption assay and values shown represent the percentage of EGFP-negative observed relative to an RGN using a perfectly matched gRNA. Experiments were performed in duplicate and means with error bars representing standard errors of the mean are shown.

Figure 5B:
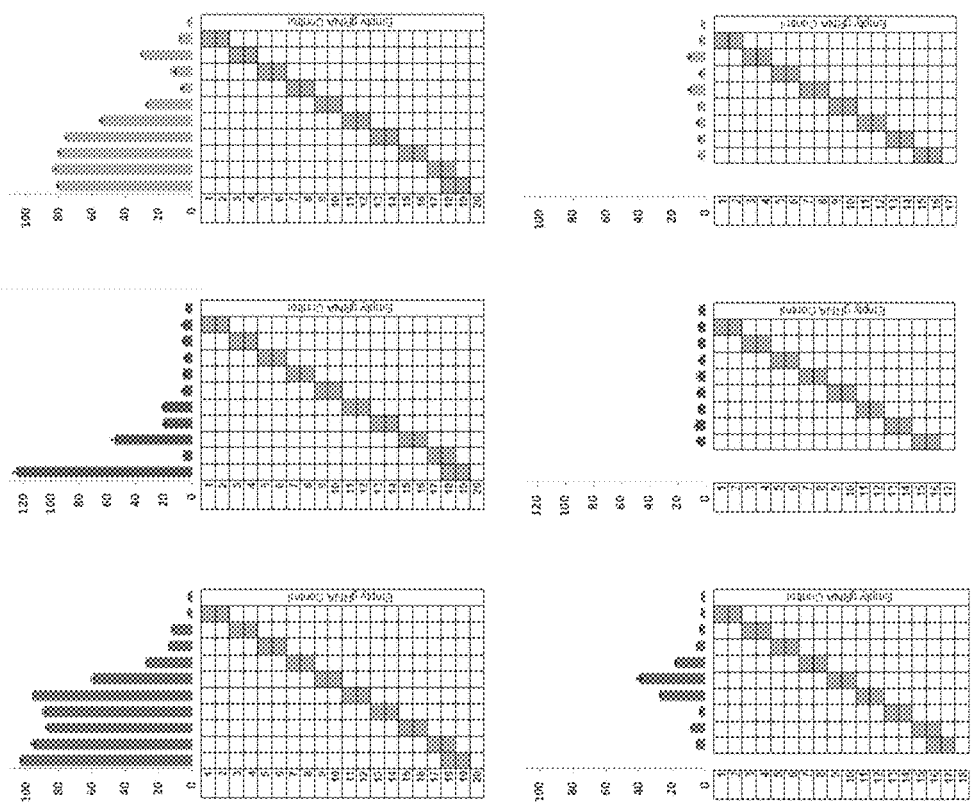

FIG. 5B: Activities of RGNs targeted to three sites in EGFP using full-length (top) or tru-gRNAs (bottom) with adjacent double mismatches at each position (except at the 5'-most base which must remain a G for efficient expression from the U6 promoter). Data presented as in 5A.

Figure 6A:
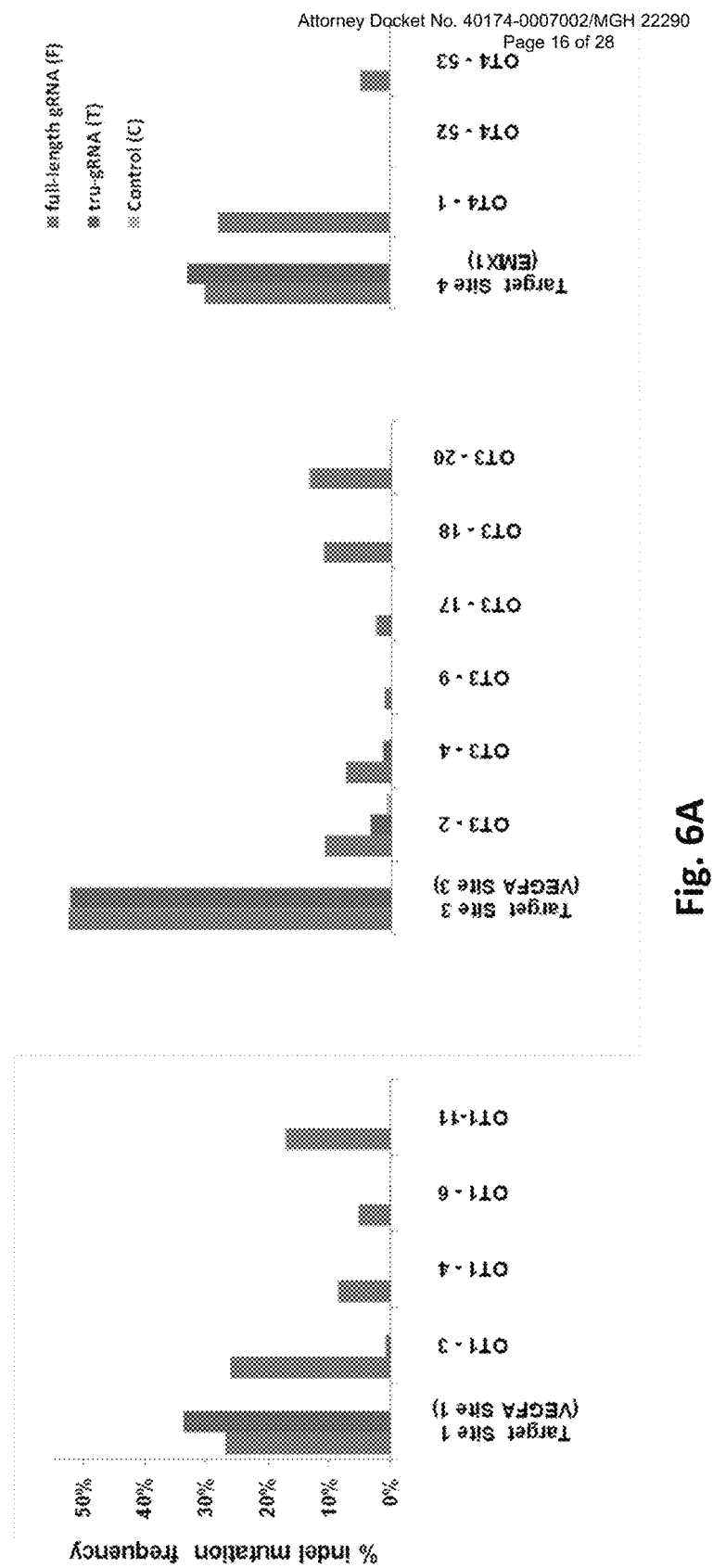

FIG. 6A: Absolute frequencies of on- and off-target indel mutations induced by RGNs targeted to three different endogenous human gene sites as measured by deep sequencing. Indel frequencies are shown for the three target sites from cells in which targeted RGNs with a full-length gRNA, a tru-gRNA, or a control gRNA lacking a complementarity region were expressed. Absolute counts of indel mutations used to make these graphs can be found in Table 3B.

FIG. 6B: Fold-improvements in off-target site specificities of three tru-RGNs. Values shown represent the ratio of on/off-target activities of tru-RGNs to on/off-target activities of standard RGNs for the off-target sites shown, calculated using the data from (A) and Table 3B. For the sites marked with an asterisk (*), no indels were observed with the tru-RGN and therefore the values shown represent conservative statistical estimates for the fold-improvements in specificities for these off-target sites (see Results and Experimental Procedures).

FIG. 6C, top: Comparison of the on-target and an off-target site identified by T7EI assay for the tru-RGN targeted to VEGFA site 1 (more were identified by deep sequencing). Note that the full-length gRNA is mismatched to the two nucleotides at the 5' end of the target site and that these are the two nucleotides not present in the tru-gRNA target site. Mismatches in the off-target site relative to the on-target are highlighted in bold underlined text. Mismatches between the gRNAs and the off-target site are shown with X's.

FIG. 6C, bottom: Indel mutation frequencies induced in the off-target site by RGNs bearing full-length or truncated gRNAs. Indel mutation frequencies were determined by T7EI assay. Note that the off-target site in this figure is one that we had examined previously for indel mutations induced by the standard RGN targeted to VEGFA site 1 and designated as site OT1-30 in that earlier study (Example 1 and Fu et al., Nat Biotechnol. 31(9):822-6 (2013)). It is likely that we did not identify off-target mutations at this site in our previous experiments because the frequency of indel mutations appears to be at the reliable detection limit of the T7EI assay (2-5%).

FIGS. 7A-D: DNA sequences of indel mutations induced by RGNs using tru-gRNAs or matched full-length gRNAs targeted to VEGFA sites 1 and 3. Sequences depicted as in FIG. 3C.

Figure 7E:
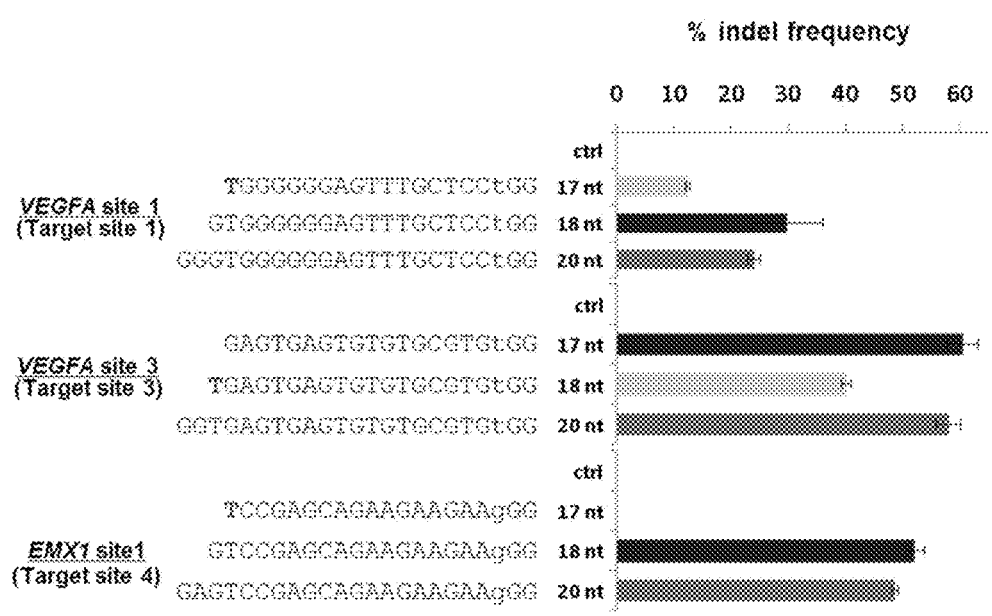

FIG. 7E. Indel mutation frequencies induced by tru-gRNAs bearing a mismatched 5' G nucleotide. Indel mutation frequencies in human U2OS.EGFP cells induced by Cas9 directed by tru-gRNAs bearing 17, 18 or 20 nt complementarity regions for VEGFA sites 1 and 3 and EMX1 site 1 are shown. Three of these gRNAs contain a mismatched 5' G (indicated by positions marked in bold text). Bars indicate results from experiments using full-length gRNA (20 nt), tru-gRNA (17 or 18 nt), and tru-gRNA with a mismatched 5' G nucleotide (17 or 18 nt with boldface T at 5' end). (Note that no activity was detectable for the mismatched tru-gRNA to EMX1 site 1.)

FIGS. 8A-C: Sequences of off-target indel mutations induced by RGNs in human U2OS.EGFP cells. Wild-type genomic off-target sites recognized by RGNs (including the PAM sequence) are highlighted in grey and numbered as in Table 1 and Table B. Note that the complementary strand is shown for some sites. Deleted bases are shown as dashes on a grey background. Inserted bases are italicized and highlighted in grey.

FIGS. 9A-C: Sequences of off-target indel mutations induced by RGNs in human HEK293 cells. Wild-type genomic off-target sites recognized by RGNs (including the PAM sequence) are highlighted in grey and numbered as in Table 1 and Table B. Note that the complementary strand is shown for some sites. Deleted bases are shown as dashes on a grey background. Inserted bases are italicized and highlighted in grey. *Yielded a large number of single bp indels.

DETAILED DESCRIPTION

CRISPR RNA-guided nucleases (RGNs) have rapidly emerged as a facile and efficient platform for genome editing. Although Marraffini and colleagues (Jiang et al., Nat Biotechnol 31, 233-239 (2013)) recently performed a systematic investigation of Cas9 RGN specificity in bacteria, the specificities of RGNs in human cells have not been extensively defined. Understanding the scope of RGN-mediated off-target effects in human and other eukaryotic cells will be critically essential if these nucleases are to be used widely for research and therapeutic applications. The present inventors have used a human cell-based reporter assay to characterize off-target cleavage of Cas9-based RGNs. Single and double mismatches were tolerated to varying degrees depending on their position along the guide RNA (gRNA)-DNA interface. Off-target alterations induced by four out of six RGNs targeted to endogenous loci in human cells were readily detected by examination of partially mismatched sites. The off-target sites identified harbor up to five mismatches and many are mutagenized with frequencies comparable to (or higher than) those observed at the intended on-target site. Thus RGNs are highly active even with imperfectly matched RNA-DNA interfaces in human cells, a finding that might confound their use in research and therapeutic applications.

The results described herein reveal that predicting the specificity profile of any given RGN is neither simple nor straightforward. The EGFP reporter assay experiments show that single and double mismatches can have variable effects on RGN activity in human cells that do not strictly depend upon their position(s) within the target site. For example, consistent with previously published reports, alterations in the 3' half of the sgRNA/DNA interface generally have greater effects than those in the 5' half (Jiang et al., Nat Biotechnol 31, 233-239 (2013); Cong et al., Science 339, 819-823 (2013); Jinek et al., Science 337, 816-821 (2012)); however, single and double mutations in the 3' end sometimes also appear to be well tolerated whereas double mutations in the 5' end can greatly diminish activities. In addition, the magnitude of these effects for mismatches at any given position(s) appears to be site-dependent. Comprehensive profiling of a large series of RGNs with testing of all possible nucleotide substitutions (beyond the Watson-Crick transversions used in our EGFP reporter experiments) may help provide additional insights into the range of potential off-targets. In this regard, the recently described bacterial cell-based method of Marraffini and colleagues (Jiang et al., Nat Biotechnol 31, 233-239 (2013)) or the in vitro, combinatorial library-based cleavage site-selection methodologies previously applied to ZFNs by Liu and colleagues (Pattanayak et al., Nat Methods 8, 765-770 (2011)) might be useful for generating larger sets of RGN specificity profiles.

Despite these challenges in comprehensively predicting RGN specificities, it was possible to identify bonafide off-targets of RGNs by examining a subset of genomic sites that differed from the on-target site by one to five mismatches. Notably, under conditions of these experiments, the frequencies of RGN-induced mutations at many of these off-target sites were similar to (or higher than) those observed at the intended on-target site, enabling the detection of mutations at these sites using the T7EI assay (which, as performed in our laboratory, has a reliable detection limit of ~2 to 5% mutation frequency). Because these mutation rates were very high, it was possible to avoid using deep sequencing methods previously required to detect much lower frequency ZFN- and TALEN-induced off-target alterations (Pattanayak et al., Nat Methods 8, 765-770 (2011); Perez et al., Nat Biotechnol 26, 808-816 (2008); Gabriel et al., Nat Biotechnol 29, 816-823 (2011); Hockemeyer et al., Nat Biotechnol 29, 731-734 (2011)). Analysis of RGN off-target mutagenesis in human cells also confirmed the difficulties of predicting RGN specificities—not all single and double mismatched off-target sites show evidence of mutation whereas some sites with as many as five mismatches can also show alterations. Furthermore, the bonafide off-target sites identified do not exhibit any obvious bias toward transition or transversion differences relative to the intended target sequence (Table E; grey highlighted rows).

Although off-target sites were seen for a number of RGNs, identification of these sites was neither comprehensive nor genome-wide in scale. For the six RGNs studied, only a very small subset of the much larger total number of potential off-target sequences in the human genome (sites that differ by three to six nucleotides from the intended target site; compare Tables E and C) was examined. Although examining such large numbers of loci for off-target mutations by T7EI assay is neither a practical nor a cost-effective strategy, the use of high-throughput sequencing in future studies might enable the interrogation of larger numbers of candidate off-target sites and provide a more sensitive method for detecting bonafide off-target mutations. For example, such an approach might enable the unveiling of additional off-target sites for the two RGNs for which we failed to uncover any off-target mutations. In addition, an improved understanding both of RGN specificities and of any epigenomic factors (e.g., DNA methylation and chromatin status) that may influence RGN activities in cells might also reduce the number of potential sites that need to be examined and thereby make genome-wide assessments of RGN off-targets more practical and affordable.

As described herein, a number of strategies can be used to minimize the frequencies of genomic off-target mutations. For example, the specific choice of RGN target site can be optimized; given that off-target sites that differ at up to five positions from the intended target site can be efficiently mutated by RGNs, choosing target sites with minimal numbers of off-target sites as judged by mismatch counting seems unlikely to be effective; thousands of potential off-target sites that differ by four or five positions within the 20 bp RNA:DNA complementarity region will typically exist for any given RGN targeted to a sequence in the human genome (see, for example, Table C). It is also possible that the nucleotide content of the gRNA complementarity region might influence the range of potential off-target effects. For example, high GC-content has been shown to stabilize RNA:DNA hybrids (Sugimoto et al., Biochemistry 34, 11211-11216 (1995)) and therefore might also be expected to make gRNA/genomic DNA hybridization more stable and more tolerant to mismatches. Additional experiments with larger numbers of gRNAs will be needed to assess if and how these two parameters (numbers of mismatched sites in the genome and stability of the RNA:DNA hybrid) influence the genome-wide specificities of RGNs. However, it is important to note that even if such predictive parameters can be defined, the effect of implementing such guidelines would be to further restrict the targeting range of RGNs.

One potential general strategy for reducing RGN-induced off-target effects might be to reduce the concentrations of gRNA and Cas9 nuclease expressed in the cell. This idea was tested using the RGNs for VEGFA target sites 2 and 3 in U2OS.EGFP cells; transfecting less sgRNA- and Cas9-expressing plasmid decreased the mutation rate at the on-target site but did not appreciably change the relative rates of off-target mutations (Tables 2A and 2B). Consistent with this, high-level off-target mutagenesis rates were also observed in two other human cell types (HEK293 and K562 cells) even though the absolute rates of on-target mutagenesis are lower than in U2OS.EGFP cells. Thus, reducing expression levels of gRNA and Cas9 in cells is not likely to provide a solution for reducing off-target effects. Furthermore, these results also suggest that the high rates of off-target mutagenesis observed in human cells are not caused by overexpression of gRNA and/or Cas9.

TABLE 2A

Indel mutation frequencies at on- and off-target genomic sites induced by different amounts of Cas9- and single gRNA-expressing plasmids for the RGN targeted to VEGFA Target Site 2

| Site | Sequence | SEQ ID NO: | 250 ng gRNA/ 750 ng Cas9 Mean indel frequency (%) ± SEM | 12.5 ng gRNA/ 50 ng Cas9 Mean indel frequency (%) ± SEM |
|---|---|---|---|---|
| T2 (On-target) | GACCCCCTCCACCCCGCCTCCGG | 12 | 50.2 ± 4.9 | 25.4 ± 4.8 |
| OT2-1 | GACCCCCCCCACCCCGCCCCGG | 13 | 14.4 ± 3.4 | 4.2 ± 0.2 |
| OT2-2 | GGGCCCCTCCACCCCGCCTCTGG | 14 | 20.0 ± 6.2 | 9.8 ± 1.1 |
| OT2-6 | CTACCCCTCCACCCCGCCTCCGG | 15 | 8.2 ± 1.4 | 6.0 ± 0.5 |
| OT2-9 | GCCCCCACCCACCCCGCCTCTGG | 16 | 50.7 ± 5.6 | 16.4 ± 2.1 |

TABLE 2A-continued

Indel mutation frequencies at on- and off-target genomic sites induced by different amounts of Cas9- and single gRNA-expressing plasmids for the RGN targeted to VEGFA Target Site 2

| Site | Sequence | SEQ ID NO: | 250 ng gRNA/ 750 ng Cas9 Mean indel frequency (%) ± SEM | 12.5 ng gRNA/ 50 ng Cas9 Mean indel frequency (%) ± SEM |
|---|---|---|---|---|
| OT2-15 | TACCCCCACACCCCGCCTCTGG | 17 | 9.7 ± 4.5 | 2.1 ± 0.0 |
| OT2-17 | ACACCCCCCACCCCGCCTCAGG | 18 | 14.0 ± 2.8 | 7.1 ± 0.0 |
| OT2-19 | ATTCCCCCCACCCCGCCTCAGG | 19 | 17.0 ± 3.3 | 9.2 ± 0.4 |
| OT2-20 | CCCCACCCCACCCCGCCTCAGG | 20 | 6.1 ± 1.3 | N.D. |
| OT2-23 | CGCCCTCCCACCCCGCCTCCGG | 21 | 44.4 ± 6.7 | 35.1 ± 1.8 |
| OT2-24 | CTCCCCACCCACCCCGCCTCAGG | 22 | 62.8 ± 5.0 | 44.1 ± 4.5 |
| OT2-29 | TGCCCCTCCCACCCCGCCTCTGG | 23 | 13.8 ± 5.2 | 5.0 ± 0.2 |
| OT2-34 | AGGCCCCCACACCCCGCCTCAGG | 24 | 2.8 ± 1.5 | N.D. |

Amounts of gRNA- and Cas9-expressing plasmids transfected into U2OS.EGFP cells for these assays are shown at the top of each column. (Note that data for 250 ng gRNA/750 ng Cas9 are the same as those presented in Table 1.) Mean indel frequencies were determined using the T7EI assay from replicate samples as described in Methods. OT = Off-target sites, numbered as in Table 1 and Table B. Mismatches from the on-target site (within the 20 bp region to which the gRNA hybridizes) are highlighted as bold, underlined text.
ND. = none detected

TABLE 2B

Indel mutation frequencies at on- and off-target genomic sites induced by different amounts of Cas9- and single gRNA-expressing plasmids for the RGN targeted to VEGFA Target Site 3

| Site | Sequence | SEQ ID NO: | 250 ng gRNA/ 750 ng Cas9 Mean indel frequency (%) ± SEM | 12.5 ng gRNA/ 250 ng Cas9 Mean indel frequency (%) ± SEM |
|---|---|---|---|---|
| T3 (On-target) | GGTGAGTGAGTGTGTGCGTGTGG | 25 | 49.4 ± 3.8 | 33.0 ± 3.7 |
| OT3-1 | GGTGAGTGAGTGTGTGTGTGAGG | 26 | 7.4 ± 3.4 | N.D. |
| OT3-2 | AGTGAGTGAGTGTGTGTGTGGGG | 27 | 24.3 ± 9.2 | 9.8 ± 4.2 |
| OT3-4 | GCTGAGTGAGTGTATGCGTGTGG | 28 | 20.9 ± 11.8 | 4.2 ± 1.2 |
| OT3-9 | GGTGAGTGAGTGCGTGCGGGTGG | 29 | 3.2 ± 0.3 | N.D. |
| OT3-17 | GTTGAGTGAATGTGTGCGTGAGG | 30 | 2.9 ± 0.2 | N.D. |
| OT3-18 | TGTGGGTGAGTGTGTGCGTGAGG | 31 | 13.4 ± 4.2 | 4.9 ± 0.0 |
| OT3-20 | AGAGAGTGAGTGTGTGCATGAGG | 32 | 16.7 ± 3.5 | 7.9 ± 2.4 |

Amounts of gRNA- and Cas9-expressing plasmids transfected into U2OS.EGFP cells for these assays are shown at the top of each column. (Note that data for 250 ng gRNA/750 ng Cas9 are the same as those presented in Table 1.) Mean indel frequencies were determined using the T7EI assay from replicate samples as described in Methods.
OT = Off-target sites, numbered as in Table 1 and Table B.
N.D. = none detected.

The finding that significant off-target mutagenesis can be induced by RGNs in three different human cell types has important implications for broader use of this genome-editing platform. For research applications, the potentially confounding effects of high frequency off-target mutations will need to be considered, particularly for experiments involving either cultured cells or organisms with slow generation times for which the outcrossing of undesired alterations would be challenging. One way to control for such effects might be to utilize multiple RGNs targeted to different DNA sequences to induce the same genomic alteration because off-target effects are not random but instead related to the targeted site. However, for therapeutic applications, these findings clearly indicate that the specificities of RGNs will need to be carefully defined and/or improved if these nucleases are to be used safely in the longer term for treatment of human diseases.

Methods for Improving Specificity

As shown herein, CRISPR-Cas RNA-guided nucleases based on the S. pyogenes Cas9 protein can have significant off-target mutagenic effects that are comparable to or higher than the intended on-target activity (Example 1). Such off-target effects can be problematic for research and in particular for potential therapeutic applications. Therefore, methods for improving the specificity of CRISPR-Cas RNA guided nucleases (RGNs) are needed.

As described in Example 1, Cas9 RGNs can induce high-frequency indel mutations at off-target sites in human cells (see also Cradick et al., 2013; Fu et al., 2013; Hsu et al., 2013; Pattanayak et al., 2013). These undesired alterations can occur at genomic sequences that differ by as many as five mismatches from the intended on-target site (see Example 1). In addition, although mismatches at the 5' end of the gRNA complementarity region are generally better tolerated than those at the 3' end, these associations are not absolute and show site-to-site-dependence (see Example 1 and Fu et al., 2013; Hsu et al., 2013; Pattanayak et al., 2013). As a result, computational methods that rely on the number and/or positions of mismatches currently have limited predictive value for identifying bonafide off-target sites. Therefore, methods for reducing the frequencies of off-target mutations remain an important priority if RNA-guided nucleases are to be used for research and therapeutic applications.

Truncated Guide RNAs (Tru-gRNAs) Achieve Greater Specificity

Guide RNAs generally speaking come in two different systems: System 1, which uses separate crRNA and tracrRNAs that function together to guide cleavage by Cas9, and System 2, which uses a chimeric crRNA-tracrRNA hybrid that combines the two separate guide RNAs in a single system (referred to as a single guide RNA or sgRNA, see also Jinek et al., Science 2012; 337:816-821). The tracrRNA can be variably truncated and a range of lengths has been shown to function in both the separate system (system 1) and the chimeric gRNA system (system 2). For example, in some embodiments, tracrRNA may be truncated from its 3' end by at least 1, 2, 3, 4, 5, 6, 7, 8, 9, 10, 15, 20, 25, 30, 35 or 40 nts. In some embodiments, the tracrRNA molecule may be truncated from its 5' end by at least 1, 2, 3, 4, 5, 6, 7, 8, 9, 10, 15, 20, 25, 30, 35 or 40 nts. Alternatively, the tracrRNA molecule may be truncated from both the 5' and 3' end, e.g., by at least 1, 2, 3, 4, 5, 6, 7, 8, 9, 10, 15 or 20 nts on the 5' end and at least 1, 2, 3, 4, 5, 6, 7, 8, 9, 10, 15, 20, 25, 30, 35 or 40 nts on the 3' end. See, e.g., Jinek et al., Science 2012; 337:816-821; Mali et al., Science. 2013 Feb. 15; 339(6121):823-6; Cong et al., Science. 2013 Feb. 15; 339 (6121):819-23; and Hwang and Fu et al., Nat Biotechnol. 2013 Mar. 31(3):227-9; Jinek et al., Elife 2, e00471 (2013)). For System 2, generally the longer length chimeric gRNAs have shown greater on-target activity but the relative specificities of the various length gRNAs currently remain undefined and therefore it may be desirable in certain instances to use shorter gRNAs. In some embodiments, the gRNAs are complementary to a region that is within about 100-800 bp upstream of the transcription start site, e.g., is within about 500 bp upstream of the transcription start site, includes the transcription start site, or within about 100-800 bp, e.g., within about 500 bp, downstream of the transcription start site. In some embodiments, vectors (e.g., plasmids) encoding more than one gRNA are used, e.g., plasmids encoding, 2, 3, 4, 5, or more gRNAs directed to different sites in the same region of the target gene.

The present application describes a strategy for improving RGN specificity based on the seemingly counterintuitive idea of shortening, rather than lengthening, the gRNA complementarity region. These shorter gRNAs can induce various types of Cas9-mediated on-target genome editing events with efficiencies comparable to (or, in some cases, higher than) full-length gRNAs at multiple sites in a single integrated EGFP reporter gene and in endogenous human genes. In addition, RGNs using these shortened gRNAs exhibit increased sensitivity to small numbers of mismatches at the gRNA-target DNA interface. Most importantly, use of shortened gRNAs substantially reduces the rates of genomic off-target effects in human cells, yielding improvements of specificity as high as 5000-fold or more at these sites. Thus, this shortened gRNA strategy provides a highly effective approach for reducing off-target effects without compromising on-target activity and without the need for expression of a second, potentially mutagenic gRNA. This approach can be implemented on its own or in conjunction with other strategies such as the paired nickase method to reduce the off-target effects of RGNs in human cells.

Figure 1:
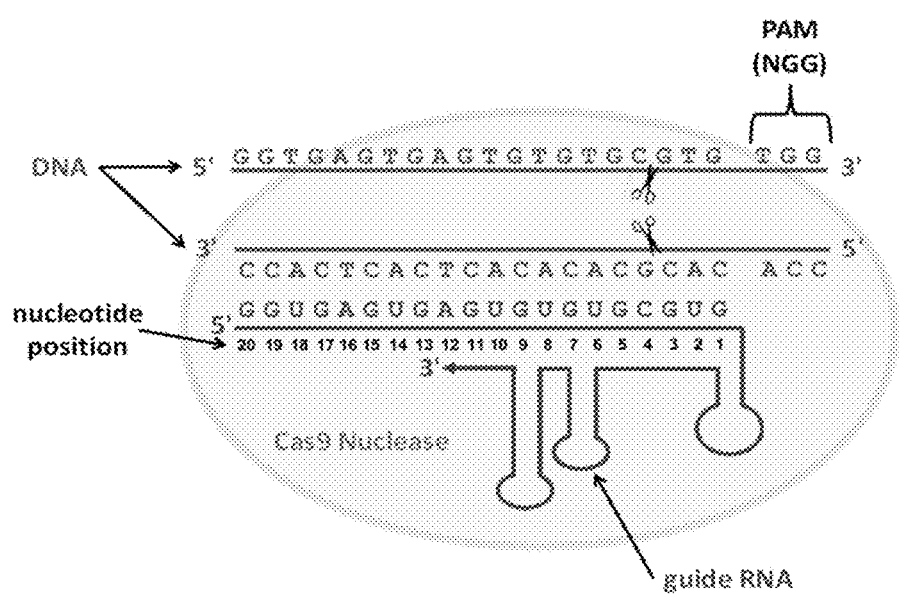
FIG. 1: Schematic illustrating a gRNA/Cas9 nuclease complex bound to its target DNA site. Scissors indicate approximate cleavage points of the Cas9 nuclease on the genomic DNA target site. Note the numbering of nucleotides on the guide RNA proceeds in an inverse fashion from 5' to 3'.

Thus, one method to enhance specificity of CRISPR/Cas nucleases shortens the length of the guide RNA (gRNA) species used to direct nuclease specificity. Cas9 nuclease can be guided to specific 17-18 nt genomic targets bearing an additional proximal protospacer adjacent motif (PAM), e.g., of sequence NGG, using a guide RNA, e.g., a single gRNA or a crRNA (paired with a tracrRNA), bearing 17 or 18 nts at its 5' end that are complementary to the complementary strand of the genomic DNA target site (FIG. 1).

Although one might expect that increasing the length of the gRNA complementarity region would improve specificity, the present inventors (Hwang et al., PLoS One. 2013 Jul. 9; 8(7):e68708) and others (Ran et al., Cell. 2013 Sep. 12; 154(6):1380-9) have previously observed that lengthening the target site complementarity region at the 5' end of the gRNA actually makes it function less efficiently at the on-target site.

By contrast, experiments in Example 1 showed that gRNAs bearing multiple mismatches within a standard length 5' complementarity targeting region could still induce robust Cas9-mediated cleavage of their target sites. Thus, it was possible that truncated gRNAs lacking these 5'-end nucleotides might show activities comparable to their full-length counterparts (FIG. 2A). It was further speculated that these 5' nucleotides might normally compensate for mismatches at other positions along the gRNA-target DNA interface and therefore predicted that shorter gRNAs might be more sensitive to mismatches and thus induce lower levels of off-target mutations (FIG. 2A).

Decreasing the length of the DNA sequence targeted might also decrease the stability of the gRNA:DNA hybrid, making it less tolerant of mismatches and thereby making the targeting more specific. That is, truncating the gRNA sequence to recognize a shorter DNA target might actually result in a RNA-guided nuclease that is less tolerant to even single nucleotide mismatches and is therefore more specific and has fewer unintended off-target effects.

This strategy for shortening the gRNA complementarity region could potentially be used with RNA guided proteins other than S. pyogenes Cas9 including other Cas proteins from bacteria or archaea as well as Cas9 variants that nick a single strand of DNA or have no-nuclease activity such as a dCas9 bearing catalytic inactivating mutations in one or both nuclease domains. This strategy can be applied to systems that utilize a single gRNA as well as those that use dual gRNAs (e.g., the crRNA and tracrRNA found in naturally occurring systems).

Thus, described herein is a single guide RNA comprising a crRNA fused to a normally trans-encoded tracrRNA, e.g., a single Cas9 guide RNA as described in Mali et al., Science 2013 Feb. 15; 339(6121):823-6, but with a sequence at the 5' end that is complementary to fewer than 20 nucleotides (nts), e.g., 19, 18, or 17 nts, preferably 17 or 18 nts, of the complementary strand to a target sequence immediately 5' of a protospacer adjacent motif (PAM), e.g., NGG, NAG, or NNGG. In some embodiments, the shortened Cas9 guide RNA consists of the sequence:

(SEQ ID NO: 2404)
($X_{17-18}$ or $X_{17-19}$) GUUUUAGAGCUA ($X_N$);

(SEQ ID NO: 2407)
($X_{17-18}$ or $X_{17-19}$) GUUUUAGAGCUAUGCUGUUUUG ($X_N$);

(SEQ ID NO: 2408)
($X_{17-18}$ or $X_{17-19}$) GUUUUAGAGCUAUGCU ($X_N$);

(SEQ ID NO: 1)
($X_{17-18}$ or $X_{17-19}$) GUUUUAGAGCUAGAAAUAGCAAGUUAAAAU

AAGGCUAGUCCG ($X_N$);

(SEQ ID NO: 2)
($X_{17-18}$ or $X_{17-19}$) GUUUUAGAGCUAUGCUGAAAAGCAUAGCAAG

UUAAAAUAAGGCUAGUCCGUUAUC ($X_N$);

(SEQ ID NO: 3)
($X_{17-18}$ or $X_{17-19}$) GUUUUAGAGCUAUGCUGUUUUGGAAACAAAA

CAGCAUAGCAAGUUAAAAUAAGGCUAGUCCGUUAUC ($X_N$);

(SEQ ID NO: 4)
($X_{17-18}$) GUUUUAGAGCUAGAAAUAGCAAGUUAAAAUAAGGCUAGUC

CGUUAUCAACUUGAAAAAGUGGCACCGAGUCGGUGC ($X_N$), (SEQ ID NO: 5)
($X_{17-18}$ or $X_{17-19}$) GUUUAAGAGCUAGAAAUAGCAAGUUUAAAUA

AGGCUAGUCCGUUAUCAACUUGAAAAAGUGGCACCGAGUCGGUGC;

(SEQ ID NO: 6)
($X_{17-18}$ or $X_{17-19}$) GUUUUAGAGCUAUGCUGGAAACAGCAUAGCA

AGUUUAAAUAAGGCUAGUCCGUUAUCAACUUGAAAAAGUGGCACCGAGU

CGGUGC;
or (SEQ ID NO: 7)
($X_{17-18}$ or $X_{17-19}$) GUUUAAGAGCUAUGCUGGAAACAGCAUAGCA

AGUUUAAAUAAGGCUAGUCCGUUAUCAACUUGAAAAAGUGGCACCGAGUC

GGUGC;

wherein $X_{17-18}$ or $X_{17-19}$ is the nucleotide sequence complementary to 17-18 or 17-19 consecutive nucleotides of the target sequence, respectively. Also described herein are DNAs encoding the shortened Cas9 guide RNAs that have been described previously in the literature (Jinek et al., Science. 337(6096):816-21 (2012) and Jinek et al., Elife. 2:e00471 (2013)).

The guide RNAs can include $X_N$ which can be any sequence, wherein N (in the RNA) can be 0-200, e.g., 0-100, 0-50, or 0-20, that does not interfere with the binding of the ribonucleic acid to Cas9.

In some embodiments, the guide RNA includes one or more Adenine (A) or Uracil (U) nucleotides on the 3' end. In some embodiments the RNA includes one or more U, e.g., 1 to 8 or more Us (e.g., U, UU, UUU, UUUU, UUUUU, UUUUUU, UUUUUUU, UUUUUUUU) at the 3' end of the molecule, as a result of the optional presence of one or more Ts used as a termination signal to terminate RNA PolIII transcription.

Modified RNA oligonucleotides such as locked nucleic acids (LNAs) have been demonstrated to increase the specificity of RNA-DNA hybridization by locking the modified oligonucleotides in a more favorable (stable) conformation. For example, 2'-O-methyl RNA is a modified base where there is an additional covalent linkage between the 2' oxygen and 4' carbon which when incorporated into oligonucleotides can improve overall thermal stability and selectivity (formula I).

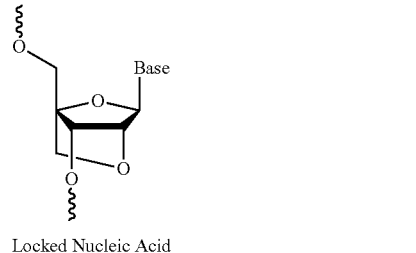

Locked Nucleic Acid

Thus in some embodiments, the tru-gRNAs disclosed herein may comprise one or more modified RNA oligonucleotides. For example, the truncated guide RNAs molecules described herein can have one, some or all of the 17-18 or 17-19 nts 5' region of the guideRNA complementary to the target sequence are modified, e.g., locked (2'-O-4'-C methylene bridge), 5'-methylcytidine, 2'-O-methyl-pseudouridine, or in which the ribose phosphate backbone has been replaced by a polyamide chain (peptide nucleic acid), e.g., a synthetic ribonucleic acid.

In other embodiments, one, some or all of the nucleotides of the tru-gRNA sequence may be modified, e.g., locked (2'-O-4'-C methylene bridge), 5'-methylcytidine, 2'-O-methyl-pseudouridine, or in which the ribose phosphate backbone has been replaced by a polyamide chain (peptide nucleic acid), e.g., a synthetic ribonucleic acid.

In a cellular context, complexes of Cas9 with these synthetic gRNAs could be used to improve the genome-wide specificity of the CRISPR/Cas9 nuclease system.

Exemplary modified or synthetic tru-gRNAs may comprise, or consist of, the following sequences:

(SEQ ID NO: 2404)
($X_{17-18}$ or $X_{17-19}$) GUUUUAGAGCUA ($X_N$);

(SEQ ID NO: 2407)
($X_{17-18}$ or $X_{17-19}$) GUUUUAGAGCUAUGCUGUUUUG ($X_N$);

(SEQ ID NO: 2408)
($X_{17-18}$ or $X_{17-19}$) GUUUUAGAGCUAUGCU ($X_N$);

(SEQ ID NO: 1)
($X_{17-18}$ or $X_{17-19}$) GUUUUAGAGCUAGAAAUAGCAAGUUAAAAU

AAGGCUAGUCCG ($X_N$);

(SEQ ID NO: 2)
($X_{17-18}$ or $X_{17-19}$) GUUUUAGAGCUAUGCUGAAAAGCAUAGCAAG

UUAAAAUAAGGCUAGUCCGUUAUC ($X_N$);

(X$_{17-18}$ or X$_{17-19}$) GUUUUAGAGCUAUGCUGUUUUGGAAACAAAA
CAGCAUAGCAAGUUAAAAUAAGGCUAGUCCGUUAUC (X$_N$); (SEQ ID NO: 3)

(X$_{17-18}$) GUUUUAGAGCUAGAAAUAGCAAGUUAAAAUAAGGCUAGUC
CGUUAUCAACUUGAAAAAGUGGCACCGAGUCGGUGC (X$_N$), (SEQ ID NO: 4)

(X$_{17-18}$ or X$_{17-19}$) GUUUAAGAGCUAGAAAUAGCAAGUUUAAAUA
AGGCUAGUCCGUUAUCAACUUGAAAAAGUGGCACCGAGUCGGUGC; (SEQ ID NO: 5)

(X$_{17-18}$ or X$_{17-19}$) GUUUUAGAGCUAUGCUGGAAACAGCAUAGCA
AGUUUAAAUAAGGCUAGUCCGUUAUCAACUUGAAAAAGUGGCACCGAGU
CGGUGC; (SEQ ID NO: 6)

or (X$_{17-18}$ or X$_{17-19}$) GUUUAAGAGCUAUGCUGGAAACAGCAUAGCA
AGUUUAAAUAAGGCUAGUCCGUUAUCAACUUGAAAAAGUGGCACCGAGUC
GGUGC; (SEQ ID NO: 7)

wherein X$_{17-18}$ or X$_{17-19}$ is a sequence complementary to 17-18 or 17-19 nts of a target sequence, respectively, preferably a target sequence immediately 5' of a protospacer adjacent motif (PAM), e.g., NGG, NAG, or NNGG, and further wherein one or more of the nucleotides are locked, e.g., one or more of the nucleotides within the sequence X$_{17-18}$ or X$_{17-19}$, one or more of the nucleotides within the sequence X$_N$, or one or more of the nucleotides within any sequence of the tru-gRNA. X$_N$ is any sequence, wherein N (in the RNA) can be 0-200, e.g., 0-100, 0-50, or 0-20, that does not interfere with the binding of the ribonucleic acid to Cas9. In some embodiments the RNA includes one or more U, e.g., 1 to 8 or more Us (e.g., U, UU, UUU, UUUU, UUUUU, UUUUUU, UUUUUUU, UUUUUUUU) at the 3' end of the molecule, as a result of the optional presence of one or more Ts used as a termination signal to terminate RNA PolIII transcription.

Although some of the examples described herein utilize a single gRNA, the methods can also be used with dual gRNAs (e.g., the crRNA and tracrRNA found in naturally occurring systems). In this case, a single tracrRNA would be used in conjunction with multiple different crRNAs expressed using the present system, e.g., the following: (X$_{17-18}$ or X$_{17-19}$)GUUUUAGAGCUA (SEQ ID NO:2404); (X$_{17-18}$ or X$_{17-19}$) GUUUUAGAGCUAUGCUGUUUUG (SEQ ID NO:2407); or (X$_{17-18}$ or X$_{17-19}$)GUUUUAGAGC-UAUGCU (SEQ ID NO:2408); and a tracrRNA sequence. In this case, the crRNA is used as the guide RNA in the methods and molecules described herein, and the tracrRNA can be expressed from the same or a different DNA molecule. In some embodiments, the methods include contacting the cell with a tracrRNA comprising or consisting of the sequence GGAACCAUUCAAAACAGCAUAGCAAGU-UAAAAUAAGGCUAGUCCGUUA UCAACUUGAA-AAAGUGGCACCGAGUCGGUGC (SEQ ID NO:8) or an active portion thereof (an active portion is one that retains the ability to form complexes with Cas9 or dCas9). In some embodiments, the tracrRNA molecule may be truncated from its 3' end by at least 1, 2, 3, 4, 5, 6, 7, 8, 9, 10, 15, 20, 25, 30, 35 or 40 nts. In another embodiment, the tracrRNA molecule may be truncated from its 5' end by at least 1, 2, 3, 4, 5, 6, 7, 8, 9, 10, 15, 20, 25, 30, 35 or 40 nts. Alternatively, the tracrRNA molecule may be truncated from both the 5' and 3' end, e.g., by at least 1, 2, 3, 4, 5, 6, 7, 8, 9, 10, 15 or 20 nts on the 5' end and at least 1, 2, 3, 4, 5, 6, 7, 8, 9, 10, 15, 20, 25, 30, 35 or 40 nts on the 3' end. Exemplary tracrRNA sequences in addition to SEQ ID NO:8 include the following:
UAGCAAGUUAAAAUAAGGCUAGUCCGUUAUCA-ACUUGAAAAAGUGGCA CCGAGUCGGUGC (SEQ ID NO:2405) or an active portion thereof;
AGCAUAGCAAGUUAAAAUAAGGCUAGUCCGUU-AUCAACUUGAAAAAGU GGCACCGAGUCGGUGC (SEQ ID NO:2407) or an active portion thereof;
CAAAACAGCAUAGCAAGUUAAAAUAAGGCUAGU-CCGUUAUCAACUUGA AAAGUGGCACCGAGUCG-GUGC (SEQ ID NO:2409) or an active portion thereof;
UAGCAAGUUAAAAUAAGGCUAGUCCGUUAUCA-ACUUGAAAAAGUG (SEQ ID NO:2410) or an active portion thereof;
UAGCAAGUUAAAAUAAGGCUAGUCCGUUAUCA (SEQ ID NO:2411) or an active portion thereof; or UAG-CAAGUUAAAAUAAGGCUAGUCCG (SEQ ID NO: 2412) or an active portion thereof.

In some embodiments wherein (X$_{17-18}$ or X$_{17-19}$) GUUUUAGAGCUAUGCUGUUUUG (SEQ ID NO:2407) is used as a crRNA, the following tracrRNA is used: GGAACCAUUCAAAACAGCAUAGCAAGUUAAAA-UAAGGCUAGUCCGUUA UCAACUUGAAAAAGUG-GCACCGAGUCGGUGC (SEQ ID NO:8) or an active portion thereof. In some embodiments wherein (X$_{17-18}$ or X$_{17-19}$)GUUUUAGAGCUA (SEQ ID NO:2404) is used as a crRNA, the following tracrRNA is used: UAGCAAGUUAAAAUAAGGCUAGUCCGUUAUCA-ACUUGAAAAAGUGGCA CCGAGUCGGUGC (SEQ ID NO:2405) or an active portion thereof. In some embodiments wherein (X$_{17-18}$ or X$_{17-19}$) GUUUUAGAGC-UAUGCU (SEQ ID NO:2408) is used as a crRNA, the following tracrRNA is used:
AGCAUAGCAAGUUAAAAUAAGGCUAGUCCGUUA-UCAACUUGAAAAAGU GGCACCGAGUCGGUGC (SEQ ID NO:2406) or an active portion thereof.

In addition, in a system that uses separate crRNA and tracrRNA, one or both can be synthetic and include one or more modified (e.g., locked) nucleotides or deoxyribonucleotides.

In some embodiments, the single guide RNAs and/or crRNAs and/or tracrRNAs can include one or more Adenine (A) or Uracil (U) nucleotides on the 3' end.

Existing Cas9-based RGNs use gRNA-DNA heteroduplex formation to guide targeting to genomic sites of interest. However, RNA-DNA heteroduplexes can form a more promiscuous range of structures than their DNA-DNA counterparts. In effect, DNA-DNA duplexes are more sensitive to mismatches, suggesting that a DNA-guided nuclease may not bind as readily to off-target sequences, making them comparatively more specific than RNA-guided nucleases. Thus, the truncated guide RNAs described herein can be hybrids, i.e., wherein one or more deoxyribonucleotides, e.g., a short DNA oligonucleotide, replaces all or part of the gRNA, e.g., all or part of the complementarity region of a gRNA. This DNA-based molecule could replace either all or part of the gRNA in a single gRNA system or alternatively might replace all of part of the crRNA in a dual crRNA/tracrRNA system. Such a system that incorporates DNA into the complementarity region should more reliably target the intended genomic DNA sequences due to the general intolerance of DNA-DNA duplexes to mismatching compared to RNA-DNA duplexes. Methods for making such duplexes are known in the art, See, e.g., Barker et al., BMC Genomics. 2005 Apr. 22; 6:57; and Sugimoto et al., Biochemistry. 2000 Sep. 19; 39(37):11270-81.

Exemplary modified or synthetic tru-gRNAs may comprise, or consist of, the following sequences:

(SEQ ID NO: 1)
$(X_{17-18}$ or $X_{17-19})$ GUUUUAGAGCUAGAAAUAGCAAGUUAAAAUA;

AGGCUAGUCCG$(X_N)$ (SEQ ID NO: 2)
$(X_{17-18}$ or $X_{17-19})$ GUUUUAGAGCUAUGCUGAAAAGCAUAGCAAG

UUAAAAUAAGGCUAGUCCGUUAUC$(X_N)$;

(SEQ ID NO: 3)
$(X_{17-18}$ or $X_{17-19})$ GUUUUAGAGCUAUGCUGUUUUGGAAACAAAA

CAGCAUAGCAAGUUAAAAUAAGGCUAGUCCGUUAUC$(X_N)$;

(SEQ ID NO: 4)
$(X_{17-18}$ or $X_{17-19})$ GUUUUAGAGCUAGAAAUAGCAAGUUAAAAUA

AGGCUAGUCCGUUAUCAACUUGAAAAAGUGGCACCGAGUCGGUGC$(X_N)$, (SEQ ID NO: 5)
$(X_{17-18}$ or $X_{17-19})$ GUUUAAGAGCUAGAAAUAGCAAGUUUAAAUA

AGGCUAGUCCGUUAUCAACUUGAAAAAGUGGCACCGAGUCGGUGC;

(SEQ ID NO: 6)
$(X_{17-18}$ or $X_{17-19})$ GUUUUAGAGCUAUGCUGGAAACAGCAUAGCA

AGUUUAAAUAAGGCUAGUCCGUUAUCAACUUGAAAAAGUGGCACCGAGU

CGGUGC;
or (SEQ ID NO: 7)
$(X_{17-18}$ or $X_{17-19})$ GUUUAAGAGCUAUGCUGGAAACAGCAUAGCA

AGUUUAAAUAAGGCUAGUCCGUUAUCAACUUGAAAAAGUGGCACCGAGU

CGGUGC;

wherein $X_{17-18}$ or $X_{17-19}$ is a sequence complementary to 17-18 or 17-19 nts of a target sequence, respectively, preferably a target sequence immediately 5' of a protospacer adjacent motif (PAM), e.g., NGG, NAG, or NNGG, and further wherein one or more of the nucleotides are deoxyribonucleotides, e.g., one or more of the nucleotides within the sequence $X_{17-18}$ or $X_{17-19}$, one or more of the nucleotides within the sequence $X_N$, or one or more of the nucleotides within any sequence of the tru-gRNA. $X_N$ is any sequence, wherein N (in the RNA) can be 0-200, e.g., 0-100, 0-50, or 0-20, that does not interfere with the binding of the ribonucleic acid to Cas9. In some embodiments the RNA includes one or more U, e.g., 1 to 8 or more Us (e.g., U, UU, UUU, UUUU, UUUUU, UUUUUU, UUUUUUU, UUUUUUUU) at the 3' end of the molecule, as a result of the optional presence of one or more Ts used as a termination signal to terminate RNA PolIII transcription.

In addition, in a system that uses separate crRNA and tracrRNA, one or both can be synthetic and include one or more deoxyribonucleotides.

In some embodiments, the single guide RNAs or crRNAs or tracrRNAs includes one or more Adenine (A) or Uracil (U) nucleotides on the 3' end.

In some embodiments, the gRNA is targeted to a site that is at least three or more mismatches different from any sequence in the rest of the genome in order to minimize off-target effects.

The methods described can include expressing in a cell, or contacting the cell with, a shortened Cas9 gRNA (tru-gRNA) as described herein (optionally a modified or DNA/RNA hybrid tru-gRNA), plus a nuclease that can be guided by the shortened Cas9 gRNAs, e.g., a Cas9 nuclease, e.g., as described in Mali et al., a Cas9 nickase as described in Jinek et al., 2012; or a dCas9-heterofunctional domain fusion (dCas9-HFD).

Cas9

A number of bacteria express Cas9 protein variants. The Cas9 from *Streptococcus pyogenes* is presently the most commonly used; some of the other Cas9 proteins have high levels of sequence identity with the *S. pyogenes* Cas9 and use the same guide RNAs. Others are more diverse, use different gRNAs, and recognize different PAM sequences as well (the 2-5 nucleotide sequence specified by the protein which is adjacent to the sequence specified by the RNA). Chylinski et al. classified Cas9 proteins from a large group of bacteria (RNA Biology 10:5, 1-12; 2013), and a large number of Cas9 proteins are listed in supplementary FIG. 1 and supplementary table 1 thereof, which are incorporated by reference herein. Additional Cas9 proteins are described in Esvelt et al., Nat Methods. 2013 Nov. 10(11):1116-21 and Fonfara et al., "Phylogeny of Cas9 determines functional exchangeability of dual-RNA and Cas9 among orthologous type II CRISPR-Cas systems." Nucleic Acids Res. 2013 Nov. 22. [Epub ahead of print] doi: 10.1093/nar/gkt1074.

Cas9 molecules of a variety of species can be used in the methods and compositions described herein. While the *S. pyogenes* and *S. thermophilus* Cas9 molecules are the subject of much of the disclosure herein, Cas9 molecules of, derived from, or based on the Cas9 proteins of other species listed herein can be used as well. In other words, while the much of the description herein uses *S. pyogenes* and *S. thermophilus* Cas9 molecules, Cas9 molecules from the other species can replace them. Such species include those set forth in the following table, which was created based on supplementary FIG. 1 of Chylinski et al., 2013.

| Alternative Cas9 proteins | |
|---|---|
| GenBank Acc No. | Bacterium |
| 303229466 | *Veillonella atypica* ACS-134-V-Col7a |
| 34762592 | *Fusobacterium nucleatum* subsp. *vincentii* |
| 374307738 | *Filifactor alocis* ATCC 35896 |
| 320528778 | *Solobacterium moorei* F0204 |
| 291520705 | *Coprococcus catus* GD-7 |
| 42525843 | *Treponema denticola* ATCC 35405 |
| 304438954 | *Peptoniphilus duerdenii* ATCC BAA-1640 |
| 224543312 | *Catenibacterium mitsuokai* DSM 15897 |
| 24379809 | *Streptococcus mutans* UA159 |
| 15675041 | *Streptococcus pyogenes* SF370 |
| 16801805 | *Listeria innocua* Clip11262 |
| 116628213 | *Streptococcus thermophilus* LMD-9 |
| 323463801 | *Staphylococcus pseudintermedius* ED99 |
| 352684361 | *Acidaminococcus intestini* RyC-MR95 |
| 302336020 | *Olsenella uli* DSM 7084 |
| 366983953 | *Oenococcus kitaharae* DSM 17330 |
| 310286728 | *Bifidobacterium bifidum* S17 |
| 258509199 | *Lactobacillus rhamnosus* GG |
| 300361537 | *Lactobacillus gasseri* JV-V03 |
| 169823755 | *Finegoldia magna* ATCC 29328 |
| 47458868 | *Mycoplasma mobile* 163K |
| 284931710 | *Mycoplasma gallisepticum* str. F |
| 363542550 | *Mycoplasma ovipneumoniae* SC01 |
| 384393286 | *Mycoplasma canis* PG 14 |
| 71894592 | *Mycoplasma synoviae* 53 |
| 238924075 | *Eubacterium rectale* ATCC 33656 |
| 116627542 | *Streptococcus thermophilus* LMD-9 |
| 315149830 | *Enterococcus faecalis* TX0012 |

| Alternative Cas9 proteins | |
|---|---|
| GenBank Acc No. | Bacterium |
| 315659848 | *Staphylococcus lugdunensis* M23590 |
| 160915782 | *Eubacterium dolichum* DSM 3991 |
| 336393381 | *Lactobacillus coryniformis* subsp. *torquens* |
| 310780384 | *Ilyobacter polytropus* DSM 2926 |
| 325677756 | *Ruminococcus albus* 8 |
| 187736489 | *Akkermansia muciniphila* ATCC BAA-835 |
| 117929158 | *Acidothermus cellulolyticus* 11B |
| 189440764 | *Bifidobacterium longum* DJO10A |
| 283456135 | *Bifidobacterium dentium* Bd1 |
| 38232678 | *Corynebacterium diphtheriae* NCTC 13129 |
| 187250660 | *Elusimicrobium minutum* Pei191 |
| 319957206 | *Nitratifractor salsuginis* DSM 16511 |
| 325972003 | *Sphaerochaeta globus* str. Buddy |
| 261414553 | *Fibrobacter succinogenes* subsp. *succinogenes* |
| 60683389 | *Bacteroides fragilis* NCTC 9343 |
| 256819408 | *Capnocytophaga ochracea* DSM 7271 |
| 90425961 | *Rhodopseudomonas palustris* BisB18 |
| 373501184 | *Prevotella micans* F0438 |
| 294674019 | *Prevotella ruminicola* 23 |
| 365959402 | *Flavobacterium columnare* ATCC 49512 |
| 312879015 | *Aminomonas paucivorans* DSM 12260 |
| 83591793 | *Rhodospirillum rubrum* ATCC 11170 |
| 294086111 | *Candidatus Puniceispirillum marinum* IMCC1322 |
| 121608211 | *Verminephrobacter eiseniae* EF01-2 |
| 344171927 | *Ralstonia syzygii* R24 |
| 159042956 | *Dinoroseobacter shibae* DFL 12 |
| 288957741 | *Azospirillum* sp-B510 |
| 92109262 | *Nitrobacter hamburgensis* X14 |
| 148255343 | *Bradyrhizobium* sp-BTAi1 |
| 34557790 | *Wolinella succinogenes* DSM 1740 |
| 218563121 | *Campylobacter jejuni* subsp. *jejuni* |
| 291276265 | *Helicobacter mustelae* 12198 |
| 229113166 | *Bacillus cereus* Rock1-15 |
| 222109285 | *Acidovorax ebreus* TPSY |
| 189485225 | uncultured Termite group 1 |
| 182624245 | *Clostridium perfringens* D str. |
| 220930482 | *Clostridium cellulolyticum* H10 |
| 154250555 | *Parvibaculum lavamentivorans* DS-1 |
| 257413184 | *Roseburia intestinalis* L1-82 |
| 218767588 | *Neisseria meningitidis* Z2491 |
| 15602992 | *Pasteurella multocida* subsp. *multocida* |
| 319941583 | *Sutterella wadsworthensis* 3 1 |
| 254447899 | gamma proteobacterium HTCC5015 |
| 54296138 | *Legionella pneumophila* str. Paris |
| 331001027 | *Parasutterella excrementihominis* YIT 11859 |
| 34557932 | *Wolinella succinogenes* DSM 1740 |
| 118497352 | *Francisella novicida* U112 |

The constructs and methods described herein can include the use of any of those Cas9 proteins, and their corresponding guide RNAs or other guide RNAs that are compatible. The Cas9 from *Streptococcus thermophilus* LMD-9 CRISPRI system has also been shown to function in human cells in Cong et al (Science 339, 819 (2013)). Cas9 orthologs from *N. meningitides* are described in Hou et al., Proc Natl Acad Sci USA. 2013 Sep. 24; 110(39):15644-9 and Esvelt et al., Nat Methods. 2013 Nov. 10(11):1116-21. Additionally, Jinek et al. showed in vitro that Cas9 orthologs from *S. thermophilus* and *L. innocua*, (but not from *N. meningitidis* or *C. jejuni*, which likely use a different guide RNA), can be guided by a dual *S. pyogenes* gRNA to cleave target plasmid DNA, albeit with slightly decreased efficiency.

In some embodiments, the present system utilizes the Cas9 protein from *S. pyogenes*, either as encoded in bacteria or codon-optimized for expression in mammalian cells, containing mutations at D10, E762, H983, or D986 and H840 or N863, e.g., D10A/D10ON and H840A/H840N/H840Y, to render the nuclease portion of the protein catalytically inactive; substitutions at these positions could be alanine (as they are in Nishimasu al., Cell 156, 935-949 (2014)) or they could be other residues, e.g., glutamine, asparagine, tyrosine, serine, or aspartate, e.g., E762Q, H983N, H983Y, D986N, N863D, N863S, or N863H (FIG. 1C). The sequence of the catalytically inactive *S. pyogenes* Cas9 that can be used in the methods and compositions described herein is as follows; the exemplary mutations of D10A and H840A are in bold and underlined.

(SEQ ID NO: 33)

```
         10         20         30         40
MDKKYSIGLA IGTNSVGWAV ITDEYKVPSK KFKVLGNTDR 50         60         70         80
HSIKKNLIGA LLFDSGETAE ATRLKRTARR RYTRRKNRIC 90        100        110        120
YLQEIFSNEM AKVDDSFFHR LEESFLVEED KKHERHPIFG 130        140        150        160
NIVDEVAYHE KYPTIYHLRK KLVDSTDKAD LRLIYLALAH 170        180        190        200
MIKFRGHFLI EGDLNPDNSD VDKLFIQLVQ TYNQLFEENP 210        220        230        240
INASGVDAKA ILSARLSKSR RLENLIAQLP GEKKNGLFGN 250        260        270        280
LIALSLGLTP NFKSNFDLAE DAKLQLSKDT YDDDLDNLLA 290        300        310        320
QIGDQYADLF LAAKNLSDAI LLSDILRVNT EITKAPLSAS 330        340        350        360
MIKRYDEHHQ DLTLLKALVR QQLPEKYKEI FFDQSKNGYA 370        380        390        400
GYIDGGASQE EFYKFIKPIL EKMDGTEELL VKLNREDLLR 410        420        430        440
KQRTFDNGSI PHQIHLGELH AILRRQEDFY PFLKDNREKI 450        460        470        480
EKILTFRIPY YVGPLARGNS RFAWMTRKSE ETITPWNFEE 490        500        510        520
VVDKGASAQS FIERMTNFDK NLPNEKVLPK HSLLYEYFTV 530        540        550        560
YNELTKVKYV TEGMRKPAFL SGEQKKAIVD LLFKTNRKVT 570        580        590        600
VKQLKEDYFK KIECFDSVEI SGVEDRFNAS LGTYHDLLKI 610        620        630        640
IKDKDFLDNE ENEDILEDIV LTLTLFEDRE MIEERLKTYA 650        660        670        680
HLFDDKVMKQ LKRRRYTGWG RLSRKLINGI RDKQSGKTIL 690        700        710        720
DFLKSDGFAN RNFMQLIHDD SLTFKEDIQK AQVSGQGDSL 730        740        750        760
HEHIANLAGS PAIKKGILQT VKVVDELVKV MGRHKPENIV 770        780        790        800
IEMARENQTT QKGQKNSRER MKRIEEGIKE LGSQILKEHP 810        820        830        840
VENTQLQNEK LYLYYLQNGR DMYVDQELDI NRLSDYDVDA

850        860        870        880
IVPQSFLKDD SIDNKVLTRS DKNRGKSDNV PSEEVVKKMK 890        900        910        920
NYWRQLLNAK LITQRKFDNL TKAERGGLSE LDKAGFIKRQ
```

```
                    -continued
       930        940        950        960
  LVETRQITKH VAQILDSRMN TKYDENDKLI REVKVITLKS 970        980        990       1000
  KLVSDFRKDF QFYKVREINN YHHAHDAYLN AVVGTALIKK 1010       1020       1030       1040
  YPKLESEFVY GDYKVYDVRK MIAKSEQEIG KATAKYFFYS 1050       1060       1070       1080
  NIMNFFKTEI TLANGEIRKR PLIETNGETG EIVWDKGRDF 1090       1100       1110       1120
  ATVRKVLSMP QVNIVKKTEV QTGGFSKESI LPKRNSDKLI 1130       1140       1150       1160
  ARKKDWDPKK YGGFDSPTVA YSVLVVAKVE KGKSKKLKSV 1170       1180       1190       1200
  KELLGITIME RSSFEKNPID FLEAKGYKEV KKDLIIKLPK 1210       1220       1230       1240
  YSLFELENGR KRMLASAGEL QKGNELALPS KYVNFLYLAS 1250       1260       1270       1280
  HYEKLKGSPE DNEQKQLFVE QHKHYLDEII EQISEFSKRV 1290       1300       1310       1320
  ILADANLDKV LSAYNKHRDK PIREQAENII HLFTLTNLGA 1330       1340       1350       1360
  PAAFKYFDTT IDRKRYTSTK EVLDATLIHQ SITGLYETRI

DLSQLGGD
```

In some embodiments, the Cas9 nuclease used herein is at least about 50% identical to the sequence of S. pyogenes Cas9, i.e., at least 50% identical to SEQ ID NO:33. In some embodiments, the nucleotide sequences are about 50%, 55%, 60%, 65%, 70%, 75%, 80%, 85%, 90%, 95%, 99% or 100% identical to SEQ ID NO:33. In some embodiments, any differences from SEQ ID NO:33 are in non-conserved regions, as identified by sequence alignment of sequences set forth in Chylinski et al., RNA Biology 10:5, 1-12; 2013 (e.g., in supplementary FIG. 1 and supplementary table 1 thereof); Esvelt et al., Nat Methods. 2013 Nov; 10(11):1116-21 and Fonfara et al., Nucl. Acids Res. (2014) 42 (4): 2577-2590. [Epub ahead of print 2013 Nov. 22]doi:10.1093/nar/gkt1074.

To determine the percent identity of two sequences, the sequences are aligned for optimal comparison purposes (gaps are introduced in one or both of a first and a second amino acid or nucleic acid sequence as required for optimal alignment, and non-homologous sequences can be disregarded for comparison purposes). The length of a reference sequence aligned for comparison purposes is at least 50% (in some embodiments, about 50%, 55%, 60%, 65%, 70%, 75%, 85%, 90%, 95%, or 100% of the length of the reference sequence is aligned). The nucleotides or residues at corresponding positions are then compared. When a position in the first sequence is occupied by the same nucleotide or residue as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For purposes of the present application, the percent identity between two amino acid sequences is determined using the Needleman and Wunsch ((1970) J. Mol. Biol. 48:444-453) algorithm which has been incorporated into the GAP program in the GCG software package, using a Blossum 62 scoring matrix with a gap penalty of 12, a gap extend penalty of 4, and a frameshift gap penalty of 5.

Cas9-HFD

Cas9-HFD are described in a U.S. Provisional Patent Application Ser. No. 61/799,647, Filed on Mar. 15, 2013, U.S. Ser. No. 61/838,148, filed on Jun. 21, 2013, and PCT International Application No. PCT/US14/27335, all of which are incorporated herein by reference in its entirety.

The Cas9-HFD are created by fusing a heterologous functional domain (e.g., a transcriptional activation domain, e.g., from VP64 or NF-κB p65), to the N-terminus or C-terminus of a catalytically inactive Cas9 protein (dCas9). In the present case, as noted above, the dCas9 can be from any species but is preferably from S. pyogenes, In some embodiments, the Cas9 contains mutations in the D10 and H840 residues, e.g., D10N/D10A and H840A/H840N/H840Y, to render the nuclease portion of the protein catalytically inactive, e.g., as shown in SEQ ID NO:33 above.

The transcriptional activation domains can be fused on the N or C terminus of the Cas9. In addition, although the present description exemplifies transcriptional activation domains, other heterologous functional domains (e.g., transcriptional repressors (e.g., KRAB, ERD, SID, and others, e.g., amino acids 473-530 of the ets2 repressor factor (ERF) repressor domain (ERD), amino acids 1-97 of the KRAB domain of KOX1, or amino acids 1-36 of the Mad mSIN3 interaction domain (SID); see Beerli et al., PNAS USA 95:14628-14633 (1998)) or silencers such as Heterochromatin Protein 1 (HP1, also known as swi6), e.g., HP1α or HP1β; proteins or peptides that could recruit long non-coding RNAs (lncRNAs) fused to a fixed RNA binding sequence such as those bound by the MS2 coat protein, endoribonuclease Csy4, or the lambda N protein; enzymes that modify the methylation state of DNA (e.g., DNA methyltransferase (DNMT) or TET proteins); or enzymes that modify histone subunits (e.g., histone acetyltransferases (HAT), histone deacetylases (HDAC), histone methyltransferases (e.g., for methylation of lysine or arginine residues) or histone demethylases (e.g., for demethylation of lysine or arginine residues)) as are known in the art can also be used. A number of sequences for such domains are known in the art, e.g., a domain that catalyzes hydroxylation of methylated cytosines in DNA. Exemplary proteins include the Ten-Eleven-Translocation (TET)1-3 family, enzymes that converts 5-methylcytosine (5-mC) to 5-hydroxymethylcytosine (5-hmC) in DNA.

Sequences for human TET1-3 are known in the art and are shown in the following table:

|      | GenBank Accession Nos. | |
| --- | --- | --- |
| Gene | Amino Acid | Nucleic Acid |
| TET1 | NP_085128.2 | NM_030625.2 |
| TET2* | NP_001120680.1 (var 1) | NM_001127208.2 |
|      | NP_060098.3 (var 2) | NM_017628.4 |
| TET3 | NP_659430.1 | NM_144993.1 |

*Variant (1) represents the longer transcript and encodes the longer isoform (a). Variant (2) differs in the 5' UTR and in the 3' UTR and coding sequence compared to variant 1. The resulting isoform (b) is shorter and has a distinct C-terminus compared to isoform a.

In some embodiments, all or part of the full-length sequence of the catalytic domain can be included, e.g., a catalytic module comprising the cysteine-rich extension and the 2OGFeDO domain encoded by 7 highly conserved exons, e.g., the Tet1 catalytic domain comprising amino acids 1580-2052, Tet2 comprising amino acids 1290-1905 and Tet3 comprising amino acids 966-1678. See, e.g., FIG. 1 of Iyer et al., Cell Cycle. 2009 Jun. 1; 8(11):1698-710. Epub 2009 Jun. 27, for an alignment illustrating the key catalytic residues in all three Tet proteins, and the supplementary materials thereof (available at ftp site ftp.ncbi.nih.gov/pub/aravind/DONS/supplementary_material_DONS.html) for full length sequences (see, e.g., seq 2c); in some embodiments, the sequence includes amino acids 1418-2136 of Tet1 or the corresponding region in Tet2/3.

Other catalytic modules can be from the proteins identified in Iyer et al., 2009.

In some embodiments, the heterologous functional domain is a biological tether, and comprises all or part of (e.g., DNA binding domain from) the MS2 coat protein, endoribonuclease Csy4, or the lambda N protein. These proteins can be used to recruit RNA molecules containing a specific stem-loop structure to a locale specified by the dCas9 gRNA targeting sequences. For example, a dCas9 fused to MS2 coat protein, endoribonuclease Csy4, or lambda N can be used to recruit a long non-coding RNA (lncRNA) such as XIST or HOTAIR; see, e.g., Keryer-Bibens et al., Biol. Cell 100:125-138 (2008), that is linked to the Csy4, MS2 or lambda N binding sequence. Alternatively, the Csy4, MS2 or lambda N protein binding sequence can be linked to another protein, e.g., as described in Keryer-Bibens et al., supra, and the protein can be targeted to the dCas9 binding site using the methods and compositions described herein. In some embodiments, the Csy4 is catalytically inactive.

In some embodiments, the fusion proteins include a linker between the dCas9 and the heterologous functional domains. Linkers that can be used in these fusion proteins (or between fusion proteins in a concatenated structure) can include any sequence that does not interfere with the function of the fusion proteins. In preferred embodiments, the linkers are short, e.g., 2-20 amino acids, and are typically flexible (i.e., comprising amino acids with a high degree of freedom such as glycine, alanine, and serine). In some embodiments, the linker comprises one or more units consisting of GGGS (SEQ ID NO:34) or GGGGS (SEQ ID NO:35), e.g., two, three, four, or more repeats of the GGGS (SEQ ID NO:34) or GGGGS (SEQ ID NO:35) unit. Other linker sequences can also be used.

Expression Systems

In order to use the guide RNAs described, it may be desirable to express them from a nucleic acid that encodes them. This can be performed in a variety of ways. For example, the nucleic acid encoding the guide RNA can be cloned into an intermediate vector for transformation into prokaryotic or eukaryotic cells for replication and/or expression. Intermediate vectors are typically prokaryote vectors, e.g., plasmids, or shuttle vectors, or insect vectors, for storage or manipulation of the nucleic acid encoding the guide RNA for production of the guide RNA. The nucleic acid encoding the guide RNA can also be cloned into an expression vector, for administration to a plant cell, animal cell, preferably a mammalian cell or a human cell, fungal cell, bacterial cell, or protozoan cell.

To obtain expression, a sequence encoding a guide RNA is typically subcloned into an expression vector that contains a promoter to direct transcription. Suitable bacterial and eukaryotic promoters are well known in the art and described, e.g., in Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 2010). Bacterial expression systems for expressing the engineered protein are available in, e.g., *E. coli, Bacillus* sp., and *Salmonella* (Palva et al., 1983, Gene 22:229-235). Kits for such expression systems are commercially available. Eukaryotic expression systems for mammalian cells, yeast, and insect cells are well known in the art and are also commercially available.

The promoter used to direct expression of a nucleic acid depends on the particular application. For example, a strong constitutive promoter is typically used for expression and purification of fusion proteins. In contrast, when the guide RNA is to be administered in vivo for gene regulation, either a constitutive or an inducible promoter can be used, depending on the particular use of the guide RNA. In addition, a preferred promoter for administration of the guide RNA can be a weak promoter, such as HSV TK or a promoter having similar activity. The promoter can also include elements that are responsive to transactivation, e.g., hypoxia response elements, Gal4 response elements, lac repressor response element, and small molecule control systems such as tetracycline-regulated systems and the RU-486 system (see, e.g., Gossen & Bujard, 1992, Proc. Natl. Acad. Sci. USA, 89:5547; Oligino et al., 1998, Gene Ther., 5:491-496; Wang et al., 1997, Gene Ther., 4:432-441; Neering et al., 1996, Blood, 88:1147-55; and Rendahl et al., 1998, Nat. Biotechnol., 16:757-761).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the gRNA, and any signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the gRNA, e.g., expression in plants, animals, bacteria, fungus, protozoa, etc. Standard bacterial expression vectors include plasmids such as pBR322 based plasmids, pSKF, pET23D, and commercially available tag-fusion expression systems such as GST and LacZ.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

The vectors for expressing the guide RNAs can include RNA Pol III promoters to drive expression of the guide RNAs, e.g., the H1, U6 or 7SK promoters. These human promoters allow for expression of gRNAs in mammalian cells following plasmid transfection. Alternatively, a T7 promoter may be used, e.g., for in vitro transcription, and the RNA can be transcribed in vitro and purified. Vectors suitable for the expression of short RNAs, e.g., siRNAs, shRNAs, or other small RNAs, can be used.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with the gRNA encoding sequence under the direction of the polyhedrin promoter or other strong baculovirus promoters.

The elements that are typically included in expression vectors also include a replicon that functions in E. coli, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., 1989, J. Biol. Chem., 264:17619-22; Guide to Protein Purification, in Methods in Enzymology, vol. 182 (Deutscher, ed., 1990)). Transformation of eukaryotic and prokaryotic cells are performed according to standard techniques (see, e.g., Morrison, 1977, J. Bacteriol. 132:349-351; Clark-Curtiss & Curtiss, Methods in Enzymology 101:347-362 (Wu et al., eds, 1983).

Any of the known procedures for introducing foreign nucleotide sequences into host cells may be used. These include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the gRNA.

The present invention includes the vectors and cells comprising the vectors.

EXAMPLES

The invention is further described in the following examples, which do not limit the scope of the invention described in the claims.

Example 1. Assessing Specificity of RNA-Guided Endonucleases

CRISPR RNA-guided nucleases (RGNs) have rapidly emerged as a facile and efficient platform for genome editing. This example describes the use of a human cell-based reporter assay to characterize off-target cleavage of Cas9-based RGNs.

Materials and Methods

The following materials and methods were used in Example 1.

Construction of Guide RNAs

DNA oligonucleotides (Table A) harboring variable 20 nt sequences for Cas9 targeting were annealed to generate short double-strand DNA fragments with 4 bp overhangs compatible with ligation into BsmBI-digested plasmid pMLM3636.

Cloning of these annealed oligonucleotides generates plasmids encoding a chimeric +103 single-chain guide RNA with 20 variable 5' nucleotides under expression of a U6 promoter (Hwang et al., Nat Biotechnol 31, 227-229 (2013); Mali et al., Science 339, 823-826 (2013)). pMLM3636 and the expression plasmid pJDS246 (encoding a codon optimized version of Cas9) used in this study are both available through the non-profit plasmid distribution service Addgene (addgene.org/crispr-cas).

TABLE A

| | | | | | | | | | | | | | | | | | | | | Oligos for generating gRNA expression plasmid | | |
|---|---|---|---|---|---|---|---|---|---|---|---|---|---|---|---|---|---|---|---|---|---|---|
| gRNA Target Sequence Position | | | | | | | | | | | | | | | | | | | | oligonucleotide 1 (5' to 3') | # | oligonucleotide 2 (5' to 3') | # |
| 20 | 19 | 18 | 17 | 16 | 15 | 14 | 13 | 12 | 11 | 10 | 9 | 8 | 7 | 6 | 5 | 4 | 3 | 2 | 1 | | | | |
| EGFP Target Site 1 | | | | | | | | | | | | | | | | | | | | | | | |
| G | G | G | C | A | C | G | G | G | C | A | G | C | T | T | G | C | C | G | G | ACACCGGGCACGGGCAGCTTGCCGG | 36. | AAAACCGGCAAGCTGCCCGTGCCCG | 230. |
| G | G | G | C | A | C | G | G | G | C | A | G | C | T | T | G | C | C | G | c | ACACCGGGCACGGGCAGCTTGCCCG | 37. | AAAACGGGCAAGCTGCCCGTGCCCG | 231. |
| G | G | G | C | A | C | G | G | G | C | A | G | C | T | T | G | C | C | G | G | ACACCGGGCACGGGCAGCTTGCCGG | 38. | AAAACCGGCAAGCTGCCCGTGCCCG | 232. |
| G | G | G | C | A | C | G | G | G | C | A | G | C | T | T | G | C | g | G | G | ACACCGGGCACGGGCAGCTTGCGGG | 39. | AAAACCCGCAAGCTGCCCGTGCCCG | 233. |
| G | G | G | C | A | C | G | G | G | C | A | G | C | T | T | g | C | C | G | G | ACACCGGGCACGGGCAGCTTCCCGG | 40. | AAAACCGGGAAGCTGCCCGTGCCCG | 234. |
| G | G | G | C | A | C | G | G | G | C | A | G | C | T | a | G | C | C | G | G | ACACCGGGCACGGGCAGCTAGCCGG | 41. | AAAACCGGCTAGCTGCCCGTGCCCG | 235. |
| G | G | G | C | A | C | G | G | G | C | A | G | C | a | T | G | C | C | G | G | ACACCGGGCACGGGCAGCATGCCGG | 42. | AAAACCGGCATGCTGCCCGTGCCCG | 236. |
| G | G | G | C | A | C | G | G | G | C | A | G | g | T | T | G | C | C | G | G | ACACCGGGCACGGGCAGGTTGCCGG | 43. | AAAACCGGCAACCTGCCCGTGCCCG | 237. |
| G | G | G | C | A | C | G | G | G | C | A | c | C | T | T | G | C | C | G | G | ACACCGGGCACGGGCACCTTGCGGG | 44. | AAAACCCGCAAGGTGCCCGTGCCCG | 238. |
| G | G | G | C | A | C | G | G | G | g | A | G | C | T | T | G | C | C | G | G | ACACCGGGCACGGGGAGCTTGCCGG | 45. | AAAACCGGCAAGCTCCCGTGCCCG | 239. |
| G | G | G | C | A | C | G | G | G | C | t | G | C | T | T | G | C | C | G | G | ACACCGGGCACGGGCTGCTTGCCGG | 46. | AAAACCGGCAAGCAGCCCGTGCCCG | 240. |
| G | G | G | C | A | C | G | G | c | C | A | G | C | T | T | G | C | C | G | G | ACACCGGGCACGGCCAGCTTGCCGG | 47. | AAAACCGGCAAGCTGGCCGTGCCCG | 241. |
| G | G | G | C | A | C | G | c | G | C | A | G | C | T | T | G | C | C | G | G | ACACCGGGCACGCGCAGCTTGCCGG | 48. | AAAACCGGCAAGCTGCGCGTGCCCG | 242. |
| G | G | G | C | A | C | c | G | G | C | A | G | C | T | T | G | C | C | G | G | ACACCGGGCACCGGCAGCTTGCCGG | 49. | AAAACCGGCAAGCTGCCGGTGCCCG | 243. |
| G | G | G | C | A | C | G | G | G | C | A | G | C | T | T | G | C | C | G | G | ACACCGGGCACGGGCAGCTTGCCGG | 50. | AAAACCGGCAAGCTGCCCGTGCCCG | 244. |
| G | G | G | C | A | G | G | G | G | C | A | G | C | T | T | G | C | C | G | G | ACACCGGGCAGGGGCAGCTTGCCGG | 51. | AAAACCGGCAAGCTGCCCCTGCCCG | 245. |
| G | G | G | C | c | C | G | G | G | C | A | G | C | T | T | G | C | C | G | G | ACACCGGGCCCGGGCAGCTTGCCGG | 52. | AAAACCGGCAAGCTGCCCGGGCCCG | 246. |
| G | G | G | t | A | C | G | G | G | C | A | G | C | T | T | G | C | C | G | G | ACACCGGGTACGGGCAGCTTGCCGG | 53. | AAAACCGGCAAGCTGCCCGTACCCG | 247. |
| G | G | g | C | A | C | G | G | G | C | A | G | C | T | T | G | C | C | G | G | ACACCGGCCACGGGCAGCTTGCCGG | 54. | AAAACCGGCAAGCTGCCCGTGGCCG | 248. |
| G | c | G | C | A | C | G | G | G | C | A | G | C | T | T | G | C | C | G | G | ACACCGCGCACGGGCAGCTTGCCGG | 55. | AAAACCGGCAAGCTGCCCGTGCGCG | 249. |
| G | G | G | C | A | C | G | G | G | C | A | G | C | T | T | G | C | C | G | c | ACACCGGGCACGCGCAGCTTGCCCG | 56. | AAAACGGGCAAGCTGCCCGTGCCCG | 250. |

TABLE A-continued

| | | | | | | | | | | | | | | | | | | | | |
|---|---|---|---|---|---|---|---|---|---|---|---|---|---|---|---|---|---|---|---|---|
| G | G | C | A | G | G | C | A | G | C | T | T | G | G | ACACCGGGCACGGGCAGCTTGGGGGG | 57. | AAAACCCCCCAAGCTGCCCGTGCCCG | 251. |
| G | G | C | A | G | G | C | A | G | C | T | T | a | g | ACACCGGGCACGGGCAGCTACCCGGG | 58. | AAAACCCGGGCAGCTAGCTGCCCGTGCCCG | 252. |
| G | G | C | A | G | G | C | t | G | C | T | T | c | G | ACACCGGGCACGGGCAGGATGCCCGG | 59. | AAAACCCGGCCATCCTGCCCGTGCCCG | 253. |
| G | G | C | A | G | c | G | A | c | G | T | T | c | G | ACACCGGGCACGGGCTCCTTGCCGGG | 60. | AAAACCCGGCAAGGAGCCCGTGCCCG | 254. |
| G | G | C | A | G | G | C | A | G | C | T | T | c | G | ACACCGGGCACGGGCAGCTTGCCGGG | 61. | AAAACCCGGCAAGCTGCCCGTGCCCG | 255. |
| G | G | C | A | G | G | C | A | G | C | T | T | c | G | ACACCGGGCACGGGCAGCTTGCCGGG | 62. | AAAACCCGGCAAGCTGCGGGTGCCCG | 256. |
| G | G | C | A | G | G | C | t | G | C | T | T | c | G | ACACCGGGCTGGGGCAGCTTGCCGGG | 63. | AAAACCCGGCAAGCTGCCCCAGCCCG | 257. |
| G | G | C | A | G | G | C | A | G | C | T | T | c | G | ACACCGGGCACGGGCAGCTTGCCGGG | 64. | AAAACCCGGCAAGCTGCCCGTCGCCG | 258. |
| G | G | C | c | G | G | C | A | G | C | T | T | c | G | ACACCGCCACGGGCAGCTTGCCGGG | 65. | AAAACCCGGCAAGCTGCCCGTGCGGG | 259. |
| G | G | C | A | G | G | C | A | G | C | T | T | c | G | ACACCGCGCACGGGCAGCTTGCCGGG | 66. | AAAACCCGGCAAGCTGCCCGTGCCCG | 260. |
| G | G | c | A | G | c | C | A | G | C | T | T | c | G | ACACCGCCGTGGGGCAGCTTGCCGGG | 67. | AAAACCCGGCAAGCTGCCCGTGCCCG | 261. |
| G | G | c | t | G | c | C | A | G | C | T | T | c | G | ACACCGCCGTGGGCAGCTTGCCGGG | 68. | AAAACCCGGCAAGCTGCCCGTCGCCG | 262. |
| G | G | c | t | G | c | c | A | G | C | T | T | c | G | ACACCGCCGCCACGGGCAGCTTGCCGGG | 69. | AAAACCCGGCAAGCTGCCCGTGCCCG | 263. |
| G | G | c | t | G | c | c | A | G | C | T | T | c | G | ACACCGCCGCGTGCCGCAGCTTGCCGGG | 70. | AAAACCCGGCAAGCTGCCCGTGCCCG | 264. |
| G | G | c | t | G | c | c | A | G | C | T | T | c | G | ACACCGCCGTGCCCCAGCTTGCCGGG | 71. | AAAACCCGGCAAGCTGCCCGTGCCCG | 265. |
| G | G | c | t | G | c | g | A | G | C | T | T | c | G | ACACCGCCCGCTGCCCGAGCTTGCCGGG | 72. | AAAACCCGGCAAGCTGCCCGTGCCCG | 266. |
| G | G | C | A | G | C | g | A | G | C | T | T | g | G | ACACCGGGCACGGGCAGCTTGCCGCG | 73. | AAAACCCGGCAAGCTGCCCGTGCCCG | 267. |
| G | G | C | A | G | G | C | A | G | C | T | T | c | g | ACACCGGGCACGGGCAGCTTCCGGGG | 74. | AAAACCCGGAAGCTGCCCGTGCCCG | 268. |
| G | G | C | A | G | G | C | A | G | C | T | a | T | g | ACACCGGGCACGGGCAGCATGCGGGG | 75. | AAAACCCCCATGCTGCCCGTGCCCG | 269. |
| G | G | C | A | G | G | C | A | G | C | T | T | c | g | ACACCGGGCACGGACCTTGCGGGG | 76. | AAAACCCGGCAAGCTGCCCGTGCCCG | 270. |
| G | G | C | A | G | G | C | A | G | C | T | T | c | g | ACACCGGGCACGGCAGCTTGCGGGG | 77. | AAAACCCCCGAAGTTCCCGTGCCCG | 271. |
| G | G | C | A | G | G | C | A | G | C | T | T | c | g | ACACCGGGCAGGGCAGCTTGCCGGG | 78. | AAAACCCGGCAAGCTGCGCCGTGCCCG | 272. |
| G | G | C | A | G | G | C | A | G | C | T | T | c | G | ACACCGGGCAGCGGCAGCTTGCCGGG | 79. | AAAACCCCCAAGCTGCCCGTCCCCG | 273. |
| G | G | C | A | G | G | C | A | G | C | T | T | g | G | ACACCGCGCCAAGGGCAGCTTGCCGGG | 80. | AAAACCCCCAAGCTGCCGTGCCCG | 274. |
| G | c | G | A | G | G | C | A | G | C | T | T | G | G | ACACCGCCACGGGCAGCTTGCGGGG | 81. | AAAACCCGGCAAGCTGCCCGTGCGCG | 275. |

TABLE A-continued

| | | | | | | | | | | | | | | | | | | | | | |
|---|---|---|---|---|---|---|---|---|---|---|---|---|---|---|---|---|---|---|---|---|---|
| G | G | G | A | C | G | g | A | G | T | T | G | C | ACACCGGGCACGGGGAGCTTGCCGCG | 82. | AAAACGGCGCAAGTCCCCGTGCCCG | 276. |
| G | C | C | C | c | G | g | A | G | T | T | C | C | ACACCGGGCACGGGGAGCTTCCCGGG | 83. | AAAACCCGGAAGTCCCCGTGCCCG | 277. |
| G | C | C | A | C | G | g | A | G | T | T | G | C | ACACCGGGCACGGGGAGCATGCCGGG | 84. | AAAACCCGGCATGTCCCCGTGCCCG | 278. |
| G | C | C | C | C | G | g | A | G | T | T | G | C | ACACCGGGCACGGGGAGCTTGCCGGG | 85. | AAAACCCGGCAAGTCCCCGTGCCCG | 279. |
| G | C | C | A | C | G | g | A | G | T | T | G | C | ACACCGGGCACGCGGAGCTTGCCGGG | 86. | AAAACCCGGCAAGTCCGCGTGCCCG | 280. |
| G | C | C | A | g | G | g | A | G | T | T | G | C | ACACCGGGCAGGGGGAGCTTGCCGGG | 87. | AAAACCCGGCAAGTCCCCGTCCCCG | 281. |
| G | C | C | A | C | G | C | A | G | T | T | G | C | ACACCGGGCACGGGGCAGCTTGCCGGG | 88. | AAAACCCGGCAAGTCCCCGTGCCGCG | 282. |
| G | C | C | A | C | G | g | A | G | T | T | G | C | ACACCGGGCACGGGGAGCTTGCCGGG | 89. | AAAACCCGGCAAGTCCCCGTGCCCG | 283. |
| c | C | C | A | C | G | c | A | G | T | T | G | C | ACACCGCGCACGGGGCAGCTTGCCGCG | 90. | AAAACGCGCAAGTGCCCGTGCCCG | 284. |
| G | C | C | A | C | G | g | A | G | T | T | C | C | ACACCGCGCACGGGGAGCTTCCCGGG | 91. | AAAACCCGGAAGTCCCCGTGCCCG | 285. |
| G | C | C | A | C | G | a | A | G | T | T | G | C | ACACCGCGCACGGGGACATGCCGGG | 92. | AAAACCCGGCATGTCCCCGTGCCG | 286. |
| G | C | C | A | C | G | g | A | G | C | T | G | C | ACACCGCGCACGGGGCAGCTTGCCGGG | 93. | AAAACCCGGCAAGTCCGCGTGCCCG | 287. |
| C | C | C | A | C | G | C | A | G | T | T | G | C | ACACCGCGCACGCGCCAGCTTGCCGGG | 94. | AAAACCCGGCAAGTGCCCTGCCCG | 288. |
| c | g | c | A | C | G | g | A | G | T | T | G | C | ACACCGCGCAGGGGCAGCTTGCCGGG | 95. | AAAACCCGGCAAGTGCCCTGCCCG | 289. |
| G | C | C | A | C | G | g | A | G | T | T | G | C | ACACCGCGACGGGACAGCTTGCCGGG | 96. | AAAACCCGGCAAGTCCCCGTCCGCG | 290. |

EGFP Target Site 2

| | | | | | | | | | | | | | | | | | | | | | |
|---|---|---|---|---|---|---|---|---|---|---|---|---|---|---|---|---|---|---|---|---|---|
| G | A | T | G | C | C | T | T | C | T | T | C | T | ACACCGATGCCGTTCTTCTGCTTGTG | 97. | AAAACAAGCAGAAGAACGGCATCG | 291. |
| G | A | T | G | C | C | T | T | C | T | T | C | G | ACACCGATGCCGTTCTTCTGCTTGAG | 98. | AAAACACAAGCAGAAGAACGGCATCG | 292. |
| G | A | T | G | C | C | T | T | C | T | T | C | T | ACACCGATGCCGTTCTTCTGCTTCTG | 99. | AAAACACAAGCAGAAGAACGGCATCG | 293. |
| G | A | T | G | C | C | T | T | C | T | T | C | T | ACACCGATGCCGTTCTTCTGCTAGTG | 100. | AAAACACAAGCAGAAGAACGGCATCG | 294. |
| G | A | T | G | C | C | T | a | C | T | T | C | a | ACACCGATGCCGTTCTTCTTGCTTGTG | 101. | AAAACACAAGCAGAAGAACGGCATCG | 295. |
| G | A | T | G | C | C | T | T | C | T | T | C | T | ACACCGATGCCGTTCTTCTGCATGTG | 102. | AAAACACAAGCAGAAGAACGGCATCG | 296. |
| G | A | T | g | C | C | T | T | c | T | T | c | G | ACACCGATGCCGTTCTTCCTTGTG | 103. | AAAACACAAGCAGAAGAACGGCATCG | 297. |
| G | A | T | G | C | C | T | T | C | T | T | C | T | ACACCGATGCCGTTCTTCCTTGTG | 104. | AAAACACAAGCAGAAGAACGGCATCG | 298. |
| G | A | T | G | C | C | T | a | C | T | T | C | T | ACACCGATGCCGTTCTTCCAGCTTGTG | 103. | AAAACACAAGCAGAAGAACGGCATCG | 299. |
| G | A | T | G | c | g | T | T | g | T | T | g | T | ACACCGATGCCGTTCTTGTGCTTGTG | 103. | AAAACACAAGCAGAAGAACGGCATCG | 299. |

TABLE A-continued

| | | | | | | | | | | | | | | | | | | | | |
|---|---|---|---|---|---|---|---|---|---|---|---|---|---|---|---|---|---|---|---|---|
| G | A | T | G | C | C | G | T | T | C | T | T | C | T | G | C | T | T | G | T | G | ACACCGATGCCGTTCTACTGCTTGTG | 106 | AAAACACAAGCAGAAGAACGGCATCG | 300. |
| G | A | T | G | C | C | G | T | T | C | a | T | C | T | G | C | T | T | G | T | G | ACACCGATGCCGTTCATCTGCTTGTG | 107 | AAAACACAAGCAGAAGAACGGCATCG | 301. |
| G | A | T | G | C | C | G | T | T | C | T | T | G | T | C | T | T | G | C | T | T | ACACCGATGCCGTTCTTGTCTTGCTTGTG | 108 | AAAACACAAGCAGAAGAACGGCATCG | 302. |
| G | A | T | G | C | C | G | a | T | C | T | a | C | T | T | C | T | G | C | T | T | ACACCGATGCCGATCTACTTCTGCTTGTG | 109 | AAAACACAAGCAGAAGAACGGCATCG | 303. |
| G | A | T | G | C | C | G | T | T | C | T | T | C | T | G | C | T | T | G | T | G | ACACCGATGCCGTTCTTCTGCTTGTG | 110 | AAAACACAAGCAGAAGAACGGCATCG | 304. |
| G | A | T | G | C | C | G | T | T | C | T | T | C | T | G | C | T | T | G | T | G | ACACCGATGCCCTTCTTCTGCTTGTG | 111 | AAAACACAAGCAGAAGAACGGCATCG | 305. |
| G | A | T | G | C | G | G | T | T | C | T | T | C | T | G | C | T | T | G | T | G | ACACCGATGCGGTTCTTCTGCTTGTG | 112 | AAAACACAAGCAGAAGAACGGCATCG | 306. |
| G | A | T | G | g | C | G | T | T | C | T | T | C | T | G | C | T | T | G | T | G | ACACCGATGGCGTTCTTCTGCTTGTG | 113 | AAAACACAAGCAGAAGAACGGCATCG | 307. |
| G | A | T | C | C | C | G | T | T | C | T | T | C | T | G | C | T | T | G | T | G | ACACCGATCCCGTTCTTCTGCTTGTG | 114 | AAAACACAAGCAGAAGAACGGCATCG | 308. |
| G | A | t | G | C | C | G | T | T | C | T | T | C | T | G | C | T | T | G | T | G | ACACCGAAGCCGTTCTTCTGCTTGTG | 115 | AAAACACAAGCAGAAGAACGGCATCG | 309. |
| G | A | T | G | C | C | G | T | T | G | C | C | G | T | T | C | T | T | C | T | G | ACACCGTTGCCGTTCTTCTGCTTGTG | 116 | AAAACACAAGCAGAAGAACGGCATCG | 310. |
| G | A | T | G | C | C | G | T | T | C | T | T | C | T | G | C | T | T | C | a | G | ACACCGATGCCGTTCTTCTGCTTCAG | 117 | AAAACTGAAGCAGAAGAACGGCATCG | 311. |
| G | A | T | G | C | C | G | T | T | C | T | T | C | T | G | C | T | T | G | T | G | ACACCGATGCCGTTCTTCTGCTTGTG | 118 | AAAACACAAGCAGAAGAACGGCATCG | 312. |
| G | A | T | G | c | G | T | a | g | c | a | T | T | c | c | T | T | G | T | T | G | ACACCGATGCCGTTCTTCTGCTTGTG | 119 | AAAACACAAGCAGAAGAACGGCATCG | 313. |
| G | A | T | G | C | C | G | T | T | C | T | T | C | T | G | a | G | C | T | T | G | ACACCGATGCCGTTCTTCTGAGCTTGTG | 120 | AAAACACAAGCTCAAGAAGAACGGCATCG | 314. |
| G | A | T | G | C | C | G | T | T | C | a | a | C | T | G | C | T | T | G | T | G | ACACCGATGCCGTTCAACTGCTTGTG | 121 | AAAACACAAGCAGAAGAACGGCATCG | 315. |
| G | A | T | G | C | C | G | T | T | a | g | T | T | C | T | G | C | T | T | G | T | ACACCGATGCCGTTAGTTCTGCTTGTG | 122 | AAAACACAAGCAGAAGAACGGCATCG | 316. |
| G | A | T | G | C | C | C | a | T | C | T | T | C | T | G | C | T | T | G | T | G | ACACCGATGCCCATCTTCTGCTTGTG | 123 | AAAACACAAGCAGAAGAACGGCATCG | 317. |
| G | A | T | G | g | g | g | T | T | C | T | T | C | T | G | C | T | T | G | T | G | ACACCGATGGGGTTCTTCTGCTTGTG | 124 | AAAACACAAGCAGAAGAACGGCATCG | 318. |
| G | A | c | c | C | G | a | C | C | C | G | T | T | C | T | T | C | T | G | T | T | ACACCGACCCGTTCTTCTGCTTGTG | 125 | AAAACACAAGCAGAAGAACGGCATCG | 319. |

TABLE A-continued

| | | | | | | | | | | | | | | Sequence | # | Sequence | # |
|---|---|---|---|---|---|---|---|---|---|---|---|---|---|---|---|---|---|
| G | t | a | C | C | G | T | T | C | T | T | C | G | T | ACACCGTAGCCGTTCTTCTGCTTGTG | 126 | AAAACACAAGCAGAAGAACGGCAAGG | 320. |
| G | t | a | C | C | G | T | T | C | T | T | C | G | T | ACACCGTACCCGTTCTTCTGCTTGTG | 127 | AAAACACAAGCAGAAGAACGGGTACG | 321. |
| G | t | a | C | C | G | T | T | C | T | T | C | G | T | ACACCGTACGGTTCTTCTGCTTGTG | 128 | AAAACACAAGCAGAGAACGGGTACG | 322. |
| G | t | a | C | g | G | T | T | C | T | T | C | G | T | ACACCGTACGGGTTCTTCTGCTTGTG | 129 | AAAACACAAGCAGAAGAACCCGTACG | 323. |
| G | t | a | c | g | G | T | T | C | T | T | C | G | T | ACACCGTACGGCTTCTTCTGCTTGTG | 130 | AAAACACAAGCAGAAGAAGCCGTACG | 324. |
| G | t | a | c | g | c | T | T | C | T | T | C | G | T | ACACCGTACGGCATCTTCTGCTTGTG | 131 | AAAACACAAGCAGAAGATGCCGTACG | 325. |
| G | t | a | c | g | c | a | T | C | T | T | C | G | T | ACACCGTACGGCAACTTCTGCTTGTG | 132 | AAAACACAAGCAGAAGAGTTGCCGTACG | 326. |
| G | t | a | c | g | c | a | a | C | T | T | C | G | T | ACACCGTACGGCAAGTTCTGCTTGTG | 133 | AAAACACAAGCAGAACTTGCCGTACG | 327. |
| G | A | T | G | T | c | T | T | g | T | T | C | G | a | ACACCGTAGCCGTTCTTCTGCTAGAG | 134 | AAAACTCTAGCAAGACGGCATCG | 328. |
| G | A | T | G | T | c | T | a | C | T | T | C | G | T | ACACCGATGCCGTTCTTCTGCTAGTG | 135 | AAAACACTACCAGAAGACGGCATCG | 329. |
| G | A | T | G | T | c | T | a | C | T | T | C | G | T | ACACCGATGCCGTTCTTCAGCTAGTG | 136 | AAAACACTAGCTGAAGACGGCATCG | 330. |
| G | A | T | G | T | c | T | a | C | T | T | C | G | T | ACACCGATGCCGTTCTACTGCTAGTG | 137 | AAAACACTAGCAGTACGGCATCG | 331. |
| G | A | T | G | T | c | a | a | C | T | T | C | G | T | ACACCGATGCCGTTGTCTGCTAGTG | 138 | AAAACACTAGCAGAACAACGGCATCG | 332. |
| G | A | T | G | T | c | T | a | C | T | T | C | G | T | ACACCGATGCCGATCTTCTGCTAGTG | 139 | AAAACACTAGCAGAGATCGGCATCG | 333. |
| G | A | T | G | T | c | T | a | C | T | T | C | G | T | ACACCGATGCCGGTTCTTCTGCTAGTG | 140 | AAAACACTAGCAGAGAACCGCATCG | 334. |
| G | A | T | G | T | c | T | a | C | T | T | C | G | T | ACACCGATGCCGTTCCGTTCTGCTAGTG | 141 | AAAACACTAGCAGAGAACGGGATCG | 335. |
| G | A | T | G | T | c | T | a | C | T | T | C | G | T | ACACCGATGCCGTTCCGTTGTTCTGCTAGTG | 142 | AAAACACTAGCAGAGAACGGCAACG | 336. |
| G | A | T | G | T | c | T | T | C | T | T | C | G | T | ACACCGATGCCGTTCCGTTGTCAGCTAGTG | 143 | AAAACTCAAGCAGACAACGGCATCG | 337. |
| G | A | T | G | T | c | T | T | C | T | T | C | G | T | ACACCGATGCCGTTGTTGTTCTTGAG | 144 | AAAACACAAGCTGAACAACGGCATCG | 338. |
| G | A | T | G | T | c | T | T | C | T | T | C | G | T | ACACCGATGCCGTTGTTCAGCTTGTG | 145 | AAAACACAAGCAGAACAACGGCATCG | 339. |
| G | A | T | G | T | c | T | T | C | T | T | C | G | T | ACACCGATGCCGTGTACTGCTTGTG | 146 | AAAACACAAGCAGTACAACGGCATCG | 340. |
| G | A | T | G | T | c | T | T | C | T | T | C | G | T | ACACCGATGCCGATGTTCTGCTTGTG | 147 | AAAACACAAGCAGACATCGGCATCG | 341. |
| G | A | T | G | T | c | T | T | C | T | T | C | G | T | ACACCGATGCCGGTTGTTCTGCTTGTG | 148 | AAAACACAAGCAGAACACCGCATCG | 342. |
| G | A | T | G | T | c | T | T | C | T | T | C | G | T | ACACCGATCCCGTTGTTCTGCTTGTG | 149 | AAAACACAAGCAGAACAACGGGATCG | 343. |

TABLE A-continued

| | | | | | | | | | | | | | | | | | | | |
|---|---|---|---|---|---|---|---|---|---|---|---|---|---|---|---|---|---|---|---|
| G | t | T | G | C | T | T | T | T | G | T | T | C | T | G | 150 | ACACCGTTGCCGTTGCCGTTCTTGCTTGTG | AAAACACAAGCAGAACAACACGGCAACG | 344 |
| G | t | T | G | C | T | T | T | T | G | T | T | C | T | G | 151 | ACACCGTTGCCGTTCTTCTGCTTGAG | AAAACTCAAGCAGAAGAACGGCAACG | 345 |
| G | t | T | G | C | T | T | T | T | G | T | T | g | T | a | 152 | ACACCGTTGCCGTTCTTCTTGGTTGTG | AAAACACAACCAGAAGAACGGCAACG | 346 |
| G | t | T | G | C | T | T | T | T | G | T | T | C | T | T | 153 | ACACCGTTGCCGTTCTTCTTCAGCTTGTG | AAAACACAAGCTGAAGAACGGCAACG | 347 |
| G | t | T | G | C | T | T | T | T | a | T | T | C | T | T | 154 | ACACCGTTGCCGTTCTACTGCTTGTG | AAAACACAAGCAGTAGAACGGCAACG | 348 |
| G | t | T | G | C | T | T | T | T | G | T | a | C | T | C | 155 | ACACCGTTGCCGATCTTCTTCTGCTTGTG | AAAACACAAGCAGAAGATCGGCAACG | 349 |
| G | t | T | G | g | T | T | T | T | G | T | T | C | T | T | 156 | ACACCGTTGCGGTTCTTCTTCTGCTTGTG | AAAACACAAGCAGAAGAACCGCAACG | 350 |
| G | t | T | G | C | T | T | T | T | G | T | T | C | T | T | 157 | ACACCGTTCCCGTTCCTTCTTCTGCTTGTG | AAAACACAAGCAGAGAACGGGAACG | 351 |

EGFP Target Site 3

| | | | | | | | | | | | | | | | | | | | |
|---|---|---|---|---|---|---|---|---|---|---|---|---|---|---|---|---|---|---|---|
| G | T | G | T | C | A | A | G | T | C | T | T | C | A | 158 | ACACCGGTGGTGCAGATGAACTTCAG | AAAACTGAAGTTCATCTGCACCACCG | 352 |
| G | T | G | T | C | A | A | G | T | C | T | T | C | A | 159 | ACACCGGTGGTGCAGATGAACTTCTG | AAAACAGAAGTTCATCTGCACCACCG | 353 |
| G | T | G | T | C | A | A | G | T | C | T | T | g | A | 160 | ACACCGGTGGTGCAGATGAACTTGAG | AAAACTCAAGTTCATCTGCACCACCG | 354 |
| G | T | G | T | C | A | A | G | T | C | T | T | C | A | 161 | ACACCGGTGGTGCAGATGAACTACAG | AAAACTGTAGTTCATCTGCACCACCG | 355 |
| G | T | G | T | C | A | A | G | T | a | T | T | C | A | 162 | ACACCGGTGGTGCAGATGAACAACAG | AAAACTGTTGTTCATCTGCACCACCG | 356 |
| G | T | G | T | C | A | A | g | T | C | T | T | C | A | 163 | ACACCGGTGGTGCAGATGAACATCAG | AAAACTGATGTTCATCTGCACCACCG | 357 |
| G | T | G | T | C | A | A | G | T | C | T | T | C | A | 164 | ACACCGGTGGTGCAGATGATCTTCAG | AAAACTGAAGATCATCTGCACCACCG | 358 |
| G | T | G | T | C | A | t | G | T | C | T | T | C | t | 165 | ACACCGGTGGTGCAGGTACTTCTG | AAAACTGAAGTACATCTGCACCACCG | 359 |
| G | T | G | T | C | A | A | G | T | C | T | T | C | A | 166 | ACACCGGTGGTGCAGATCAACTTCAG | AAAACTGAAGTTGATCTGCACCACCG | 360 |
| G | T | G | T | c | A | A | G | t | C | T | T | C | A | 167 | ACACCGGTGGTGCAGATTGATCTGCACCACCG | AAAACTGAAGTTCTTCTGCACCACCG | 361 |
| G | T | G | T | C | A | A | G | T | C | T | T | C | A | 168 | ACACCGGTGGTGCAGAAGAACTTCAG | AAAACTGAAGTTCAACTGCACCACCG | 362 |
| G | T | G | T | C | A | A | G | T | C | T | T | C | A | 169 | ACACCGGTGGTGCAGATGTTGAACTTCAG | AAAACTGAAGATCATCGCACCACCG | 363 |
| G | T | G | T | C | A | A | G | T | C | T | T | C | A | 170 | ACACCGGTGGTGCACATGTGATGAACTTCAG | AAAACTGAAGTTCATCAGCACCACCG | 364 |
| G | T | G | T | C | A | A | G | T | C | T | T | C | A | 171 | ACACCGGTGGTGCTGTGGAGATGAACTTCAG | AAAACTGAAGTTCATCTCCACCACCG | 365 |
| G | T | G | T | C | A | A | G | T | C | T | T | C | A | 172 | ACACCGGTGGTTGGTCCAGATGAACTTCAG | AAAACTGAAGTTCATCTGGACCACCG | 366 |
| G | a | G | a | c | A | t | G | T | C | T | T | C | A | 173 | ACACCGTGGAGCAGAGATGAACTTCAG | AAAACTGAAGTTCATCTGCTCCACCG | 367 |

TABLE A-continued

| | | | | | | | | | | | | | | | | | | | | | |
|---|---|---|---|---|---|---|---|---|---|---|---|---|---|---|---|---|---|---|---|---|---|
| G | T | G | G | T | G | C | A | A | T | G | A | A | C | T | T | C | A | ACACCGGTGCTGCAGATGAACTTCAG | 174 | AAAACTGAAGTTCATCTGCAGCACCG | 368. |
| G | T | G | G | T | G | C | A | A | T | G | A | A | C | T | T | C | A | ACACCGGTCGTGCAGATGAACTTCAG | 175 | AAAACTGAAGTTCATCTGCACGACCG | 369. |
| G | a | G | G | T | G | C | A | A | T | G | A | A | C | T | T | C | A | ACACCGGAGGTGCAGATGAACTTCAG | 176 | AAAACTGAAGTTCATCTGCACTTCCG | 370. |
| G | T | G | G | T | G | C | A | A | T | G | A | A | C | T | T | C | A | ACACCGCTGGTGCAGATGAACTTCAG | 177 | AAAACTGAAGTTCATCTGCACCAGCG | 371. |
| G | T | G | G | T | G | C | A | A | T | G | A | A | C | T | T | g | t | ACACCGGTGGTGCAGATGAACTTGTG | 178 | AAAACACAAGTTCATCTGCACCACCG | 372. |
| G | T | G | G | T | G | C | A | A | T | G | A | A | C | T | T | C | A | ACACCGGTGGTGCAGATGAACACAG | 179 | AAAACTGTTGTTCATCTGCACCACCG | 373. |
| G | T | G | G | T | G | C | A | A | T | G | A | t | a | T | T | C | A | ACACCGGTGGTGCAGATGATGTTCAG | 180 | AAAACTGAACATCATCTGCACCACCG | 374. |
| G | T | G | G | T | G | C | A | A | T | g | A | A | C | T | T | C | A | ACACCGGTGGTGCAGATCTACTTCAG | 181 | AAAACTGAAGTAGATCTGCACCACCG | 375. |
| G | T | G | G | T | G | C | A | A | T | G | A | A | C | T | T | C | A | ACACCGGTGGTGCAGTAGAACTTCAG | 182 | AAAACTGAAGTTACTGCACCACCG | 376. |
| G | T | G | G | T | G | C | A | A | T | G | A | A | C | T | T | C | A | ACACCGGTGGTGTCATGAACTTCAG | 183 | AAAACTGAAGTTCATGAGCACCACCG | 377. |
| G | T | G | G | T | G | g | A | A | T | G | A | A | C | T | T | C | A | ACACCGGTGGTGCAGCAGAACTTCAG | 184 | AAAACTGAAGTTCATCTGCTGCACCG | 378. |
| G | T | G | G | T | G | C | A | A | T | G | A | A | C | T | T | C | A | ACACCGGACGTGCAGGTGAACTTCAG | 185 | AAAACTGAAGTTCATCTGCACGTCCG | 379. |
| G | c | G | c | a | c | C | A | A | T | G | A | A | C | T | T | C | A | ACACCGCAGGTGCAGGTGAACTTCAG | 186 | AAAACTGAAGTTCATCTGCACCGTCG | 380. |
| G | T | G | c | a | c | C | A | A | T | G | A | A | C | T | T | C | A | ACACCGCACCTGCAGATGAACTTCAG | 187 | AAAACTGAAGTTCATCTGCACCAGGG | 381. |
| G | c | G | c | a | c | C | A | A | T | G | A | A | C | T | T | C | A | ACACCGCACGTGCAGATGAACTTCAG | 188 | AAAACTGAAGTTCATCTGCACGTGCG | 382. |
| G | c | G | c | a | c | C | A | A | T | G | A | A | C | T | T | C | A | ACACCGCACTGCAGATGATGAACTTCAG | 189 | AAAACTGAAGTTCATCTGCACGGTGCG | 383. |
| G | c | G | c | a | c | C | A | t | c | C | t | A | C | T | T | C | A | ACACCGCACCAGCAGATGAACTTCAG | 190 | AAAACTGAAGTTCATCTGCTGGTGCG | 384. |
| G | c | G | c | a | c | C | A | t | g | C | t | A | C | T | T | C | A | ACACCGCACCAGATGATGAACTTCAG | 191 | AAAACTGAAGTTCATCTGTGGTGCG | 385. |
| G | c | G | c | a | c | C | A | A | T | G | A | A | C | T | T | C | A | ACACCGCACCACCAGAGATGAACTTCAG | 192 | AAAACTGAAGTTCATCTGGTGTGCG | 386. |
| G | c | G | c | a | c | g | A | A | T | G | A | A | C | T | T | C | A | ACACCGCACCACAGGTGATGAACTTCAG | 193 | AAAACTGAAGTTCATCTGGTGTGCG | 387. |
| G | c | G | c | a | c | g | A | t | g | C | t | A | C | T | T | C | A | ACACCGCACCGCCGACACGTGATGAACTTCAG | 194 | AAAACTGAAGTTCATCACGGTGGTGCG | 388. |
| G | T | G | G | T | G | C | A | A | T | G | A | A | C | T | T | a | t | ACACCGGTGGTGCAGATGCATGAACTTCAG | 195 | AAAACTGAAGTTCATGACTGGTGGCG | 389. |
| G | T | G | G | T | G | C | A | A | T | G | t | t | g | T | T | a | c | ACACCGGTGGTGCAGATGAAGTACTG | 196 | AAAACTGTACTTCATCTGCACCACCG | 390. |
| G | T | G | G | T | G | C | A | A | T | G | A | A | C | T | a | C | A | ACACCGGTGCTGCAGATGTACTACAG | 197 | AAAACTGTAGTACATCTGCACCACCG | 391. |

TABLE A-continued

| | | | | | | | | | | | | | | | | | | | |
|---|---|---|---|---|---|---|---|---|---|---|---|---|---|---|---|---|---|---|---|
| G | T | G | T | G | C | T | G | A | A | A | A | C | T | a | A | ACACCGGTGGTGCAGAAGAACTACAG | 198 | AAAACTGTAGTTCTTCTGCACCACCG | 392 |
| G | T | G | T | G | C | T | G | A | A | A | A | C | T | a | A | ACACCGGTGGTGCACATGAACTACAG | 199 | AAAACTGTAGTTCATGTGCACCACCG | 393 |
| G | T | G | T | G | g | T | G | A | A | A | A | C | T | a | A | ACACCGGTGGTGGAGCAGATGAACTACAG | 200 | AAAACTGTAGTTCATCTCCACCACCG | 394 |
| G | T | G | T | G | C | T | G | A | A | A | A | C | T | a | A | ACACCGGTGGTCGCAGATGAACTACAG | 201 | AAAACTGTAGTTCATCTGCTCCACCG | 395 |
| G | a | G | T | G | C | T | G | A | A | A | A | C | T | a | A | ACACCGGTGGTCGCAGATGAACTACAG | 202 | AAAACTGTAGTTCATCTGCACGACCG | 396 |
| G | T | G | T | G | C | T | G | A | A | A | A | C | T | a | A | ACACCGCTGGTGCAGATGAACTACAG | 203 | AAAACTGTAGTTCATCTGCACCAGCG | 397 |
| c | T | G | T | G | C | T | G | A | A | A | t | C | T | T | t | ACACCGCTGGTGCACATGAACTTCTG | 204 | AAAACAGAAGTTCATGTGCACCACCG | 398 |
| G | T | G | T | G | C | T | G | A | A | A | A | C | T | T | A | ACACCGCTGGTGCACATGAAGTTCAG | 205 | AAAACTGAACTTCATGTGCACCACCG | 399 |
| G | T | G | T | G | C | T | G | A | A | A | A | g | T | T | A | ACACCGCTGGTGCACATGTACTTCAG | 206 | AAAACTGAAGTACATGTGCACCACCG | 400 |
| G | T | G | T | G | C | T | G | A | A | A | A | C | T | T | A | ACACCGCTGGTGCACAAGAACTTCAG | 207 | AAAACTGAAGTTCTTGTGCACCACCG | 401 |
| G | T | G | T | G | C | a | G | A | A | A | A | C | T | T | A | ACACCGCTGGTGGACATGAACTTCAG | 208 | AAAACTGAAGTTCATGTCCACCACCG | 402 |
| G | c | G | T | G | C | T | G | A | A | A | A | g | T | T | A | ACACCGCTGGAGCACACATGAACTTCAG | 209 | AAAACTGAAGTTCATGTGCTCCACCG | 403 |
| G | T | G | a | G | C | T | G | A | A | A | A | C | T | T | A | ACACCGGTGTCTGCACATGAACTTCAG | 210 | AAAACTGAAGTTCATGTGCACGACCG | 404 |
| G | T | G | T | G | C | T | G | A | A | A | A | C | T | T | A | ACACCGGTGCTGGTGCACATGAACTTCAG | 211 | AAAACTGAAGTTCATGTGCACCAGCG | 405 |
| c | T | G | T | G | C | T | G | A | A | A | t | C | T | T | t | ACACCGCTGGTGCAGATGAACTTCTG | 212 | AAAACAGAAGTTCATCTGCACCAGCG | 406 |
| G | T | G | c | G | C | T | G | A | A | A | A | C | T | T | A | ACACCGCTGGTGCAGATGTACTTCAG | 213 | AAAACTGAACTTCATGTACCACCAGCG | 407 |
| G | T | G | T | G | C | T | G | A | A | A | A | C | T | T | A | ACACCGCTGGTGCAGAAGAACTTCAG | 214 | AAAACTGAAGTTCTTCTGCACCAGCG | 408 |
| G | c | G | T | G | C | T | G | A | A | A | A | C | T | T | A | ACACCGCTGGTGGAGATGAACTTCAG | 215 | AAAACTGAAGTTCATCTGCACCAGCG | 409 |
| G | T | G | T | G | g | T | G | A | A | A | A | C | T | T | A | ACACCGCTGGTGCATCATGAACTTCAG | 216 | AAAACTGAAGTTCATCTCCACCAGCG | 410 |
| c | T | G | a | G | C | T | G | A | A | A | A | C | T | T | A | ACACCGCTGGAGCAGATGAACTTCAG | 217 | AAAACTGAAGTTCATCTGCTCCAGCG | 411 |
| c | T | G | T | G | C | T | G | A | A | A | A | C | T | T | A | ACACCGCTCGTGCAGATGAACTTCAG | 218 | AAAACTGAAGTTCATCTGCACGAGCG | 412 |

TABLE A-continued

| Endogenous Target | Sequence | SEQ ID NO |
|---|---|---|
| Endogenous Target 1 (VEGFA Site 1) | GGGTGGGGGGAGTTTGCTCCG | 219 |
|  |  | 220 |
|  | ACACCGGGTGGGGGGAGTTTGCTCCG | 413 |
|  | AAAACGGAGCAAACTCCCCCACCCG | 414 |
| Endogenous Target 2 (VEGFA Site 2) | GACCCCCCTCCACCCCGCCTCG | 221 |
|  |  | 222 |
|  | ACACCGACCCCCCTCCACCCCGCCTCG | 415 |
|  | AAAACGAGGCGGGGTGGAGGGGGTCG | 416 |
| Endogenous Target 3 (VEGFA Site 3) | GGTGAGTGAGTGTGTGCGTGG | 223 |
|  |  | 224 |
|  | ACACCGGTGAGTGAGTGTGTGCGTGG | 417 |
|  | AAAACCACGCACACACTCACTCACCG | 418 |
| Endogenous Target 4 (EMX1) | GAGTCCGAGCAGAAGAAGAA | 225 |
|  |  | 226 |
|  | ACACCGAGTCCGAGCAGAAGAAGAA | 419 |
|  | AAAACTTCTTCTTCTGCTCGGACTCG | 420 |
| Endogenous Target 5 (RNF2) | GTCATCTTAGTCATTACCTGG | 227 |
|  |  | 228 |
|  | ACACCGTCATCTTAGTCATTACCTGG | 421 |
|  | AAAACCAGTAATGACTAAGATGACG | 422 |
|  | GAATCCCTTCTGCAGCACCG | 229 |
|  | ACACCGAATCCCTTCTGCAGCACCG | — |
|  | AAAACGGTGCTGCAGAAGGGATTCCG | 423 | sequences of oligonucleotides used to generate expression plasmids encoding single gRNAs/variant single gRNAs targeted to sites in the EGFP reporter gene and single gRNAs targeted to six endogenous human gene targets.
, SEQ ID NO:.

EGFP Activity Assays

U2OS.EGFP cells harboring a single integrated copy of an EGFP-PEST fusion gene were cultured as previously described (Reyon et al., Nat Biotech 30, 460-465 (2012)). For transfections, 200,000 cells were Nucleofected with the indicated amounts of sgRNA expression plasmid and pJDS246 together with 30 ng of a Td-tomato-encoding plasmid using the SE Cell Line 4D-Nucleofector™ X Kit (Lonza) according to the manufacturer's protocol. Cells were analyzed 2 days post-transfection using a BD LSRII flow cytometer. Transfections for optimizing gRNA/Cas9 plasmid concentration were performed in triplicate and all other transfections were performed in duplicate.

PCR Amplification and Sequence Verification of Endogenous Human Genomic Sites

PCR reactions were performed using Phusion Hot Start II high-fidelity DNA polymerase (NEB) with PCR primers and conditions listed in Table B. Most loci amplified successfully using touchdown PCR (98° C., 10 s; 72-62° C., −1° C./cycle, 15 s; 72° C., 30 s]10 cycles, [98° C., 10 s; 62° C., 15 s; 72° C., 30 s]25 cycles). PCR for the remaining targets were performed with 35 cycles at a constant annealing temperature of 68° C. or 72° C. and 3% DMSO or 1M betaine, if necessary. PCR products were analyzed on a QIAXCEL capillary electrophoresis system to verify both size and purity. Validated products were treated with ExoSap-IT (Affymetrix) and sequenced by the Sanger method (MGH DNA Sequencing Core) to verify each target site.

TABLE B

| Actual Target in U2OS.EGFP cells | Forward PCR Primer | SEQ ID NO | Reverse PCR Primer | SEQ ID NO: | PCR Conditions | Watson-Crick Transversions | non-Watson-Crick Transversions | Transitions |
|---|---|---|---|---|---|---|---|---|
| | TCCAGATGGCACATTGTCAG | 436. | AGGGAGCAGGAAAGTGAGGT | 748. | DMSO | 0 | 0 | 1 |
| | GGGGCCACTCTTCTTCCAT | 437. | ACCCAGACTCCTGTGTGGC | 749. | No DMSO | 2 | 0 | 0 |
| | GCTAAGCAGAGATGCCTATGCC | 438. | ACCACCCTTTCCCCAGAAA | 750. | DMSO | 0 | 0 | 2 |
| | ACCCCACAGCCAGGTTTTCA | 439. | GAATCACTGCACCTGGCCATC | 751. | DMSO | 1 | 1 | 0 |
| | TGCGGCAACTTCAGACAACC | 440. | TAAAGGGCGTGCTGGGAGAG | 752. | DMSO | 0 | 2 | 0 |
| | GCATGTCAGGATCTGACCC | 441. | TGCAGGGCCATCTTGTGT | 753. | DMSO | 1 | 1 | 1 |
| | CCACCACATGTTCTGGGTGC | 442. | CTGGGTCTGTTCCCTGTGG | 754. | DMSO | 0 | 2 | 1 |
| | GGCTCTCCCTGCCCTAGTTT | 443. | GCAGTCAAGTTGGAACCCG | 755. | DMSO | 1 | 0 | 2 |
| | GGGGTGAGAACATGAGATGCA | 444. | AGATTTGTGCACTGCCTGCCT | 756. | DMSO | 0 | 1 | 0 |
| | CCCGACCTCCGCTCCAAAGC | 445. | GGACCCTGCACACCCTGGC | 757. | DMSO | 2 | 1 | 1 |
| | TGCAAGGTCGCATAGTCCCA | 446. | CAGGAGGGGAAGTTGTCC | 758. | DMSO | 1 | 1 | 2 |
| | GCCCATTCTTTTTGCAGTGGA | 447. | GAGAGCAAGTTTGTTCCCCAGG | 759. | DMSO | 0 | 1 | 0 |
| | GCCCCCAGCCCCTCGTTTC | 448. | GCTGCTGGTAGGGGAGCTGG | 760. | DMSO | 1 | 2 | 2 |
| | CGGCTGCCTTCCCTGAGTCC | 449. | GGGTGACGCTTGCCATGAGC | 761. | 72C Anneal, 3% DMSO | 1 | 2 | 0 |
| | TGACCCTGGAGTACAAAATGTTCCCA | 450. | GCTGAGACAACCAGCCCAGCT | 762. | 72C Anneal, 3% DMSO | 2 | 1 | 0 |
| | TGCCTCCACCCTTAGCCCCT | 451. | GCAGCCGATCCCACACTGGGG | 763. | DMSO | 1 | 0 | 2 |
| | AACTCAGGACACACTGCCTGT | 452. | CCCAGGAGCAGGGTACAATGC | 764. | DMSO | 0 | 1 | 2 |
| | TCCTCCTTGGAGAGGGGCCC | 453. | CCTTTGGAAGGGGCCTTGGGTGG | 765. | DMSO | 0 | 3 | 0 |
| | CCGAGGGCATGGGCAATCCT | 454. | GGCTGCTGCGAGTTGCCAAC | 766. | DMSO | 0 | 1 | 3 |
| | TGCTTTTGCATGGGGTCAGACA | 455. | GGGGTTGCTTGCCCTCTGT | 767. | DMSO | 0 | 2 | 2 |
| | AGTCCTCCTTCTCATTTCTCTTCTGCTGT | 456. | CACAGAAGGATGTGTGCAGGTT | 768. | DMSO | 0 | 2 | 2 |
| | AGCAGACACAGTCAGGTGAATGCTGCT | 457. | GGTCAGGTGTGCTGCTAGGCA | 769. | DMSO | 1 | 1 | 2 |
| | CCTGTGGGGCTCTCAGGTGT | 458. | ACTGCCTGCCAAAGTGGGTGT | 770. | No DMSO TD | 1 | 1 | 2 |
| | AGCTGCACTGGGGAATGAGT | 459. | TGCCGGGTAATAGCTGGCTT | 771. | DMSO | 0 | 1 | 3 |
| | CCAGCCTGGGCAACAAAGCG | 460. | GGGGGCTTCCAGGTCACAGG | 772. | 72C Anneal, 3% DMSO, 6% DMSO | 0 | 3 | 1 |
| | TACCCCCACTGCCCCATTGC | 461. | ACAAGTCCATGCTTAGCAGAGGG | 773. | DMSO | 0 | 1 | 3 |

TABLE B-continued

| | | | | | 0/1 | | |
|---|---|---|---|---|---|---|---|
| GGGTGATTGAAGTTTGCT CCAGG GGGTGATTGAAGTTTGCT GCAGG (SEQ ID NO: 424) | ACGGATTCACGACGGAGTGC | 462. | CCGAGTCCGTGCAGAGAGC | 774. | DMSO | 3 | 2 | 2 |
| | TGTGGTTGAAGTAGGGGACAGGT | 463. | TGGCCCAATTGGAAGTGATTTCGT | 775. | DMSO | 0 | 1 | 0 |
| | TGGGATGCGCAGAGTCATCAACGT | 464. | GGCCCAATCGTAGAGGATGCA | 776. | DMSO | 0 | 3 | 1 |
| | ATGGGGCCTCCAGTCTGTG | 465. | TGCACCCACACAGCCAGCAA | 777. | DMSO | 0 | 3 | 1 |
| | GGGGAGGGAGGACCAGGGAA | 466. | AATTAGCTGGGCGCGGTGGT | 778. | 72C Anneal, 3% DMSO | 0 | 1 | 3 |
| | ATCCCGTGCAGGAAGTCGCC | 467. | CAGGCGGCCCCTTGAGGAAT | 779. | DMSO | 3 | 1 | 0 |
| | CCCCAACCCTTTGCTCAGCG | 468. | TGAGGAGAACACCAGGCAGA | 780. | DMSO | 1 | 2 | 1 |
| | ATCGACGAGGAGGGGCCTT | 469. | CCCCTCACTCAAGCAGGCCC | 781. | DMSO | 0 | 3 | 1 |
| | TGCTCAAGGGGCCTGTTCCA | 470. | CAGGGGCAGTGGCAGAGTC | 782. | No DMSO | 1 | 3 | 0 |
| | TGCCTGGCACGCAGTAGTG | 471. | GGGAAGGGGGAACAGTGCA | 783. | DMSO | 0 | 0 | 5 |
| | Not optimized | | | | | 1 | 1 | 3 |
| | ACCTGGGCTTGCCACTAGGG | 472. | GCTGCTCGCAGTTAAGCACCA | 784. | DMSO | 1 | 3 | 1 |
| | GTGGCCCGGCTACTGCTACC | 473. | GGTTCCACAAGCTGGGGGCA | 785. | DMSO | 3 | 2 | 0 |
| | Not optimized | | | | | 1 | 3 | 1 |
| | GCAAGAGGCGGAGGAGACCC | 474. | AGAGTCATCATCCATTTCCTGGGGGC | 786. | DMSO | 2 | 3 | 0 |
| | GGGGTCAGTGGTGGTGATATCCCCT | 475. | AGGGAATCCTTTTTCCATTGCTTGTTT | 787. | 1M betaine, TD | 1 | 4 | 0 |
| | AGAGAGGCCACGTGGAGGGT | 476. | GCCTCCCCTCCTCCTTCCCA | 788. | DMSO | 1 | 3 | 1 |
| | GACAGTGCCTTGCGATGCAC | 477. | TCTGACCGGTATGCCTGACG | 789. | DMSO | 3 | 2 | 0 |
| | TGTGTGAACGCAGCCTGCT | 478. | TGGTCTAGTACTTCCTCCAGCCTT | 790. | DMSO | 3 | 1 | 1 |
| | GGTTCTCCCTTGGCTCCTGTGA | 479. | CCCACTGCTCCTAGCCCTGC | 791. | DMSO | 1 | 3 | 1 |
| | TGAAGTCAACAATCTAAGCTTCCACCT | 480. | AGCTTTGGTAGTTGGAGTCTTTGAAGG | 792. | DMSO | 3 | 1 | 2 |
| | TGATTGGGCTGCAGTTCATGTACT | 481. | GCACAGCCTGCCCTTGAAG | 793. | DMSO | 2 | 1 | 3 |
| | TCCATGGGCCCCTCTGAAAGA | 482. | AGCGGCTTCTCTTCTGCGA | 794. | DMSO | 1 | 0 | 5 |

TABLE B-continued

| | | | | | |
|---|---|---|---|---|---|
| GCGGTTGCGTGGGGTTGATGC | 483. | GAGTTCCTCCTCCCCGCCAGT | 795. | DMSO | 2 | 0 | 4 |
| AGGCAAGATTTTCCAGTGTGCAAGA | 484. | GCTTTTGCCTGGGACTCCGC | 796. | DMSO | 2 | 0 | 4 |
| GCTGCTGGTCGGGCTCTCTG | 485. | GCTCTGTCCCACTTCCCCTGG | 797. | No DMSO TD | 3 | 1 | 2 |
| GCTGCGAGGCTTCCGTGAGA | 486. | CGCCCCTAGAGCTAAGGGGT | 798. | DMSO | 3 | 2 | 1 |
| CCAGGAGCCTGAGAGCTGCC | 487. | AGGGCTAGGACTGCCAGTGAGC | 799. | DMSO | 1 | 3 | 2 |
| CTGTGCTTCAGCCTGGGTCT | 488. | GCCTGGGGCTGTGAGTAGTTT | 800. | DMSO | 2 | 3 | 1 |
| AGCTCGCGCCAGATCTGTGG | 489. | ACTTCGCAGGCTGAGGCAGG | 801. | 72C Anneal, 3% DMSO | 4 | 2 | 0 |
| AGAGAAGTCGAGGAAGAGAGAG | 490. | CAGCAGAAAGTTCATGGTTTCG | 802. | DMSO | | | |
| TGGACAGCTGCAGTACTCCCTG | 491. | ACTGATCGATGATGGCCTATGGGT | 803. | DMSO | 0 | 0 | 2 |
| CAAGATGTGCACTTGGGCTA | 492. | GCAGCCTATTGTCTCCTGGT | 804. | DMSO | 1 | 0 | 1 |
| GTCCAGTGCCTGACCCTGGC | 493. | AGCATCATGCCTCCAGCTTCA | 805. | DMSO | 1 | 1 | 1 |
| GCTCCCGATCCTCTGCCACC | 494. | GCAGCTCCCACCACCCTCAG | 806. | DMSO | 1 | 2 | 0 |
| GGGGACAGGCAGGCAAGGAG | 495. | GTGCGTGTCCGTTCACCCT | 807. | DMSO | 1 | 1 | 1 |
| AAGGGCTGCTGGTAGGAC | 496. | CGTGATTCGAGTTCCTGGCA | 808. | DMSO | 2 | 1 | 0 |
| GACCCTCAGGAAGCTGGGAG | 497. | CTGCGAGATGCCCCAAATCG | 809. | 1M betaine, TD | 1 | 0 | 2 |
| CCGCGGCCGCTCTGCTAGA | 498. | TGCTGGGATTACAGGCGCGA | 810. | DMSO | 1 | 1 | 1 |
| CCAGGTGGTGTCAGCGGAGG | 499. | TGCCTGGCCCTCTCTGAGTCT | 811. | DMSO | 0 | 2 | 1 |
| CGACTCCACGGCGTCTCAGG | 500. | CAGCGCAGTCCAGCCCGATG | 812. | 1M betaine, TD | 2 | 1 | 0 |
| CTTTCCCTCCCCCAGCACCAC | 501. | GCTACACAGGTTGCACAGTGAGAGGT | 813. | DMSO | 1 | 1 | 1 |
| CCCCGGGGAGTCTGTCCTGA | 502. | CCCAGCCGTTCCAGGTCTTCC | 814. | 72C Anneal, 3% DMSO | 1 | 0 | 2 |
| GAAGCGCGAAAACCCGGCTC | 503. | TCCAGGGTCCTTCTCGGCCC | 815. | DMSO | 1 | 0 | 2 |
| AGGGTGGTCAGGGAGGCCTT | 504. | CATGGGGCTCGGACCTCGTC | 816. | DMSO | 2 | 0 | 1 |
| GGGAAGAGGCAGGGCTGTCG | 505. | TGCCAGGAAGGAAGTGGCC | 817. | 72C Anneal, 3% DMSO | 0 | 2 | 1 |

TABLE B-continued

| | | | | | |
|---|---|---|---|---|---|
| GAGTGACGATGAGCCCCGGG | 818. | CCCTTAGCTGCAGTGCCCC | 0 | 1 | 3 |
| CCCATGAGGGGTTTGAGTGC | 506. | | | | |
| CACCTGGGCATCTGGGTGG | 507. | TGAAGATGGGCAGTTTGGGG | 0 | 2 | 2 |
| TCATGATCCCCAAAAGGGCT | 508. | ACTGGGGTTGGGAGGGGAT | 2 | 0 | 2 |
| TGGTGCCCAGAATAGTGGCCA | 509. | CCATTTGTGCTGATCTGTGGGT | 1 | 0 | 3 |
| GCCTCAGACAACCCTGCCC | 510. | AGGAAATGTGTTGTGCCAGGGC | 1 | 2 | 1 |
| | 511. | GCCAAGTGTTACTCATCAAGAAAGTGG | 2 | 1 | 1 |
| GCCGGGACAAGACTGAGTTGGG | 512. | TCCCGAACTCCCGCAAAACG | 1 | 2 | 1 |
| TGCTGCAGGTGGTTCCGAG | 513. | CTGGAACCGCATCCTCCGCA | 1 | 0 | 3 |
| ACACTGGTCCAGGTCCCGTCT | 514. | GGCTGTGCCTTCCGATGAA | 2 | 1 | 1 |
| ATCGCGCCAAAGCACAGGT | 515. | AGGCTTCTGAAAAGTCCTCAATGCA | 3 | 0 | 2 |
| CTCTCCCCCCCACCCCCCCCTCTGG (SEQ ID NO: 425) | | | | | |
| Not optimized | | | | | |
| CCCTCATGGTGGTCTTACGGCA | 516. | AGCCACACATCTTTCTGGTAGGG | 1 | 1 | 2 |
| TGCGTCGCTCATCTGGGAG | 517. | AGGGTGGGGTGTACTGGCTCA | 1 | 1 | 2 |
| GAGCTGAGACGGCACCACTG | 518. | TGGCCTTGAACTCTTGGGCT | 0 | 3 | 1 |
| Not optimized | | | | | |
| AGTGAGAGTGGCACGAACCA | 519. | CAGTAGGTGGTCCCTTCCGC | 1 | 2 | 1 |
| Not optimized | | | | | |
| GGGAGAACCTTGTCCAGCCT | 520. | AAGCCGAAAAGCTGGGCAAA | 2 | 1 | 1 |
| CTTCCCAGTGTGCCCCGTCC | 521. | ACACAGTCAGAGCTCCGCCG | 1 | 1 | 3 |
| Not optimized | | | | | |
| CTGAGAGGGGAGGGGGAGG | 522. | TCGACTGGTCTTGTCCTCCCA | 0 | 2 | 3 |
| CAGCCTGCTGATCGGAAAA | 523. | TGCAGCCAAGAGAAAAAGCCT | 3 | 0 | 4 |
| TCCCCTCTGACCCGGAACCCA | 524. | ACCCGACTTCCTCCCCATTGC | 1 | 0 | 2 |
| TGGGGGTTTGCGTGCTTGTCA | 525. | GCCAGGAGGACACCAGGACC | 2 | 1 | 4 |
| ATCAGGTGCCAGGAGAGACAC | 526. | GGCCCTGAGAGTGGAGAGTGG | 4 | 1 | 0 |
| | | | 4 | 1 | 0 |

| | |
|---|---|
| 818. | 68C Anneal, 3% DMSO |
| 819. | DMSO |
| 820. | DMSO |
| 821. | DMSO |
| 822. | DMSO |
| 823. | No DMSO TD |
| 824. | DMSO |
| 825. | No DMSO TD |
| 826. | DMSO |
| 827. | DMSO |
| 828. | DMSO |
| 829. | DMSO |
| 830. | 1M betaine, TD |
| 831. | DMSO |
| 833. | DMSO |
| 834. | DMSO |
| 835. | 68C Anneal, 3% DMSO |
| 836. | 1M betaine, TD |
| 837. | DMSO |
| 838. | DMSO |
| 839. | DMSO |

TABLE B-continued

| | | | | | | |
|---|---|---|---|---|---|---|
| ATTTCCTCCCCCCCC-CCTCAGG (SEQ ID NO: 426) | Not optimized | | | | | |
| | TGAGCCACATGAATCAAGGCCTCC | ACCTCTCCAAGTCTCAGTAACTCTCT | 527. | 840. | DMSO | 1 | 4 | 0 |
| | GGTCCCTCTGTGCAGTGAA | CTTTGTGGACCTGCACAGC | 528. | 841. | DMSO | 1 | 3 | 1 |
| | GCGAGGCTGCTGACTGCCT | GCTGGGACTACAGACATGTGCCA | 529. | 842. | DMSO | 2 | 2 | 2 |
| | ATTGCAGGCGTGTCCAGCA | AAATCCTGCATGGTGATGGGAGT | 530. | 843. | DMSO | 2 | 2 | 2 |
| | | | | | | 1 | 1 | 5 |
| | TGCTCTGCCATTTATGTCCTATGAACT | ACAGCCTCTTCTCCATGACTGAGC | 531. | 844. | DMSO | 1 | 3 | 2 |
| | TCCGCCCAAACAGGAGGCAG | GCGGTGGGGAAGCCATTGAG | 532. | 845. | DMSO | 2 | 3 | 1 |
| | GGGGGTCTGGCTCACCTGA | CCTGTCGGGAGAGTGCCTGC | 533. | 846. | DMSO | 3 | 1 | 2 |
| | TCCTGGTCATTTGCTAGAACTCTGGA | ACTCCAGATGCAACCAGGGCT | 534. | 847. | DMSO | 3 | 2 | 1 |
| | CGTGTGGTGAGCCTGAGTCT | GCTTCACCGTAGAGTCTGCT | 535. | 848. | DMSO | 3 | 0 | 3 |
| | AGGCCCTGATAATTCATGCTACCAA | TCAGTGACACCTTTTGTATTCGGCA | 536. | 849. | DMSO | 0 | 2 | 4 |
| | Not optimized | | 537. | | | 2 | 2 | 2 |
| | TCCAGATGGCACATTGTCAG | AGGGAGCAGGAAAGTGAGGT | 538. | 850. | DMSO | | | |
| | GCAGGCAAGCTGTCAAGGGT | CACCGACACACCCACTCACC | 539. | 851. | DMSO | 0 | 0 | 1 |
| | GAGGGGAAAGTCACCGACAA | TACCCGGGCCGTCTGTTAGA | 540. | 852. | DMSO | 0 | 0 | 2 |
| | GACACCCCACACCACTCTCATGC | TGAATCCCTTCACCCCCAAG | 541. | 853. | DMSO | 1 | 0 | 1 |
| | TCCTTTGAGGTTCATCCCCC | CCAATCCAGGATGATTCCGC | 542. | 854. | DMSO | 1 | 1 | 0 |
| | CAGGGCCAGGAACACAGGAA | GGGAGTATGTGCGGAGTG | 543. | 855. | DMSO | 1 | 0 | 1 |
| | TGCAGCCTGAGTGAGCAAGTGT | GCCCAGGTGCTAAGCCCCTC | 544. | 856. | DMSO | 1 | 1 | 0 |
| | TACAGCCTGGGTGATGAGC | TGTGTCATGGACTTTCCCATTGT | 545. | 857. | 1M betaine, TD | 1 | | 2 |
| | GGCAGGCATTAAACTCATCAGTCC | TCTCCCCAAGGTATCAGAGAGCT | 546. | 858. | DMSO | 1 | 1 | 0 |
| | GGGCCTCCCTGCTGGTTCTC | GCTGCCGTCCGAACCCAAGA | 547. | 859. | DMSO | 0 | 1 | 1 |
| | ACAAACCAGGTGGACCGAA | ACTCCGAAAATGCCCCGCAGT | 548. | 860. | DMSO | 1 | 1 | 0 |
| | AGGGGAGGGTTCAGTGGTTGC | TTGAGAGGGTTCAGTGGTTGC | 549. | 861. | DMSO | 1 | 0 | 1 |
| | CTAATGCTTACCGCTGCGGG | AGCCAACGGCAGATGCAAAT | 550. | 862. | DMSO | 1 | 0 | 1 |

TABLE B-continued

| Sequence 1 | SEQ ID | Sequence 2 | SEQ ID | Condition | | | |
|---|---|---|---|---|---|---|---|
| GAGCGAAGTTAACCCACCGC | 551. | CACACATGCACATGCCCCTG | 863. | 68C, 3% DMSO | 2 | 0 | 0 |
| GCATGTGTCTAACTGGAGACAATAGCA | 552. | TCCCCCATATCAACACACACA | 864. | DMSO | 2 | 0 | 0 |
| GCCCCTCCCGCCTTTGTGT | 553. | TGGGCAAAGGACATGAAACAGACA | 865. | DMSO | 2 | 0 | 0 |
| GCCTCAGCTCTGCTCTTAAGCCC | 554. | ACGAACAGAGATCATTTTTCATGGCTTCC | 866. | DMSO | 2 | 0 | 0 |
| CTCCAGACCTGGCTACCA | 555. | CCCTCTCCGGAAGTGCCTTG | 867. | DMSO | 0 | 1 | 1 |
| TCTGTCTCACCACACAGTTACCACC | 556. | GTTGCCTGGGGATGGGGTAT | 868. | DMSO | 0 | 1 | 1 |
| GGGGACCCTCAAGAGGCACT | 557. | GGGCATCAAAGGATGGGGAT | 869. | DMSO | 2 | 0 | 1 |
| TGTGGAGGGTGGGACCTGGT | 558. | ACAGTGAGGTGCGGTCTTTGGG | 870. | DMSO | 1 | 0 | 2 |
| CGGGGTGGCAGTGACGTCAA | 559. | GGTGCAGTCCAAGAGCCCCC | 871. | DMSO | 0 | 0 | 3 |
| AGCTGAGGCAGAGTCCCCGA | 560. | GGGAGACAAGAGCAGCGCCTC | 872. | DMSO | 1 | 1 | 1 |
| ACCACCAGACCCCACCTCCA | 561. | AGGACGACTTGTGCCCCATTCA | 873. | 72C Anneal, 3% DMSO | 1 | 1 | 1 |
| GGGTCAGGACGCAGGTCAGA | 562. | TCCACCACCCACCCATCCT | 874. | 72C Anneal, 3% DMSO | 2 | 0 | 1 |
| ACACTCTGGGCTAGTGCTGGA | 563. | GCCCCCTCACCACATGATGCT | 875. | DMSO | 2 | 0 | 1 |
| GGGGCCATTCCTCTGCTGCA | 564. | TGGGGATCCTTGCTCATGGC | 876. | DMSO | 3 | 0 | 0 |
| ACACACTGGCTGCATTCACCA | 565. | CCTGCACGAGGCCAGTGTT | 877. | DMSO | 2 | 1 | 0 |
| TGGGCACGTAGTAAACTGCACCA | 566. | CTCGCCGCCTGACTGTAGG | 878. | DMSO | 0 | 3 | 1 |
| TCAGCTGGTCCTGGGCTTGG | 567. | AGAGACACTGGGTAGCAGTCAGT | 879. | DMSO | 2 | 1 | 0 |
| AGACACAGCCAGGGCCTCAG | 568. | GGTGGGCGTGTGTGTGTACC | 880. | 68C, 3% DMSO | 1 | 1 | 1 |
| ACACTCTCACACACGACCAA | 569. | GAGAAGTCAGGGCTGGCGGG | 881. | 72C Anneal, 3% DMSO | 1 | 2 | 0 |
| ACTGCCTGCATTTCCCCGT | 570. | TGGTGAGGGCTTCAGGGAGC | 882. | DMSO | 1 | 1 | 1 |
| GCCAGGTTCATTGACTGCCC | 571. | TCCTTCTACACATCGGCGGC | 883. | DMSO | 2 | 1 | 0 |
| CGAGGGAGCCGAGTTCGTAA | 572. | CTGACCTGGGGCTCTTGGTAC | 884. | DMSO | 1 | 2 | 0 |
| TCCTCGGGAAGTCATGGCTTCA | 573. | GCACTGAGCAACCAGGAGCAC | 885. | DMSO | 2 | 1 | 0 |
| Not optimized | | | | | 1 | 0 | 3 |
| TAAACCGTTGCCCCGCCTC | 574. | GCTCCCCTGCCAGGTGAACC | 886. | DMSO | 2 | 1 | 1 |

TABLE B-continued

| | | | | | | | |
|---|---|---|---|---|---|---|---|
| CCTGTGAGACTCCAGGTCC | 575. | CTGCGGAGTGGCTGGCTATA | 887. | DMSO | 2 | 0 | 2 |
| CTCGGGACTGACAAGCCGG | 576. | GGAGCAGTCTTCCAGGGCC | 888. | DMSO | 3 | 0 | 1 |
| CCCCGACCAAAGCAGGAGCA | 577. | CTGGCAGCCTCTGGATGGGG | 889. | DMSO | 1 | 2 | 1 |
| Not optimized | | | | | 0 | 3 | 1 |
| ATTTCAGAGCCCCGGGGAAA | 578. | AGGCCGCGTGTTATGGTTA | 890. | DMSO | 1 | 2 | 1 |
| GCCAGTGGCTTAGTGTCTTTGTGT | 579. | TGACATATTTCCTGGGCCATGGGT | 891. | DMSO | 2 | 1 | 1 |
| TGCCAGAAGAACATGGCCAGA | 580. | CCATGCTGACATCATATACTGGGAAGC | 892. | DMSO | 3 | 1 | 0 |
| GCGTGTCTCTGTGTGCCTGC | 581. | CCAGGCTGGGCACACAGGTT | 893. | DMSO | 3 | 1 | 0 |
| Not optimized | | | | | 2 | 2 | 0 |
| TGCCCAGTCCAATATTTCAGCAGCT | 582. | AGGATGAGTTCATGTCCTTTGTGGGG | 894. | DMSO | 2 | 2 | 0 |
| GGGTGAAAATTTGGTACTGTTAGCTGT | 583. | AATGACTCATTCCCTGGGTATCTCCCA | 895. | DMSO | 2 | 2 | 0 |
| TGCCCCATCAATCACCTCGGC | 584. | CAAGGTCGGCAGGGCAGTGA | 896. | DMSO | 1 | 2 | 2 |
| GCCTCCTCGCCGCTGGTAA | 585. | TGAGAGTTCCTGTTGCTCCACACT | 897. | DMSO | 1 | 2 | 2 |
| Not optimized | | | | | 2 | 2 | 1 |
| GCCACCAAAATAGCCAGCGT | 586. | ACATGCATCTGTGTGCGT | 898. | DMSO | 3 | 0 | 2 |
| ACAGACTGACCCTTGAAAATACCAGT | 587. | TGTATCTTTCTTGCCAATGGTTTTCCC | 899. | DMSO | 2 | 1 | 2 |
| AGCCAAATTTCTCAACAGCAGCACT | 588. | TCCTGGAGAGCAGGCATTTTTGT | 900. | DMSO | 3 | 1 | 1 |
| ACCTCCTTGTGTCGCTGGGC | 589. | GGGCGGAAGGTAACCCTGGG | 901. | DMSO | 2 | 1 | 2 |
| CACAAAGCTCTACCTTTCCAGTAGTGT | 590. | TGATCCGATGGTTGTTCACAGCT | 902. | DMSO | 3 | 1 | 1 |
| TGTGGGGATTACCTGCCTGGC | 591. | ACGCACAAAAATGCCCTGTCA | 903. | DMSO | 2 | 2 | 1 |
| TGAGGCAGACCCAGTCATCCAGC | 592. | GCCCGAGCACAGTGTAGGGC | 904. | DMSO | 2 | 3 | 0 |
| ATTAGCTGGGCGTGGCGGAG | 593. | ACTGCATCTCATCTCAGGCAGCT | 905. | DMSO | 2 | 1 | 3 |
| TGAAGCAGAAGGAGTGGAGAAGGA | 594. | TCAGCTTCACATCTGTTTCAGTTCAGT | 906. | DMSO | 4 | 0 | 2 |
| TGGTGGAGTGTGTGTGTGGT | 595. | AGAGCAGAAAGAGAGTGCCCA | 907. | DMSO | 1 | 3 | 2 |
| GCCCCTGTACGTCCTGACAGC | 596. | TGCACAAGCCACTTAGCCTCTCT | 908. | DMSO | 3 | 1 | 2 |
| AGCGCAGGTAAACAGGCCCA | 597. | TCTCTCGCCCCGTTTCCTTGT | 909. | DMSO | 3 | 1 | 2 |

TABLE B-continued

| | | | | | | |
|---|---|---|---|---|---|---|
| | ATGGGTGCCAGGTACCACGC | 598. | ACAGCAGGAGGAGCCGCAG | 910. | DMSO | 2 | 3 | 1 |
| | CGGGCGGGTGGACAGAATGAG | 599. | AGGAGGTCTCGAGCCAGGGG | 911. | DMSO | 2 | 3 | 1 |
| | TCAACCTAGTGAACACAGACCACTGA | 600. | GTCTATATACAGCCCACAACCTCATGT | 912. | DMSO | 1 | 2 | 3 |
| | GCCAGGGCCAGTGGATTGCT | 601. | TGTCATTTCTTAGTATGTCAGCCGGA | 913. | DMSO | 2 | 4 | 0 |
| | GAGCCCCACCGGTTCAGTCC | 602. | GCCAGAGCTACCCACTCGCC | 914. | DMSO | 1 | 3 | 2 |
| | | 603. | | | | | |
| | GGAGCAGCTGGTCAGAGGGG | 604. | GGGAAGGGGACACTGGGGA | 915. | DMSO | 0 | 1 | |
| | TCTCTCCTTCAACTCATGACCAGCT | 605. | ATCTGCACATGTATGTACAGAGAGTCAT | 916. | DMSO | 2 | 1 | 1 |
| AAGACAGAGGAGGAAGAAG AAGGG (SEQ ID NO: 427) | TGGGGAATCTCCAAAGAACCCCC | 606. | AGGGTGTACTGTGGAACTTTGCA | 917. | DMSO | 1 | 1 | 1 |
| | GATGGCCCCACTGAGCACGT | 607. | ACTTCGTAGAGCCTTAAACATGTGGC | 918. | DMSO | 1 | 0 | 2 |
| | AGGATTAATGTTTAAAGTCACTGGTGG | 608. | TCAAACAAGGTGCAGATACAGCA | 919. | 1M betaine, TD | 1 | 0 | 2 |
| | TCCAAGCCACTGGTTTCTCAGTCA | 609. | TGCTCTGTGGATCATATTTTGGGGGA | 920. | DMSO | 0 | 1 | 2 |
| | ACTTTCAGAGCTTGGGGCAGGT | 610. | CCCACGCTGAAGTGCAATGGC | 921. | DMSO | 1 | 1 | 1 |
| | CAAAGCATGCCTTTCAGCCG | 611. | GGCTCTTTCGATTTGGCACCT | 922. | 1M betaine, TD | 1 | 1 | 1 |
| | Not optimized | | | | | | |
| | GGACTCCCTGCAGCTCCAGC | 612. | AGGAACACAGGCCAGCTGG | 923. | 72C Anneal, 6% DMSO | 0 | 0 | 2 |
| | CCCTTTAGGCACCTTCCCCA | 613. | CCGACCTTCATCCCTCTG | 924. | DMSO | 0 | 0 | 3 |
| | TGATTCTGCCTTAGAGTCCCAGGT | 614. | TGGGCTCTGTGTCCCTACCCA | 925. | DMSO | 0 | 3 | 2 |
| | Not optimized | | | | | 2 | 1 | 0 |
| | AGGCAGGAGAGCAAGCAGGT | 615. | ACCCTGACTACTGACTGACCGCT | 926. | DMSO | 0 | 1 | 2 |
| | CTCCCATTGCGACCCGAG | 616. | AGAGGCATTGACTTGGAGCACCT | 927. | DMSO | 1 | 2 | 0 |
| | CTGGAGCCCAGCAGGAAGGC | 617. | CCTCAGGGAGGGGGCCTGAT | 928. | DMSO | 1 | 2 | 0 |

TABLE B-continued

| Sequence 1 | # | Sequence 2 | Conditions | | | |
|---|---|---|---|---|---|---|
| ACTGTGGGCGTTGTCCCAC | 618. | AGGTCGGTGCAGGGTTTAAGGA | 929. | DMSO | 1 | 0 | 3 |
| GGCGCTCCCTTTTTCCCTTTGT | 619. | CGTCACCCATCGTCTCGTGGA | 930. | DMSO | 2 | 0 | 2 |
| TGCCATCTATAGCAGCCCCCT | 620. | GCATCTTGCTAACCGTACTTCTTCTGA | 931. | DMSO | 1 | 0 | 3 |
| GTGGAGACGCTAAACCTGTGAGGT | 621. | GCTCCTGGCCTCTTCCTACAGC | 932. | DMSO | 1 | 2 | 1 |
| CCGAACTTCTGCTGAGCTTGATGC | 622. | CCAAGTCAATGGGCAACAAGGGA | 933. | DMSO | 0 | 2 | 2 |
| Not optimized | | | | | 1 | 1 | 2 |
| TGCCCCCAAGACCTTTCTCC | 623. | ATGGCAGGCAGAGGAGGAAG | 934. | DMSO | 2 | 0 | 2 |
| GGGTGGGGCCATTGTGGGTT | 624. | CTGGGGCCAGGGTTTCTGCC | 935. | DMSO | 3 | 0 | 1 |
| TGGAGAACATGAGAGGCTTGCAA | 625. | TCCTTCTGTAGGCAATGGAACAA | 936. | DMSO | 3 | 0 | 1 |
| GCCACACATGGTAGAAGTCGG | 626. | GGCAGATTTCCCCCATGCTG | 937. | 1M betaine, TD | 1 | 2 | 1 |
| TGTACACCCCAAGTCCTCCC | 627. | AAGGGGAGTGTGCAAGCCTC | 938. | DMSO | 3 | 1 | 0 |
| AGGTCTGCTAGAGATGCAGCA | 628. | AGTCCAACACTCAGTGAGACCCT | 939. | DMSO | 3 | 1 | 0 |
| CCAAGAGGACCCAGCTGTTGGA | 629. | GGGTATGGAATTCTGGATTAGCAGAGC | 940. | DMSO | 0 | 2 | 2 |
| ACCATCTCTTCATTGATGAGTCCCAA | 630. | ACACTGTGAGTATGCTTGGCGT | 941. | DMSO | 2 | 2 | 0 |
| GGCTGCGGGAGATGAGCTC | 631. | TCGGATGCTTTTCCACAGGCT | 942. | DMSO | 2 | 2 | 1 |
| TCTTCCAGGAGGGCAGCTCC | 632. | CCAATCCTGAGCTCCTACAAGGCT | 943. | DMSO | 1 | 0 | 4 |
| GAGCTGCACTGGATGGCACT | 633. | TGCTGGTTAAGGGGTGTTTTGGA | 944. | DMSO | 0 | 1 | 3 |
| TCTGGAAGGTGAGGAGGCCA | 634. | TGGGGACAATGGAAAAGCAATGA | 945. | DMSO | 2 | 2 | 3 |
| CTTGCTCCCAGCCTGACCC | 635. | AGCCCTTGCCATGCAGGACC | 946. | DMSO | 3 | 1 | 1 |
| GGGATTTTTATCTGTTGGGTGCGAA | 636. | AACCACAGATGTACCCTCAAAGCT | 947. | DMSO | 2 | 2 | 1 |
| ACCCATCAGGACCGCAGCAC | 637. | TCTGGAACCTGGGAGGCGGA | 948. | 72C Anneal, 3% DMSO | 3 | 1 | 1 |
| CGTCCCTTGGGCCTGGGGTTC | 638. | CCTCCTTGGGCCTGGGGTTC | 949. | DMSO | 1 | 3 | 1 |
| CCCTCTGCAAGGTGGAGTCTC | 639. | AGATGTTCTGTCCCCAGGCCT | 950. | DMSO | 1 | 3 | 1 |
| GGCTTCCACTGCTGAAGGCCT | 640. | TGCCGCTCCACATACCCTCC | 951. | DMSO | 2 | 1 | 2 |

TABLE B-continued

| | | | | | |
|---|---|---|---|---|---|
| AGCCATTGCCTGTCGGGTGATGT | 641. | AGCACCTATTGGACACTGGTTCTCT | 952. | DMSO | 1 | 3 | 1 |
| TCTAGAGCAGGGCACAATGC | 642. | TGGAGATGGAGCCTGGTGGGA | 953. | DMSO | 2 | 2 | 1 |
| GGTCTCAGAAAATGGAGAAAGCACG | 643. | CCCAGAGAAACCTGGGCCCT | 954. | DMSO | 1 | 2 | 3 |
| GGTTGCTGATACCAAAACGTTTGCCT | 644. | TGGGTCCTCTCCACCTCTGCA | 955. | DMSO | 0 | 3 | 3 |
| ACTCTCCTTAAGTACTGATATGGCTGT | 645. | CAGAATCTTGCTCTGTTGCCCA | 956. | DMSO | 0 | 4 | 2 |
| Not optimized | | | | | 2 | 2 | 2 |
| Not optimized | | | | | 2 | 2 | 2 |
| CAATGCCTGCAGTCCTCAGGA | 646. | TCCCAAGAGAAAACTCTGTCCTGACA | 957. | DMSO | 4 | 1 | 1 |
| GCATTGGCTGCCAGGGAAA | 647. | TGGCTGTGCTGGGCTGTGTT | 958. | DMSO | 2 | 2 | 2 |
| CCACAAGCCTCAGCCTACCCG | 648. | ACAGGTGCCAAAACACTGCCT | 959. | DMSO | 2 | 1 | 3 |
| GCCTCTTGCAAATGAGACTCCTTTT | 649. | CGATCAGTCCCCTGCGTCC | 960. | DMSO | 2/1 | 2/3 | 2 |
| TCCCAGAATCTGCCTCCCCA | 650. | AGGGGTTTCCAGGCACATGGG | 961. | DMSO | 0 | 4 | 2 |
| | | | 962. | | | | |
| TCCTAAAATCAGTTTTGAGATTTACTTCC | 651. | AAAGTGTTAGCCAACATACAGAAGTCAGGA | 963. | DMSO | | | |
| ACATCTGGGAAAGCAAAAGTCAACA | 652. | TGTCTGAGTATCTAGGCTAAAAGTGGT | 964. | DMSO | 1/2 | 1 | 1 |
| ACGATCTTGCTTCATTTCCCTGTACA | 654. | AGTGCTTTGTGAACTGAAAAGCAAACA | 965. | DMSO | 0 | 3 | 0 |
| GCACCTTGGTGCTGCTAAATGCC | 655. | GGGCAACTGAACAGGCATGAATGG | 966. | DMSO | 1 | 2 | 0 |
| AACTGTCCTGCATCCCCGCC | 656. | GGTGCACCTGGATCCACCCA | 967. | DMSO | 1 | 1 | 1 |
| Not optimized | | | | | 1 | 1 | 1 |

TABLE B-continued

| | | | | | | |
|---|---|---|---|---|---|---|
| | 657. | ACCACTGCTGCAGGGTCCAG | 968. | CATCACCCTCCACCAGGCCC | 0 | 0 |
| | | | | | 2 | 2 |
| | 658. | TGGTGCGTGGTGTGTGTGGT | 969. | Not optimized | 1 | 1 |
| | | | | CCTGACCCGTGGTTCCCGAC | | |
| | 659. | CCATGTGACTACTGGGCTGCCC | 970. | TGGGAACATTGGAGAAGTTCCTGA | 1 | 2 |
| | 660. | GGTTCTCTCTCCAGAAAAGAAA GAGG | 971. | AGCCTTGGCAAGCAACTCCCT | 1 | 3 |
| | 661. | GCCAGAGGCTCTCAGCAGTGC | 972. | GGCAGCCGACTTCAGAGCCA | 1 | 3 |
| | 662. | ACTGTGCCCAGCCCCATATT | 973. | CCAGCCTTGGTCAATATGGCA | 2 | 1 |
| | 663. | CGGGTTGTGCCACCGGGTTA | 974. | ATGCCAACACTCGAGGGGCC | 2 | 1 |
| | 664. | AGAGTTCAGGCATGAAAAGAAGC AACA | 975. | TTGCTCTAGTGGGGAGGGGG | 3 | 1 |
| | 665. | TGCAATTTGAGGGGCTCTCTTCA | 976. | AGCTGAAGATAGCAGTGTTTAAGCCT | 1 | 2 |
| | 666. | TGCCAGCCAAAAGTTGTTAGTGT GT | 977. | AGTCACTGGAGTAAGCCTGCCT | 2 | 2 |
| | 667. | TGTGTGGTAGGGAGCAAAACGAC A | 978. | GGGTCTCCTCAGTGCCCTG | 2 | 2 |
| | 668. | TGACCACACACCCCACG | 979. | TGGGGGCTGTTAAGAGGCACA | 2 | 1 |
| | 669. | TGTGTTTTTAAGCTGCACCCCAGG | 980. | TCAAAACAGATTGACCAAGGCCAAAT | 1 | 3 |
| | 670. | GCACGCAGCTGACTCCCAGA | 981. | TCTGGCACCAGGACTGATTGTACA | 2 | 1 |
| | | | | Not optimized | | |
| | 671. | ACCAGGGCTGCCACAGAGTC | 982. | AGCATCTGTGATACCCTACCTGTCT | 1 | 3 |
| | 672. | CTCGGCCCCTGAGAGTTCAT | 983. | TAGTCTTGTTGCCCAGGCTG | 2 | 1 |
| | 673. | GAGCAGCAGCAAAGCCACCG | 984. | CTGCAACCAGGGGCCCTTACC | 1 | 2 |
| TCCATCTCACTCATTACC TGAGGTCCATCTCACTCA TTACCTGATG (SEQ ID NO: 430) | | | | | | |
| | 674. | AGCCGAGACAATCTGCCCCG | 985. | GCCTGGAGAGCAAGCCTGGG | 1 | 2 |
| | 675. | GGCAGTCTGACCAGTGGGG | 986. | AGTGAAACAAACAAGCAGCAGTCTGA | 1 | 1 |
| TTTATATTAGTGATTACC TGCGG (SEQ ID NO: 431) | | | | | | |

Condition column (between SEQ number and last numeric columns):
- 968: 72C Anneal, 3% DMSO
- 969: 72C Anneal, 3% DMSO
- 970-984: DMSO
- 985: DMSO
- 986: No DMSO TD TABLE B-continued

| | | | | |
|---|---|---|---|---|
| AGGCTCAGAGAGGTAAGCAATGGA | 676. | TGAGTAGACAGAAATGTTACCGGTGTT | 987. | DMSO | 3 | 0 | 2 |
| TCAGAGATGTTAAAGCCTTGGTGGG | 677. | AGTGAACCAAGGGAATGGGGGA | 988. | DMSO | 3 | 0 | 2 |
| TGTGCTTTCTGGGGTAGTGGCA | 678. | CACCTCAGCCCTGTAGTCCTGG | 989. | DMSO | 0 | 4 | 1 |
| CCATTGGGTGACTGAATGCACA | 679. | GCCACTGTCCCCAGCCTATT | 990. | 1M betaine, TD | 1 | 3 | 1 |
| ACCAAGAAAGTGAAAAGGAAACCC | 680. | TGAGATGGCATACGATTTACCCA | 991. | DMSO | 1 | 2 | 2 |
| AGGGTGGGGACTGAAAGGAGCT | 681. | TGGCATCACTCAGAGATTGAAACACA | 992. | DMSO | 3 | 1 | 1 |
| ACCAGTGCTGTGTGACCTTGGA | 682. | TCCTATGGGAGGGAGGCTTCT | 993. | DMSO | 3 | 1 | 1 |
| CCAGGTGTGGTGGTTCATGAC | 683. | GCATACGGCAGTAGAATGAGCC | 994. | 68C, 3% DMSO | 4 | 0 | 1 |
| CAGGCGCTGGGTTCTTAGCCT | 684. | CCTTCCTGGGCCCCATGGTG | 995. | DMSO | 2 | 3 | 0 |
| TGGGGTCCAAGATGTCCCT | 685. | TGAAACTGCTTGATGAGGTGTGGA | 996. | DMSO | 1 | 2 | 2 |
| GCTGGGCTTGGTGTGTATATGC | 686. | ACTTGCAAAGCTGATAACTGACTGA | 997. | DMSO | 5 | 0 | 1 |
| AGTTGGTGTCACTGACAATGGGA | 687. | CGCAGCGCACGAGTTCATCA | 998. | DMSO | 3 | 0 | 3 |
| AGAGGAGGCACAATTCAACCCT | 688. | GGCTGGGGAGGCCTCACAAT | 999. | DMSO | 1 | 1 | 4 |
| GGGAAAGTTTGGGAAAGTCAGCA | 689. | AGGACAAGCTACCCCACACC | 1000. | DMSO | 1 | 3 | 2 |
| TGGTGCATCAAAGGGTTGCTTCT | 690. | TCATTCCAGCACGCCGGGAG | 1001. | DMSO | 0 | 3 | 3 |
| CCCAGGCTGCCCCATCACACT | 691. | TGGAGTAAGTATACCTTGGGGACCT | 1002. | DMSO | 1 | 3 | 2 |
| TCAGTGCCCCTGGGTCCTCA | 692. | TGTGCAAATACCTAGCACGGTGC | 1003. | DMSO | 4 | 2 | 0 |
| AGCACTCCCTTTTGAATTTTGGTGCT | 693. | ACTGAAGTCCAGCCTCTTCCATTTCA | 1004. | DMSO | 2 | 1 | 3 |
| GAAACCGGTCCCTGGTGCCA | 694. | GGGGAGTAGAGGGTAGTGTTGCC | 1005. | DMSO | 2 | 0 | 4 |
| TTGCGGGTCCCCTGTGGAGTC | 695. | AGGTGCCGTGTTGTGCCCAA | 1006. | DMSO | 1 | 2 | 3 |
| GCCCTACAATCTGCTCTCCCTCCA | 696. | | 1007. | | | | |
| TTGGAGTGTGGCCCGGGTTG | 697. | GGGCCCGGGAAAGAGTTGCTG | 1008. | DMSO | | | |
| | 698. | ACCTCTCTTTCTCTGCCTCACTGT | 1009. | DMSO | 0 | 1 | 1 |

TABLE B-continued

| | | | | | | |
|---|---|---|---|---|---|---|
| CACACCATGCTGATCCAAGGC | GCAGTACGGAAGCACGAAGC | 699. | | | 1 | 1 |
| CTCCAGGGCTCGCTGTCCAC | CTGGGCTCTGCTGGTTCCCC | 700. | DMSO | 0 | 2 | 1 |
| CTGTGGTAGCCGTGGCCAGG | CCCCATACCACCTCTCCGGGA | 701. | DMSO | 0 | 2 | 1 |
| GGTGGCGGGACTTGAATGAG | CCAGCGTGTTTCCAAGGGAT | 702. | DMSO | 0 | 1 | 2 |
| CCAGAGGTGGGCCCTGTGA | TTTCCACACTCAGTTCTGCAGGA | 703. | 1M betaine, TD | 1 | 1 | 1/2 |
| GGAATCCCCCTCTCCAGCC CCTGG GGAATCCCCCTCTCCAGCC TCTGG (SEQ ID NO: 432) | | | DMSO | | | |
| GGAATCTCTTCCTTGGCA TCTGG (SEQ ID NO: 433) | | | | | | |
| TGTGACTGGTTGTCCTGCTTTCCT | GCAGTGTTTTGTGGGTGATGGGCA | 704. | 1M betaine, TD | 0 | 1 | 5 |
| CTGGCCAAGGGGTGAGTGGG | TGGGACCCCAGCAGCCAATG | 705. | DMSO | 1 | 0 | 2 |
| ACGGTGTGCTGGCTGCTCTT | ACAGTGCTGACCGTGCTGGG | 706. | DMSO | 1 | 1 | 1 |
| TGGTTTGGGCCTCAGGGATGG | TGCCTCCCACAAAAATGTCTACCT | 707. | DMSO | 0 | 0 | 3 |
| TGGTTTGGGCCTCAGGGATGG | ACCCCTTATCCCAGAACCCATGA | 708. | DMSO | 0 | 0 | 3 |
| TCCAAGTCAGCGATGAGGGCT | TGGGAGCTGTTCCTTTTTGGCCA | 709. | DMSO | 0 | 3 | 0 |
| CACCCCTCTCAGCTTCCAA | GCTAGAGGGTCTGCTGCCTT | 710. | DMSO | 1 | 2 | 0 |
| AGACCCCTTGGCCAAGCACA | CTTGCTCTCACCCCGCCTCC | 711. | DMSO | 2 | 1 | 0 |
| ACATGTGGGAGGCGGACAGA | TCTCACTTTGCTGTTACCGATGTCG | 712. | DMSO | 0 | 1 | 3 |
| GGACGACTGTGCCTGGGACA | AGTGCCCAGAGTGTTGTAACTGCT | 713. | 72C Anneal, 3% DMSO | 0 | 1 | 3 |
| GGAGAGCTCAGCGCCAGGTC | CAGCGTGGCCCGTGGGAATA | 714. | DMSO | 1 | 1 | 2 |
| GCTGAAGTGCTCTTGGGGTGCT | ACCCCACTGTGGATGAATTGGTA CC | 715. | DMSO | 1 | 1 | 2 |
| TCGGGGTGCACATGGCCATC | TTGCCTCGCAGGGGAAGCAG | 716. | DMSO | 0 | 1 | 3 |
| CTCGTGGGAGGCCAACACCT | AGCCACCAAACATACCAGGCT | 717. | DMSO | 2 | 0 | 2 |
| GCATGCCTTTAATCCCGGCT | AGGATTTCAGAGTGATGGGCT | 718. | DMSO | 2 | 1 | 1 |
| CGCCCAGCCACAAAGTGCAT | GCAAATTTCTGCACCTACTCTTAGG CCT | 719. | DMSO | 1 | 1 | 2 |

TABLE B-continued

| | | | | | |
|---|---|---|---|---|---|
| AGCTCACAAGAATTGGAGGTAACAGT | 720. | GCAGTCACCCTTCACTGCCTGT | 1031. | DMSO | 1 | 1 | 2 |
| | 721. | GGGGCTAAGCATTGTCAGACCCC | 1032. | DMSO | 2 | 0 | 2 |
| | 722. | TCTCCTGCCTCAGCCTCCCA | 1033. | 1M betaine, TD | 1 | 2 | 1 |
| | 723. | TCTCCTGCCTCAGCCTCCCA | 1034. | 1M betaine, TD | 1 | 2 | 1 |
| | 724. | TCTCCTGCCTCAGCCTCCCA | 1035. | 1M betaine, TD | 1 | 2 | 1 |
| | 725. | GGCCTGTCAACCAACCAACC | 1036. | DMSO | 2 | 2 | 0 |
| | 726. | AAATCCTGCAGCCTCCCCTT | 1037. | DMSO | 0 | 2 | 2 |
| | 727. | TCCTCCCCACTCAGCCTCCC | 1038. | DMSO | 0 | 3 | 1 |
| | 728. | AGGGACCAGCCACTACCCTTCA | 1039. | DMSO | 2 | 2 | 0 |
| | 729. | GGGGAGAGATTGGAGTTCCCC | 1040. | DMSO | 1 | 0 | 4 |
| | 730. | TCTGCCTGGGGTGCTTTCCC | 1041. | DMSO | 1 | 1 | 3 |
| | 731. | GCCCCGACAGATGAGGCCTC | 1042. | DMSO | 1 | 2 | 2 |
| | 732. | ACCCAGGAATTGCCACCCCA | 1043. | DMSO | 1 | 2 | 3 |
| CAGATTACTGCTGACGCA CCGGG (SEQ ID NO: 434) | 733. | GCAGACACTAGAGACCCGCCC | 1044. | DMSO | 3 | 2 | 0 |
| | 734. | ACCTGCGTCTCTGTGCTGCA | 1045. | DMSO | 2 | 3 | 0 |
| | 735. | CCTGCCCCATGCTGCCTG | 1046. | DMSO | 2 | 2 | 1 |
| | 736. | AGGGAATGATGTTTTCCACCCCCT | 1047. | DMSO | 2 | 3 | 0 |
| | 737. | TGCATTGACGTACGATGGCTCA | 1048. | DMSO | 1 | 3 | 1 |
| | 738. | ACCTGAGCAACATGAACTCACCTG G | 1049. | DMSO | 2 | 1 | 2 |
| ACACAAACTTCTGCAGCA CCTGG ACACAAACTTCTGCAGCA CGTGG (SEQ ID NO: 435) | 739. | ACCATTGGTGAACCCAGTCA | 1050. | 1M betaine, TD | 3/2 | 3 | 1 |
| | 740. | TCAGCTATAACCTGGGACTTGTGC T | 1051. | DMSO | 2 | 1 | 3 |

TABLE B-continued

| | | | | |
|---|---|---|---|---|
| AGCAGCCAGTCCAGTGTCCTG | 741. | CCCTTTCATCGAGAACCCCAGGG | 1052. | DMSO | 3 | 1 | 2 |
| TGGACGCTGCTGGGAGGAGA | 742. | GAGGTCTCGGGCTGCTCGTG | 1053. | DMSO | 0 | 3 | 3 |
| AGGTTTGCACTCTGTTGCCTGG | 743. | TGGGGTGATTGGTTGCCAGT | 1054. | DMSO | 3 | 2 | 1 |
| TCTTCCTTTGCCAGGCAGCACA | 744. | TGCAGGAATAGCAGGTATGAGGAGT | 1055. | DMSO | 4 | 0 | 2 |
| GGACGCCTACTGCCTGGACC | 745. | GCCCTGGCAGCCCATGGTAC | 1056. | DMSO | 3 | 0 | 3 |
| AGGCAGTCATCGCCTTGCTA | 746. | GGTCCCACCTTCCCCTACAA | 1057. | DMSO | 2 | 3 | 1 |
| Not optimized | | | | | 3 | 1 | 2 |
| CCCCAGCCCCCACCAGTTTC | 747. | CAGCCCAGGCCACAGCTTCA | 1058. | DMSO | 1 | 4 | 1 |

Sequences and characteristics of genomic on- and off-target sites for six RGNs targeted to endogenous human genes and primers and PCR conditions used to amplify these sites.

Determination of RGN-Induced On- and Off-Target Mutation Frequencies in Human Cells For U2OS.EGFP and K562 cells, $2\times10^5$ cells were transfected with 250 ng of gRNA expression plasmid or an empty U6 promoter plasmid (for negative controls), 750 ng of Cas9 expression plasmid, and 30 ng of td-Tomato expression plasmid using the 4D Nucleofector System according to the manufacturer's instructions (Lonza). For HEK293 cells, $1.65\times10^5$ cells were transfected with 125 ng of gRNA expression plasmid or an empty U6 promoter plasmid (for the negative control), 375 ng of Cas9 expression plasmid, and 30 ng of a td-Tomato expression plasmid using Lipofectamine LTX reagent according to the manufacturer's instructions (Life Technologies). Genomic DNA was harvested from transfected U2OS.EGFP, HEK293, or K562 cells using the QIAamp DNA Blood Mini Kit (QIAGEN), according to the manufacturer's instructions. To generate enough genomic DNA to amplify the off-target candidate sites, DNA from three Nucleofections (for U2OS.EGFP cells), two Nucleofections (for K562 cells), or two Lipofectamine LTX transfections was pooled together before performing T7EI. This was done twice for each condition tested, thereby generating duplicate pools of genomic DNA representing a total of four or six individual transfections. PCR was then performed using these genomic DNAs as templates as described above and purified using Ampure XP beads (Agencourt) according to the manufacturer's instructions. T7EI assays were performed as previously described (Reyon et al., 2012, supra).

DNA Sequencing of NHEJ-Mediated Indel Mutations

Purified PCR products used for the T7EI assay were cloned into Zero Blunt TOPO vector (Life Technologies) and plasmid DNAs were isolated using an alkaline lysis miniprep method by the MGH DNA Automation Core. Plasmids were sequenced using an M13 forward primer (5'-GTAAAACGACGGCCAG-3' (SEQ ID NO: 1059) by the Sanger method (MGH DNA Sequencing Core).

Example 1a. Single Nucleotide Mismatches

To begin to define the specificity determinants of RGNs in human cells, a large-scale test was performed to assess the effects of systematically mismatching various positions within multiple gRNA/target DNA interfaces. To do this, a quantitative human cell-based enhanced green fluorescent protein (EGFP) disruption assay previously described (see Methods above and Reyon et al., 2012, supra) that enables rapid quantitation of targeted nuclease activities (FIG. 2B) was used. In this assay, the activities of nucleases targeted to a single integrated EGFP reporter gene can be quantified by assessing loss of fluorescence signal in human U2OS.EGFP cells caused by inactivating frameshift insertion/deletion (indel) mutations introduced by error prone non-homologous end-joining (NHEJ) repair of nuclease-induced double-stranded breaks (DSBs) (FIG. 2B). For the studies described here, three ~100 nt single gRNAs targeted to different sequences within EGFP were used, as follows:

```
EGFP Site 1
                          (SEQ ID NO: 9)
GGGCACGGGCAGCTTGCCGGTGG EGFP Site 2
                          (SEQ ID NO: 10)
GATGCCGTTCTTCTGCTTGTCGG EGFP Site 3
                          (SEQ ID NO: 11)
GGTGGTGCAGATGAACTTCAGGG
```

Each of these gRNAs can efficiently direct Cas9-mediated disruption of EGFP expression (see Example 1e and 2a, and FIGS. 3E (top) and 3F (top)).

In initial experiments, the effects of single nucleotide mismatches at 19 of 20 nucleotides in the complementary targeting region of three EGFP-targeted gRNAs were tested. To do this, variant gRNAs were generated for each of the three target sites harboring Watson-Crick transversion mismatches at positions 1 through 19 (numbered 1 to 20 in the 3' to 5' direction; see FIG. 1) and the abilities of these various gRNAs to direct Cas9-mediated EGFP disruption in human cells tested (variant gRNAs bearing a substitution at position 20 were not generated because this nucleotide is part of the U6 promoter sequence and therefore must remain a guanine to avoid affecting expression.)

For EGFP target site #2, single mismatches in positions 1-10 of the gRNA have dramatic effects on associated Cas9 activity (FIG. 2C, middle panel), consistent with previous studies that suggest mismatches at the 5' end of gRNAs are better tolerated than those at the 3' end (Jiang et al., Nat Biotechnol 31, 233-239 (2013); Cong et al., Science 339, 819-823 (2013); Jinek et al., Science 337, 816-821 (2012)). However, with EGFP target sites #1 and #3, single mismatches at all but a few positions in the gRNA appear to be well tolerated, even within the 3' end of the sequence. Furthermore, the specific positions that were sensitive to mismatch differed for these two targets (FIG. 2C, compare top and bottom panels)—for example, target site #1 was particularly sensitive to a mismatch at position 2 whereas target site #3 was most sensitive to mismatches at positions 1 and 8.

Example 1b. Multiple Mismatches

To test the effects of more than one mismatch at the gRNA/DNA interface, a series of variant gRNAs bearing double Watson-Crick transversion mismatches in adjacent and separated positions were created and the abilities of these gRNAs to direct Cas9 nuclease activity were tested in human cells using the EGFP disruption assay. All three target sites generally showed greater sensitivity to double alterations in which one or both mismatches occur within the 3' half of the gRNA targeting region. However, the magnitude of these effects exhibited site-specific variation, with target site #2 showing the greatest sensitivity to these double mismatches and target site #1 generally showing the least. To test the number of adjacent mismatches that can be tolerated, variant gRNAs were constructed bearing increasing numbers of mismatched positions ranging from positions 19 to 15 in the 5' end of the gRNA targeting region (where single and double mismatches appeared to be better tolerated).

Testing of these increasingly mismatched gRNAs revealed that for all three target sites, the introduction of three or more adjacent mismatches results in significant loss of RGN activity. A sudden drop off in activity occurred for three different EGFP-targeted gRNAs as one makes progressive mismatches starting from position 19 in the 5' end and adding more mismatches moving toward the 3' end. Specifically, gRNAs containing mismatches at positions 19 and 19+18 show essentially full activity whereas those with mismatches at positions 19+18+17, 19+18+17+16, and 19+18+17+16+15 show essentially no difference relative to a negative control (FIG. 2F). (Note that we did not mismatch position 20 in these variant gRNAs because this position needs to remain as a G because it is part of the U6 promoter that drives expression of the gRNA.)

Additional proof of that shortening gRNA complementarity might lead to RGNs with greater specificities was obtained in the following experiment: for four different EGFP-targeted gRNAs (FIG. 2H), introduction of a double mismatch at positions 18 and 19 did not significantly impact activity. However, introduction of another double mismatch at positions 10 and 11 then into these gRNAs results in near complete loss of activity. Interestingly introduction of only the 10/11 double mismatches does not generally have as great an impact on activity.

Taken together, these results in human cells confirm that the activities of RGNs can be more sensitive to mismatches in the 3' half of the gRNA targeting sequence. However, the data also clearly reveal that the specificity of RGNs is complex and target site-dependent, with single and double mismatches often well tolerated even when one or more mismatches occur in the 3' half of the gRNA targeting region. Furthermore, these data also suggest that not all mismatches in the 5' half of the gRNA/DNA interface are necessarily well tolerated.

In addition, these results strongly suggest that gRNAs bearing shorter regions of complementarity (specifically ~17 nts) will be more specific in their activities. We note that 17 nts of specificity combined with the 2 nts of specificity conferred by the PAM sequence results in specification of a 19 bp sequence, one of sufficient length to be unique in large complex genomes such as those found in human cells.

Example 1c. Off-Target Mutations

To determine whether off-target mutations for RGNs targeted to endogenous human genes could be identified, six single gRNAs that target three different sites in the VEGFA gene, one in the EMX1 gene, one in the RNF2 gene, and one in the FANCF gene were used (Table 1 and Table A). These six gRNAs efficiently directed Cas9-mediated indels at their respective endogenous loci in human U2OS.EGFP cells as detected by T7 Endonuclease 1 (T7EI) assay (Methods above and Table 1). For each of these six RGNs, we then examined dozens of potential off-target sites (ranging in number from 46 to as many as 64) for evidence of nuclease-induced NHEJ-mediated indel mutations in U2OS.EGFP cells. The loci assessed included all genomic sites that differ by one or two nucleotides as well as subsets of genomic sites that differ by three to six nucleotides and with a bias toward those that had one or more of these mismatches in the 5' half of the gRNA targeting sequence (Table B). Using the T7EI assay, four off-target sites (out of 53 candidate sites examined) for VEGFA site 1, twelve (out of 46 examined) for VEGFA site 2, seven (out of 64 examined) for VEGFA site 3 and one (out of 46 examined) for the EMX1 site (Table 1 and Table B) were readily identified. No off-target mutations were detected among the 43 and 50 potential sites examined for the RNF2 or FANCF genes, respectively (Table B). The rates of mutation at verified off-target sites were very high, ranging from 5.6% to 125% (mean of 40%) of the rate observed at the intended target site (Table 1). These bonafide off-targets included sequences with mismatches in the 3' end of the target site and with as many as a total of five mismatches, with most off-target sites occurring within protein coding genes (Table 1). DNA sequencing of a subset of off-target sites provided additional molecular confirmation that indel mutations occur at the expected RGN cleavage site (FIGS. 8A-C).

TABLE 1

On- and off-target mutations induced by RGNs designed to endogenous human genes

| Target | Site name | Sequence | SEQ ID NO: | Indel Mutation Frequency (%) ± SEM U2OS.EGFP | HEK293 | K562 | Gene |
|---|---|---|---|---|---|---|---|
| Target 1 (VEGFA Site 1) | T1 | GGGTGGGGGGAGTTTGCTCcTGG | 1059. | 26.0 ± 2.9 | 10.5 ± 0.07 | 3.33 ± 0.42 | VEGFA |
| | OT1-3 | GGATGGAGGGAGTTTGCTCCTGG | 1060. | 25.7 ± 9.1 | 18.9 ± 0.77 | 2.93 ± 0.04 | IGDCC3 |
| | OT1-4 | GGGAGGGTGGAGTTTGCTCCTGG | 1061. | 9.2 ± 0.8 | 8.32 ± 0.51 | N.D. | LOC116437 |
| | OT1-6 | CGGGGGAGGGAGTTTGCTCCTGG | 1062. | 5.3 ± 0.2 | 3.67 ± 0.09 | N.D. | CACNA2D |
| | OT1-11 | GGGGAGGGGAAGTTTGCTCCTGG | 1063. | 17.1 ± 4.7 | 8.54 ± 0.16 | N.D. | |
| Target 2 (VEGFA Site 2) | T2 | GACCCCCTCCACCCCGCCTCCGG | 1064. | 50.2 ± 4.9 | 38.6 ± 1.92 | 15.0 ± 0.25 | VEGFA |
| | OT2-1 | GACCCCCCCCACCCCGCCCCCGG | 1065. | 14.4 ± 3.4 | 33.6 ± 1.17 | 4.10 ± 0.05 | FMN1 |
| | OT2-2 | GGGCCCCTCCACCCCGCCTCTGG | 1066. | 20.0 ± 6.2 | 15.6 ± 0.30 | 3.00 ± 0.06 | PAX6 |
| | OT2-6 | CTACCCCTCCACCCCGCCTCCGG | 1067. | 8.2 ± 1.4 | 15.0 ± 0.64 | 5.24 ± 0.22 | PAPD7 |
| | OT2-9 | GCCCCCACCCACCCCGCCTCCGG | 1068. | 50.7 ± 5.6 | 30.7 ± 1.44 | 7.05 ± 0.48 | LAMA3 |
| | OT2-15 | TACCCCCCACACCCCGCCTCTGG | 1069. | 9.7 ± 4.5 | 6.97 ± 0.10 | 1.34 ± 0.15 | SPNS3 |
| | OT2-17 | ACACCCCCCCACCCCGCCTCAGG | 1070. | 14.0 ± 2.8 | 12.3 ± 0.45 | 1.80 ± 0.03 | |
| | OT2-19 | ATTCCCCCCCACCCCGCCTCAGG | 1071. | 17.0 ± 3.3 | 19.4 ± 1.35 | N.D. | HDLBP |
| | OT2-20 | CCCCACCCCCCACCCCGCCTCAGG | 1072. | 6.1 ± 1.3 | N.D. | N.D. | ABLIM1 |
| | OT2-23 | CGCCCTCCCCACCCCGCCTCAGG | 1073. | 44.4 ± 6.7 | 28.7 ± 1.15 | 4.18 ± 0.37 | CALY |
| | OT2-24 | CTCCCCACCCACCCCGCCTCAGG | 1074. | 62.8 ± 5.0 | 29.8 ± 1.08 | 21.1 ± 1.68 | |
| | OT2-29 | TGCCCCTCCCACCCCGCCTCTGG | 1075. | 13.8 ± 5.2 | N.D. | N.D. | ACLY |
| | OT2-34 | AGGCCCCCACACCCCGCCTCAGG | 1076. | 2.8 ± 1.5 | N.D. | N.D. | |
| Target 3 (VEGFA Site 3) | T3 | GGTGAGTGAGTGTGTGcGTGTGG | 1077. | 49.4 ± 3.8 | 35.7 ± 1.26 | 27.9 ± 0.52 | VEGFA |
| | OT3-1 | GGTGAGTGAGTGTGTGTGTGAGG | 1078. | 7.4 ± 3.4 | 8.97 ± 0.80 | N.D. | (abParts) |
| | OT3-2 | AGTGAGTGAGTGTGTGTGTGGGG | 1079. | 24.3 ± 9.2 | 23.9 ± 0.08 | 8.9 ± 0.16 | MAX |
| | OT3-4 | GCTGAGTGAGTGTATGCGTGTGG | 1080. | 20.98 ± 11.8 | 11.2 ± 0.23 | N.D. | |
| | OT3-9 | GGTGAGTGAGTGCGTGCGGGTGG | 1081. | 3.2 ± 0.3 | 2.34 ± 0.21 | N.D. | TPCN2 |
| | OT3-17 | GTTGAGTGAATGTGTGcGTGAGG | 1082. | 2.9 ± 0.2 | 1.27 ± 0.02 | N.D. | SLIT1 |
| | OT3-18 | TGTGGGTGAGTGTGTGCGTGAGG | 1083. | 13.4 ± 4.2 | 12.1 ± 0.24 | 2.42 ± 0.07 | COMDA |
| | OT3-20 | AGAGAGTGAGTGTGTGCATGAGG | 1084. | 16.7 ± 3.5 | 7.64 ± 0.05 | 1.18 ± 0.01 | |
| Target 4 (EMX1) | T4 | GAGTCCGAGCAGAAGAAGAAGGG | 1085. | 42.1 ± 0.4 | 26.0 ± 0.70 | 10.7 ± 0.50 | EMX1 |
| | OT4-1 | GAGTTAGAGCAGAAGAAGAAAGG | 1086. | 16.8 ± 0.2 | 8.43 ± 1.32 | 2.54 ± 0.02 | HCN1 |

TABLE 1-continued

On- and off-target mutations induced by RGNs designed to endogenous human genes

| Target | Site name | Sequence | SEQ ID NO: | Indel Mutation Frequency (%) ± SEM | | | Gene |
|---|---|---|---|---|---|---|---|
| | | | | U2OS.EGFP | HEK293 | K562 | |
| Target 5 (RNF2) | T5 | GTCATCTTAGTCATTACCTGTGG | 1087. | 26.6 ± 6.0 | — | — | RNF2 |
| Target 6 (FANCF) | T6 | GGAATCCCTTCTGCAGCACCAGG | 1088. | 33.2 ± 6.5 | — | — | FANCF |

"OT" indicates off-target sites (with numbering of sites as in Table E). Mismatches from the on-target (within the 20 bp region to which the gRNA hybridizes) are highlighted as bold, underlined text. Mean indel mutation frequencies in U2OS.EGFP, HEK293, and K562 cells were determined as described in Methods. Genes in which sites were located (if any) are shown. All sites listed failed to show any evidence of modification in cells transfected with Cas9 expression plasmid and a control U6 promoter plasmid that did not express a functional gRNA.
N.D. = none detected;
— = not tested.

Example 1d. Off-Target Mutations in Other Cell Types

Having established that RGNs can induce off-target mutations with high frequencies in U2OS.EGFP cells, we next sought to determine whether these nucleases would also have these effects in other types of human cells. We had chosen U2OS.EGFP cells for our initial experiments because we previously used these cells to evaluate the activities of TALENs[15] but human HEK293 and K562 cells have been more widely used to test the activities of targeted nucleases. Therefore, we also assessed the activities of the four RGNs targeted to VEGFA sites 1, 2, and 3 and the EMX1 site in HEK293 and K562 cells. We found that each of these four RGNs efficiently induced NHEJ-mediated indel mutations at their intended on-target site in these two additional human cell lines (as assessed by T7EI assay) (Table 1), albeit with somewhat lower mutation frequencies than those observed in U2OS.EGFP cells. Assessment of the 24 off-target sites for these four RGNs originally identified in U2OS.EGFP cells revealed that many were again mutated in HEK293 and K562 cells with frequencies similar to those at their corresponding on-target site (Table 1). As expected, DNA sequencing of a subset of these off-target sites from HEK293 cells provided additional molecular evidence that alterations are occurring at the expected genomic loci (FIGS. 9A-C). We do not know for certain why in HEK293 cells four and in K562 cells eleven of the off-target sites identified in U2OS.EGFP cells did not show detectable mutations. However, we note that many of these off-target sites also showed relatively lower mutation frequencies in U2OS.EGFP cells. Therefore, we speculate that mutation rates of these sites in HEK293 and K562 cells may be falling below the reliable detection limit of our T7EI assay (~2-5%) because RGNs generally appear to have lower activities in HEK293 and K562 cells compared with U2OS.EGFP cells in our experiments. Taken together, our results in HEK293 and K562 cells provide evidence that the high-frequency off-target mutations we observe with RGNs will be a general phenomenon seen in multiple human cell types.

Example 1e. Titration of gRNA- and Cas9-Expressing Plasmid Amounts Used for the EGFP Disruption Assay Single gRNAs were generated for three different sequences (EGFP SITES 1-3, shown above) located upstream of EGFP nucleotide 502, a position at which the introduction of frameshift mutations via non-homologous end-joining can robustly disrupt expression of EGFP (Maeder, M. L. et al., Mol Cell 31, 294-301 (2008); Reyon, D. et al., Nat Biotech 30, 460-465 (2012)).

For each of the three target sites, a range of gRNA-expressing plasmid amounts (12.5 to 250 ng) was initially transfected together with 750 ng of a plasmid expressing a codon-optimized version of the Cas9 nuclease into our U2OS.EGFP reporter cells bearing a single copy, constitutively expressed EGFP-PEST reporter gene. All three RGNs efficiently disrupted EGFP expression at the highest concentration of gRNA-encoding plasmid (250 ng) (FIG. 3E (top)). However, RGNs for target sites #1 and #3 exhibited equivalent levels of disruption when lower amounts of gRNA-expressing plasmid were transfected whereas RGN activity at target site #2 dropped immediately when the amount of gRNA-expressing plasmid transfected was decreased (FIG. 3E (top)).

The amount of Cas9-encoding plasmid (range from 50 ng to 750 ng) transfected into our U2OS.EGFP reporter cells was titrated and EGFP disruption assayed. As shown in FIG. 3F (top), target site #1 tolerated a three-fold decrease in the amount of Cas9-encoding plasmid transfected without substantial loss of EGFP disruption activity. However, the activities of RGNs targeting target sites #2 and #3 decreased immediately with a three-fold reduction in the amount of Cas9 plasmid transfected (FIG. 3F (top)). Based on these results, 25 ng/250 ng, 250 ng/750 ng, and 200 ng/750 ng of gRNA-/Cas9-expressing plasmids were used for EGFP target sites #1, #2, and #3, respectively, for the experiments described in Examples 1a-1d.

The reasons why some gRNA/Cas9 combinations work better than others in disrupting EGFP expression is not understood, nor is why some of these combinations are more or less sensitive to the amount of plasmids used for transfection. Although it is possible that the range of off-target sites present in the genome for these three gRNAs might influence each of their activities, no differences were seen in the numbers of genomic sites that differ by one to six bps for each of these particular target sites (Table C) that would account for the differential behavior of the three gRNAs.

TABLE C

Numbers of off-target sites in the human genome for six RGNs targeted to endogenous human genes and three RGNs targeted to the EGFP reporter gene

| Target Site | Number of mismatches to on-target site | | | | | | |
|---|---|---|---|---|---|---|---|
| | 0 | 1 | 2 | 3 | 4 | 5 | 6 |
| Target 1 (VEGFA Site 1) | 1 | 1 | 4 | 32 | 280 | 2175 | 13873 |
| Target 2 (VEGFA Site 2) | 1 | 0 | 2 | 35 | 443 | 3889 | 17398 |

TABLE C-continued

Numbers of off-target sites in the human genome for six RGNs targeted to endogenous human genes and three RGNs targeted to the EGFP reporter gene

| Target Site | Number of mismatches to on-target site | | | | | | |
|---|---|---|---|---|---|---|---|
| | 0 | 1 | 2 | 3 | 4 | 5 | 6 |
| Target 3 (VEGFA Site 3) | 1 | 1 | 17 | 377 | 6028 | 13398 | 35517 |
| Target 4 (EMX) | 1 | 0 | 1 | 18 | 276 | 2309 | 15731 |
| Target 5 (RNF2) | 1 | 0 | 0 | 6 | 116 | 976 | 7443 |
| Target 6 (FANCF) | 1 | 0 | 1 | 18 | 271 | 1467 | 9551 |
| EGFP Target Site #1 | 0 | 0 | 3 | 10 | 156 | 1365 | 9755 |
| EGFP Target Site #2 | 0 | 0 | 0 | 11 | 96 | 974 | 7353 |
| EGFP Target Site #3 | 0 | 0 | 1 | 14 | 165 | 1439 | 10361 |

Off-target sites for each of the six RGNs targeted to the VEGFA, RNF2, FANCF, and EMX1 genes and the three RGNs targeted to EGFP Target Sites #1, #2 and #3 were identified in human genome sequence build GRCh37. Mismatches were only allowed for the 20 nt region to which the gRNA anneals and not to the PAM sequence.

Example 2: Shortening gRNA Complementarity Length to Improve RGN Cleavage Specificity It was hypothesized that off-target effects of RGNs might be minimized without compromising on-target activity simply by decreasing the length of the gRNA-DNA interface, an approach that at first might seem counterintuitive. Longer gRNAs can actually function less efficiently at the on-target site (see below and Hwang et al., 2013a; Ran et al., 2013). In contrast, as shown above in Example 1, gRNAs bearing multiple mismatches at their 5' ends could still induce robust cleavage of their target sites (FIGS. 2A and 2C-2F), suggesting that these nucleotides might not be required for full on-target activity. Therefore, it was hypothesized that truncated gRNAs lacking these 5' nucleotides might show activities comparable to full-length gRNAs (FIG. 2A). It was speculated that if the 5' nucleotides of full-length gRNAs are not needed for on-target activity then their presence might also compensate for mismatches at other positions along the gRNA-target DNA interface. If this were true, it was hypothesized that gRNAs might have greater sensitivity to mismatches and thus might also induce substantially lower levels of Cas9-mediated off-target mutations (FIG. 2A).

Experimental Procedures

The following experimental procedures were used in Example 2.

Plasmid Construction

All gRNA expression plasmids were assembled by designing, synthesizing, annealing, and cloning pairs of oligonucleotides (IDT) harboring the complementarity region into plasmid pMLM3636 (available from Addgene) as described above (Example 1). The resulting gRNA expression vectors encode a ~100 nt gRNA whose expression is driven by a human U6 promoter. The sequences of all oligonucleotides used to construct gRNA expression vectors are shown in Table D. The Cas9 D10A nickase expression plasmid (pJDS271) bearing a mutation in the RuvC endonuclease domain was generated by mutating plasmid pJDS246 using a QuikChange kit (Agilent Technologies) with the following primers: Cas9 D10A sense primer 5'-tggataaaaagtattctattggtttagccatcggcactaattccg-3' (SEQ ID NO: 1089); Cas9 DI OA antisense primer 5'-cggaattagtgccgatggctaaaccaatagaatactttttatcca-3' (SEQ ID NO:1090). All the targeted gRNA plasmids and the Cas9 nickase plasmids used in this study are available through the non-profit plasmid distribution service Addgene (addgene.org/crispr-cas).

TABLE D

Sequences of oligonucleotides used to construct gRNA expression plasmids

| 20 | 19 | 18 | 17 | 16 | 15 | 14 | 13 | 12 | 11 | 10 | 9 | 8 | 7 | 6 | 5 | 4 | 3 | 2 | 1 | oligonucleotide 1 (5' to 3') | SEQ ID NO: | oligonucleotide 2 (5' to 3') | SEQ ID NO: |
|---|---|---|---|---|---|---|---|---|---|---|---|---|---|---|---|---|---|---|---|---|---|---|---|
| | | G | C | A | C | G | G | G | C | A | G | C | T | T | G | C | C | G | G | ACACCGCACGGGCAGCTTGCCGCGG | 1091 | AAAACGGGGCAAGCTGCCCGTGCG | 1180 |
| | | G | C | A | C | G | G | G | C | A | G | C | T | T | G | C | C | G | c | ACACCGCACGGGCAGCTTGCCGCGG | 1092 | AAAACGCGGCAAGCTGCCCGTGCG | 1181 |
| | | G | C | A | C | G | G | G | C | A | G | C | T | T | G | C | C | C | G | ACACCGCACGGGCAGCTTGCCCGGG | 1093 | AAAACCGGGCAAGCTGCCCGTGCG | 1182 |
| | | G | C | A | C | G | G | G | C | A | G | C | T | T | G | C | g | G | G | ACACCGCACGGGCAGCTTGCGCCGG | 1094 | AAAACCCGCAAGCTGCCCGTGCG | 1183 |
| | | G | C | A | C | G | G | G | C | A | G | C | T | T | G | g | C | G | G | ACACCGCACGGGCAGCTTGGCCGGG | 1095 | AAAACCCGGAAGCTGCCCGTGCG | 1184 |
| | | G | C | A | C | G | G | G | C | A | G | C | T | T | c | C | C | G | G | ACACCGCACGGGCAGCTTCCCGGGG | 1096 | AAAACCCGGGAAGCTGCCCGTGCG | 1185 |
| | | G | C | A | C | G | G | G | C | A | G | T | a | a | G | C | C | G | G | ACACCGCACGGGCAGTAGCCGGGG | 1097 | AAAACCGGCTAGCTGCCCGTGCG | 1186 |
| | | G | C | A | C | G | G | G | C | A | G | c | T | T | G | C | C | G | G | ACACCGCACGGGCAGCATGCCGGG | 1098 | AAAACCCGGCATGCTGCCCGTGCG | 1187 |
| | | G | C | A | C | G | G | G | C | A | c | C | T | T | G | C | C | G | G | ACACCGCACGGGCACCTGCCTGCGG | 1099 | AAAACCCGGCAACTGCCCGTGCG | 1188 |
| | | G | C | A | C | G | G | G | C | t | G | C | T | T | G | C | C | G | G | ACACCGCACGGGCTGCTTGCCGGG | 1100 | AAAACCCGGCAAGCTCCCCGTGCG | 1189 |
| | | G | C | A | C | G | G | G | g | A | G | C | T | T | G | C | C | G | G | ACACCGCACGGGGAGCTTGCCGGG | 1101 | AAAACCCGGCAAGCTCCCCGTGCG | 1190 |
| | | G | C | A | C | G | G | c | C | A | G | C | T | T | G | C | C | G | G | ACACCGCACGGCCAGCTTGCCGCGG | 1102 | AAAACCCGGCAAGCTGGCCGTGCG | 1191 |
| | | G | C | A | C | G | G | G | C | A | G | C | T | T | G | C | C | G | G | ACACCGCACGGGCAGCTTGCCGCGG | 1103 | AAAACCCGGCAAGCTGCCGGTGCG | 1192 |
| | | G | C | A | C | G | c | G | C | A | G | C | T | T | G | C | C | G | G | ACACCGCACGCGCAGCTTGCCGGG | 1104 | AAAACCCGGCAAGCTGCCGGTGCG | 1193 |
| | | G | C | A | C | c | G | G | C | A | G | C | T | T | G | C | C | G | G | ACACCGCACCGGCAGCTTGCCGGG | 1105 | AAAACCCGGCAAGCTGCCGGTGCG | 1194 |
| | | G | C | A | g | G | G | G | C | A | G | C | T | T | G | C | C | G | G | ACACCGCAGGGGCAGCTTGCCGCGG | 1106 | AAAACCCGGCAAGCTGCCCTGCG | 1195 |
| | | G | C | t | C | G | G | G | C | A | G | C | T | T | G | C | C | G | G | ACACCGCTCGGGCAGCTTGCCGCGG | 1107 | AAAACCCGGCAAGCTGCCCGAGCG | 1196 |
| | | G | C | A | C | G | G | G | C | A | G | C | T | T | G | C | C | G | G | ACACCGGACGGGCAGCTTGCCGCCG | 1108 | AAAACGGGGCAAGCTGCCCGTCCG | 1197 |
| | | G | g | A | C | G | G | G | C | A | G | C | T | T | G | C | C | G | G | ACACCGCACGGGCAGCTTGCCCCG | 1109 | AAAACGGGGCAAGCTGCCCGTGCG | 1198 |
| | | G | C | A | C | G | G | G | C | A | G | C | T | a | G | C | C | G | G | ACACCGCACGGGCAGCTACCGGG | 1110 | AAAACCCCCAAGCTGCCCGTGCG | 1199 |
| | | G | C | A | C | G | G | G | C | A | G | C | a | T | G | C | C | G | G | ACACCGCACGGGCAGTACCCGGG | 1111 | AAAACCCGGTAGCTGCCGGTGCG | 1200 |
| | | G | C | A | C | G | G | G | C | A | G | a | T | T | G | C | C | G | G | ACACCGCACGGGCAAGATGCCGCG | 1112 | AAAACCCGATCTTCTGCCGTGCG | 1201 |
| | | G | C | A | C | G | G | c | C | t | c | c | T | T | G | C | C | G | G | ACACCGCACGGGGCTCCTTCCTGGG | 1113 | AAAACCCGGGAAGGAGCCCGTGCC | 1202 |
| | | G | C | A | C | G | G | G | g | A | G | C | T | T | G | C | C | G | G | ACACCGCACGGCGGCCAGCTTGCCGG | 1114 | AAAACCCGGCAAGTCGCCGTGCG | 1203 |
| | | G | A | A | C | c | G | c | C | A | C | C | T | T | G | C | C | C | C | ACACCGCACCGCACCCCAGCTTGCCCG | 1115 | AAAACCCGGCAAGTCGCCGGTGCG | 1204 |
| | | G | c | t | g | G | c | G | C | t | G | g | a | T | c | C | C | G | G | ACACCGCTGGGCGCTACCCGGG | 1116 | AAAACCCGGGAGCATCCTGCCCAGCG | 1205 |
| | | G | g | t | C | G | c | G | C | A | G | g | a | T | G | C | C | G | G | ACACCGGTCGGGCAGCTTGCCGGG | 1117 | AAAACCCGGCAAGCTGCCCGACCG | 1206 |

TABLE D-continued

| | | | | | | | | | | | | | | | |
|---|---|---|---|---|---|---|---|---|---|---|---|---|---|---|---|
| G | C | G | T | C | A | G | T | T | C | T | G | ACACCGCCGTTCTTTCTGCTTGTG | 1118 | AAAACAAGCAGAAGAACGGCG | 1207 |
| G | C | G | T | C | A | G | T | T | C | A | G | ACACCGCCGTTCTTTCTGCTTGAG | 1119 | AAAACTCAAGCAGAAGAACGGCG | 1208 |
| G | C | G | T | C | A | G | T | T | C | T | G | ACACCGCCGTTCTTTCTGCTTCTG | 1120 | AAAACAGAAGCAGAAGAACGGCG | 1209 |
| G | C | G | T | C | A | G | T | T | C | T | G | ACACCGCCGTTCTTTCTGCTAGTG | 1121 | AAAACACTAGCAGAAGAACGGCG | 1210 |
| G | C | G | T | C | A | G | T | T | C | T | G | ACACCGCCGTTCTTCTGCATGTG | 1122 | AAAACACATGCAGAAGAACGGCG | 1211 |
| G | C | G | T | C | A | G | T | T | C | T | G | ACACCGCCGTTCTTCTGGTTGTG | 1123 | AAAACAAGGAGCAGAAGAACGGCG | 1212 |
| G | C | G | T | C | A | G | T | T | C | T | G | ACACCGCCGTTCTTCTCAGCTTGTG | 1124 | AAAACAAGCTGAAGAACGGCG | 1213 |
| G | C | G | T | C | A | G | T | T | C | T | G | ACACCGCCGTTCTTGTGCTTGTG | 1125 | AAAACACAAGCACAAGAACGGCG | 1214 |
| G | C | G | T | C | A | G | T | T | C | T | G | ACACCGCCGTTCTACTTGCTTCTG | 1126 | AAAACAAGCAGTAGAACGGCG | 1215 |
| G | C | G | T | C | A | G | T | T | C | T | G | ACACCGCCGTTCATCTGCTTCTG | 1127 | AAAACACAAGCAGATCGGCG | 1216 |
| G | C | G | T | C | A | G | T | T | C | T | G | ACACCGCCGTTCATGAACGGCG | 1128 | AAAACACAAGCAGTGAACGGCG | 1217 |
| G | C | G | T | C | A | G | T | T | C | T | G | ACACCGCCGTTCTGTTCTGCTTGTG | 1129 | AAAACACAAGCAGACACGGCG | 1218 |
| G | C | G | T | C | A | G | T | T | C | T | G | ACACCGCCGTTCTTCTCTGCTTGTG | 1130 | AAAACAAGCAGCAGAAGTACGGCG | 1219 |
| G | C | G | T | C | A | G | T | T | C | T | G | ACACCGCCGTTCTTCTGCTTGTG | 1131 | AAAACAAGCAGAAGATCGGCG | 1220 |
| G | C | G | T | C | A | G | T | T | C | T | G | ACACCGCCGTTCTTCTGCTTGTG | 1132 | AAAACAAGCAGAGAAGGGCG | 1221 |
| G | C | G | T | C | A | G | T | T | C | T | G | ACACCGCCCCTTCTTCTGCTTGTG | 1133 | AAAACAAGCAGAACAACGGCG | 1222 |
| G | C | G | T | C | A | G | T | T | C | T | G | ACACCGCGTTCTTCTGCTTGTG | 1134 | AAAACTGAAGCAGAAGAACGGCG | 1223 |
| G | C | G | T | C | A | G | T | T | C | T | a | ACACCGCCGTTCTTCTGCTTCAG | 1135 | AAAACTGAAGCAGAAGAACGCCG | 1224 |
| G | C | G | T | a | G | T | T | c | G | T | G | ACACCGCCGTTCTTCTCAAGTG | 1136 | AAAACACTTGCAGAGAAGAACGGCG | 1225 |
| G | C | G | T | C | A | G | T | T | C | T | G | ACACCGCCGTTCTTCTCTGTTGTG | 1137 | AAAACACAAGCTCAAGAACGGCG | 1226 |
| G | C | G | T | C | A | G | T | T | C | T | G | ACACCGCCGTTCCGTTCTGCTTGTG | 1138 | AAAACAAGCAGCAGTTGAACGGCG | 1227 |
| G | C | G | T | C | A | G | T | T | C | T | G | ACACCGCCGTTCCGTTCTGCTTGTG | 1139 | AAAACAAGCAGAACTACGGCG | 1228 |
| G | C | G | T | C | A | G | T | T | C | T | G | ACACCGCCGCCGTAGTTCTGCTTGTG | 1140 | AAAACAAGCAGCAGAAGAACGGCG | 1229 |
| G | C | G | T | C | A | G | T | T | C | T | G | ACACCGCCGCCCATCTTCTGCTTGTG | 1141 | AAAACAAGCAGCAGAAGATGGGCG | 1230 |
| G | C | G | T | C | A | G | T | T | C | T | G | ACACCGGGGTTCTTCTGCTTCAG | 1142 | AAAACTGAAGCAGAAGAACCCCG | 1231 |
| G | T | G | C | A | A | T | T | T | C | T | A | ACACCGGTGCAGATGAACTTCAG | 1143 | AAAACTGAAGTTCATCTGCACCG | 1232 |
| G | T | G | C | A | A | T | T | T | C | T | t | ACACCGGTGCAGATGAACTTCTG | 1144 | AAAACTCAAGTTCATCTGCACCG | 1233 |
| G | T | G | C | A | A | T | T | T | C | T | A | ACACCGGTGCAGATGAACTTGAG | 1145 | AAAACTGTAGTTCATCTGCACCG | 1234 |
| G | T | G | C | A | A | T | T | T | g | T | A | ACACCGGTGCAGATGAACTACAG | 1146 | AAAACTGATGTTCATCTGCACCG | 1235 |
| G | T | G | C | A | A | T | T | T | C | T | A | ACACCGGTGCAGATGAACATCAG | 1147 | AAAACTGAACTTCATCTGCACCG | 1236 |
| G | T | G | C | A | A | T | T | T | C | T | A | ACACCGGTGCAGATGAAGTTCAG | 1148 | AAAACTGAAGATCATCTGCACCG | 1237 |
| G | T | G | C | A | A | T | T | T | C | T | A | ACACCGGTGCAGATGATCTTCAG | 1149 | AAAACTGAAGTACATCTGCACCG | 1238 |
| G | T | G | C | A | A | T | T | T | C | T | A | ACACCGGTGCAGATGTACTTCAG | 1150 | AAAACTGAAGTTGATCTGCACCG | 1239 |
| G | T | G | C | A | t | T | T | T | C | T | A | ACACCGGTGCAGATCAACTTCAG | 1151 | AAAACTGAAGTTCTTCTGCACCG | 1240 |
| G | T | G | C | A | A | T | T | T | C | T | A | ACACCGGTGCAGAAGAACTTCAG | 1152 | AAAACTGAAGTTCAACTGCACCG | 1241 |
| G | T | G | C | A | A | T | T | T | C | T | A | ACACCGGTGCAGTTGAACTTCAG | 1153 | AAAACTGAAGTTCATGTGCACCG | 1242 |
| G | T | G | C | A | A | T | T | T | C | T | A | ACACCGGTGCACATGAACTTCAG | 1154 | AAAACTGAAGTTCATCAGCACCG | 1243 |
| G | T | G | C | A | A | T | T | T | C | T | A | ACACCGGTGCTGATGAACTTCAG | 1155 | AAAACTGAAGTTCATCCACCG | 1244 |
| G | T | G | C | A | A | T | T | T | g | C | A | ACACCGGTGGAGATGATGAACTTCAG | 1156 | AAAACTGAAGTTCATCTGGACCG | 1245 |
| G | T | G | C | A | A | T | T | T | C | T | A | ACACCGGTCCAGATGAACTTCAG | 1157 | AAAACTGAAGTTCATCTCTCCG | 1246 |
| G | a | G | C | A | A | T | T | T | C | T | C | ACACCGGAGCAGATGAACTTCAG | 1158 | AAAACTGAAGTTCATCTGCAGCG | 1247 |

TABLE D-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| | | | G | C | T | G | A | A | T | C | T | T | C | A | ACACCGGTGCAGATGAACTTCAG | 1159 | AAAACTGAAGTTCATCTCAGCG | 1248 |
| | | | G | C | T | G | A | A | C | T | C | T | T | t | ACACCGGTGCAGATGAACTTGTG | 1160 | AAAACACAAGTTCATCTGCACCG | 1249 |
| | | | G | G | T | G | A | A | C | a | T | T | C | C | ACACCGGTGCAGATGAACAACAG | 1161 | AAAACTGTTGTTCATCTGCACCG | 1250 |
| | | | G | G | T | G | A | A | T | g | T | T | C | A | ACACCGGTGCAGATGATGTTCAG | 1162 | AAAACTGAACATCATCTGCACCG | 1251 |
| | | | G | G | T | G | A | A | T | C | T | T | C | A | ACACCGGTGCAGATCTACTTCAG | 1163 | AAAACTGAAGTAGATCTGCACCG | 1252 |
| | | | G | G | T | G | A | A | G | T | a | T | C | A | ACACCGGTGCAGTAGAACTTCAG | 1164 | AAAACTGAAGTTCTACTGCACCG | 1253 |
| | | | G | G | T | C | A | t | T | C | T | T | C | A | ACACCGGTGCTCATGAACTTCAG | 1165 | AAAACTGAAGTTCATGAGCACCG | 1254 |
| | | | G | G | T | G | A | A | T | C | T | T | C | A | ACACCGGTGCGAGATGAACTTCAG | 1166 | AAAACTGAAGTTCATCTCGACCG | 1255 |
| | | | G | C | a | G | A | A | T | C | T | T | C | A | ACACCGCAGCAGATGAACTTCAG | 1167 | AAAACTGAAGTTCATCTGCTGCG | 1256 |
| | | | | | | | | | Endogenous Target 1 (VEGFA site 1 tru-gRNA): | | | | | | | | |
| | G | T | G | G | G | G | A | T | T | G | C | T | C | C | ACACCGTGGGGGAGTTTGCTCCG | 1168 | AAAACGGAGCAAACTCCCCCACG | 1257 |
| | | | | | | | | | Endogenous Target 3 (VEGFA Site 3 tru-gRNA): | | | | | | | | |
| | | | G | A | C | G | T | G | T | G | C | T | G | G | ACACCGAGTGAGTGTGTGCGTGG | 1169 | AAAACCACGCACACACTCACTCG | 1258 |
| | | | | | | | | | Endogenous Target 4 (EMX1 Site 1 tru-gRNA): | | | | | | | | |
| | G | T | C | C | G | A | G | C | A | G | A | A | G | A | ACACCGTCCGAGCAGAAGAAGAAG | 1170 | AAAACTTCTTCTTCTGCTCGGACG | 1259 |
| | | | | | | | | | CTLA full-length gRNA | | | | | | | | |
| | G | A | T | G | T | A | G | T | G | T | T | T | C | C | ACACCGCAGATGTAGTGTTTCCACAG | 1171 | AAAACTGTGGAAACACTACATCTGCG | 1260 |
| | | | | | | | | | CTLA tru-gRNA | | | | | | | | |
| | | | G | A | T | G | T | A | G | T | G | T | T | T | ACACCGATGTAGTGTTTCCACAG | 1172 | AAAACTGTGGAAACACTACATCG | 1261 |
| | | | | | | | | | VEGFA site 4 full-length gRNA | | | | | | | | |
| | T | C | T | T | T | T | A | G | C | C | A | G | C | C | ACACCTCCCTCTTTTAGCCAGAGCCGG | 1173 | AAAACCGGCTCTGGCTAAAGAGGGAG | 1262 |
| | | | | | | | | | EMX1 site 2 full-length gRNA | | | | | | | | |
| | G | C | T | T | T | G | T | A | C | T | T | T | G | T | ACACCGCCGTTTGTACTTTGTCCTCG | 1174 | AAAACGAGGACAAAGTACAAACGGCG | 1263 |
| | | | | | | | | | EMX1 site 2 tru-gRNA | | | | | | | | |
| | | | G | T | T | T | G | T | A | C | T | T | T | G | ACACCGTTTGTACTTTGTCCTCG | 1175 | AAAACGAGGACAAAGTACAAACG | 1264 |
| | | | | | | | | | EMX1 site 3 full-length gRNA | | | | | | | | |
| | G | A | A | G | A | C | T | G | A | G | G | C | T | A | ACACCGGAAGACTGAGGCTACATAG | 1176 | AAAACTATGTAGCCTCAGTCTTCCG | 1265 |
| | | | | | | | | | EXM1 site 3 tru-gRNA | | | | | | | | |
| | | | G | A | A | G | A | C | T | G | A | G | G | C | ACACCGAAGACTGAGGCTACATAG | 1177 | AAAACTATGTAGCCTCAGTCTTCG | 1266 |
| | | | | | | | | | EMX1 site 4 full-length gRNA | | | | | | | | |
| | G | A | G | G | C | C | C | C | C | A | G | A | G | C | ACACCGAGGCCCCCAGAGCAGCCACG | 1178 | AAAACGTGGCTGCTCTGGGGGCCTCG | 1267 |
| | | | | | | | | | EXM1 site 4 tru-gRNA | | | | | | | | |
| | | | G | C | C | C | C | C | A | G | A | G | C | A | ACACCGCCCCCAGAGCAGCCACG | 1179 | AAAACGTGGCTGCTCTGGGGGCG | 1268 |

Human Cell-Based EGFP Disruption Assay

U2OS.EGFP cells harboring a single-copy, integrated EGFP-PEST gene reporter have been previously described (Reyon et al., 2012). These cells were maintained in Advanced DMEM (Life Technologies) supplemented with 10% FBS, 2 mM GlutaMax (Life Technologies), penicillin/streptomycin and 400 µg/ml G418. To assay for disruption of EGFP expression, $2 \times 10^5$ U2OS.EGFP cells were transfected in duplicate with gRNA expression plasmid or an empty U6 promoter plasmid as a negative control, Cas9 expression plasmid (pJDS246) (Example 1 and Fu et al., 2013), and 10 ng of td-Tomato expression plasmid (to control for transfection efficiency) using a LONZA 4D-Nucleofector™, with SE solution and DN100 program according to the manufacturer's instructions. We used 25 ng/250 ng, 250 ng/750 ng, 200 ng/750 ng, and 250 ng/750 ng of gRNA expression plasmid/Cas9 expression plasmid for experiments with EGFP site #1, #2, #3, and #4, respectively. Two days following transfection, cells were trypsinized and resuspended in Dulbecco's modified Eagle medium (DMEM, Invitrogen) supplemented with 10% (vol/vol) fetal bovine serum (FBS) and analyzed on a BD LSRII flow cytometer. For each sample, transfections and flow cytometry measurements were performed in duplicate.

Transfection of Human Cells and Isolation of Genomic DNA

To assess the on-target and off-target indel mutations induced by RGNs targeted to endogenous human genes, plasmids were transfected into U2OS.EGFP or HEK293 cells using the following conditions: U2OS.EGFP cells were transfected using the same conditions as for the EGFP disruption assay described above. HEK293 cells were transfected by seeding them at a density of $1.65 \times 10^5$ cells per well in 24 well plates in Advanced DMEM (Life Technologies) supplemented with 10% FBS and 2 mM GlutaMax (Life Technologies) at 37° C. in a $CO_2$ incubator. After 22-24 hours of incubation, cells were transfected with 125 ng of gRNA expression plasmid or an empty U6 promoter plasmid (as a negative control), 375 ng of Cas9 expression plasmid (pJDS246) (Example 1 and Fu et al., 2013), and 10 ng of a td-Tomato expression plasmid, using Lipofectamine LTX reagent according to the manufacturer's instructions (Life Technologies). Medium was changed 16 hours after transfection. For both types of cells, genomic DNA was harvested two days post-transfection using an Agencourt DNAdvance genomic DNA isolation kit (Beckman) according to the manufacturer's instructions. For each RGN sample to be assayed, 12 individual 4D transfection replicates were performed, genomic DNA was isolated from each of these 12 transfections, and then these samples were combined to create two "duplicate" pools each consisting of six pooled genomic DNA samples. Indel mutations were then assessed at on-target and off-target sites from these duplicate samples by T7EI assay, Sanger sequencing, and/or deep sequencing as described below.

To assess frequencies of precise alterations introduced by HDR with ssODN donor templates, $2 \times 10^5$ U2OS.EGFP cells were transfected 250 ng of gRNA expression plasmid or an empty U6 promoter plasmid (as a negative control), 750 ng Cas9 expression plasmid (pJDS246), 50 pmol of ssODN donor (or no ssODN for controls), and 10 ng of td-Tomato expression plasmid (as the transfection control). Genomic DNA was purified three days after transfection using Agencourt DNAdvance and assayed for the introduction of a BamHI site at the locus of interest as described below. All of these transfections were performed in duplicate.

For experiments involving Cas9 nickases, $2 \times 10^5$ U2OS.EGFP cells were transfected with 125 ng of each gRNA expression plasmid (if using paired gRNAs) or 250 ng of gRNA expression plasmid (if using a single gRNA), 750 ng of Cas9-D10A nickase expression plasmid (pJDS271), 10 ng of td-Tomato plasmid, and (if performing HDR) 50 pmol of ssODN donor template (encoding the BamHI site). All transfections were performed in duplicate. Genomic DNA harvested two days after transfection (if assaying for indel mutations) or three days after transfection (if assaying for HDR/ssODN-mediated alterations) using the Agencourt DNAdvance genomic DNA isolation kit (Beckman).

T7EI Assays for Quantifying Frequencies of Indel Mutations

T7EI assays were performed as previously described (Example 1 and Fu et al., 2013). In brief, PCR reactions to amplify specific on-target or off-target sites were performed with Phusion high-fidelity DNA polymerase (New England Biolabs) using one of the two following programs: (1) Touchdown PCR program [(98° C., 10 s; 72-62° C., −1° C./cycle, 15 s; 72° C., 30 s)×10 cycles, (98° C., 10 s; 62° C., 15 s; 72° C., 30 s)×25 cycles] or (2) Constant Tm PCR program [(98° C., 10 s; 68° C. or 72° C., 15 s; 72° C., 30 s)×35 cycles], with 3% DMSO or 1 M betaine if necessary. All primers used for these amplifications are listed in Table E. Resulting PCR products ranged in size from 300 to 800 bps and were purified by Ampure XP beads (Agencourt) according to the manufacturer's instructions. 200 ng of purified PCR products were hybridized in 1×NEB buffer 2 in a total volume of 19 µl and denatured to form heteroduplexes using the following conditions: 95° C., 5 minutes; 95 to 85° C., −2° C./s; 85 to 25° C., −0.1° C./s; hold at 4° C. 1 µl of T7 Endonuclease I (New England Biolabs, 10 units/µl) was added to the hybridized PCR products and incubated at 37° C. for 15 minutes. The T7EI reaction was stopped by adding 2 µl of 0.25 M EDTA solution and the reaction products were purified using AMPure XP beads (Agencourt) with elution in 20 µl 0.1×EB buffer (QIAgen). Reactions products were then analyzed on a QIAXCEL capillary electrophoresis system and the frequencies of indel mutations were calculated using the same formula as previously described (Reyon et al., 2012).

TABLE E

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | non-Watson-Crick Transversions | Transitions |
|---|---|---|---|---|---|---|---|---|---|---|---|---|
| Target 1 | GGGTGGGGGAG TTTGCTCCTGG | 1269. | 0 | | TCCAGATGGCACA TTGTCAG | 1270. | AGGGAGCA GGAAAGTG AGGT | 1271. | DMSO | | | |
| OT1-1 | GGGTGGGGGAG TTTGCCCCAGG | 1272. | 1 | | GGGGCCCACTCTT CTTCCAT | 1273. | ACCCAGAC TCCTGGTG TGGC | 1274. | No DMSO | 0 | 0 | 1 |
| OT1-2 | GCGTGGGGGTG TTTGCTCCTGG | 1275. | 2 | | GCTAAGCAGAGAT GCCTATGCC | 1276. | ACCACCCT TTCCCCCA GAAA | 1277. | DMSO | 2 | 0 | 0 |
| OT1-3 | GGATGGAGGGAG TTTGCTCCTGG | 1278. | 2 | | ACCCCACAGCCAG GTTTTCA | 1279. | GAATCACT GCACCTGG CCATC | 1280. | DMSO | 0 | 0 | 2 |
| OT1-4 | GGGAGGGTGGAG TTTGCTCCTGG | 1281. | 2 | | TGCCGCAACTTCA GACAACC | 1282. | TAAAGGGC GTGCTGGG AGAG | 1283. | DMSO | 1 | 1 | 0 |
| OT1-5 | GGGTGGTGGAG TTTGCTACTGG | 1284. | 2 | | GCATGTCAGGATC TGACCCC | 1285. | TGCAGGGC CATCTTGT GTGT | 1286. | DMSO | 0 | 2 | 0 |
| OT1-6 | CGGGGGAGGGAG TTTGCTCCTGG | 1287. | 3 | | CCACCACATGTTC TGGGTGC | 1288. | CTGGTCT GTTCCCTG TGGG | 1289. | DMSO | 1 | 1 | 1 |
| OT1-7 | GAGTGGGTGGAG TTTGCTACAGG | 1290. | 3 | | GGCTCTCCCTGCC CTAGTTT | 1291. | GCAGGTCA AGTTGGAA CCCG | 1292. | DMSO | 0 | 2 | 1 |
| OT1-8 | GGGAGGGGAGAG TTTGTTCCAGG | 1293. | 3 | | GGGGCTGAGAACA CATGAGATGCA | 1294. | AGATTTGT GCACTGCC TGCCT | 1295. | DMSO | 1 | 0 | 2 |
| OT1-9 | GGGAGGGGCAG GTTGCTCCAGG | 1296. | 3 | | CCCGACCTCCGCT CCAAAGC | 1297. | GGACCTCT GCACACCC TGGC | 1298. | DMSO | 2 | 1 | 0 |
| OT1-10 | GGGAGGGGGAG TGTGTTCCGGG | 1299. | 3 | | TGCAAGGTCCAT AGTCCCA | 1300. | CAGGAGG GGAAGTGT GTCC | 1301. | DMSO | 1 | 1 | 1 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | non-Watson-Crick Transversions | Transitions |
|---|---|---|---|---|---|---|---|---|---|---|---|---|
| OT1-11 | GGGGAGGGGAAG TTTGCTCCTGG | 1302. | 3 | | GCCCATTCTTTT GCAGTGGA | 1303. | GAGAGCAA GTTTGTTC CCCAGG | 1304. | DMSO | 0 | 1 | 2 |
| OT1-12 | GGGGGTGGGGAC TTTGCTCCAGG | 1305. | 3 | | GCCCCCAGCCCCT CTGTTTC | 1306. | GCTGCTGG TAGGGAG CTGG | 1307. | DMSO | 1 | 2 | 0 |
| OT1-13 | GGGTCGGGGAG TGGGCTCCAGG | 1308. | 3 | | CGGCTGCCTTCCC TGAGTCC | 1309. | GGGTGACG CTTGCCAT GAGC | 1310. | 72 C. Anneal, 3% DMSO | 1 | 2 | 0 |
| OT1-14 | GGGTGGCTGGAG TTTGCTGCTGG | 1311. | 3 | | TGACCCTGGAGTA CAAAATGTTCCCA | 1312. | GCTGAGAC AACCAGCC CAGCT | 1313. | 72 C. Anneal, 3% DMSO | 2 | 1 | 0 |
| OT1-15 | GGGTGGGGGTG CCTGCTCCAGG | 1314. | 3 | | TGCCTCCACCCTT AGCCCT | 1315. | GCAGCCGA TCCACACT GGGG | 1316. | DMSO | 1 | 0 | 2 |
| OT1-16 | GGTTGAGGGGAG TCTGCTCCAGG | 1317. | 3 | | AACTCAGGACAAC ACTGCCTGT | 1318. | CCCAGGAG CAGGGTAC AATGC | 1319. | DMSO | 0 | 1 | 2 |
| OT1-17 | GTGTGGGTGGCG TTTGCTCCAGG | 1320. | 3 | | TCCTCCTTGGAGA GGGGCCC | 1321. | CCTTGAA GGGGCTT GGTGG | 1322. | DMSO | 0 | 3 | 0 |
| OT1-18 | AGTTGGTGGGAG CTTGTTCCTGG | 1323. | 4 | | CCGAGGGCATGGG CAATCCT | 1324. | GGCTGCTG CGAGTTGC CAAC | 1325. | DMSO | 0 | 1 | 3 |
| OT1-19 | AGTTTGGGGAG TTTGCCCCAGG | 1326. | 4 | | TGCTTTGCATGGG GTCTCAGACA | 1327. | GGGTTGCT TGCCCTCT GTGT | 1328. | DMSO | 0 | 2 | 2 |
| OT1-20 | ATCTGTGGGGAA TTTGCTCCAGG | 1329. | 4 | | AGCTCCTTCTCAT TTCTCTTCTGCTGT | 1330. | CACAGAAG GATGTGTG CAGGTT | 1331. | DMSO | 0 | 2 | 2 |
| OT1-21 | CAGTGGGGGAG CTTTCTCCTGG | 1332. | 4 | | AGCAGACACAGGT GAATGCTGCT | 1333. | GGTCAGGT GTGCTGCT AGGCA | 1334. | DMSO | 1 | 1 | 2 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | non-Watson-Crick Transversions | Transitions |
|---|---|---|---|---|---|---|---|---|---|---|---|---|
| OT1-22 | GAGGGGGAGCAGTTTGCTCCAGG | 1335. | 4 | | CCTGTGGGGCTCTCAGGTGC | 1336. | ACTGCCTGCCAAAGTGGGTGT | 1337. | No DMSO TD | 1 | 1 | 2 |
| OT1-23 | GGAGGAGGGGAGTCTGCTCCAGG | 1338. | 4 | | AGCTGCACTGGGGAATGAGT | 1339. | TGCCGGGTAATAGCTGGCTT | 1340. | DMSO | 0 | 1 | 3 |
| OT1-24 | GGAGGGGGGCTTTTTGCTCCAGG | 1341. | 4 | | CCAGCCTGGGCAACAAAGCG | 1342. | GGGGGCTTCCAGTCACAGG | 1343. | 72 C. Anneal, 3% DMSO, 6% DMSO | 0 | 3 | 1 |
| OT1-25 | GGGCAAGGGGAGGTTGCTCCTGG | 1344. | 4 | | TACCCCCACTGCCCCATTGC | 1345. | ACAGGTCCATGCTTAGCAGAGGG | 1346. | DMSO | 0 | 1 | 3 |
| OT1-26 | GGGTGATTGAAGTTTGCTCCAGG | 1347. | 4 | GGGTGATTGAAGTTTGCTCCAGG (SEQ ID NO: 2225) GGGTGATTGAAGTTGCTGCAGG (SEQ ID NO: 2226) | ACGGATTCACGACGGAGTGC | 1348. | CCGAGTCCGTGGCAGAGAGC | 1349. | DMSO | 0/1 | 2 | 2 |
| OT1-27 | GGGTGTGGGGTCATTGCTCCAGG | 1350. | 4 | | TGTGTGTTGAAGTAGGGGACAGT | 1351. | TGGCCCAATTGGAAGTGATTTCGT | 1352. | DMSO | 3 | 0 | 1 |
| OT1-28 | GGTGGGGGTGGGTTTGCTCCTGG | 1353. | 4 | | TGGGATGGCAGAGTCATCAACGT | 1354. | GGCCCAATCGGTAGAAGGATGCA | 1355. | DMSO | 0 | 3 | 1 |
| OT1-29 | GTGGGGGTAGAGTTTGCTCCAGG | 1356. | 4 | | ATGGGGCGCTCCAGTCTGTG | 1357. | TGCACCCACACAGCCAGCAA | 1358. | DMSO | 0 | 3 | 1 |
| OT1-30 | TAGTGGAGGGAGCTTGCTCCTGG | 1359. | 4 | | GGGGAGGGAGGACCAGGGAA | 1360. | AATTAGCTGGGCGCGGTGGT | 1361. | 72 C. Anneal, 3% DMSO | 0 | 1 | 3 |
| OT1-31 | TGCTCGGGGGAGTTTGCACCAGG | 1362. | 4 | | ATCCCGTGCAGGAAGTCGCC | 1363. | CAGGCGCCCCTTGAGGAAT | 1364. | DMSO | 3 | 1 | 0 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | non-Watson-Crick Transversions | Transitions |
|---|---|---|---|---|---|---|---|---|---|---|---|---|
| OT1-32 | TGAGAGGGGAGTTGGCTCCTGG | 1365. | 4 | | CCCCAACCCTTTGCTCAGCG | 1366. | TGAGGAGAACACCACAGGCAGA | 1367. | DMSO | 1 | 2 | 1 |
| OT1-33 | TGGTGTTGGAGTCTGCTCCAGG | 1368. | 4 | | ATCGACGAGAGGGGGCCTT | 1369. | CCCCTCACTCAAGCAGGCCC | 1370. | DMSO | 0 | 3 | 1 |
| OT1-34 | TTTGGGGGGCAGTTTGCTCCTGG | 1371. | 4 | | TGCTCAAGGGGCCTGTTCCA | 1372. | CAGGGGCAGTGGCAGGAGTC | 1373. | No DMSO | 1 | 3 | 0 |
| OT1-35 | AAGTAAGGGAAGTTTGCTCCTGG | 1374. | 5 | | TGCCTGGCACGCAGTAGTG | 1375. | GGGAAGGGGGAACAGGTGCA | 1376. | DMSO | 0 | 0 | 5 |
| OT1-36 | AGAAGAGGGGATTTTGCTCCTGG | 1377. | 5 | | Not optimized | | | | | 1 | 1 | 3 |
| OT1-37 | ATCTGGGGTGATTTTGCTCCTGG | 1378. | 5 | | ACCTGGGCTTGCCACTAGGG | 1379. | GCTGCTCGCAGTTAAGCACCA | 1380. | DMSO | 1 | 3 | 1 |
| OT1-38 | CTCTGCTGGGAGTTTGCTCCTGG | 1381. | 5 | | GTGGCCGGGCTACTGCTACC | 1382. | GGTTCCACAAGCTGGGGGCA | 1383. | DMSO | 3 | 2 | 0 |
| OT1-39 | CTGGTGGGGAGCTTGCTCCAGG | 1384. | 5 | | Not optimized | | | | | 1 | 3 | 1 |
| OT1-40 | CTTTCGGGGAGTTTGCGCCGGG | 1385. | 5 | | GCAAGAGGCCGAGGAGACCC | 1386. | AGAGTCATCCATTTCCTGGGGGC | 1387. | DMSO | 2 | 3 | 0 |
| OT1-41 | CTTTGGGGTTAGTTTGCTCCTGG | 1388. | 5 | | GGGGTCAGTGGTGATATCCCCT | 1389. | AGGGAATCCTTTTTCCATTGCTTGTTT | 1390. | 1M betaine, TD | 1 | 4 | 0 |
| OT1-42 | GCTCTGGGGTAGTTTGCTCCAGG | 1391. | 5 | | AGAGAGGCCACGTGGAGGGT | 1392. | GCCTCCCCTCCTCCTTCCCA | 1393. | DMSO | 1 | 3 | 1 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | non-Watson-Crick Transversions | Transitions |
|---|---|---|---|---|---|---|---|---|---|---|---|---|
| OT1-43 | GTCTCTCGGGAG TTTGCTCCGGG | 1394 | 5 | | GACAGTGCCTTGC GATGCAC | 1395 | TCTGACCG GTATGCCT GACG | 1396 | DMSO | 3 | 2 | 0 |
| OT1-44 | TCCTGAGGGCAG TTTGCTCCAGG | 1397 | 5 | | TGTGTGAACGCAG CCTGCT | 1398 | TGGTCTAG TACTTCCT CCAGCCTT | 1399 | DMSO | 3 | 1 | 1 |
| OT1-45 | TCTTTGGGAGAG TTTGCTCCAGG | 1400 | 5 | | GGTTCTCCCTTGG CTCCTGTGA | 1401 | CCCACTGC TCCTAGCC CTGC | 1402 | DMSO | 1 | 3 | 1 |
| OT1-46 | ACAACTGGGGAG TTTGCTCCTGG | 1403 | 6 | | TGAAGTCAACAAT CTAAGCTTCCACCT | 1404 | AGCTTTGG TAGTTGGA GTCTTTGA AGG | 1405 | DMSO | 3 | 1 | 2 |
| OT1-47 | ACAAGGTGGAAG TTTGCTCCTGG | 1406 | 6 | | TGATTGGGCTGCA GTTCATGTACA | 1407 | GCACAGCC TGCCCTTG GAAG | 1408 | DMSO | 2 | 1 | 3 |
| OT1-48 | ACATAGAAGGAG TTTGCTCCAGG | 1409 | 6 | | TCCATGGGCCCCT CTGAAAGA | 1410 | AGCGGCTT CTGCTTCT GCGA | 1411 | DMSO | 1 | 0 | 5 |
| OT1-49 | AGACCCAGGGAG TTTGCTCCGGG | 1412 | 6 | | GCGGTTGGTGGGG TTGATGC | 1413 | GAGTTCCT CCTCCCGC CAGT | 1414 | DMSO | 2 | 0 | 4 |
| OT1-50 | AGACCCAGGGAG TTTGCTCCGGG | 1415 | 6 | | AGGCAAGATTTTC CAGTGCAAGA | 1416 | GCTTTTGC CTGGGACT CCGC | 1417 | DMSO | 2 | 0 | 4 |
| OT1-51 | CACGGAGGGGTG TTTGCTCCTGG | 1418 | 6 | | GCTGCTGGTCGGG CTCTCTG | 1419 | GCTCTGTC CCACTTCC CCTGG | 1420 | No DMSO TD | 3 | 1 | 2 |
| OT1-52 | CAGAGCTTGGAG TTTGCTCCAGG | 1421 | 6 | | GCTGCGAGGCTTC CGTGAGA | 1422 | CGCCCCTA GAGCTAAG GGGGT | 1423 | DMSO | 3 | 2 | 1 |
| OT1-53 | CTATTGATGGAG TTTGCTCCTGG | 1424 | 6 | | CCAGGAGCCTGAG AGCTGCC | 1425 | AGGGCTAG GACTGCAG TGAGC | 1426 | DMSO | 1 | 3 | 2 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | Watson-Crick Transitions | non-Watson-Crick Transversions | Transitions |
|---|---|---|---|---|---|---|---|---|---|---|---|---|---|
| OT1-54 | CTTTCTAGGGAG TTTGCTCCTGG | 1427. | 6 | | CTGTGCTCAGCCT GGGTGCT | 1428. | GCCTGGGG CTGTGAGT AGTTT | 1429. | DMSO | 2 | 3 | | 1 |
| OT1-55 | GCCATGCTGGAG TTTGCTCCAGG | 1430. | 6 | | AGCTCGCGCCAGA TCTGTGG | 1431. | ACTTGGCA GGCTGAGG CAGG | 1432. | 72 C. Anneal, 3% DMSO | 4 | 2 | | 0 |
| | | 1433. | | | | 1434. | | 1435. | | | | | |
| Target 2 | GACCCCCTCCAC CCCGCCTCCGG | 1436. | 0 | | AGAGAAGTCAGG AAGAGAG | 1437. | CAGCAGAA AGTTCATG GTTTCG | 1438. | DMSO | | | | |
| OT2-1 | GACCCCCCCCAC CCCGCCCCCGG | 1439. | 2 | | TGGACAGCTGCAG TACTCCCTG | 1440. | ACTGATCG ATGATGGC CTATGGGT | 1441. | DMSO | 0 | 0 | | 2 |
| OT2-2 | GGGCCCCTCCAC CCCGCCTCTGG | 1442. | 2 | | CAAGATGTGCACT TGGGCTA | 1443. | GCAGCCTA TTGTCTCC TGGT | 1444. | DMSO | 1 | 0 | | 1 |
| OT2-3 | AACCCCATCCAC CCGGCCTCAGG | 1445. | 3 | | GTCCAGTGCCTGA CCCTGGC | 1446. | AGCATCAT GCCTCCAG CTTCA | 1447. | DMSO | 1 | 1 | | 1 |
| OT2-4 | CACCCCCTCAAC CCGGCCTCAGG | 1448. | 3 | | GCTCCCGATCCTC TGCCACC | 1449. | GCAGTCC CACCACCC TCAG | 1450. | DMSO | 1 | 2 | | 0 |
| OT2-5 | CACCCCCTCCCC TCCCGCCTCAGG | 1451. | 3 | | GGGGACAGGCAGG CAAGGAG | 1452. | GTGCGTGT CCGTTCAC CCCT | 1453. | DMSO | 1 | 1 | | 1 |
| OT2-6 | CTACCCCTCCAC CCGGCCTCCGG | 1454. | 3 | | AAGGGGCTGCTGG GTAGGAC | 1455. | CGTGATTC GAGTTCCT GGCA | 1456. | DMSO | 2 | 1 | | 0 |
| OT2-7 | GACCCGCCCCGC CCCGCCTCTGG | 1457. | 3 | | GACCCTCAGGAAG CTGGGAG | 1458. | CTGCGAGA TGCCCCAA ATCG | 1459. | 1M betaine, TD | 1 | 0 | | 2 |
| OT2-8 | GATCGACTCCAC CCCGCCTCTGG | 1460. | 3 | | CCGGGCGCGCTCTG CTAGA | 1461. | TGCTGGGA TTACAGGC GCGA | 1462. | DMSO | 1 | 1 | | 1 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | Watson-Crick Transversions | non-Watson-Crick Transversions | Transitions |
|---|---|---|---|---|---|---|---|---|---|---|---|---|---|
| OT2-9 | GCCCCCACCCAC CCCGCCTCTGG | 1463. | 3 | | CCAGTGTGTCA GCGGAGG | 1464. | TGCCTGGC CCTCTCTG AGTCT | 1465. | DMSO | 0 | 2 | | 1 |
| OT2-10 | GCCCCGTTCCTC CCCGCCTCCGG | 1466. | 3 | | CGACTCCACGGCG TCTCAGG | 1467. | CAGGCGCAG TCCAGCCC GATG | 1468. | 1M betaine, TD | 2 | 1 | | 0 |
| OT2-11 | GGCCCCCTCCAC CAGGCCTCAGG | 1469. | 3 | | CTTCCCTCCCCCA GCACCAC | 1470. | GCTACAGG TTGCACAG TGAGAGGT | 1471. | DMSO | 1 | 1 | | 1 |
| OT2-12 | GGCCCCCTCCTC CTCGCCTCTGG | 1472. | 3 | | CCCCGGGGAGTCT GTCCTGA | 1473. | CCCAGCCG TTCCAGGT CTTCC | 1474. | 72 C. Anneal, 3% DMSO | 1 | 0 | | 2 |
| OT2-13 | GGCGCCCTCCAC CCTGCCTCGGG | 1475. | 3 | | GAAGCGCGAAAAC CCGGCTC | 1476. | TCCAGGGT CCTTCTCG GCCC | 1477. | DMSO | 1 | 0 | | 2 |
| OT2-14 | GTCCTCCACCAC CCCGCCTCTGG | 1478. | 3 | | AGGGTGGTCAGGG AGGCCTT | 1479. | CATGGGGC TCGGACCT CGTC | 1480. | DMSO | 2 | 0 | | 1 |
| OT2-15 | TACCCCCACCAC CCCGCCTCTGG | 1481. | 3 | | GGGAAGAGGCAGG GCTGTCG | 1482. | TGCCAGGA AGGAAGCT GGCC | 1483. | 72 C. Anneal, 3% DMSO | 0 | 2 | | 1 |
| OT2-16 | AACCCATTCCAC CCTGCCTCAGG | 1484. | 4 | | GAGTGACGATGAG CCCCGGG | 1485. | CCCTTAGC TGCAGTCG CCCC | 1486. | 68 C. Anneal, 3% DMSO | 0 | 1 | | 3 |
| OT2-17 | ACACCCCCCCAC CCCGCCTCAGG | 1487. | 4 | | CCCATGAGGGGTT TGAGTGC | 1488. | TGAAGATG GGCAGTTT GGGG | 1489. | DMSO | 0 | 2 | | 2 |
| OT2-18 | AGCCCCCACCTC CCCGCCTCGGG | 1490. | 4 | | CACCTGGGCATC TGGGTGG | 1491. | ACTGGGGT TGGGAGG GGAT | 1492. | DMSO | 2 | 0 | | 2 |
| OT2-19 | ATTCCCCCCCAC CCCGCCTCAGG | 1493. | 4 | | TCATGATCCCCAA AAGGGCT | 1494. | CCATTTGT GCTGATCT GTGGGT | 1495. | DMSO | 1 | 0 | | 3 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | Watson-Crick Transversions | non-Watson-Crick Transversions | Transitions |
|---|---|---|---|---|---|---|---|---|---|---|---|---|---|
| OT2-20 | CCCCACCCCAC CCGCCTCAGG | 1496. | 4 | | TGGTGCCCAGAAT AGTGCCCA | 1497. | AGGAAATG TGTTGTGC CAGGGCA | 1498. | DMSO | 1 | 2 | | 1 |
| OT2-21 | CCCCCCACCAC CCGCCTCGGG | 1499. | 4 | | GCCTCAGACAACC CTGCCCC | 1500. | GCCAAGTG TTACTCAT CAAGAAAG TGG | 1501. | No DMSO TD | 2 | 1 | | 1 |
| OT2-22 | CCCCCCCCCC CCGCCTCAGG | 1502. | 4 | | GCCGGGACAAGAC TGAGTGGG | 1503. | TCCCGAAC TCCCGCAA AACG | 1504. | DMSO | 1 | 2 | | 1 |
| OT2-23 | CGCCCTCCCAC CCGCCTCCGG | 1505. | 4 | | TGCTGCAGGTGGT TCCGGAG | 1506. | CTGGAACC GCATCCTC CGCA | 1507. | No DMSO TD | 1 | 0 | | 3 |
| OT2-24 | CTCCCCACCCAC CCGCCTCAGG | 1508. | 4 | | ACACTGGTCCAGG TCCCGTCT | 1509. | GGCTGTGC CTTCCGAT GGAA | 1510. | DMSO | 2 | 1 | | 1 |
| OT2-25 | CTCTCCCCCCAC CCGCCTCGGG | 1511. | 4 | CTCTCCCCCCACCC CCCCTCTGG (SEQ ID NO: 2227) | ATCCGCCCAAAG CACAGGT | 1512. | AGGCTTCT GGAAAAGT CCTCAATG CA | 1513. | DMSO | 3 | 0 | | 2 |
| OT2-26 | GCCTCTCTGCAC CCGCCTCAGG | 1514. | 4 | | Not optimized | | | | | 1 | 1 | | 2 |
| OT2-27 | GTCACTCCCCAC CCCGCCTCTGG | 1515. | 4 | | CCCTCATGTGGT CTTACGGCA | 1516. | AGCCACAC ATCTTTCT GGTAGGG | 1517. | DMSO | 1 | 1 | | 2 |
| OT2-28 | TGCCCCCCTCCC CCAGCCTCTGG | 1518. | 4 | | TGCGTGCGCTCATG CTGGAG | 1519. | GGGGTGGG GTGTACTG GCTCA | 1520. | DMSO | 0 | 3 | | 1 |
| OT2-29 | TGCCCCTCCCAC CCCGCCTCTGG | 1521. | 4 | | GAGCTGAGACGGC ACCACTG | 1522. | TGGCCTTG AACTCTTG GGCT | 1523. | 1M betaine, TD | 0 | 1 | | 3 |
| OT2-30 | TTCCCCTTCCAC CCAGCCTCTGG | 1524. | 4 | | Not optimized | | | | | 1 | 2 | | 1 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | Watson-Crick Transitions | non-Watson-Crick Transversions | non-Watson-Crick Transitions |
|---|---|---|---|---|---|---|---|---|---|---|---|---|---|
| OT2-31 | TTCTCCCTCCTC CCCGCCTCGGG | 1525. | 4 | | AGTGAGAGTGGCA CGAACCA | 1526. | CAGTAGGT GGTCCCTT CCGC | 1527. | DMSO | 2 | 1 | | 1 |
| OT2-32 | ACCCTGCCCAC CCCGCCTCAGG | 1528. | 5 | | Not optimized | | | | | | 1 | 1 | 3 |
| OT2-33 | AGCCAACCCCAC CCCGCCTCTGG | 1529. | 5 | | GGGAGAACCTTGT CCAGCCT | 1530. | AAGCCGAA AAGCTGGG CAAA | 1531. | DMSO | 0 | 2 | | 3 |
| OT2-34 | AGGCCCCACAC CCCGCCTCC | 1532. | 5 | | CTTCCCAGTGTGG CCCGTCC | 1533. | ACACAGTC AGAGCTCC GCCG | 1534. | DMSO | 1 | 1 | | 3 |
| OT2-35 | AGGCCCCCCGC CCCGCCTCAGG | 1535. | 5 | | Not optimized | | | | | 1 | 0 | | 4 |
| OT2-36 | ATCTGCACCAC CCCGCCTCCGG | 1536. | 5 | | CTGAGAGGGGAG GGGGAGG | 1537. | TCGACTGG TCTTGTCC TCCCA | 1538. | 68 C. Anneal, 3% DMSO | 3 | 0 | | 2 |
| OT2-37 | CATCTTCCCCAC CCCGCCTCTGG | 1539. | 5 | | CAGCTGCTGCAT CGGAAAA | 1540. | TGCAGCCA AGAGAAAA AGCCT | 1541. | 1M betaine, TD | 1 | 0 | | 4 |
| OT2-38 | CTTTCCCTCCAC CCAGCCTCTGG | 1542. | 5 | | TCCCTCTGACCCG GAACCCA | 1543. | ACCCGACT TCCTCCCC ATTGC | 1544. | DMSO | 2 | 1 | | 2 |
| OT2-39 | GTCGAGGTCCAC CCCGCCTCAGG | 1545. | 5 | | TGGGGGTTGCGTG CTTGTCA | 1546. | GCCAGGAG GACACCAG GACC | 1547. | DMSO | 4 | 1 | | 0 |
| OT2-40 | GTCGAGGTCCAC CCCGCCTCAGG | 1548. | 5 | | ATCAGGTGCCAGG AGGACAC | 1549. | GGCCTGAG AGTGGAGA GTGG | 1550. | DMSO | 4 | 1 | | 0 |
| OT2-41 | TCAGACCTCCAC CCCGCCTCAGG | 1551. | 5 | | Not optimized | | | | | 1 | 4 | | 0 |
| OT2-42 | TGCAACCTCCTC CCCGCCTCGGG | 1552. | 5 | | TGAGCCACATGAA TCAAGGCCTCC | 1553. | ACCTCTCC AAGTCTCA GTAACTCT CT | 1554. | DMSO | 1 | 3 | | 1 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | Watson-Crick Transversions | non-Watson-Crick Transversions | Transitions |
|---|---|---|---|---|---|---|---|---|---|---|---|---|---|
| OT2-43 | ACCAGTTGCAC CCCGCCTCTGG | 1555. | 6 | | GGTCCTCCTGTGC AGTGAA | 1556. | CTTTGTG GACCTGCA CAGC | 1557. | DMSO | | 2 | 2 | 2 |
| OT2-44 | ACTACCCACCTC CCCGCCTCAGG | 1558. | 6 | | GCGAGGCTGCTGA CTTCCCT | 1559. | GCTGGGAC TACAGACA TGTGCCA | 1560. | DMSO | | 2 | 2 | 2 |
| OT2-45 | ATTTCCCCCCCC CCCGCCTCAGG | 1561. | 6 | ATTTCCTCCCCCCC C-CCTCAGG (SEQ ID NO: 2228) | ATTGCAGGCGTGT CCAGCA | 1562. | AAATCCTG CATGGTGA TGGGAGT | 1563. | DMSO | | 1 | 1 | 5 |
| OT2-46 | CCACCATCCCAC CCCGCCTCTGG | 1564. | 6 | | TGCTCTGCCATTT ATGTCCTATGAACT | 1565. | ACAGCCTC TTCTCCAT GACTGAGC | 1566. | DMSO | | 1 | 3 | 2 |
| OT2-47 | CCCAAGCCCAC CCCGCCTCGGG | 1567. | 6 | | TCCGCCCAAACAG GAGGCAG | 1568. | GCGGTGGG GAAGCCAT TGAG | 1569. | DMSO | | 2 | 3 | 1 |
| OT2-48 | CCGCGCTTCCGC CCCGCCTCTGG | 1570. | 6 | | GGGGGTCTGGCTC ACCTGA | 1571. | CCTGTCGG GAGAGTGC CTGC | 1572. | DMSO | | 3 | 1 | 2 |
| OT2-49 | CCTGCCATGCAC CCCGCCTCAGG | 1573. | 6 | | TCCTGGTTCATTT GCTAGAACTCTGGT | 1574. | ACTCCAGA TGCAACCA GGGCT | 1575. | DMSO | | 3 | 2 | 1 |
| OT2-50 | CTGCCTCCTCAC CCCGCCTCAGG | 1576. | 6 | | CGTGTGGTGAGCC TGAGTCT | 1577. | GCTTCACC GTAGAGGC TGCT | 1578. | DMSO | | 3 | 0 | 3 |
| OT2-51 | TCTTCTTTCCAC CCCGCCTCAGG | 1579. | 6 | | AGGCCCTGATAAT TCATGCTACCAA | 1580. | TCAGTGAC AACCTTTT GTATTCGG CA | 1581. | DMSO | | 0 | 2 | 4 |
| OT2-52 | TTGACCCCCGC CCCGCCTCAGG | 1582. | 6 | | Not optimized | | | | | | 2 | 2 | 2 |
| Target 3 | GGTGAGTGAGTG TGTGCGTGTGG | 1583. | 0 | | TCCAGATGGCACA TTGTCAG | 1584. | AGGGAGCA GGAAGTG AGGT | 1585. | DMSO | | | | |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | Watson-Crick Transitions | non-Watson-Crick Transversions | Transitions |
|---|---|---|---|---|---|---|---|---|---|---|---|---|---|
| OT3-1 | GGTGAGTGAGTG TGTGTGAGG | 1586 | 1 | | GCAGGCAAGCTGT CAAGGGT | 1587 | CACCGACA CACCCACT CACC | 1588 | DMSO | 0 | 0 | | 1 |
| OT3-2 | AGTGAGTGAGTG TGTGTGGGG | 1589 | 2 | | GAGGGGGAAGTCA CCGACAA | 1590 | TACCCGGG CCGTCTGT TAGA | 1591 | DMSO | 0 | 0 | | 2 |
| OT3-3 | AGTGTGTGAGTG TGTGCGTGTGG | 1592 | 2 | | GACACCCCACACA CTCTCATGC | 1593 | TGAATCCC TTCACCCC CAAG | 1594 | DMSO | 1 | 0 | | 1 |
| OT3-4 | GCTGAGTGAGTG TATGCGTGTGG | 1595 | 2 | | TCCTTTGAGGTTC ATCCCCC | 1596 | CCAATCCA GGATGATT CCGC | 1597 | DMSO | 1 | 0 | | 1 |
| OT3-5 | GGTGAGTCAGTG TGTGAGTGAGG | 1598 | 2 | | CAGGGCCAGGAAC ACAGGAA | 1599 | GGGAGGTA TGTGCGGG AGTG | 1600 | DMSO | 1 | 1 | | 0 |
| OT3-6 | GGTGAGTGAGAG TGTGTGTGG | 1601 | 2 | | TGCAGCCTGAGTG AGCAAGTGT | 1602 | GCCCAGT GCTAAGCC CCTC | 1603 | DMSO | 1 | 0 | | 1 |
| OT3-7 | GGTGAGTGAGTG AGTGAGTGAGG | 1604 | 2 | | TACAGCCTGGGTG ATGGAGC | 1605 | TGTGTCAT GGACTTTC CCATTGT | 1606 | 1M betaine, TD | 1 | 1 | | 0 |
| OT3-8 | GGTGAGTGAGTG AGTGAGTGAGG | 1607 | 2 | | GGCAGGCATTAAA CTCATCAGGTCC | 1608 | TCTCCCCC AAGGTATC AGAGAGCT | 1609 | DMSO | 1 | 1 | | 0 |
| OT3-9 | GGTGAGTGAGTG CGTGCGGGTGG | 1610 | 2 | | GGGCCTCCCCTGCT GGTTCTC | 1611 | GCTGCCGT CCGAACCC AAGA | 1612 | DMSO | 0 | 1 | | 1 |
| OT3-10 | GGTGAGTGTGTG TGTGAGTGTGG | 1613 | 2 | | ACAAACGCAGGTG GACCGAA | 1614 | ACTCCGAA AATGCCCC GCAGT | 1615 | DMSO | 1 | 1 | | 0 |
| OT3-11 | GGTGAGTGTGTG TGTGCATGTGG | 1616 | 2 | | AGGGGAGGGGACA TTGCCT | 1617 | TTGAGAGG GTTCAGTG GTTGC | 1618 | DMSO | 1 | 0 | | 1 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | non-Watson-Crick Transversions | Transitions |
|---|---|---|---|---|---|---|---|---|---|---|---|---|
| OT3-12 | GGTGTGTGAGTG TGTGTGTGG | 1619. | 2 | | CTAATGCTTACGG CTGCGGG | 1620. | AGCCAACG GCAGATGC AAAT | 1621. | DMSO | 1 | 0 | 1 |
| OT3-13 | GGTGTGTGTGTG TGTGCGTGG | 1622. | 2 | | GAGCGAAGTTAAC CCACCGC | 1623. | CACACATG CACATGCC CCTG | 1624. | 68 C., 3% DMSO | 2 | 0 | 0 |
| OT3-14 | GGTGTGTGTGTG TGTGCGTGG | 1625. | 2 | | GCATGTGTCTAAC TGGAGACAATAGCA | 1626. | TCCCCCAT ATCAACAC ACACA | 1627. | DMSO | 2 | 0 | 0 |
| OT3-15 | GGTGTGTGTGTG TGTGCGTGG | 1628. | 2 | | GCCCCTCCCCCCT TTTGTGT | 1629. | TGGGCAAA GGACATGA AACAGACA | 1630. | DMSO | 2 | 0 | 0 |
| OT3-16 | GGTGTGTGTGTG TGTGCGTGG | 1631. | 2 | | GCCTCAGCTCTGC TCTTAAGCCC | 1632. | ACGAACAG ATCATTTT TCATGGCT TCC | 1633. | DMSO | 2 | 0 | 0 |
| OT3-17 | GTTGAGTGAATG TGTGCGTGAGG | 1634. | 2 | | CTCCAGAGCCTGG CCTACCA | 1635. | CCCTCTCC GGAAGTGC CTTG | 1636. | DMSO | 0 | 1 | 1 |
| OT3-18 | TGTGGGTGAGTG TGTGCGTGAGG | 1637. | 2 | | TCTGTCACCACAC AGTACCACC | 1638. | GTTGCCTG GGGATGGG GTAT | 1639. | DMSO | 0 | 1 | 1 |
| OT3-19 | ACTCTGTGAGTG TGTGCGTGAGG | 1640. | 3 | | GGGGACCCCTCAAG AGGCACT | 1641. | GGGCATCA AAGGATGG GGAT | 1642. | DMSO | 2 | 0 | 1 |
| OT3-20 | AGAGAGTGAGTG TGTGCATGAGG | 1643. | 3 | | TGTGGAGGGTGGG ACCTGGT | 1644. | ACAGTGAG GTGCGGTC TTTGGG | 1645. | DMSO | 1 | 0 | 2 |
| OT3-21 | AGCCAGTGGGTG TGTGCGTGGG | 1646. | 3 | | CGGGGTGGCAGTG ACGTCAA | 1647. | GGTGCAGT CCAAGAGC CCCC | 1648. | DMSO | 0 | 0 | 3 |
| OT3-22 | AGGGAGTGACTG TGTGCGTGTGG | 1649. | 3 | | AGCTGAGGCAGAG TCCCCGA | 1650. | GGGAGACA GAGCAGCG CCTC | 1651. | DMSO | 1 | 1 | 1 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | non-Watson-Crick Transversions | Transitions |
|---|---|---|---|---|---|---|---|---|---|---|---|---|
| OT3-23 | AGTGAGTGAGTG AGTGAGTGAGG | 1652. | 3 | | ACCACCAGACCCCC ACCTCCA | 1653. | AGGACGAC TTGTGCCC CATTCA | 1654. | 72 C. Anneal, 3% DMSO | 1 | 1 | 1 |
| OT3-24 | CATGAGTGAGTG TGTGGGTGGGG | 1655. | 3 | | GGGTCAGGACGCA GGTCAGA | 1656. | TCCACCCA CCCACCCA TCCT | 1657. | 72 C. Anneal, 3% DMSO | 2 | 0 | 1 |
| OT3-25 | CGTGAGTGTGTG TATGCGTGGGA | 1658. | 3 | | ACACTCTGGGCTA GGTGCTGGA | | GCCCCCTC ACCACATG ATGCT | 1660. | DMSO | 2 | 0 | 1 |
| OT3-26 | GGACTGTGAGTG TGTGCGTGGGG | 1661. | 3 | | GGGGCCATTCCTC TGCTGCA | 1662. | TGGGGATC CTTGCTCA TGGC | 1663. | DMSO | 3 | 0 | 0 |
| OT3-27 | GGTGTGTGCCTG CATTCACCA | 1664. | 3 | | ACACACTGGCTCG CATTCACCA | 1665. | CCTGCACG AGGCCAGG TGTT | 1666. | DMSO | 2 | 1 | 0 |
| OT3-28 | GTTTCATGAGTG TGTGCGTGGGG | 1667. | 3 | | TGGGCACGTAGTA AACTGCACCA | 1668. | CTCGCCGC CGTGACTG TAGG | 1669. | DMSO | 0 | 3 | 1 |
| OT3-29 | TGAGTGTGAGTG TGTGCGTGGGG | 1670. | 3 | | TCAGCTGGTCCTG GGCTTGG | 1671. | AGAGACACT GGGTAGCA GTCAGT | 1672. | DMSO | 2 | 1 | 0 |
| OT3-30 | TGCCAGTGAGTG TGTGCGTGGGG | 1673. | 3 | | AGACACAGCCAGG GCCTCAG | 1674. | GGTGGGCG TGTGTGTG TACC | 1675. | 68 C., 3% DMSO | 1 | 1 | 1 |
| OT3-31 | TGGGTGTGAGTG TGTGCGTGGGG | 1676. | 3 | | ACACTCTCACACA CGCACCAA | 1677. | GAGAAGTC AGGGCTGG CGGG | 1678. | 72 C. Anneal, 3% DMSO | 1 | 2 | 0 |
| OT3-32 | TGTATGTGAGTG TGTGCGTGGGG | 1679. | 3 | | ACTGCCTGCATTT CCCCGGT | 1680. | TGGTGAGG GCTTCAGG GAGC | 1681. | DMSO | 1 | 1 | 1 |
| OT3-33 | TGTGAGAGAG TGTGCGTGGGG | 1682. | 3 | | GCCAGGTTCATTG ACTGCCC | 1683. | TCCTTCTA CACATCGG CGGC | 1684. | DMSO | 2 | 1 | 0 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | non-Watson-Crick Transversions | Transitions |
|---|---|---|---|---|---|---|---|---|---|---|---|---|
| OT3-34 | TGTGCCTGAGTG TGTGCGTGTGG | 1685. | 3 | | CGAGGGAGCCGAG TTCGTAA | 1686. | CTGACCTG GGGCTCTG GTAC | 1687. | DMSO | 1 | 2 | 0 |
| OT3-35 | TGTGTGTGTGTG TGTGCGTGTGG | 1688. | 3 | | TCCTCGGGAAGTC ATGGCTTCA | 1689. | GCACTGAG CAACCAGG AGCAC | 1690. | DMSO | 2 | 1 | 0 |
| OT3-36 | AGCGTGTGAGTG TATGCGTGGGG | 1691. | 4 | | Not optimized | | | | | 1 | 0 | 3 |
| OT3-37 | ATTGAGTGTGTG AGTGCGTGGGG | 1692. | 4 | | TAAACCGTTGCCC CCGCCTC | 1693. | GCTCCCCT GCCAGGTG AACC | 1694. | DMSO | 2 | 1 | 1 |
| OT3-38 | CATCTGTGGGTG TGTGCGTGTGG | 1695. | 4 | | CCTGCTGAGACTC CAGTCC | 1696. | CTGCGGAG TGGCTGGC TATA | 1697. | DMSO | 2 | 0 | 2 |
| OT3-39 | CCCCAGTGTGTG TGTGCGTGTGG | 1698. | 4 | | CTCGGGGACTGAC AAGCCGG | 1699. | GGAGCAGC TCTTCCAG GGCC | 1700. | DMSO | 3 | 0 | 1 |
| OT3-40 | CTGGAGTGAGTG TGTGTGTGTGG | 1701. | 4 | | CCCCGACCAAAGC AGGAGCA | 1702. | CTGGCAGC CTCTGGAT GGGG | 1703. | DMSO | 1 | 2 | 1 |
| OT3-41 | GTTTCATGAGTG TGTGCGTGGGG | 1704. | 4 | | Not optimized | | | | | 0 | 3 | 1 |
| OT3-42 | TATCTGTGCCGTG TGTGCGTGTGG | 1705. | 4 | | ATTTCAGAGCCCCC GGGGAAA | 1706. | AGGCCCCG GTGTTATG GTTA | 1707. | DMSO | 1 | 2 | 1 |
| OT3-43 | TATCTGTGTGTG TGTGCGTGTGG | 1708. | 4 | | GCCAGTGGCTTAG TGTCTTTGT | 1709. | TGACATAT TTTCCTGG GCCATGGGT | 1710. | DMSO | 2 | 1 | 1 |
| OT3-44 | TCTCTGTGTGTG TGTGCGTGGGG | 1711. | 4 | | TGCCAGAAGAACA TGGGCCAGA | 1712. | CCATGCTG ACATCATA TACTGGGA AGC | 1713. | DMSO | 3 | 1 | 0 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | Watson-Crick Transitions | non-Watson-Crick Transversions | Transitions |
|---|---|---|---|---|---|---|---|---|---|---|---|---|---|
| OT3-45 | TCTGTGTGTGTG TGTGCGTGTGG | 1714 | 4 | | GCGTGTCTCTGTG TGCGTGC | 1715 | CCAGGCTG GGCACACA GGTT | 1716 | DMSO | 3 | 1 | | 0 |
| OT3-46 | TGAGCGTGAGTG TGAGCGTGTGG | 1717 | 4 | | Not optimized | | | | | 2 | 2 | | 0 |
| OT3-47 | TGTCTTTGAGTG TGTGCGTGTGG | 1718 | 4 | | TGCCCAGTCCAAT ATTTCAGCAGCT | 1719 | AGGATGAG TTCATGTC CTTTGTGG GG | 1720 | DMSO | 2 | 2 | | 0 |
| OT3-48 | TTTCTGTGTGTG TGTGCGTGTGG | 1721 | 4 | | GGGTGAAAATTTG GTACTGTTAGCTGT | 1722 | AATGACTC ATTCCCTG GGTATCTC CCA | 1723 | DMSO | 2 | 2 | | 0 |
| OT3-49 | AAGGCGTGTGTG TGTGCGTGTGG | 1724 | 5 | | TGCCCCATCAATC ACCTCGGC | 1725 | CAAGTCG GCAGGGCA GTGA | 1726 | DMSO | 1 | 2 | | 2 |
| OT3-50 | AATTCGTGTGTG TGTGCGTGTGGG | 1727 | 5 | | GCCTCTCTCTGCCG CTGGTAA | 1728 | TGAGAGTT CCTGTTGC TCCACACT | 1729 | DMSO | 1 | 2 | | 2 |
| OT3-51 | ATGGTGTGTGTG TGTGCGTGTGG | 1730 | 5 | | Not optimized | | | | | 2 | 2 | | 1 |
| OT3-52 | CACGTGTGTGTG TGTGCGTGTGG | 1731 | 5 | | GCCACCAAAATAG CCAGCGT | 1732 | ACATGCAT CTGTGTGT GCGT | 1733 | DMSO | 3 | 0 | | 2 |
| OT3-53 | GAAATTGAGTG TGTGCGTGTGG | 1734 | 5 | | ACAGACTGACCCT TGAAAAATACCAGT | 1735 | TGTATCTT TCTTGCCA ATGGTTTT CCC | 1736 | DMSO | 2 | 1 | | 2 |
| OT3-54 | TAAGTGTGTGTG TGTGCGTGTGG | 1737 | 5 | | AGCCAAATTTCTC AACAGCAGCACT | 1738 | TCCTGGAG AGCAGGCA TTTTTGT | 1739 | DMSO | 3 | 1 | | 1 |
| OT3-55 | TATATGTGTGTG TGTGCGTGTGGG | 1740 | 5 | | ACCTCCTTGTGCT GCCTGGC | 1741 | GGCGGGAA GGTAACCC TGGG | 1742 | DMSO | 2 | 1 | | 2 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | Watson-Crick Transitions | non-Watson-Crick Transversions | non-Watson-Crick Transitions |
|---|---|---|---|---|---|---|---|---|---|---|---|---|---|
| OT3-56 | TATCTGTGTGTG TGTGCGTGTGG | 1743. | 5 | | CACAAAGCTCTAC CTTTCCAGTAGTGT | 1744. | TGATCCGA TGGTTGTT CACAGCT | 1745. | DMSO | 3 | 1 | 1 | 1 |
| OT3-57 | TTTATGTGTGTG TGTGCGTGTGG | 1746. | 5 | | TGTGGGGATTACC TGCCTGGC | 1747. | ACGCACAA AAATGCCC TTGTCA | 1748. | DMSO | 2 | 2 | 2 | 1 |
| OT3-58 | TTTTTGTGTGTG TGTGCGTGTGGG | 1749. | 5 | | TGAGGCAGAGACCAG TCATCCAGC | 1750. | GCCCGAGC ACAGTGTA GGGC | 1751. | DMSO | 2 | 3 | 3 | 0 |
| OT3-59 | AAAAATTGTGTG TGTGCGTGGGG | 1752. | 6 | | ATTAGCTGGGCGT GGCGGAG | 1753. | ACTGCATC TCATCTCA GGCAGCT | 1754. | DMSO | 2 | 1 | 1 | 3 |
| OT3-60 | ACAATGTGTGTG TGTGCGTGTGG | 1755. | 6 | | TGAAGCAGAAGGA GTGAGAAGGA | 1756. | TCAGCTTC ACATCTGT TTCAGTTC AGT | 1757. | DMSO | 4 | 0 | 2 | 2 |
| OT3-61 | ATGTGGTGTGTG TGTGCGTGTGG | 1758. | 6 | | TGGTGGAGTGTGT GTGTGT | 1759. | AGAGACAGA AAGAGAGT GCCCA | 1760. | DMSO | 1 | 3 | 3 | 2 |
| OT3-62 | CAAAATTGTGTG TGTGCGTGTGG | 1761. | 6 | | GCCCCTGTACGTC CTGACAGC | 1762. | TGCACAAG CCACTTAG CCTCTCT | 1763. | DMSO | 3 | 1 | 2 | 2 |
| OT3-63 | CCCTGGTGTGTG TGTGCGTGTGG | 1764. | 6 | | AGCGCAGGTAAAC AGGCCCA | 1765. | TCTCTCGC CCCGTTTC CTTGT | 1766. | DMSO | 3 | 1 | 2 | 2 |
| OT3-64 | TCCCCTTGTGTG TGTGCGTGGGG | 1767. | 6 | | ATGGGTGCCAGGT ACCACGC | 1768. | ACAGCAGG AAGGAGCC GCAG | 1769. | DMSO | 2 | 3 | 3 | 1 |
| OT3-65 | TCCTCGTGTGTG TGTGCGTGTGG | 1770. | 6 | | CGGGCGGGTGGAC AGATGAG | 1771. | AGGAGGTC TCGAGCCA GGGG | 1772. | DMSO | 2 | 3 | 3 | 1 |
| OT3-66 | TTAAGGTGGTG TGTGCGTGGGG | 1773. | 6 | | TCAACCTAGTGAA CACAGACCACTGA | 1774. | GTCTATAT ACAGCCCA CAACCTCA TGT | 1775. | DMSO | 1 | 2 | 2 | 3 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | Watson-Crick Transversions | non-Watson-Crick Transversions | Transitions |
|---|---|---|---|---|---|---|---|---|---|---|---|---|---|
| OT3-67 | TTATATTGTGTG TGTGCGTGGGG | 1776. | 6 | | GCCAGGGCCAGTG GATTGCT | 1777. | TGTCATTT CTTAGTAT GTCAGCCG GA | 1778. | DMSO | | 2 | 4 | 0 |
| OT3-68 | TTGAGGAGAGTG TGTGCGTGAGG | 1779. | 6 | | GAGCCCCACCGGT TCAGTCC | 1780. | GCCAGAGC TACCCACT CGCC | 1781. | DMSO | | 1 | 3 | 2 |
| Target 4 | GAGTCCGAGCAG AAGAGAAGG | 1785. | 0 | | GGAGCAGCTGGTC AGAGGGG | 1786. | GGGAAGGG GGACACTG GGGA | 1787. | DMSO | | 1782. | | |
| OT4-1 | GAGTTAGAGCAG AAGAGAAAGG | 1788. | 2 | | TCTCTCCTTCAAC TCATGACCAGCT | 1789. | ATCTGCAC ATGTATGT ACAGGAGT CAT | 1790. | DMSO | | 0 | 1 | 1 |
| OT4-2 | AAGTCAGAGGAG AAGAGAAGG | 1791. | 3 | AAGACAGAGAGAA GAAGAAGGG (SEQ ID NO: 2229) | TGGGGAATCTCCA AAGAACCCCC | 1792. | AGGGTGTA CTGTGGGA ACTTTGCA | 1793. | DMSO | | 2 | 1 | 2 |
| OT4-3 | AAGTCCGAGGAG AGGAGAAAGG | 1794. | 3 | | GATGCCCCACTG AGCACGT | 1795. | ACTTCGTA GAGCCTTA AACATGTG GC | 1796. | DMSO | | 1 | 0 | 2 |
| OT4-4 | AAGTCTGAGCAC AAGAGAATGG | 1797. | 3 | | AGGATTAATGTTT AAAGTCACTGGTGG | 1798. | TCAAACAA GGTGCAGA TACAGCA | 1799. | 1M betaine, TD | | 1 | 0 | 2 |
| OT4-5 | ACGTCTGAGCAG AAGAGAATGG | 1800. | 3 | | TCCAAGCCACTGG TTTCTCAGTCA | 1801. | TGCTCTGT GGATCATA TTTTGGGG GA | 1802. | DMSO | | 0 | 1 | 2 |
| OT4-6 | GACTCCTAGCAA AAGAGAATGG | 1803. | 3 | | ACTTTCAGAGCTT GGGGCAGGT | 1804. | CCCACGCT GAAGTGCA ATGGC | 1805. | DMSO | | 1 | 1 | 1 |
| OT4-7 | GAGACTGAGAAG AAGAGAAAGG | 1806. | 3 | | CAAAGCATGCCTT TCAGCCG | 1807. | GGCTCTTC GATTTGGC ACCT | 1808. | 1M betaine, TD | | 1 | 1 | 1 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | non-Watson-Crick Transversions | Transitions |
|---|---|---|---|---|---|---|---|---|---|---|---|---|
| OT4-8 | GAGCCGAGCAG AAGAAGGAGGG | 1809. | 3 | | Not optimized | | | | | 1 | 0 | 2 |
| OT4-9 | GAGCCTGAGCAG AAGGAGAAGGG | 1810. | 3 | | GGACTCCCTGCAG CTCCAGC | 1811. | AGGAACAC AGGCCAGG CTGG | 1812. | 72 C. Anneal, 6% DMSO | 0 | 0 | 3 |
| OT4-10 | GAGGCCGAGCAG AAGAAAGACGG | 1813. | 3 | | CCCTTTAGGCACC TTCCCCA | 1814. | CCGACCTT CATCCCTC CTGG | 1815. | DMSO | 0 | 1 | 2 |
| OT4-11 | GAGTAAGAGAAG AAGAAGAAGGG | 1816. | 3 | | TGATTCTGCCTTA GAGTCCCAGGT | 1817. | TGGGCTCT GTGTCCCT ACCCA | 1818. | DMSO | 0 | 3 | 0 |
| OT4-12 | GAGTAGGAGGAG AAGAAGAAAGG | 1819. | 3 | | Not optimized | | | | | 2 | 1 | 0 |
| OT4-13 | GAGTCCGGGAAG GGAGAGAAAGG | 1820. | 3 | | AGGCAGGAGAGCA AGCAGGT | 1821. | ACCCTGAC TACTGACT GACCGCT | 1822. | DMSO | 0 | 1 | 2 |
| OT4-14 | GATTCCTACCAG AAGAAGAATGG | 1823. | 3 | | CTCCCCATTGCGA CCCGAGG | 1824. | AGAGGCAT TGACTTGG AGCACCT | 1825. | DMSO | 1 | 2 | 0 |
| OT4-15 | GCCACAGAGCAG AAGAAGAAGGG | 1826. | 3 | | CTGGAGCCCAGCA GGAAGGC | 1827. | CCTCAGGG AGGGGCC TGAT | 1828. | DMSO | 1 | 2 | 0 |
| OT4-16 | AAATCCAACCAG AAGAAGAAAGG | 1829. | 4 | | ACTGTGGGCCTTG TCCCCAC | 1830. | AGGTCGGT GCAGGGTT TAAGGA | 1831. | DMSO | 1 | 0 | 3 |
| OT4-17 | AAGTCTGAGGAC AAGAAGAATGG | 1832. | 4 | | GGCGCTCCCTTTT TCCCTTTGT | 1833. | CGTCACCC ATCGTCTC GTGGA | 1834. | DMSO | 2 | 0 | 2 |
| OT4-18 | AAGTTGGAGCAG GAGAAGAGGG | 1835. | 4 | | TGCCATCTATAGC AGCCCCT | 1836. | GCATCTTG CTAACCGT ACTTCTTC TGA | 1837. | DMSO | 1 | 0 | 3 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | non-Watson-Crick Transversions | Transitions |
|---|---|---|---|---|---|---|---|---|---|---|---|---|
| OT4-19 | AATACAGAGCAG AAGAAGAATGG | 1838. | 4 | | GTGGAGACGCTAA ACCTGTGAGT | 1839. | GCTCCTGG CCTCTTCC TACAGC | 1840. | DMSO | 1 | 2 | 1 |
| OT4-20 | AGGTACTAGCAG AAGAAGAAAGG | 1841. | 4 | | CCGAACTTCTGCT GAGCTTGATGC | 1842. | CCAAGTCA ATGGCAA CAAGGGA | 1843. | DMSO | 0 | 2 | 2 |
| OT4-21 | AGGTGCTAGCAG AAGAAGAAGGG | 1844. | 4 | | Not optimized | | | | | 1 | 1 | 2 |
| OT4-22 | AGGTGGGAGCAG AAGAAGAAAGG | 1845. | 4 | | TGCCCCCAAGACC TTTCTCC | 1846. | ATGGCAGG CAGAGGAG GAAG | 1847. | DMSO | 2 | 0 | 2 |
| OT4-23 | CAAACGGAGCAG AAGAAGAAAGG | 1848. | 4 | | GGGTGGGGCCATT GTGGGTT | 1849. | CTGGGGCC AGGGTTTC TGCC | 1850. | DMSO | 3 | 0 | 1 |
| OT4-24 | CACTCTGAGGAG AAGAAGAAAGG | 1851. | 4 | | TGGAGAACATGAG AGGCTTGCAA | 1852. | TCCTTCTG TAGGCAAT GGGAACAA | 1853. | DMSO | 3 | 0 | 1 |
| OT4-25 | CAGTCATGGCAG AAGAAGAAAGG | 1854. | 4 | | GCCACATGTGTAGA AGTCGGC | 1855. | GGCAGATT TCCCCCAT GCTG | 1856. | 1M betaine, TD | 1 | 2 | 1 |
| OT4-26 | CCGTCCCAGCAG TAGAAGAATGG | 1857. | 4 | | TGTACACCCCAAG TCCTCCC | 1858. | AAGGGGAG TGTGCAAG CCTC | 1859. | DMSO | 3 | 1 | 0 |
| OT4-27 | GTCTGTGCGATCAG AAGAAGAAAGG | 1860. | 4 | | AGGTCTGGCTAGA GATGCAGCA | 1861. | AGTCCAAC ACTCAGGT GAGACCCT | 1862. | DMSO | 3 | 1 | 0 |
| OT4-28 | TAATCCAATCAG AAGAAGAAGGG | 1863. | 4 | | CCAAGAGGACCCA GCTGTTGGA | 1864. | GGGTATGG AATTCTGG ATTAGCAG AGC | 1865. | DMSO | 0 | 2 | 2 |
| OT4-29 | TATACGGAGCAG AAGAAGAATGG | 1866. | 4 | | ACCATCTCTTCAT TGATGAGTCCAA | 1867. | ACACTGTG AGTATGCT TGGCGT | 1868. | DMSO | 2 | 2 | 0 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | non-Watson-Crick Transversions | Transitions |
|---|---|---|---|---|---|---|---|---|---|---|---|---|
| OT4-30 | ACTTCCCTGCAG AAGAAGAAAGG | 1869. | 5 | | GGCTGCGGGGAGA TGAGCTC | 1870. | TCGGATGC TTTTCCAC AGGGCT | 1871. | DMSO | 2 | 2 | 1 |
| OT4-31 | AGGACTGGGCAG AAGAAGAAGGG | 1872. | 5 | | TCTTCCAGGAGGG CAGCTCC | 1873. | CCAATCCT GAGCTCCT ACAAGGCT | 1874. | DMSO | 1 | 0 | 4 |
| OT4-32 | AGGTTGGAGAAG AAGAAGAAGGG | 1875. | 5 | | GAGCTGCACTGGA TGGCACT | 1876. | TGCTGGTT AAGGGGTG TTTTGGA | 1877. | DMSO | 1 | 1 | 3 |
| OT4-33 | AGTTCAGAGCAG GAGAAGAATGG | 1878. | 5 | | TCTGGGAAGGTGA GGAGGCCA | 1879. | TGGGGGAC AATGAAAA AGCAATGA | 1880. | DMSO | 0 | 2 | 3 |
| OT4-34 | ATGACACAGCAG AAGAAGAAGGG | 1881. | 5 | | CTTGCTCCCAGCC TGACCCC | 1882. | AGCCCTTG CCATGCAG GACC | 1883. | DMSO | 3 | 1 | 1 |
| OT4-35 | ATGACAGAGAAG AAGAAGAAAGG | 1884. | 5 | | GGGATTTTTATCT GTTGGGTGCGAA | 1885. | AACCACAG ATGTACCC TCAAAGCT | 1886. | DMSO | 2 | 2 | 1 |
| OT4-36 | CCGCCCCTGCAG AAGAAGAACGG | 1887. | 5 | | ACCCATCAGGACC GCAGCAC | 1888. | TCTGGAAC CTGGAGG CGGA | 1889. | 72 C. Anneal, 3% DMSO | 3 | 1 | 1 |
| OT4-37 | GCAGGAGAGCAG AAGAAGAAAGG | 1890. | 5 | | CGTCCCTCACAGC CAGGCTC | 1891. | CCTCCTTG GGCCTGGG GTTC | 1892. | DMSO | 1 | 3 | 1 |
| OT4-38 | GTTCAAGAGCAG AAGAAGAATGG | 1893. | 5 | | CCCTCTGCAAGGT GGAGTCTCC | 1894. | AGATGTTC TGTCCCCA GGCCT | 1895. | DMSO | 1 | 3 | 1 |
| OT4-39 | GTTTTGAAGCAG AAGAAGAAAGG | 1896. | 5 | | GGCTTCCACTGCT GAAGGCCT | 1897. | TGCCGCTC CACATACC CTCC | 1898. | DMSO | 2 | 1 | 2 |
| OT4-40 | TATGGCAAGCAG AAGAAGAAAGG | 1899. | 5 | | AGCATTGCCTGTC GGGTGATGT | 1900. | AGCACCTA TTGGACAC TGGTTCTCT | 1901. | DMSO | 1 | 3 | 1 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | Watson-Crick Transitions | non-Watson-Crick Transversions | Transitions |
|---|---|---|---|---|---|---|---|---|---|---|---|---|---|
| OT4-41 | TGGTGGGATCAG AAGAAGAAGG | 1902. | 5 | | TCTAGAGCAGGGG CACAATGC | 1903. | TGGAGATG GAGCCTGG TGGGA | 1904. | DMSO | 2 | 2 | | 1 |
| OT4-42 | ACCCACGGGCAG AAGAAGAAGGG | 1905. | 6 | | GGTCTCAGAAAAT GGAGAGAAAGCACG | 1906. | CCCACAGA AACCTGGG CCCT | 1907. | DMSO | 1 | 2 | | 3 |
| OT4-43 | ACTCCTGATCAG AAGAAGAAGGG | 1908. | 6 | | GGTTGCTGATACC AAAACGTTTGCCT | 1909. | TGGGTCCT CTCCACCT CTGCA | 1910. | DMSO | 0 | 3 | | 3 |
| OT4-44 | ACTGATGAGCAG AAGAAGAAGG | 1911. | 6 | | ACTCTCCTTAAGT ACTGATATGGCTGT | 1912. | CAGAATCT TGCTCTGT TGCCCA | 1913. | DMSO | 0 | 4 | | 2 |
| OT4-45 | ATTTTAGTGCAG AAGAAGAAGG | 1914. | 6 | | Not optimized | | | | | | | | 2 |
| OT4-46 | ATTTTAGTGCAG AAGAAGAAGG | 1915. | 6 | | Not optimized | | | | | | | | 2 |
| OT4-47 | CCATGGCAGCAG AAGAAGAAGGG | 1916. | 6 | | CAATGCCTGCAGT CCTCAGGA | 1917. | TCCCAAGA GAAAACTC TGTCCTGA CA | 1918. | DMSO | 4 | 1 | | 1 |
| OT4-48 | CCATTACAGCAG AAGAAGAAGG | 1919. | 6 | | GCATTGGCTGCCC AGGGAAA | 1920. | TGGCTGTG CTGGGCTG TGTT | 1921. | DMSO | 2 | 2 | | 2 |
| OT4-49 | CGAGGCGGGCAG AAGAAGAAGG | 1922. | 6 | | CCACAAGCCTCAG CCTACCCG | 1923. | ACAGGTGC CAAAACAC TGCCT | 1924. | DMSO | 2 | 1 | | 3 |
| OT4-50 | TCATTGCAGCAG AAGAAGAAGG | 1925. | 6 | TCATTGCAGCAGAA GAAGAAGG TCATTGTAGCAGAA GAAGAAGG (SEQ ID NO: 2230) | GCCTCTTGCAAAT GAGACTCCTTTT | 1926. | CGATCAGT CCCCTGGC GTCC | 1927. | DMSO | 2/1 | 2/3 | | 2 |
| OT4-51 | TCTCCAGGGCAG AAGAAGAAGG | 1928. | 6 | | TCCCAGAATCTGC CTCCGCA | 1929. | AGGGGTTT CCAGGCAC ATGGG | 1930. | DMSO | 0 | 4 | | 2 |
| | | 1931. | | | | 1932. | | 1933. | | | | | |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | non-Watson-Crick Transversions | Transitions |
|---|---|---|---|---|---|---|---|---|---|---|---|---|
| Target 5 | GTCATCTTAGTC ATTACCTGAGGG | 1934. | 0 | | TCCTAAAAATCAG TTTTGAGATTTAC TTCC | 1935. | AAAGTGTT AGCCAACA TACAGAAG TCAGGA | 1936. | DMSO | | | |
| OT5-1 | GGTATCTAAGTC ATTACCTGTGG | 1937. | 3 | GGTATCTAAGTCAT TACCTGTGG (SEQ ID NO: 2231) GGTATCTAAGTCAA TACCTGTGG (SEQ ID NO: 2232) | ACATCTGGGAAA GCAAAAGTCAACA | 1938. | TGTCTCAG TATCTAGG CTAAAAGT GGT | 1939. | DMSO | 1/2 | 1 | 1 |
| OT5-2 | GTAATATTAGTC ATTACCGGTGG | 1940. | 3 | | ACGATCTTGCTTC ATTTCCCTGTACA | 1941. | AGTGCTTT GTGAACTG AAAAGCAA ACA | 1942. | DMSO | 0 | 3 | 0 |
| OT5-3 | GTAATCTGAGTC ATTTCCTGGGG | 1943. | 3 | | GCACCTTGGTGCT GCTAAATGCC | 1944. | GGGCACT GAACAGGC ATGAATGG | 1945. | DMSO | 1 | 2 | 0 |
| OT5-4 | GTCATCTCTAGTC ATTTACTGGGG | 1946. | 3 | | AACTGTCCTGCAT CCCCGCC | 1947. | GGTGCACC TGGATCCA CCCA | 1948. | DMSO | 1 | 1 | 1 |
| OT5-5 | GTCATCCTAGTG CTTACCTGAGG | 1949. | 3 | | Not optimized | 1950. | | 1951. | | 1 | 1 | 1 |
| OT5-6 | GTCATCTGAGGC ATTAACTGGGG | 1952. | 3 | | CATCACCCTCCAC CAGGCCC | 1953. | ACCACTGC TGCAGGCT CCAG | 1954. | 72 C. Anneal, 3% DMSO | 0 | 3 | 0 |
| OT5-7 | AATATGTTAGTC ATTACCTGAGG | 1955. | 4 | | Not optimized | | | | | 2 | 0 | 2 |
| OT5-8 | ATAAACGTAGTC ATTACCTGGGG | 1956. | 4 | | CCTGACCCGTGGT TCCCGAC | 1957. | TGGTGCGT GGTGTGTG TGGT | 1958. | 72 C. Anneal, 3% DMSO | 1 | 2 | 1 |
| OT5-9 | ATCATCATCGTC ATTATCTGGGG | 1959. | 4 | | TGGGAACATTGGA GAAGTTCCTGA | 1960. | CCATGTGA CTACTGGG CTGCCC | 1961. | DMSO | 1 | 1 | 2 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | Watson-Crick Transversions | non-Watson-Crick Transversions | Transitions |
|---|---|---|---|---|---|---|---|---|---|---|---|---|---|
| OT5-10 | ATCATTTTACTC ATTACTGTGG | 1962. | 4 | | AGCCTTGGCAAGC AACTCCCT | 1963. | GGTTCTCT CTCTCAGA AAAGAAAG AGG | 1964. | DMSO | 1 | 0 | 3 |
| OT5-11 | ATCATTTTAGTC ATCTCCTGTGG | 1965. | 4 | | GGCAGCGGACTTC AGAGCCA | 1966. | GCCAGAGG CTCTCAGC AGTGC | 1967. | DMSO | 1 | 0 | 3 |
| OT5-12 | CACAGCTTAGTC ATCACCTGGGG | 1968. | 4 | | CCAGCCTGGTCAA TATGCA | 1969. | ACTGTGCC CAGCCCCA TATT | 1970. | DMSO | 2 | 1 | 1 |
| OT5-13 | CCCAGCTTAGTC ATTAGCTGTGG | 1971. | 4 | | ATGCCAACACTCG AGGGCC | 1972. | CGGGTTGT GGCACCGG GTTA | 1973. | DMSO | 2 | 1 | 1 |
| OT5-14 | CTCACCTTTGTC ATTTCCTGAGG | 1974. | 4 | | TTGCTCTAGTGGG GAGGGGG | 1975. | AGAGTTCA GGCATGAA AAGAAGCA ACA | 1976. | DMSO | 3 | 0 | 1 |
| OT5-15 | CTCATTTTATTC ATTGCCTGGGG | 1977. | 4 | | AGCTGAAGATAGC AGTGTTTAAGCCT | 1978. | TGCAATTT GAGGGGCT CTCTTCA | 1979. | DMSO | 1 | 1 | 2 |
| OT5-16 | CTCTCCTTAGTC ACTACCTGAGG | 1980. | 4 | | AGTCACTGAGTA AGCCTGCCT | 1981. | TGCCAGCC AAAAGTTG TTAGTGTGT | 1982. | DMSO | 2 | 0 | 2 |
| OT5-17 | CTTATCTCTGTC ATTACCTGGGG | 1983. | 4 | | GGGTCTCCCTCAG TGCCCTG | 1984. | TGTGTGGT AGGGAGCA AAACGACA | 1985. | DMSO | 2 | 0 | 2 |
| OT5-18 | GACAGCTTCCGTC ATTAGCTGGGG | 1986. | 4 | | TGGGGGCTGTTAA GAGGCACA | 1987. | TGACCACA CACACCCC CACG | 1988. | DMSO | 1 | 2 | 1 |
| OT5-19 | GCCACCTTCAGTC ATTAGCTGGGG | 1989. | 4 | | TCAAAACAGATTG ACCAAGGCCAAAT | 1990. | TGTGTTTT TAAGCTGC ACCCCAGG | 1991. | DMSO | 1 | 0 | 3 |
| OT5-20 | GGAATCTTACTC ATTACTGGGG | 1992. | 4 | | TCTGGCACCAGGA CTGATTGTACA | 1993. | GCACCCAG CTGACTCC CAGA | 1994. | DMSO | 1 | 2 | 1 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | non-Watson-Crick Transversions | Transitions |
|---|---|---|---|---|---|---|---|---|---|---|---|---|
| OT5-21 | GTGGCCTCAGTC ATTACCTGCGG | 1995. | 4 | | Not optimized | | | | | 1 | 0 | 3 |
| OT5-22 | GTTGTTTAGTG ATTACCTGAGG | 1996. | 4 | | AGCATCTGTGATA CCCTACCTGTCT | 1997. | ACCAGGGC TGCCACAG AGTC | 1998. | DMSO | 1 | 0 | 3 |
| OT5-23 | TACATCTTAGTC CTCACCTGTGG | 1999. | 4 | | TAGTCTTGTTGCC CAGGCTG | 2000. | CTCGGCCC CTGAGAGT TCAT | 2001. | DMSO | 1 | 2 | 1 |
| OT5-24 | TCCATCTCACTC ATTACCTGAGG | 2002. | 4 | TCCATCTCACTCAT TACCTGAGG (SEQ ID NO: 2233) TCCATCTCACTCAT TACCTGATG (SEQ ID NO: 2234) | CTGCAACCAGGGC CCTTACC | 2003. | GAGCAGCA GCAAAGCC ACCG | 2004. | DMSO | 1 | 1 | 2 |
| OT5-25 | TTCATCCTAGTC AACACCTGGGG | 2005. | 4 | | GCCTGGAGAGCAA GCCTGGG | 2006. | AGCCGAGA CAATCTGC CCCG | 2007. | DMSO | 1 | 1 | 2 |
| OT5-26 | TTTATATTAGTG ATTACCTGTGG | 2008. | 4 | TTTATATTAGTGAT TACCTGCGG (SEQ ID NO: 2235) | AGTGAAACAAACA AGCAGCAGTCTGA | 2009. | GGCAGTC TGACCAGT GGGG | 2010. | No DMSO TD | 1 | 2 | 1 |
| OT5-27 | AACGTGTAAGTC ATTACCTGAGG | 2011. | 5 | | AGGGTCAGAGAGG TAAGCAATGA | 2012. | TGAGTAGA CAGAAATG TTACCGGT GTT | 2013. | DMSO | 3 | 0 | 2 |
| OT5-28 | AAGATCACAGTC AGCCTTGGTGG | 2014. | 5 | | TCAGAGATGTTAA AGCCTTGGTGGG | 2015. | AGTGAACC AAGGGAAT GGGGGA | 2016. | DMSO | 3 | 0 | 2 |
| OT5-29 | AGAATATTAGTC CTTACCTGGGG | 2017. | 5 | | TGTGCTTTCTGGG GTAGTGGCA | 2018. | CACCTCAG CCCTGTAG TCCTGG | 2019. | DMSO | 0 | 4 | 1 |
| OT5-30 | AGCAGATTAGTG ATTACCTGGGG | 2020. | 5 | | CCATTGGGTGACT GAATGCACA | 2021. | GCCACTGT CCCCAGCC TATT | 2022. | 1M betaine, TD | 1 | 3 | 1 |
| OT5-31 | AGTAGCTTAGTG ATTACCTGGGG | 2023. | 5 | | ACCAAGAAAGTGA AAAGGAAACCC | 2024. | TGAGATGG CATACGAT TTACCCA | 2025. | DMSO | 1 | 2 | 2 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | Watson-Crick Transitions | non-Watson-Crick Transversions | Transitions |
|---|---|---|---|---|---|---|---|---|---|---|---|---|---|
| OT5-32 | CACGGGCTTACTC ATTACCTGGGG | 2026. | 5 | | AGGGTGGGGACTG AAAGGAGCT | 2027. | TGGCATCA CTCAGAGA TTGGAACA CA | 2028. | DMSO | 3 | 1 | 1 | 1 |
| OT5-33 | CATATGTTAGGC ATTACCTGGGG | 2029. | 5 | | ACCAGTGCTGTGT GACCTTGGA | 2030. | TCCTATGG GAGGGGAG GCTTCT | 2031. | DMSO | 3 | 1 | 1 | 1 |
| OT5-34 | CATTTCTTAGTC ATTTCCTGAGG | 2032. | 5 | | CCAGTGTGTGGTGG TTCATGAC | 2033. | GCATACGG CAGTAGAA TGAGCC | 2034. | 68 C., 3% DMSO | 4 | 0 | 1 | 1 |
| OT5-35 | TGCAGCTAACTC ATTACCTGCGG | 2035. | 5 | | CAGGCGCTGGGTT CTTAGCCT | 2036. | CCTTCCTG GGCCCCAT GGTG | 2037. | DMSO | 2 | 3 | 0 | 0 |
| OT5-36 | TTGCTTTTAGTT ATTACCTGGGG | 2038. | 5 | | TGGGGTCCAAGAT GTCCCCT | 2039. | TGAAACTG CTTGATGA GGTGTGA | 2040. | DMSO | 1 | 2 | 2 | 2 |
| OT5-37 | AACTTGAAAGTC ATTACCTGTTG | 2041. | 6 | | GCTGGGCTTGGTG GTATATGC | 2042. | ACTTGCAA AGCTGATA ACTGACTGA | 2043. | DMSO | 5 | 0 | 0 | 1 |
| OT5-38 | AAGGTCACAGTC ATTACCTGGGG | 2044. | 6 | | AGTTGGTGTCACT GACAATGGGA | 2045. | CGCAGCGC ACGAGTTC ATCA | 2046. | DMSO | 3 | 0 | 0 | 3 |
| OT5-39 | AATGTCTTCATC ATTACCTGAGG | 2047. | 6 | | AGAGAGGACACAA TTCAACCCCT | 2048. | GGCTGGGG AGGCCTCA CAAT | 2049. | DMSO | 1 | 1 | 1 | 4 |
| OT5-40 | AGATGCTTGGTC ATTACCTGTGG | 2050. | 6 | | GGGAAAGTTTGGG AAAGTCAGCA | 2051. | AGGACAAG CTACCCCA CACC | 2052. | DMSO | 1 | 3 | 3 | 2 |
| OT5-41 | AGTAGATTAGTT ATTACCTGGGG | 2053. | 6 | | TGGTGCATCAAAG GGTTGCTTCT | 2054. | TCATTCCA GCACGCCG GGAG | 2055. | DMSO | 0 | 3 | 3 | 3 |
| OT5-42 | AGTAGGTTAGTA ATTACCTGGGG | 2056. | 6 | | CCCAGGCTGCCCA TCACACT | 2057. | TGGAGTAA GTATACCT TGGGGACCT | 2058. | DMSO | 1 | 3 | 3 | 2 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | non-Watson-Crick Transversions | Transitions |
|---|---|---|---|---|---|---|---|---|---|---|---|---|
| OT5-43 | CAAATGAGAGTC ATTACCTGAGG | 2059. | 6 | | TCAGTGCCCCTGG GTCCTCA | 2060. | TGTGCAAA TACCTAGC ACGGTGC | 2061. | DMSO | 4 | 2 | 0 |
| OT5-44 | CATGTCTGAATC ATTACCTGAGG | 2062. | 6 | | AGCACTCCCTTTT GAATTTTGGTGCT | 2063. | ACTGAAGT CCAGCCTC TTCCATTT CA | 2064. | DMSO | 2 | 1 | 3 |
| OT5-45 | CCTGACTTGGTC ATTACCTGTGG | 2065. | 6 | | GAAACCGGTCCCT GGTGCCA | 2066. | GGGGAGTA GAGGGTAG TGTTGCC | 2067. | DMSO | 2 | 0 | 4 |
| OT5-46 | CGTGCATTAGTC ATTACCTGAGG | 2068. | 6 | | TTGCGGGTCCCTG TGGAGTC | 2069. | AGGTGCCG TGTTGTGC CCAA | 2070. | DMSO | 1 | 2 | 3 |
| Target 6 | GGAATCCCTTCT GCAGCACCTGG | 2071. | 0 | | GCCCTACATCTGC TCTCCCTCCA | 2072. | GGGCCGGG AAAGAGTT GCTG | 2073. | DMSO | | | |
| OT6-1 | GGAACCCGTCT GCAGCACCAGG | 2074. | 2 | | TTGGAGTGTGGCC CGGGTTG | 2075. | ACCTCTCT TTCTCTGC CTCACTGT | 2076. | DMSO | 0 | 1 | 1 |
| OT6-2 | GGAACACCTTCT GCAGCTCCAGG | 2077. | 3 | | CACACCATGCTGA TCCAGGC | 2078. | GCAGTACG GAAGCACG AAGC | 2079. | DMSO | 1 | 1 | 1 |
| OT6-3 | GGAAGCTCTGCT GCAGCACCTGG | 2080. | 3 | | CTCCAGGGCTCGC TGTCCAC | 2081. | CTGGGCTC TGCTGGTT CCCC | 2082. | DMSO | 0 | 2 | 1 |
| OT6-4 | GGAATATCTTCT GCAGCCCCAGG | 2083. | 3 | | CTGTGGTAGCCGT GGCCAGG | 2084. | CCCCATAC CACCTCTC CGGGA | 2085. | DMSO | 0 | 2 | 1 |
| OT6-5 | GGAATCACTTTT ACAGCACCAGG | 2086. | 3 | | GGTGGCGGGACTT GAATGAG | 2087. | CCAGCGTG TTTCCAAG GGAT | 2088. | 1M betaine, TD | 0 | 1 | 2 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | Watson-Crick Transversions | non-Watson-Crick Transversions | Transitions |
|---|---|---|---|---|---|---|---|---|---|---|---|---|---|
| OT6-6 | GGAATCCCCTCT CCAGCCCCTGG | 2089. | 3 | GGAATCCCCTCTCC AGCCCCTGG (SEQ ID NO: 2236) GGAATCCCCCTCTCC AGCCTCTGG (SEQ ID NO: 2237) | CCAGAGGTGGGGC CCTGTGA | 2090. | TTTCCACA CTCAGTTC TGCAGGA | 2091. | DMSO | 1 | 1 | 1/2 |
| OT6-7 | GGAATCTCTTCT TCAGCATCTGG | 2092. | 3 | GGAATCTCTTCTTCCTT GGCATCTGG (SEQ ID NO: 2238) | TGTGACTGGTTGT CCTGCTTTCCT | 2093. | GCAGTGTT TTGTGGTG ATGGGCA | 2094. | 1M betaine, TD | 0 | 1 | 5 |
| OT6-8 | GGAATTGCTTCT GCAGCGCCAGG | 2095. | 3 | | CTGGCCAAGGGGT GAGTGGG | 2096. | TGGGACCC CAGCAGCC AATG | 2097. | DMSO | 1 | 0 | 2 |
| OT6-9 | GGACTCCCCTCT GCAGCAGTTGG | 2098. | 3 | | ACGGTGTGCTGGC TGCTCTT | 2099. | ACAGTGCT GACCGTGC TGGG | 2100. | DMSO | 1 | 1 | 1 |
| OT6-10 | GGAGTCCCTCCT ACAGCACCAGG | 2101. | 3 | | TGGTTTGGGCCTC AGGGATGG | 2102. | TGCCTCCC ACAAAAT GTCTACCT | 2103. | DMSO | 0 | 0 | 3 |
| OT6-11 | GGAGTCCCTCCT ACAGCACCAGG | 2104. | 3 | | TGGTTTGGGCCTC AGGGATGG | 2105. | ACCCCTTA TCCCAGAA CCCATGA | 2106. | DMSO | 0 | 0 | 3 |
| OT6-12 | GGCATCCATTCT GCAGCCCCTGG | 2107. | 3 | | TCCAAGTCAGCGA TGAGGGCT | 2108. | TGGGAGCT GTTCCTTT TTGGCCA | 2109. | DMSO | 0 | 3 | 0 |
| OT6-13 | GGCTTCCCTTCT GCAGCCCCAGG | 2110. | 3 | | CACCCCCTCTCAGC TTCCCAA | 2111. | GCTAGAGG GTCTGCTG CCTT | 2112. | DMSO | 1 | 2 | 0 |
| OT6-14 | TGAATCCATTCT CCAGCACCAGG | 2113. | 3 | | AGACCCCCTTGGCC AAGCACA | 2114. | CTTGCTCT CACCCCGC CTCC | 2115. | DMSO | 2 | 1 | 0 |
| OT6-15 | AAAATACCTTCT GCAGTACCAGG | 2116. | 4 | | ACATGTGGGAGGC GGACAGA | 2117. | TCTCACTT TGCTGTTA CCGATGTCG | 2118. | DMSO | 0 | 1 | 3 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | non-Watson-Crick Transversions | Transitions |
|---|---|---|---|---|---|---|---|---|---|---|---|---|
| OT6-16 | AAAATCCCTTCT TCAACACCTGG | 2119. | 4 | | GGACGACTGTGCC TGGGACA | 2120. | AGTGCCCA GAGTGTTG TAACTGCT | 2121. | 72 C. Anneal, 3% DMSO | 0 | 1 | 3 |
| OT6-17 | ACACTCCCTTCT GCAGCACCTGG | 2122. | 4 | | GGAGAGCTCAGCG CCAGTC | 2123. | CAGCGTGG CCCGTGGG AATA | 2124. | DMSO | 1 | 1 | 2 |
| OT6-18 | ACCATCCCTTCT GCAGCACCAGG | 2125. | 4 | | GCTGAAGTGCTCT GGGGTGCT | 2126. | ACCCCACT GTGGATGA ATTGGTACC | 2127. | DMSO | 1 | 1 | 2 |
| OT6-19 | AGAGGCCCTCT GCAGCACCAGG | 2128. | 4 | | TCGGGGTGCACAT GGCCATC | 2129. | TTGCCTCG CAGGGGAA GCAG | 2130. | DMSO | 0 | 1 | 3 |
| OT6-20 | AGGATCCCTTGT GCAGCTCCTGG | 2131. | 4 | | CTCGTGGGAGGCC AACACCT | 2132. | AGCCACCA ACACATAC CAGGCT | 2133. | DMSO | 2 | 0 | 2 |
| QT6-21 | CCACTCCCTTCT GCAGCACCCGG | 2134. | 4 | | GCATGCCTTTAAT CCCGCT | 2135. | AGGATTTC AGAGTGAT GGGGCT | 2136. | DMSO | 2 | 1 | 1 |
| OT6-22 | GAAGGCCCTTCA GCAGCACCTGG | 2137. | 4 | | CGCCCAGCCACAA AGTGCAT | 2138. | GCAAATTT CTGCACCT ACTCTAGG CCT | 2139. | DMSO | 1 | 1 | 2 |
| OT6-23 | GATATCCCTTCT GTATCACCTGG | 2140. | 4 | | AGCTCACAGAAT TGGAGGTAACAGT | 2141. | GCAGTCAC CCTTCACT GCCTGT | 2142. | DMSO | 1 | 1 | 2 |
| OT6-24 | GGGTCCGCTTCT GCAGCACCTGG | 2143. | 4 | | AAACTGGGCTGGG CTTCCGG | 2144. | GGGGCTAA GGCATTGT CAGACCC | 2145. | DMSO | 2 | 0 | 2 |
| OT6-25 | GTCTCCCCTTCT GCAGCACCAGG | 2146. | 4 | | GCAGTAGGCAGT CTGGGGC | 2147. | TCTCCTGC CTCAGCCT CCCA | 2148. | 1M betaine, TD | 1 | 2 | 1 |
| OT6-26 | GTCTCCCCTTCT GCAGCACCAGG | 2149. | 4 | | GCAGTAGGCAGT CTGGGGC | 2150. | TCTCCTGC CTCAGCCT CCCA | 2151. | 1M betaine, TD | 1 | 2 | 1 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | Watson-Crick Transitions | non-Watson-Crick Transversions | non-Watson-Crick Transitions |
|---|---|---|---|---|---|---|---|---|---|---|---|---|---|
| OT6-27 | GTCTCCCCTTCT GCAGCACCAGG | 2152. | 4 | | GCAGGTAGGCAGT CTGGGGC | 2153. | TCTCCTGC CTCAGCCT CCCA | 2154. | 1M betaine, TD | 1 | | 2 | 1 |
| OT6-28 | TCATTCCCGTCT GCAGCACCCGG | 2155. | 4 | | GCTCTGGGTAGA AGGAGGC | 2156. | GGCCTGTC AACCAACC AACC | 2157. | DMSO | 2 | | 2 | 0 |
| OT6-29 | TGCACCCCTCCT GCAGCACCAGG | 2158. | 4 | | TGACATGTTCTGT GCTGGGC | 2159. | AAATCCTG CAGCCTCC CCTT | 2160. | DMSO | 0 | | 2 | 2 |
| OT6-30 | TGCATACCCTCT GCAGCACCAGG | 2161. | 4 | | TCCTGGTGAGATC GTCCACAGGA | 2162. | TCCTCCCC ACTCAGCC TCCC | 2163. | DMSO | 0 | | 3 | 1 |
| OT6-31 | TGCATGGCTTCT GCAGCACCAGG | 2164. | 4 | | TCCTAATCCAAGT CCTTTGTTCAGACA | 2165. | AGGGACCA GCCACTAC CCTTCA | 2166. | DMSO | 2 | | 2 | 0 |
| OT6-32 | AATATTCCCTCT GCAGCACCAGG | 2167. | 5 | | GGGACACCAGTTC CTTCCAT | 2168. | GGGGGAGA TTGGAGTT CCCC | 2169. | DMSO | 1 | | 0 | 4 |
| OT6-33 | ACCATTTCTTCT GCAGCACCTGG | 2170. | 5 | | ACACCACTATCAA GGCAGAGTAGT | 2171. | TCTGCCTG GGGTGCTT TCCC | 2172. | DMSO | 1 | | 1 | 3 |
| OT6-34 | AGCTCCCATTCT GCAGCACCCGG | 2173. | 5 | | CTGGGAGCCGAGG GAAGTGC | 2174. | GCCCCGAC AGATGAGG CCTC | 2175. | DMSO | 1 | | 2 | 2 |
| OT6-35 | CAGATTCCTGCT GCAGCACCCGG | 2176. | 5 | CAGATTACTGCTGC AGCACCGGG (SEQ ID NO: 2239) | CGGGTCTCGAAT GCCTCCA | 2177. | ACCAGGA ATTGCCAC CCCC | 2178. | DMSO | 1 | | 2 | 3 |
| OT6-36 | CCAGAGCTTTCT GCAGCACCTGG | 2179. | 5 | | TTGCTGTGGTCCC GGTGGTG | 2180. | GCAGACAC TAGAGCCC GCCC | 2181. | DMSO | 3 | | 2 | 0 |
| OT6-37 | CCCAGCCCTGCT GCAGCACCCGG | 2182. | 5 | | GGTGTGGTGACAG GTCGGGT | 2183. | ACCTGCGT CTCTGTGC TGCA | 2184. | DMSO | 2 | | 3 | 0 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | Watson-Crick Transitions | non-Watson-Crick Transversions | Transitions |
|---|---|---|---|---|---|---|---|---|---|---|---|---|---|
| OT6-38 | CCCCTCCCTCCT GCAGCACCTGG | 2185. | 5 | | CTCCCAGGACAGT GCTCGGC | 2186. | CCTGGCCC CATGCTGC CTG | 2187. | DMSO | | 2 | 2 | 1 |
| OT6-39 | CTACTGACTTCT GCAGCACCTGG | 2188. | 5 | | TGCGTAGGTTTTG CCTCTGTGA | 2189. | AGGGAATG ATGTTTTC CACCCCCT | 2190. | DMSO | | 2 | 3 | 0 |
| OT6-40 | CTCCTCCCTCCT GCAGCACCTGG | 2191. | 5 | | CTCCCCAGCCACC GTTGTA | 2192. | TGCATTGA CGTACGAT GGCTCA | 2193. | DMSO | | 1 | 3 | 1 |
| OT6-41 | TCTGTCCCTCCT GCAGCACCTGG | 2194. | 5 | | ACCTGCAGCATGA ACTCTCGCA | 2195. | ACCTGAGC AACATGAC TCACCTGG | 2196. | DMSO | | 2 | 1 | 2 |
| OT6-42 | ACACAAACTTCT GCAGCACCTGG | 2197. | 6 | ACACAAACTTCTGC AGCACCTGG ACACAAACTTCTGC AGCACGTGG (SEQ ID NO: 2240) | TCTCCAGTTTCTT GCTCTCATGG | 2198. | ACCATTGG TGAACCCA GTCA | 2199. | 1M betaine, TD | 3/2 | 3 | 1 |
| OT6-43 | ACTGTCATTCT GCAGCACCTGG | 2200. | 6 | | TGGGGTGGTGGTC TTGAATCCA | 2201. | TCAGTGTAT AACCTGGG ACTTGTGCT | 2202. | DMSO | | 2 | 1 | 3 |
| OT6-44 | ACTTTATCTTCT GCAGCACCTGG | 2203. | 6 | | AGCAGCCAGTCCA GTGTCCTG | 2204. | CCCTTTCA TCGAGAAC CCCAGGG | 2205. | DMSO | | 3 | 1 | 2 |
| OT6-45 | ATCCTTTCTTCT GCAGCACCTGG | 2206. | 6 | | TGGACGCTGCTGG GAGGAGA | 2207. | GAGGTCTC GGGCTGCT CGTG | 2208. | DMSO | | 0 | 3 | 3 |
| OT6-46 | CACCACCGTTCT GCAGCACCAGG | 2209. | 6 | | AGGTTTGCACTCT GTTGCCTGG | 2210. | TGGGGTGA TTGGTTGC CAGGT | 2211. | DMSO | | 3 | 2 | 1 |
| OT6-47 | CATGTGGCTTCT GCAGCACCTGG | 2212. | 6 | | TCTTCCTTTGCCA GGCAGCACA | 2213. | TGCAGGAA TAGCAGGT ATGAGGAGT | 2214. | DMSO | | 4 | 0 | 2 |
| OT6-48 | CATTTTCTTCT GCAGCACCTGG | 2215. | 6 | | GGACGCCCTACTGC CTGGACC | 2216. | GCCCTGGC AGCCATG GTAC | 2217. | DMSO | | 3 | 0 | 3 |

TABLE E-continued

| Publications ID | Expected Off-Target Sequences (Expected) - HS GRCh37 | SEQ ID NO: | Mismatches in target compared to on-target site | Actual Target in U2OS.EGFP cells | Forward PCR Primer | SEQ ID NO: | Reverse PCR Primer | SEQ ID NO: | PCR Conditions | Watson-Crick Transversions | Watson-Crick Transversions | non-Watson-Crick Transitions |
|---|---|---|---|---|---|---|---|---|---|---|---|---|
| OT6-49 | CTCTGTCCTTCT GCAGCACCTGG | 2218. | 6 | | AGGCAGTCATCGC CTTGCTA | 2219. | GGTCCCAC CTTCCCCT ACAA | 2220. | DMSO | 2 | 3 | 1 |
| OT6-50 | CTGTACCCTCCT GCAGCACCAGG | 2221. | 6 | | Not optimized | | | | | 3 | 1 | 2 |
| OT6-51 | TTTGAGGCCGTCT GCAGCACCGGG | 2222. | 6 | | CCCCAGCCCCCAC CAGTTTC | 2223. | CAGCCCAG GCCACAGC TTCA | 2224. | DMSO | 1 | 4 | 1 |

Sanger Sequencing for Quantifying Frequencies of Indel Mutations

Purified PCR products used for T7EI assay were ligated into a Zero Blunt TOPO vector (Life Technologies) and transformed into chemically competent Top 10 bacterial cells. Plasmid DNAs were isolated and sequenced by the Massachusetts General Hospital (MGH) DNA Automation Core, using an M13 forward primer (5'-GTAAAACGACG-GCCAG-3') (SEQ ID NO:1059).

Restriction Digest Assay for Quantifying Specific Alterations Induced by HDR with ssODNs PCR reactions of specific on-target sites were performed using Phusion high-fidelity DNA polymerase (New England Biolabs). The VEGF and EMX1 loci were amplified using a touchdown PCR program ((98° C., 10 s; 72-62° C., −1° C./cycle, 15 s; 72° C., 30 s)×10 cycles, (98° C., 10 s; 62° C., 15 s; 72° C., 30 s)×25 cycles), with 3% DMSO. The primers used for these PCR reactions are listed in Table E. PCR products were purified by Ampure XP beads (Agencourt) according to the manufacturer's instructions. For detection of the BamHI restriction site encoded by the ssODN donor template, 200 ng of purified PCR products were digested with BamHI at 37° C. for 45 minutes. The digested products were purified by Ampure XP beads (Agencourt), eluted in 20 ul 0.1×EB buffer and analyzed and quantified using a QIAXCEL capillary electrophoresis system.

TruSeq Library Generation and Sequencing Data Analysis

Locus-specific primers were designed to flank on-target and potential and verified off-target sites to produce PCR products ~300 bp to 400 bps in length. Genomic DNAs from the pooled duplicate samples described above were used as templates for PCR. All PCR products were purified by Ampure XP beads (Agencourt) per the manufacturer's instructions. Purified PCR products were quantified on a QIAXCEL capillary electrophoresis system. PCR products for each locus were amplified from each of the pooled duplicate samples (described above), purified, quantified, and then pooled together in equal quantities for deep sequencing. Pooled amplicons were ligated with dual-indexed Illumina TruSeq adaptors as previously described (Fisher et al., 2011). The libraries were purified and run on a QIAXCEL capillary electrophoresis system to verify change in size following adaptor ligation. The adapter-ligated libraries were quantified by qPCR and then sequenced using Illumina MiSeq 250 bp paired-end reads performed by the Dana-Farber Cancer Institute Molecular Biology Core Facilities. We analyzed between 75,000 and 1,270,000 (average ~422,000) reads for each sample. The TruSeq reads were analyzed for rates of indel mutagenesis as previously described (Sander et al., 2013). Specificity ratios were calculated as the ratio of observed mutagenesis at an on-target locus to that of a particular off-target locus as determined by deep sequencing. Fold-improvements in specificity with tru-RGNs for individual off-target sites were calculated as the specificity ratio observed with tru-gRNAs to the specificity ratio for that same target with the matched full-length gRNA. As mentioned in the text, for some of the off-target sites, no indel mutations were detected with tru-gRNAs. In these cases, we used a Poisson calculator to determine with a 95% confidence that the upper limit of the actual number of mutated sequences would be three in number. We then used this upper bound to estimate the minimum fold-improvement in specificity for these off-target sites.

Example 2a. Truncated gRNAs can Efficiently Direct Cas9-Mediated Genome Editing in Human Cells To test the hypothesis that gRNAs truncated at their 5' end might function as efficiently as their full-length counterparts, a series of progressively shorter gRNAs were initially constructed as described above for a single target site in the EGFP reporter gene, with the following sequence: 5'-GGC GAGGGCGATGCCACCTAcGG-3' (SEQ ID NO:2241). This particular EGFP site was chosen because it was possible to make gRNAs to it with 15, 17, 19, and 20 nts of complementarity that each have a G at their 5' end (required for efficient expression from the U6 promoter used in these experiments). Using a human cell-based reporter assay in which the frequency of RGN-induced indels could be quantified by assessing disruption of a single integrated and constitutively expressed enhanced green fluorescent protein (EGFP) gene (Example 1 and Fu et al., 2013; Reyon et al., 2012) (FIG. 2B), the abilities of these variable-length gRNAs to direct Cas9-induced indels at the target site were measured.

As noted above, gRNAs bearing longer lengths of complementarity (21, 23, and 25 nts) exhibit decreased activities relative to the standard full-length gRNA containing 20 nts of complementary sequence (FIG. 2H), a result that matches those recently reported by others (Ran et al., Cell 2013). However, gRNAs bearing 17 or 19 nts of target complementarity showed activities comparable to or higher than the full-length gRNA, while a shorter gRNA bearing only 15 nts of complementary failed to show significant activity (FIG. 2H).

To test the generality of these initial findings, full-length gRNAs and matched gRNAs bearing 18, 17 and/or 16 nts of complementarity to four additional EGFP reporter gene sites (EGFP sites #1, #2, #3, and #4; FIG. 3A) were assayed. At all four target sites, gRNAs bearing 17 and/or 18 nts of complementarity functioned as efficiently as (or, in one case, more efficiently than) their matched full-length gRNAs to induce Cas9-mediated disruption of EGFP expression (FIG. 3A). However, gRNAs with only 16 nts of complementarity showed significantly decreased or undetectable activities on the two sites for which they could be made (FIG. 3A). For each of the different sites tested, we transfected the same amounts of the full-length or shortened gRNA expression plasmid and Cas9 expression plasmid. Control experiments in which we varied the amounts of Cas9 and truncated gRNA expression plasmids transfected for EGFP sites #1, #2, and #3 suggested that shortened gRNAs function equivalently to their full-length counterparts (FIGS. 3E (bottom) and 3F (bottom)) and that therefore we could use the same amounts of plasmids when making comparisons at any given target site. Taken together, these results provide evidence that shortened gRNAs bearing 17 or 18 nts of complementarity can generally function as efficiently as full-length gRNAs and hereafter the truncated gRNAs with these complementarity lengths are referred to as "tru-gRNAs" and RGNs using these tru-gRNAs as "tru-RGNs".

Whether tru-RGNs could efficiently induce indels on chromatinized endogenous gene targets was tested next. Tru-gRNAs were constructed for seven sites in three endogenous human genes (VEGFA, EMX1, and CLTA), including four sites that had previously been targeted with standard full-length gRNAs in three endogenous human genes: VEGFA site 1, VEGFA site 3, EMX1, and CTLA (Example 1 and Fu et al., 2013; Hsu et al., 2013; Pattanayak et al., 2013) (FIG. 3B). (It was not possible to test a tru-gRNA for VEGFA site 2 from Example 1, because this target sequence does not have the G at either position 17 or 18 of the complementarity region required for gRNA expression from a U6 promoter.) Using a well-established T7 Endonuclease I (T7EI) genotyping assay (Reyon et al., 2012) as described above, the Cas9-mediated indel mutation frequencies induced by each of these various gRNAs at their respective target sites was quantified in human U2OS.EGFP cells. For all five of the seven four sites, tru-RGNs robustly induced indel mutations with efficiencies comparable to those mediated by matched standard RGNs (FIG. 3B). For the two sites on which tru-RGNs showed lower activities than their full-length counterparts, we note that the absolute rates of mutagenesis were still high (means of 13.3% and 16.6%) at levels that would be useful for most applications. Sanger sequencing for three of these target sites (VEGFA sites 1 and 3 and EMX1) confirmed that indels induced by tru-RGNs originate at the expected site of cleavage and that these mutations are essentially indistinguishable from those induced with standard RGNs (FIG. 3C and FIGS. 7A-D).

We also found that tru-gRNAs bearing a mismatched 5' G and an 18 nt complementarity region could efficiently direct Cas9-induced indels whereas those bearing a mismatched 5' G and a 17 nt complementarity region showed lower or undetectable activities compared with matched full-length gRNAs (FIG. 7E), consistent with our findings that a minimum of 17 nts of complementarity is required for efficient RGN activity.

To further assess the genome-editing capabilities of tru-RGNs, their abilities to induce precise sequence alterations via HDR with ssODN donor templates were tested. Previous studies have shown that Cas9-induced breaks can stimulate the introduction of sequence from a homologous ssODN donor into an endogenous locus in human cells (Cong et al., 2013; Mali et al., 2013c; Ran et al., 2013; Yang et al., 2013). Therefore, the abilities were compared of matched full-length and tru-gRNAs targeted to VEGFA site 1 and to the EMXJ site to introduce a BamHI restriction site encoded on homologous ssODNs into these endogenous genes. At both sites, tru-RGNs mediated introduction of the BamHI site with efficiencies comparable to those seen with standard RGNs harboring their full-length gRNA counterparts (FIG. 3D). Taken together, this data demonstrate that tru-RGNs can function as efficiently as standard RGNs to direct both indels and precise HDR-mediated genome editing events in human cells.

Example 2b. Tru-RGNs Exhibit Enhanced Sensitivities to gRNA/DNA Interface Mismatches Having established that tru-RGNs can function efficiently to induce on-target genome editing alterations, whether these nucleases would show greater sensitivity to mismatches at the gRNA/DNA interface was tested. To assess this, a systematic series of variants was constructed for the tru-gRNAs that were previously tested on EGFP sites #1, #2, and #3 (FIG. 3A above). The variant gRNAs harbor single Watson-Crick substitutions at each position within the complementarity region (with the exception of the 5' G required for expression from the U6 promoter) (FIG. 5A). The human cell-based EGFP disruption assay was used to assess the relative abilities of these variant tru-gRNAs and an analogous set of matched variant full-length gRNAs made to the same three sites as described in Example 1 to direct Cas9-mediated indels. The results show that for all three EGFP target sites, tru-gRNAs generally showed greater sensitivities to single mismatches than standard RGNs harboring matched full-length gRNAs (compare bottom and top panels of FIG. 5A). The magnitude of sensitivity varied by site, with the greatest differences observed for sites #2 and #3, whose tru-gRNAs harbored 17 nts of complementarity.

Encouraged by the increased sensitivity of tru-RGNs to single nucleotide mismatches, we next sought to examine the effects of systematically mismatching two adjacent positions at the gRNA-DNA interface. We therefore made variants of the tru-gRNAs targeted to EGFP target sites #1, #2, and #3, each bearing Watson-Crick transversion substitutions at two adjacent nucleotide positions (FIG. 5B). As judged by the EGFP disruption assay, the effects of adjacent double mismatches on RGN activity were again substantially greater for tru-gRNAs than for the analogous variants made in Example 1 for matched full-length gRNAs targeted to all three EGFP target sites (compare bottom to top panels in FIG. 5B). These effects appeared to be site-dependent with nearly all of the double-mismatched tru-gRNAs for EGFP sites #2 and #3 failing to show an increase in EGFP disruption activities relative to a control gRNA lacking a complementarity region and with only three of the mismatched tru-gRNA variants for EGFP site #1 showing any residual activities (FIG. 5B). In addition, although double mutations generally showed greater effects on the 5' end with full-length gRNAs, this effect was not observed with tru-gRNAs. Taken together, our data suggest that tru-gRNAs exhibit greater sensitivities than full-length gRNAs to single and double Watson-Crick transversion mismatches at the gRNA-DNA interface.

Example 2c. Tru-RGNs Targeted to Endogenous Genes Show Improved Specificities in Human Cells The next experiments were performed to determine whether tru-RGNs might show reduced genomic off-target effects in human cells relative to standard RGNs harboring full-length gRNA counterparts. We examined matched full-length and tru-gRNAs targeted to VEGFA site 1, VEGFA site 3, and EMX1 site 1 (described in FIG. 3B above) because previous studies (see Example 1 and Fu et al., 2013; Hsu et al., 2013) had defined 13 bona fide off-target sites for the full-length gRNAs targeted to these sites. (We were unable to test a tru-gRNA for VEGFA site 2 from our original study6 because this target sequence does not have the G at either position 17 or 18 of the complementarity region required for efficient gRNA expression from a U6 promoter.) Strikingly, we found that tru-RGNs showed substantially reduced mutagenesis activity in human U2OS.EGFP cells relative to matched standard RGNs at all 13 of these bona fide off-target sites as judged by T7EI assay (Table 3A); for 11 of the 13 off-target sites, the mutation frequency with tru-RGNs dropped below the reliable detection limit of the T7EI assay (2-5%) (Table 3A). We observed similar results when these matched pairs of standard and tru-RGNs were tested at the same 13 off-target sites in another human cell line (FT-HEK293 cells) (Table 3A).

To quantify the magnitude of specificity improvement observed with tru-RGNs, we measured off-target mutation frequencies using high-throughput sequencing, which provides a more sensitive method for detecting and quantifying low frequency mutations than the T7EI assay. We assessed a subset of 12 of the 13 bona fide off-target sites for which we had seen decreased mutation rates with tru-gRNAs by T7EI assay (for technical reasons, we were unable to amplify the required shorter amplicon for one of the sites) and also examined an additional off-target site for EMX1 site 1 that had been identified by another group7 (FIG. 6A).

For all 13 off-target sites we tested, tru-RGNs showed substantially decreased absolute frequencies of mutagenesis relative to matched standard RGNs (FIG. 6A and Table 3B) and yielded improvements in specificity of as much as ~5000-fold or more relative to their standard RGN counterparts (FIG. 6B). For two off-target sites (OT1-4 and OT1-11), it was difficult to quantify the on-target to off-target ratios for tru-RGNs because the absolute number and frequency of indel mutations induced by tru-RGNs fell to background or near-background levels. Thus, the ratio of on-target to off-target rates would calculate to be infinite in these cases. To address this, we instead identified the maximum likely indel frequency with a 95% confidence level for these sites and then used this conservative estimate to calculate the minimum likely magnitude of specificity improvement for tru-RGNs relative to standard RGNs for these off-targets. These calculations suggest tru-RGNs yield improvements of ~10,000-fold or more at these sites (FIG. 6B).

To further explore the specificity of tru-RGNs, we examined their abilities to induce off-target mutations at additional closely related sites in the human genome. For the tru-gRNAs to VEGFA site 1 and EMX1, which each possess 18 nts of target site complementarity, we computationally identified all additional sites in the human genome mismatched at one or two positions within the complementarity region (not already examined above in Table 3A) and a subset of all sites mismatched at three positions among which we favored mismatches in the 5' end of the site as described in Example 1. For the tru-gRNA to VEGFA site 3, which possesses 17 nts of target site complementarity, we identified all sites mismatched at one position and a subset of all sites mismatched at two positions among which mismatches in the 5' end were favored (again not already examined in Table 3A). This computational analysis yielded a total of 30, 30, and 34 additional potential off-target sites for the tru-RGNs targeted to VEGFA site 1, VEFGA site 3, and the EMX1 site, respectively, which we then assessed for mutations using T7EI assay in human U2OS.EGFP and HEK293 cells in which the RGNs had been expressed.

Strikingly, the three tru-RGNs to VEGFA site 1, VEFGA site 3, and EMX1 did not induce detectable Cas9-mediated indel mutations at 93 of the 94 potential off-target sites examined in human U2OS.EGFP cells or at any of the 94 potential off-target sites in human HEK293 cells (Table 3C). For the one site at which off-target mutations were seen, whether the standard RGN with a full-length gRNA targeted to VEGFA site 1 could also mutagenize this same off-target site was examined; it induced detectable mutations albeit at a slightly lower frequency (FIG. 6C). The lack of improvement observed with shortening of the gRNA at this off-target site can be understood by comparing the 20 and 18 nt sequences for the full-length and tru-gRNAs, which shows that the two additional bases in the full-length 20 nt target are both mismatched (FIG. 6C). In summary, based on this survey of 94 additional potential off-target sites, shortening of the gRNA does not appear to induce new high-frequency off-target mutations.

Deep sequencing of a subset of the 30 most closely matched potential off-target sites from this set of 94 site (i.e.—those with one or two mismatches) showed either undetectable or very low rates of indel mutations (Table 3D) comparable to what we observed at other previously identified off-target sites (Table 3B). We conclude that tru-RGNs generally appear to induce either very low or undetectable levels of mutations at sites that differ by one or two mismatches from the on-target site. This contrasts with standard RGNs for which it was relatively easy to find high-frequency off-target mutations at sites that differed by as many as five mismatches (see Example 1).

TABLE 3A

On- and off-target mutation frequencies of matched tru-RGNs and standard RGNs targeted to endogenous genes in human U2OS.EGFP and HEK293 cells

| Target ID | 20mer Target | SEQ ID NO: | Indel mutation frequency (%) ± s.e.m. U2OS.EGFP | HEK293 |
|---|---|---|---|---|
| T1 | GGGTGGGGGGAGTTTGCTCCtGG | 2242. | 23.69 ± 1.99 | 6.98 ± 1.33 |
| OT1-3 | GGATGGAGGGAGTTTGCTCCtGG | 2244. | 17.25 ± 2.97 | 7.26 ± 0.62 |
| OT1-4 | GGGAGGGTGGAGTTTGCTCCtGG | 2246. | 6.23 ± 0.20 | 2.66 ± 0.30 |
| OT1-6 | CGGGGAGGGAGTTTGCTCCtGG | 2248. | 3.73 ± 0.23 | 1.41 ± 0.07 |
| OT1-11 | GGGGAGGGGAAGTTTGCTCCtGG | 2250. | 10.4 ± 0.7 | 3.61 ± 0.02 |
| T3 | GGTGAGTGAGTGTGTGCGTGtGG | 2252. | 54.08 ± 1.02 | 22.97 ± 0.17 |
| OT3-1 | GGTGAGTGAGTGTGTGTGTGaGG | 2254. | 6.16 ± 0.98 | 6.02 ± 0.11 |
| OT3-2 | AGTGAGTGAGTGTGTGTGTGggGG | 2256. | 19.64 ± 1.06 | 11.29 ± 0.27 |
| OT3-4 | GCTGAGTGAGTGTATGCGTGtGG | 2258. | 7.95 ± 0.11 | 4.50 ± 0.02 |
| OT3-9 | GGTGAGTGAGTGCGTGCGGGtGG | 2260. | N.D. | 1.09 ± 0.17 |
| OT3-17 | GTTGAGTGAATGTGTGCGTGaGG | 2262. | 1.85 ± 0.08 | N.D. |
| OT3-18 | TGTGGGTGAGTGTGTGCGTGaGG | 2264. | 6.16 ± 0.56 | 6.27 ± 0.09 |
| OT3-20 | AGAGAGTGAGTGTGTGCATGaGG | 2266. | 10.47 ± 1.08 | 4.38 ± 0.58 |
| T4 | GAGTCCGAGCAGAAGAAGAAgGG | 2268. | 41.56 ± 0.20 | 12.65 ± 0.31 |
| OT4-1 | GAGTTAGAGCAGAAGAAGAAaGG | 2270. | 19.26 ± 0.73 | 4.14 ± 0.66 |
| OT-4_Hsu31 | GAGTCTAAGCAGAAGAAGAAgAG | 2272. | 4.37 ± 0.58 | N.D. |

| Target ID | TruncatedTarget | SEQ ID NO: | Indel mutation frequency (%) ± s.e.m U2OS.EGFP | HEK293 | Gene |
|---|---|---|---|---|---|
| T1 | GTGGGGGGAGTTTGCTCCtGG | 2243. | 23.93 ± 4.37 | 8.34 ± 0.01 | VEGFA |
| OT1-3 | ATGGAGGGAGTTTGCTCCtGG | 2245. | N.D. | N.D. | IGDCC3 |

TABLE 3A-continued

On- and off-target mutation frequencies of matched tru-RGNs and standard RGNs targeted to endogenous genes in human U2OS.EGFP and HEK293 cells

| | | | | | |
|---|---|---|---|---|---|
| OT1-4 | GAGGGTGGAGTTTGCTCCtGG | 2247. | N.D. | N.D. | LOC116437 |
| OT1-6 | GGGGAGGGAGTTTGCTCCtGG | 2249. | N.D. | N.D. | CACNA2D |
| OT1-11 | GGAGGGGAAGTTTGCTCCtGG | 2251. | N.D. | N.D. | |
| | | | | | |
| T3 | GAGTGAGTGTGTGCGTGtGG | 2253. | 50.49 ± 1.25 | 20.05 ± 0.01 | VEGFA |
| OT3-1 | GAGTGAGTGTGTGTGTGaGG | 2255. | N.D. | N.D. | (abParts) |
| OT3-2 | GAGTGAGTGTGTGTGTGgGG | 2257. | 5.52 ± 0.25 | 3.41 ± 0.07 | MAX |
| OT3-4 | GAGTGAGTGTATGCGTGtGG | 2259. | 1.69 ± 0.26 | 1.27 ± 0.10 | |
| OT3-9 | GAGTGAGTGCGTGCGGGtGG | 2261. | N.D. | N.D. | TPCN2 |
| OT3-17 | GAGTGAATGTGTGCGTGaGG | 2263. | N.D. | N.D. | SLIT1 |
| OT3-18 | GGGTGAGTGTGTGCGTGaGG | 2265. | N.D. | N.D. | COMDA |
| OT3-20 | GAGTGAGTGTGTGCATGaGG | 2267. | N.D. | N.D. | |
| | | | | | |
| T4 | GTCCGAGCAGAAGAAGAAgGG | 2269. | 43.01 ± 0.87 | 17.25 ± 0.64 | EMX1 |
| OT4-1 | GTTAGAGCAGAAGAAGAAaGG | 2271. | N.D. | N.D. | HCN1 |
| OT-4_Hsu31 | GTCTAAGCAGAAGAAGAAgAG | 2273. | N.D. | N.D. | MFAP1 |

Mutation frequencies were measured by T7EI assay.
Means of duplicate measurements are shown with error bars representing standard errors of the mean.
*Off-target site OT4_53 is the same as EMX1 target 3 OT31 from Hsu et al., 2013.

TABLE 3B

Numbers of wild-type (WT) and indel mutation sequencing reads from deep sequencing experiments

| | Control | | | tru-RGN | | | Standard RGN | | |
|---|---|---|---|---|---|---|---|---|---|
| Site | Indel | WT | Freq. | Indel | WT | Freq. | Indel | WT | Freq. |
| VEGFA site 1 | 45 | 140169 | 0.03% | 122858 | 242127 | 33.66% | 150652 | 410479 | 26.85% |
| OT1-3 | 0 | 132152 | 0.00% | 1595 | 205878 | 0.77% | 50973 | 144895 | 26.02% |
| OT1-4 | 0 | 133508 | 0.00% | 0 | 223881 | 0.00% | 22385 | 240873 | 8.50% |
| OT1-6 | 3 | 213642 | 0.00% | 339 | 393124 | 0.09% | 24332 | 424458 | 5.21% |
| OT1-11 | 1 | 930894 | 0.00% | 0 | 274779 | 0.00% | 43738 | 212212 | 17.09% |
| VEGFA site 3 | 5 | 212571 | 0.00% | 303913 | 292413 | 50.96% | 183626 | 174740 | 51.24% |
| OT3-2 | 1169 | 162545 | 0.71% | 9415 | 277616 | 3.28% | 26545 | 222482 | 10.66% |
| OT3-4 | 7 | 383006 | 0.00% | 15551 | 1135673 | 1.35% | 42699 | 546203 | 7.25% |
| OT3-9 | 73 | 145367 | 0.05% | 113 | 227874 | 0.05% | 1923 | 168293 | 1.13% |
| OT3-17 | 8 | 460498 | 0.00% | 31 | 1271276 | 0.00% | 16760 | 675708 | 2.42% |
| OT3-18 | 7 | 373571 | 0.00% | 284 | 1275982 | 0.02% | 72354 | 599030 | 10.78% |
| OT3-20 | 5 | 140848 | 0.00% | 593 | 325162 | 0.18% | 30486 | 202733 | 13.07% |
| EMX1 site 1 | 1 | 158838 | 0.00% | 49104 | 102805 | 32.32% | 128307 | 307584 | 29.44% |
| OT4-1 | 10 | 169476 | 0.01% | 13 | 234431 | 0.01% | 47426 | 125683 | 27.40% |
| OT4-52 | 2 | 75156 | 0.00% | 10 | 231090 | 0.00% | 429 | 340201 | 0.13% |
| OT4-53 | 0 | 234069 | 0.00% | 6 | 367811 | 0.00% | 17421 | 351667 | 4.72% |

Freq. = frequency of indel mutations = number of indel sequences/number of wild-type sequences.
Control gRNA = gRNA lacking a complementarity region

TABLE 3C

Indel mutation frequencies at potential off-target sites of tru-RGNs targeted to endogenous genes in human cells

| Target ID | Target Site + PAM | SEQ ID NO: | Number of mismatches | Indel mutation frequency (%) ± s.e.m. U2OS.EGFP cells | HEK293 cells |
|---|---|---|---|---|---|
| VEGFA Site 1 | GTGGGGGGAGTTTGCTCCtGG | 2274. | 0 (on-target) | 23.93 ± 4.37 | 8.34 ± 0.01 |
| | GTGGGGGGAGTTTGCCCCaGG | 2275. | 1 | Not detected | Not detected |
| | GTGGGGGGTGTTTGCTCCcGG | 2276. | 1 | Not detected | Not detected |
| | GTGGGTGGAGTTTGCTACtGG | 2277. | 2 | Not detected | Not detected |
| | GTGGGGGGAGCTTTCTCCtGG | 2278. | 2 | Not detected | Not detected |
| | GTGGGTGGCGTTTGCTCCaGG | 2279. | 2 | Not detected | Not detected |
| | GTGGAGGGAGCTTGCTCCtGG | 2280. | 2 | 6.88 ± 0.19 | Not detected |
| | GTGGGTGGAGTTTGCTACaGG | 2281. | 2 | Not detected | Not detected |

TABLE 3C-continued

Indel mutation frequencies at potential off-target sites of tru-RGNs targeted to endogenous genes in human cells

| Target ID | Target Site + PAM | SEQ ID NO: | Number of mismatches | Indel mutation frequency (%) ± s.e.m. U2OS.EGFP cells | HEK293 cells |
|---|---|---|---|---|---|
| | GGGGGGGCAGTTTGCTCCtGG | 2282. | 2 | Not detected | Not detected |
| | GTGTGGGGAATTTGCTCCaGG | 2283. | 2 | Not detected | Not detected |
| | CTGCTGGGAGTTTGCTCCtGG | 2284. | 3 | Not detected | Not detected |
| | TTTGGGAGAGTTTGCTCCaGG | 2285. | 3 | Not detected | Not detected |
| | CTGAGGGCAGTTTGCTCCaGG | 2286. | 3 | Not detected | Not detected |
| | GTAAGGGAAGTTTGCTCCtGG | 2287. | 3 | Not detected | Not detected |
| | GGGGGTAGAGTTTGCTCCaGG | 2288. | 3 | Not detected | Not detected |
| | GGGTGGGGACTTTGCTCCaGG | 2289. | 3 | Not detected | Not detected |
| | GGGGGAGCAGTTTGCTCCaGG | 2290. | 3 | Not detected | Not detected |
| | TTGGGGTTAGTTTGCTCCtGG | 2291. | 3 | Not detected | Not detected |
| | TTGAGGGGAGTCTGCTCCaGG | 2292. | 3 | Not detected | Not detected |
| | CTGGGGTGATTTTGCTCCtGG | 2293. | 3 | Not detected | Not detected |
| | GAGAGGGGAGTTGGCTCCtGG | 2294. | 3 | Not detected | Not detected |
| | TTTGGGGGAGTTTGCCCCaGG | 2295. | 3 | Not detected | Not detected |
| | TTCGGGGGAGTTTGCGCCgGG | 2296. | 3 | Not detected | Not detected |
| | CTCGGGGGAGTTTGCACCaGG | 2297. | 3 | Not detected | Not detected |
| | GTGTTGGGAGTCTGCTCCaGG | 2298. | 3 | Not detected | Not detected |
| | GAGGGGGCAGGTTGCTCCaGG | 2299. | 3 | Not detected | Not detected |
| | GAGGGGAGAGTTTGTTCCaGG | 2300. | 3 | Not detected | Not detected |
| | GTGGCTGGAGTTTGCTGCtGG | 2301. | 3 | Not detected | Not detected |
| | GTCGGGGGAGTGGGCTCCaGG | 2302. | 3 | Not detected | Not detected |
| | GAGGGGGGAGTGTGTTCCgGG | 2303. | 3 | Not detected | Not detected |
| | GTGGTGGGAGCTTGTTCCtGG | 2304. | 3 | Not detected | Not detected |
| | GTGGGGGGTGCCTGCTCCaGG | 2305. | 3 | Not detected | Not detected |
| VEGFA Site 3 | GAGTGAGTGTGTGCGTGtGG | 2306. | 0 (on-target) | 50.49 ± 1.25 | 20.05 ± 0.01 |
| | CAGTGAGTGTGTGCGTGtGG | 2307. | 1 | Not detected | Not detected |
| | GTGTGAGTGTGTGCGTGgGG | 2308. | 1 | Not detected | Not detected |
| | GTGTGAGTGTGTGCGTGaGG | 2309. | 1 | Not detected | Not detected |
| | GTGTGAGTGTGTGCGTGtGG | 2310. | 1 | Not detected | Not detected |
| | GAGTGTGTGTGTGCGTGtGG | 2311. | 1 | Not detected | Not detected |
| | GAGTGGGTGTGTGCGTGgGG | 2312. | 1 | Not detected | Not detected |
| | GAGTGACTGTGTGCGTGtGG | 2313. | 1 | Not detected | Not detected |
| | GAGTGAGTGTGTGGGTGgGG | 2314. | 1 | Not detected | Not detected |
| | GAGTGAGTGTGTGTGTGtGG | 2315. | 1 | Not detected | Not detected |
| | GAGTGAGTGTGTGTGTGtGG | 2316. | 1 | Not detected | Not detected |
| | GAGTGAGTGTGTGTGTGgGG | 2317. | 1 | Not detected | Not detected |
| | GAGTGAGTGTGTGTGTGtGG | 2318. | 1 | Not detected | Not detected |
| | GAGTGAGTGTGTGCGCGgGG | 2319. | 1 | Not detected | Not detected |
| | CTGTGAGTGTGTGCGTGaGG | 2320. | 2 | Not detected | Not detected |
| | ATGTGAGTGTGTGCGTGtGG | 2321. | 2 | Not detected | Not detected |
| | GCCTGAGTGTGTGCGTGtGG | 2322. | 2 | Not detected | Not detected |
| | GTGTGTGTGTGTGCGTGtGG | 2323. | 2 | Not detected | Not detected |
| | GTGTGGGTGTGTGCGTGtGG | 2324. | 2 | Not detected | Not detected |
| | GCGTGTGTGTGTGCGTGtGG | 2325. | 2 | Not detected | Not detected |
| | GTGTGTGTGTGTGCGTGgGG | 2326. | 2 | Not detected | Not detected |
| | GTGTGCGTGTGTGCGTGtGG | 2327. | 2 | Not detected | Not detected |
| | GTGTGTGTGTGTGCGTGcGG | 2328. | 2 | Not detected | Not detected |
| | GAGAGAGAGTGTGCGTGtGG | 2329. | 2 | Not detected | Not detected |
| | GAGTGTGTGAGTGCGTGgGG | 2330. | 2 | Not detected | Not detected |
| | GTGTGAGTGTGTGTGTGtGG | 2331. | 2 | Not detected | Not detected |
| | GAGTGTGTGTATGCGTGtGG | 2332. | 2 | Not detected | Not detected |
| | GAGTCAGTGTGTGAGTGaGG | 2333. | 2 | Not detected | Not detected |
| | GAGTGTGTGTGTGAGTGtGG | 2334. | 2 | Not detected | Not detected |
| | GAGTGTGTGTGTGCATGtGG | 2335. | 2 | Not detected | Not detected |
| | GAGTGAGAGTGTGTGTGtGG | 2336. | 2 | Not detected | Not detected |
| | GAGTGAGTGAGTGAGTGaGG | 2337. | 2 | Not detected | Not detected |
| EMX1 site | GTCCGAGCAGAAGAAGAAgGG | 2338. | 0 (on-target) | 43.01 ± 0.87 | 17.25 ± 0.64 |
| | GTCTGAGCAGAAGAAGAAtGG | 2339. | 1 | Not detected | Not detected |
| | GTCCCAGCAGTAGAAGAAtGG | 2340. | 2 | Not detected | Not detected |
| | GTCCGAGGAGAGGAAGAAaGG | 2341. | 2 | Not detected | Not detected |
| | GTCAGAGGAGAAGAAGAAgGG | 2342. | 2 | Not detected | Not detected |
| | GACAGAGCAGAAGAAGAAgGG | 2343. | 2 | Not detected | Not detected |
| | GTGGGAGCAGAAGAAGAAgGG | 2344. | 2 | Not detected | Not detected |
| | GTACTAGCAGAAGAAGAAaGG | 2345. | 2 | Not detected | Not detected |
| | GTCTGAGCACAAGAAGAAtGG | 2346. | 2 | Not detected | Not detected |
| | GTGCTAGCAGAAGAAGAAgGG | 2347. | 2 | Not detected | Not detected |
| | TACAGAGCAGAAGAAGAAtGG | 2348. | 3 | Not detected | Not detected |
| | TACGGAGCAGAAGAAGAAtGG | 2349. | 3 | Not detected | Not detected |

TABLE 3C-continued

Indel mutation frequencies at potential off-target sites of tru-RGNs targeted to endogenous genes in human cells

| Target ID | Target Site + PAM | SEQ ID NO: | Number of mismatches | Indel mutation frequency (%) ± s.e.m. U2OS.EGFP cells | HEK293 cells |
|---|---|---|---|---|---|
| | AACGGAGCAGAAGAAGAAaGG | 2350. | 3 | Not detected | Not detected |
| | GACACAGCAGAAGAAGAAgGG | 2351. | 3 | Not detected | Not detected |
| | CTGCGATCAGAAGAAGAAaGG | 2352. | 3 | Not detected | Not detected |
| | GACTGGGCAGAAGAAGAAgGG | 2353. | 3 | Not detected | Not detected |
| | TTCCCTGCAGAAGAAGAAaGG | 2354. | 3 | Not detected | Not detected |
| | TTCCTACCAGAAGAAGAAtGG | 2355. | 3 | Not detected | Not detected |
| | CTCTGAGGAGAAGAAGAAaGG | 2356. | 3 | Not detected | Not detected |
| | ATCCAATCAGAAGAAGAAgGG | 2357. | 3 | Not detected | Not detected |
| | GCCCCTGCAGAAGAAGAAcGG | 2358. | 3 | Not detected | Not detected |
| | ATCCAACCAGAAGAAGAAaGG | 2359. | 3 | Not detected | Not detected |
| | GACTGAGAAGAAGAAGAAaGG | 2360. | 3 | Not detected | Not detected |
| | GTGGGATCAGAAGAAGAAaGG | 2361. | 3 | Not detected | Not detected |
| | GACAGAGAAGAAGAAGAAaGG | 2362. | 3 | Not detected | Not detected |
| | GTCATGCAGAAGAAGAAaGG | 2363. | 3 | Not detected | Not detected |
| | GTTGGAGAAGAAGAAGAgGG | 2364. | 3 | Not detected | Not detected |
| | GTAAGAGAAGAAGAAGAAgGG | 2365. | 3 | Not detected | Not detected |
| | CTCCTAGCAAAAGAAGAAtGG | 2366. | 3 | Not detected | Not detected |
| | TTCAGAGCAGGAGAAGAAtGG | 2367. | 3 | Not detected | Not detected |
| | GTTGGAGCAGGAGAAGAAgGG | 2368. | 3 | Not detected | Not detected |
| | GCCTGAGCAGAAGGAGAAgGG | 2369. | 3 | Not detected | Not detected |
| | GTCTGAGGACAAGAAGAAtGG | 2370. | 3 | Not detected | Not detected |
| | GTCCGGGAAGGAGAAGAAaGG | 2371. | 3 | Not detected | Not detected |
| | GGCCGAGCAGAAGAAAGAcGG | 2372. | 3 | Not detected | Not detected |
| | GTCCTAGCAGGAGAAGAAgAG | 2373. | 3 | Not detected | Not detected |

TABLE 3D

Frequencies of tru-RGN-induced indel mutations at potential off-target sites in human U2OS.EGFP as determined by deep sequencing

| On-target site | Off-target site sequence | S#. | tru-RGN Indel | tru-RGN WT | tru-RGN Freq. | Control Indel | Control WT | Control Freq |
|---|---|---|---|---|---|---|---|---|
| VEGFA site 1 | GTGGGGGGAGTTTGCCCCaGG | 2374. | 1500 | 225640 | 0.66% | 3 | 135451 | 0.00% |
| | GTGGGGGGTGTTTGCTCCcGG | 2375. | 1552 | 152386 | 1.01% | 0 | 86206 | 0.00% |
| | GTGGGTGGAGTTTGCTACtGG | 2376. | 1 | 471818 | 0.00% | 0 | 199581 | 0.00% |
| | GTGGGTGGAGTTTGCTACaGG | 2377. | 0 | 337298 | 0.00% | 1 | 211547 | 0.00% |
| | GTGGGTGGCGTTTGCTCCaGG | 2378. | 2 | 210174 | 0.00% | 1 | 105531 | 0.00% |
| | GTGTGGGGAATTTGCTCCaGG | 2379. | 673 | 715547 | 0.09% | 1 | 387097 | 0.00% |
| | GTGGGGGGAGCTTTCTCCtGG | 2380. | 5 | 107757 | 0.00% | 1 | 58735 | 0.00% |
| | GGGGGGGCAGTTTGCTCCtGG | 2381. | 1914 | 566548 | 0.34% | 3 | 297083 | 0.00% |
| VEGFA site 3 | GTGTGAGTGTGTGCGTGtGG | 2382. | 58 | 324881 | 0.02% | 9 | 122216 | 0.01% |
| | GTGTGAGTGTGTGCGTGaGG | 2383. | 532 | 194914 | 0.27% | 11 | 73644 | 0.01% |
| | GAGTGGGTGTGTGCGTGgGG | 2384. | 70 | 237029 | 0.03% | 10 | 178258 | 0.01% |
| | GAGTGACTGTGTGCGTGtGG | 2385. | 6 | 391894 | 0.00% | 0 | 239460 | 0.00% |
| | GAGTGAGTGTGTGGGTGgGG | 2386. | 15 | 160140 | 0.01% | 10 | 123324 | 0.01% |
| | GTGTGAGTGTGTGCGTGgGG | 2387. | 19 | 138687 | 0.01% | 1 | 196271 | 0.00% |
| | CAGTGAGTGTGTGCGTGtGG | 2388. | 78 | 546865 | 0.01% | 41 | 355953 | 0.01% |
| | GTGTGAGTGTGTGCGTGtGG | 2389. | 128 | 377451 | 0.03% | 56 | 133978 | 0.04% |
| | GAGTGTGTGTGTGCGTGtGG | 2390. | 913 | 263028 | 0.35% | 78 | 178979 | 0.04% |
| | GAGTGAGTGTGTGTGtGG | 2391. | 40 | 106933 | 0.04% | 36 | 58812 | 0.06% |
| | GAGTGAGTGTGTGTGTGtGG | 2392. | 681 | 762999 | 0.09% | 63 | 222451 | 0.03% |
| | GAGTGAGTGTGTGTGTGgGG | 2393. | 331 | 220289 | 0.15% | 100 | 113911 | 0.09% |
| | GAGTGAGTGTGTGTGTGtGG | 2394. | 0 | 35725 | 0.00% | 8 | 186495 | 0.00% |
| | GAGTGAGTGTGTGCGCGgGG | 2395. | 94 | 246893 | 0.04% | 16 | 107623 | 0.01% |
| EMX1 site 1 | GTCAGAGGAGAAGAAGAAgGG | 2396. | 0 | 201483 | 0.00% | 4 | 148416 | 0.00% |
| | GTCAGAGGAGAAGAAGAAgGG | 2397. | 10 | 545662 | 0.00% | 5 | 390884 | 0.00% |
| | GTCTGAGCACAAGAAGAAtGG | 2398. | 2 | 274212 | 0.00% | 0 | 193837 | 0.00% |
| | GTCTGAGCAGAAGAAGAAtGG | 2399. | 440 | 375646 | 0.12% | 10 | 256181 | 0.00% |
| | GACAGAGCAGAAGAAGAAgGG | 2400. | 2 | 212472 | 0.00% | 1 | 158860 | 0.00% |
| | GTACTAGCAGAAGAAGAAaGG | 2401. | 152 | 229209 | 0.07% | 103 | 157717 | 0.07% |

TABLE 3D-continued

Frequencies of tru-RGN-induced indel mutations at potential off-target sites in human U2OS.EGFP as determined by deep sequencing

| On-target site | Off-target site sequence | S# | tru-RGN | | | Control | | |
|---|---|---|---|---|---|---|---|---|
| | | | Indel | WT | Freq. | Indel | WT | Freq |
| | GTGGGAGCAGAAGAAGAAgGG | 2402. | 50 | 207401 | 0.02% | 36 | 111183 | 0.03% |
| | GTCCCAGCAGTAGAAGAAtGG | 2403. | 0 | 226477 | 0.00% | 1 | 278948 | 0.00% |

S#: SEQ ID NO:

Example 2d. Tru-gRNAs can be Used with Dual Cas9 Nickases to Efficiently Induce Genome Editing in Human Cells tru-gRNAs were tested with the recently described dual Cas9 nickase approach to induce indel mutations. To do this, the Cas9-D10A nickase together with two full-length gRNAs targeted to sites in the human VEGFA gene (VEGFA site 1 and an additional sequence we refer to as VEGFA site 4) were co-expressed in U2OS.EGFP cells (FIG. 4A). As described previously (Ran et al., 2013), this pair of nickases functioned cooperatively to induce high rates of indel mutations at the VEGFA target locus (FIG. 4B). Interestingly, Cas9-D10A nickase co-expressed with only the gRNA targeted to VEGFA site 4 also induced indel mutations at a high frequency, albeit at a rate somewhat lower than that observed with the paired full-length gRNAs (FIG. 4B). Importantly, use of a tru-gRNA for VEGFA site 1 in place of a full-length gRNA did not affect the efficacy of the dual nickase approach to induce indel mutations (FIG. 4B).

The dual nickase strategy has also been used to stimulate the introduction of specific sequence changes using ssODNs (Mali et al., 2013a; Ran et al., 2013) and so whether tru-gRNAs might be used for this type of alteration was also tested. Paired full-length gRNAs for VEGFA sites 1 and 4 together with Cas9-D10A nickase cooperatively enhanced efficient introduction of a short insertion from a ssODN donor (FIG. 3A) into the VEGFA locus in human U2OS.EGFP cells as expected (FIG. 3C). Again, the efficiency of ssODN-mediated sequence alteration by dual nicking remained equally high with the use of a tru-gRNA in place of the full-length gRNA targeted to VEGFA site 1 (FIG. 3C). Taken together, these results demonstrate that tru-gRNAs can be utilized as part of a dual Cas9 nickase strategy to induce both indel mutations and ssODN-mediated sequence changes, without compromising the efficiency of genome editing by this approach.

Having established that use of a tru-gRNA does not diminish the on-target genome editing activities of paired nickases, we next used deep sequencing to examine mutation frequencies at four previously identified bonafide off-target sites of the VEGFA site 1 gRNA. This analysis revealed that mutation rates dropped to essentially undetectable levels at all four of these off-target sites when using paired nickases with a tru-gRNA (Table 4). By contrast, neither a tru-RGN (Table 3B) nor the paired nickases with full-length gRNAs (Table 4) was able to completely eliminate off-target mutations at one of these four off-target sites (OT1-3). These results demonstrate that the use of tru-gRNAs can further reduce the off-target effects of paired Cas9 nickases (and vice versa) without compromising the efficiency of on-target genome editing.

TABLE 4

Frequencies of paired nickase-induced indel mutations at on- and off-target sites of VEGFA site 1 using full-length and tru-gRNAs

| Site | Paired full-length gRNAs | | | tru-gRNA/full-length gRNA | | | Control | | |
|---|---|---|---|---|---|---|---|---|---|
| | Indel | WT | Freq. | Indel | WT | Freq. | Indel | WT | Freq. |
| VEGFA site 1 | 78905 | 345696 | 18.583% | 65754 | 280720 | 18.978% | 170 | 308478 | 0.055% |
| OT1-3 | 184 | 85151 | 0.216% | 0 | 78658 | 0.000% | 2 | 107850 | 0.002% |
| OT1-4 | 0 | 89209 | 0.000% | 1 | 97010 | 0.001% | 0 | 102135 | 0.000% |
| OT1-6 | 2 | 226575 | 0.001% | 0 | 208218 | 0.000% | 0 | 254580 | 0.000% |
| OT1-11 | 0 | 124729 | 0.000% | 0 | 121581 | 0.000% | 0 | 155173 | 0.000% |

REFERENCES

Cheng, A. W., Wang, H., Yang, H., Shi, L., Katz, Y., Theunissen, T. W., Rangarajan, S., Shivalila, C. S., Dadon, D. B., and Jaenisch, R. Multiplexed activation of endogenous genes by CRISPR-on, an RNA-guided transcriptional activator system. Cell Res 23, 1163-1171. (2013).

Cho, S. W., Kim, S., Kim, J. M. & Kim, J. S. Targeted genome engineering in human cells with the Cas9 RNA-guided endonuclease. Nat Biotechnol 31, 230-232 (2013).

Cong, L. et al. Multiplex genome engineering using CRISPR/Cas systems. Science 339, 819-823 (2013).

Cradick, T. J., Fine, E. J., Antico, C. J., and Bao, G. CRISPR/Cas9 systems targeting beta-globin and CCR5 genes have substantial off-target activity. Nucleic Acids Res. (2013).

Dicarlo, J. E. et al. Genome engineering in *Saccharomyces cerevisiae* using CRISPR-Cas systems. Nucleic Acids Res (2013).

Ding, Q., Regan, S. N., Xia, Y., Oostrom, L. A., Cowan, C. A., and Musunuru, K. Enhanced efficiency of human pluripotent stem cell genome editing through replacing TALENs with CRISPRs. Cell Stem Cell 12, 393-394. (2013).

Fisher, S., Barry, A., Abreu, J., Minie, B., Nolan, J., Delorey, T. M., Young, G., Fennell, T. J., Allen, A., Ambrogio, L., et al. A scalable, fully automated process for construction of sequence-ready human exome targeted capture libraries. Genome Biol 12, R1. (2011).

Friedland, A. E., Tzur, Y. B., Esvelt, K. M., Colaiacovo, M. P., Church, G. M., and Calarco, J. A. Heritable genome editing in C. elegans via a CRISPR-Cas9 system. Nat Methods 10, 741-743. (2013).

Fu, Y., Foden, J. A., Khayter, C., Maeder, M. L., Reyon, D., Joung, J. K., and Sander, J. D. High-frequency off-target mutagenesis induced by CRISPR-Cas nucleases in human cells. Nat Biotechnol 31, 822-826. (2013).

Gabriel, R. et al. An unbiased genome-wide analysis of zinc-finger nuclease specificity. Nat Biotechnol 29, 816-823 (2011).

Gilbert, L. A., Larson, M. H., Morsut, L., Liu, Z., Brar, G. A., Torres, S. E., Stern-Ginossar, N., Brandman, O., Whitehead, E. H., Doudna, J. A., et al. (2013). CRISPR-Mediated Modular RNA-Guided Regulation of Transcription in Eukaryotes. Cell 154, 442-451.

Gratz, S. J. et al. Genome engineering of Drosophila with the CRISPR RNA-guided Cas9 nuclease. Genetics (2013).

Hockemeyer, D. et al. Genetic engineering of human pluripotent cells using TALE nucleases. Nat Biotechnol 29, 731-734 (2011).

Horvath, P. & Barrangou, R. CRISPR/Cas, the immune system of bacteria and archaea. Science 327, 167-170 (2010).

Hsu, P. D., Scott, D. A., Weinstein, J. A., Ran, F. A., Konermann, S., Agarwala, V., Li, Y., Fine, E. J., Wu, X., Shalem, O., et al. DNA targeting specificity of RNA-guided Cas9 nucleases. Nat Biotechnol 31, 827-832. (2013).

Hwang, W. Y. et al. Efficient genome editing in zebrafish using a CRISPR-Cas system. Nat Biotechnol 31, 227-229 (2013).

Hwang, W. Y., Fu, Y., Reyon, D., Maeder, M. L., Kaini, P., Sander, J. D., Joung, J. K., Peterson, R. T., and Yeh, J. R. Heritable and Precise Zebrafish Genome Editing Using a CRISPR-Cas System. PLoS One 8, e68708. (2013a).

Jiang, W., Bikard, D., Cox, D., Zhang, F. & Marraffini, L. A. RNA-guided editing of bacterial genomes using CRISPR-Cas systems. Nat Biotechnol 31, 233-239 (2013).

Jinek, M. et al. A programmable dual-RNA-guided DNA endonuclease in adaptive bacterial immunity. Science 337, 816-821 (2012).

Jinek, M. et al. RNA-programmed genome editing in human cells. Elife 2, e00471 (2013).

Li, D., Qiu, Z., Shao, Y., Chen, Y., Guan, Y., Liu, M., Li, Y., Gao, N., Wang, L., Lu, X., et al. Heritable gene targeting in the mouse and rat using a CRISPR-Cas system. Nat Biotechnol 31, 681-683. (2013a).

Li, W., Teng, F., Li, T., and Zhou, Q. Simultaneous generation and germline transmission of multiple gene mutations in rat using CRISPR-Cas systems. Nat Biotechnol 31, 684-686. (2013b).

Maeder, M. L., Linder, S. J., Cascio, V. M., Fu, Y., Ho, Q. H., and Joung, J. K. CRISPR RNA-guided activation of endogenous human genes. Nat Methods 10, 977-979. (2013).

Mali, P., Aach, J., Stranges, P. B., Esvelt, K. M., Moosburner, M., Kosuri, S., Yang, L., and Church, G. M. CAS9 transcriptional activators for target specificity screening and paired nickases for cooperative genome engineering. Nat Biotechnol 31, 833-838. (2013a).

Mali, P., Esvelt, K. M., and Church, G. M. Cas9 as a versatile tool for engineering biology. Nat Methods 10, 957-963. (2013b).

Mali, P. et al. RNA-guided human genome engineering via Cas9. Science 339, 823-826 (2013c).

Pattanayak, V., Lin, S., Guilinger, J. P., Ma, E., Doudna, J. A., and Liu, D. R. High-throughput profiling of off-target DNA cleavage reveals RNA-programmed Cas9 nuclease specificity. Nat Biotechnol 31, 839-843. (2013).

Pattanayak, V., Ramirez, C. L., Joung, J. K. & Liu, D. R. Revealing off-target cleavage specificities of zinc-finger nucleases by in vitro selection. Nat Methods 8, 765-770 (2011).

Perez, E. E. et al. Establishment of HIV-1 resistance in CD4+ T cells by genome editing using zinc-finger nucleases. Nat Biotechnol 26, 808-816 (2008).

Perez-Pinera, P., Kocak, D. D., Vockley, C. M., Adler, A. F., Kabadi, A. M., Polstein, L. R., Thakore, P. I., Glass, K. A., Ousterout, D. G., Leong, K. W., et al. RNA-guided gene activation by CRISPR-Cas9-based transcription factors. Nat Methods 10, 973-976. (2013).

Qi, L. S., Larson, M. H., Gilbert, L. A., Doudna, J. A., Weissman, J. S., Arkin, A. P., and Lim, W. A. Repurposing CRISPR as an RNA-guided platform for sequence-specific control of gene expression. Cell 152, 1173-1183. (2013).

Ran, F. A., Hsu, P. D., Lin, C. Y., Gootenberg, J. S., Konermann, S., Trevino, A. E., Scott, D. A., Inoue, A., Matoba, S., Zhang, Y., et al. Double nicking by RNA-guided CRISPR Cas9 for enhanced genome editing specificity. Cell 154, 1380-1389. (2013).

Reyon, D. et al. FLASH assembly of TALENs for high-throughput genome editing. Nat Biotech 30, 460-465 (2012).

Sander, J. D., Maeder, M. L., Reyon, D., Voytas, D. F., Joung, J. K., and Dobbs, D. ZiFiT (Zinc Finger Targeter): an updated zinc finger engineering tool. Nucleic Acids Res 38, W462-468. (2010).

Sander, J. D., Ramirez, C. L., Linder, S. J., Pattanayak, V., Shoresh, N., Ku, M., Foden, J. A., Reyon, D., Bernstein, B. E., Liu, D. R., et al. In silico abstraction of zinc finger nuclease cleavage profiles reveals an expanded landscape of off-target sites. Nucleic Acids Res. (2013).

Sander, J. D., Zaback, P., Joung, J. K., Voytas, D. F., and Dobbs, D. Zinc Finger Targeter (ZiFiT): an engineered zinc finger/target site design tool. Nucleic Acids Res 35, W599-605. (2007).

Shen, B. et al. Generation of gene-modified mice via Cas9/RNA-mediated gene targeting. Cell Res (2013).

Sugimoto, N. et al. Thermodynamic parameters to predict stability of RNA/DNA hybrid duplexes. Biochemistry 34, 11211-11216 (1995).

Terns, M. P. & Terns, R. M. CRISPR-based adaptive immune systems. Curr Opin Microbiol 14, 321-327 (2011).

Wang, H. et al. One-Step Generation of Mice Carrying Mutations in Multiple Genes by CRISPR/Cas-Mediated Genome Engineering. Cell 153, 910-918 (2013).

Wiedenheft, B., Sternberg, S. H. & Doudna, J. A. RNA-guided genetic silencing systems in bacteria and archaea. Nature 482, 331-338 (2012).

Yang, L., Guell, M., Byrne, S., Yang, J. L., De Los Angeles, A., Mali, P., Aach, J., Kim-Kiselak, C., Briggs, A. W., Rios, X., et al. (2013). Optimization of scarless human stem cell genome editing. Nucleic Acids Res 41, 9049-9061.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10415059B2). An electronic copy of the "Sequence Listing" will also be available from the USPTO upon request and payment of the fee set forth in 37 CFR 1.19(b)(3).

What is claimed is:

1. A method of RNA-guided genome editing in a cell, the method comprising contacting the cell with a guide RNA (gRNA) that includes a complementarity region consisting of 17-18 nucleotides that are complementary to 17-18 consecutive nucleotides of the complementary strand of a target genomic sequence, wherein the gRNA comprises SEQ ID NO:1, SEQ ID NO:2, SEQ ID NO:3, SEQ ID NO:4, SEQ ID NO:5, SEQ ID NO:6, SEQ ID NO:7, SEQ ID NO:2404, SEQ ID NO:2407, or SEQ ID NO: 2408, and wherein in the presence of a S. pyogenes Cas9 nuclease, the gRNA complementarity region binds and directs the Cas9 nuclease to the target genomic sequence, and the Cas9 nuclease edits the target genomic sequence.

2. A Streptococcus pyogenes gRNA molecule that includes a complementarity region at the 5' end of the gRNA consisting of 17-18 nucleotides that are complementary to 17-18 consecutive nucleotides of the complementary strand of a target genomic sequence, wherein the target genomic sequence is immediately 5' of a protospacer adjacent motif, wherein the gRNA is a single gRNA or a CRISPR RNA (crRNA), and wherein in the presence of an S. pyogenes Cas9 nuclease, the gRNA complementarity region binds and directs the Cas9 nuclease to the target genomic sequences, and the Cas9 nuclease edits the target genomic sequence.

3. The gRNA of claim 2, wherein the complementarity region of the gRNA consists of 17 nucleotides.

4. The gRNA of claim 2, comprising a ribonucleic acid consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:2404, SEQ ID NO:2407, or SEQ ID NO: 2408.

5. The gRNA of claim 2, comprising a ribonucleic acid that includes one or more uracil (U) at the 3' end of the molecule.

6. The gRNA of claim 2, comprising a ribonucleic acid that includes one or more additional nucleotides at the 5' end of the RNA molecule that is not complementary to the target genomic sequence.

7. The gRNA of claim 2, comprising a ribonucleic acid that includes one, two, or three additional nucleotides at the 5' end of the RNA molecule that are not complementary to the target genomic sequence.

8. The gRNA of claim 2, wherein the complementarity region is complementary to 17 consecutive nucleotides of the complementary strand of a target genomic sequence.

9. The gRNA of claim 2, wherein the complementarity region is complementary to 18 consecutive nucleotides of the complementary strand of a target genomic sequence.

10. A DNA molecule encoding the gRNA of claim 2.

11. A vector comprising the DNA molecule of claim 10.

12. A host cell expressing the vector of claim 11.

13. The host cell of claim 12, wherein the cell is a eukaryotic cell.

14. The host cell of claim 13, wherein the cell is a mammalian cell.

15. The gRNA of claim 2, wherein the complementarity region of the gRNA consists of 18 nucleotides.

16. The gRNA of claim 2, and wherein the gRNA retains the ability to form a complex with a Cas9 nuclease or a catalytically inactive Cas9 (dCas9) nuclease.

17. A complex comprising:
a Streptococcus pyogenes Cas9 nuclease and
a Streptococcus pyogenes gRNA molecule that includes a complementarity region at the 5' end of the gRNA consisting of 17-18 nucleotides that are complementary to 17-18 consecutive nucleotides of the complementary strand of a target genomic sequence, wherein the target genomic sequence is immediately 5' of a protospacer adjacent motif,
wherein the gRNA is a single gRNA or a CRISPR RNA (crRNA), and
wherein in the presence of the S. pyogenes Cas9 nuclease, the gRNA complementarity region binds and directs the Cas9 nuclease to the target genomic sequence, and the Cas9 nuclease edits the target genomic sequence.

18. The complex of claim 17, wherein the Cas9 nuclease is a dCas9 nuclease.

19. The complex of claim 17, wherein the complementarity region of the gRNA consists of 17 nucleotides.

20. The complex of claim 17, wherein the gRNA comprises a ribonucleic acid consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:2404, SEQ ID NO:2407, or SEQ ID NO: 2408.

21. The complex of claim 17, wherein the gRNA includes one or more uracil (U) at the 3' end of the molecule.

22. The complex of claim 17, wherein the gRNA includes one or more additional nucleotides at the 5' end of the gRNA that is not complementary to the target genomic sequence.

23. The complex of claim 17, wherein the gRNA includes one, two, or three additional nucleotides at the 5' end of the RNA molecule that are not complementary to the target genomic sequence.

24. The complex of claim 17, wherein the complementarity region is complementary to 17 consecutive nucleotides of the complementary strand of a target genomic sequence.

25. The complex of claim 17, wherein the complementarity region is complementary to 18 consecutive nucleotides of the complementary strand of a target genomic sequence.

26. The complex of claim 17, wherein the complementarity region of the gRNA consists of 18 nucleotides.

27. A DNA molecule encoding the complex of claim 17.

28. A vector comprising the DNA molecule of claim 27.

29. A host cell expressing the vector of claim 28.

30. The host cell of claim 29, wherein the cell is a eukaryotic cell.

31. The host cell of claim 30, wherein the cell is a mammalian cell.

* * * * *